(12) United States Patent
George et al.

(10) Patent No.: US 8,029,803 B2
(45) Date of Patent: *Oct. 4, 2011

(54) CHIMERIC ANTIGENS FOR ELICITING AN IMMUNE RESPONSE

(75) Inventors: Rajan George, Edmonton (CA); Lorne Tyrrell, Edmonton (CA); Antoine Noujaim, Edmonton (CA)

(73) Assignee: Paladin Labs, Inc. (CA)

( * ) Notice: Subject to any disclaimer, the term of this patent is extended or adjusted under 35 U.S.C. 154(b) by 1275 days.

This patent is subject to a terminal disclaimer.

(21) Appl. No.: 10/365,620

(22) Filed: Feb. 13, 2003

(65) Prior Publication Data

US 2004/0001853 A1  Jan. 1, 2004

Related U.S. Application Data

(60) Provisional application No. 60/423,578, filed on Nov. 5, 2002, provisional application No. 60/390,564, filed on Jun. 20, 2002.

(51) Int. Cl.
*A61K 399/29* (2006.01)
*C12P 21/00* (2006.01)

(52) U.S. Cl. .................. 424/227.1; 424/178.1; 424/93.1

(58) Field of Classification Search .............. 424/192.1, 424/227.1, 193.1, 194.1, 196.1, 191.1; 530/387.3, 530/389.1, 391.5, 391.7, 391.9
See application file for complete search history.

(56) References Cited

U.S. PATENT DOCUMENTS

| | | | |
|---|---|---|---|
| 4,088,748 A | 5/1978 | McAleer et al. | |
| 4,181,713 A | 1/1980 | McAleer et al. | |
| 4,235,871 A | 11/1980 | Papahadjopoulos et al. | |
| 4,428,941 A | 1/1984 | Galibert et al. | |
| 4,433,059 A | 2/1984 | Chang et al. | |
| 4,501,728 A | 2/1985 | Geho et al. | |
| 4,569,794 A | 2/1986 | Smith et al. | |
| 4,599,230 A | 7/1986 | Milich et al. | |
| 4,599,231 A | 7/1986 | Milich et al. | |
| 4,722,840 A | 2/1988 | Valenzuela et al. | |
| 4,816,249 A | 3/1989 | Levy et al. | |
| 4,816,567 A | 3/1989 | Cabilly et al. | |
| 4,837,028 A | 6/1989 | Allen | |
| 4,877,830 A | 10/1989 | Dobeli et al. | |
| 5,019,369 A | 5/1991 | Presant et al. | |
| 5,023,252 A | 6/1991 | Hseih | |
| 5,047,513 A | 9/1991 | Dobeli et al. | |
| 5,053,224 A | 10/1991 | Koprowski et al. | |
| 5,098,833 A | 3/1992 | Lasky et al. | |
| 5,116,964 A | 5/1992 | Capon et al. | |
| 5,155,027 A | 10/1992 | Sledziewski et al. | |
| 5,196,194 A | 3/1993 | Rutter et al. | |
| 5,216,131 A | 6/1993 | Lasky et al. | |
| 5,225,538 A | 7/1993 | Capon et al. | |
| 5,284,933 A | 2/1994 | Dobeli et al. | |
| 5,310,663 A | 5/1994 | Dobeli et al. | |
| 5,336,603 A | 8/1994 | Capon et al. | |
| 5,346,994 A | 9/1994 | Chomczynski | |
| 5,420,264 A | 5/1995 | Seed et al. | |
| 5,428,130 A | 6/1995 | Capon et al. | |
| 5,455,030 A * | 10/1995 | Ladner et al. | 424/135.1 |
| 5,455,165 A | 10/1995 | Capon et al. | |
| 5,514,582 A | 5/1996 | Capon et al. | |
| 5,565,335 A | 10/1996 | Capon et al. | |
| 5,567,584 A | 10/1996 | Sledziewski et al. | |
| 5,589,466 A | 12/1996 | Felgner et al. | |
| 5,686,600 A * | 11/1997 | Carozzi et al. | 536/23.53 |
| 5,715,147 A | 2/1998 | Nagano | |
| 5,750,375 A | 5/1998 | Sledziewski et al. | |
| 5,792,463 A | 8/1998 | Valenzuela et al. | |
| 5,840,844 A | 11/1998 | Lasky et al. | |
| 5,843,725 A | 12/1998 | Sledziewski et al. | |
| 5,928,902 A | 7/1999 | De Wilde et al. | |
| 5,942,234 A | 8/1999 | Ralston et al. | |
| 5,965,140 A | 10/1999 | Valenzuela et al. | |
| 5,969,109 A | 10/1999 | Bona et al. | |
| 5,977,315 A * | 11/1999 | Chatterjee et al. | 530/387.2 |
| 6,004,781 A | 12/1999 | Seed | |
| 6,018,026 A | 1/2000 | Sledziewski et al. | |
| 6,074,846 A | 6/2000 | Ralston et al. | |
| 6,074,852 A | 6/2000 | Ralston et al. | |
| 6,086,873 A | 7/2000 | Sykes et al. | |

(Continued)

FOREIGN PATENT DOCUMENTS

WO  WO 92/01470  2/1992

(Continued)

OTHER PUBLICATIONS

Wikipedia Free encyclopedia in website: Immunoglubulin basic unit. svg, pp. 1-12, published on Aug. 17, 2007.*
Dalhouse University on website pim.medine.dal.ca/abfc.htm, pp. 1-2, published in 2005, modified on Nov. 29, 2006.*
Bruss et al. J. Virol. 1994, vol. 68, No. 3, pp. 1643-1650.*
Zhou et al. Zhonghua Weishengwuxue He Mianyixue Zazhi 1998, vol. 18, No. 4, pp. 331-335.*
McCluskie et al. Viral Immunology 1998, vol. 11, No. 4, pp. 245-252.*
Zhou et al. Zhonghua Weishengwuxue He Mianyixue Zazhi 1998, vol. 18, No. 4, pp. 331-335, Translated version.*
Wei et al. Clinical Chemica Acta, 2002, vol. 317, pp. 159-169.*

(Continued)

*Primary Examiner* — Bao Li
(74) *Attorney, Agent, or Firm* — Sheridan Ross P.C.

(57) ABSTRACT

Disclosed herein are the nucleotide sequences, deduced amino acid sequences as well as methods and compositions necessary to elicit immune responses against chronic Hepatitis B infections in animals and humans. Immune response is enhanced by fusing relevant viral antigens with xenotypic immunoglobulin heavy chain region through a peptide linker and producing the fusion proteins in Baculovirus expression system to incorporate high mannose glycosylation. By virtue of the antibody component, the fusion proteins bind to Fc receptors on the surface of antigen presenting cells, are taken up, processed and derived peptides are presented on MHC Class I, which elicit a CTL (Th1) response. In a similar fashion, due to cross priming and presentation on MHC Class II, will elicit a humoral (Th2) response. In addition, disclosed are the methods of cloning, expression and production of the fusion proteins.

40 Claims, 64 Drawing Sheets

U.S. PATENT DOCUMENTS

| | | | |
|---|---|---|---|
| 6,087,476 | A | 7/2000 | Kenten et al. |
| 6,117,655 | A | 9/2000 | Capon et al. |
| 6,207,153 | B1 | 3/2001 | Dan et al. |
| 6,241,985 | B1 | 6/2001 | Madiyalakan et al. |
| 6,242,195 | B1 | 6/2001 | Idusogie et al. |
| 6,274,148 | B1 | 8/2001 | Ralston et al. |
| 6,277,375 | B1 | 8/2001 | Ward |
| 6,291,212 | B1 | 9/2001 | Sledziewski et al. |
| 6,291,646 | B1 | 9/2001 | Sledziewski et al. |
| 6,300,099 | B1 | 10/2001 | Sledziewski et al. |
| 6,323,323 | B1 | 11/2001 | Sledziewski et al. |
| 6,406,697 | B1 | 6/2002 | Capon et al. |
| 6,500,641 | B1 | 12/2002 | Chen et al. |
| 6,521,423 | B1 | 2/2003 | Houghton et al. |
| 6,555,114 | B1 | 4/2003 | Leroux-Roels et al. |
| 6,613,333 | B1 | 9/2003 | Leroux-Roels et al. |
| 6,689,355 | B2 | 2/2004 | Schultes et al. |
| 6,710,169 | B2 | 3/2004 | Capon et al. |
| 6,716,623 | B2 | 4/2004 | Chen et al. |
| 6,716,966 | B1 | 4/2004 | Madiyalakan |
| 6,808,901 | B1 | 10/2004 | Neuberger et al. |
| 6,838,281 | B2 | 1/2005 | Scott et al. |
| 7,067,110 | B1 * | 6/2006 | Gillies et al. ................. 424/1.49 |
| 7,105,303 | B2 | 9/2006 | Ralston et al. |
| 7,273,752 | B2 | 9/2007 | Chen et al. |
| 7,429,385 | B2 | 9/2008 | Houghton et al. |
| 2001/0044135 | A1 | 11/2001 | Stahl et al. |
| 2001/0048922 | A1 | 12/2001 | Romet-Lemonne et al. |
| 2002/0048583 | A1 | 4/2002 | Schultes et al. |
| 2003/0118592 | A1 | 6/2003 | Ledbetter et al. |
| 2003/0149254 | A1 | 8/2003 | Anderson et al. |
| 2003/0235536 | A1 | 12/2003 | Blumberg et al. |
| 2004/0047877 | A1 | 3/2004 | Leroux-Roels et al. |
| 2004/0063912 | A1 | 4/2004 | Blumberg et al. |
| 2005/0089843 | A1 | 4/2005 | Ralston et al. |
| 2005/0186662 | A1 | 8/2005 | Low |
| 2009/0238822 | A1 | 9/2009 | George et al. |

FOREIGN PATENT DOCUMENTS

| | | |
|---|---|---|
| WO | 92/05793 | 4/1992 |
| WO | WO 96/01650 | 1/1996 |
| WO | WO 96/08570 | 3/1996 |
| WO | WO 96/40941 | 12/1996 |
| WO | 97/07218 | 2/1997 |
| WO | WO 97/36932 | 10/1997 |
| WO | 98/20141 | 5/1998 |
| WO | 99/65517 | 12/1999 |
| WO | WO 00/20460 | 4/2000 |
| WO | WO 01/07081 | 2/2001 |
| WO | WO01/07081 A * | 2/2001 |
| WO | 01/32893 | 5/2001 |
| WO | WO 01/32714 | 5/2001 |
| WO | WO 01/77137 | 10/2001 |
| WO | WO 01/85203 | 11/2001 |
| WO | WO 02/04484 | 1/2002 |
| WO | WO 02/056830 | 7/2002 |
| WO | WO 2004/004798 | 1/2004 |
| WO | WO 2004/100882 | 11/2004 |
| WO | WO 2004/101740 | 11/2004 |
| WO | WO2004/108885 | 12/2004 |
| WO | WO 2005/001025 | 1/2005 |
| WO | WO 2005/014838 | 2/2005 |
| WO | WO 2005/073383 | 8/2005 |
| WO | WO 2005/087813 | 9/2005 |

OTHER PUBLICATIONS

Shiraki et al. J. General Virol. 1992, vol. 73, pp. 1401-1407.*
Dieckman et al. Protein Expression and Purification published on line Jun. 19, 2002, vol. 25, No. 1, pp. 8-15.*
Wen et al. Inter. Rev. Immunol. 1999 vol. 18, pp. 251-258.*
He et al, "A novel human cancer vaccine elicits cellular responses to the tumor-associated antigen, human chorionic gonadotropin" Clin Cancer Res. 10(6): 1920-1927, (2004).
Motyka et al., "CD8+ T Cell Responses to a Novel Class of Therapeutic Vaccines for the Treatment of Chronic Hepatitis B Infection", Abstract No. 2481, 12th International Congress of Immunology and 4th Annual Conference of FOCIS, [online] Jul. 18-23, 2004 [retrieved Nov. 19, 2004] retrieved from the Internet URL: http://www.immuno2004.org/onlineabstracts/index.html.
Stevenson et al., "Vaccine therapy in NGL: Future Promises and Current Limitations", Leuk Lymphoma 44 Suppl 3: S85-90 (2003).
Wang et al., "Characterization of Immne Resp;onses ot a Novel Therapeutic Vaccine for the Treatment of Chronic Heaptitis B Virus Infections", Abstract No. 2293, 12th International Congress of Immunology and 4th Annual Conference of FOCIS,(2004), [online] Jul. 18-23, 2004 [retrieved Nov. 19, 2004] retrieved from the Internet URL: http://www.immuno2004.org/onlineabstracts/index.html.
You, Z., et al., "A retrogen strategy for presentation of an intracellular tumor antigen as an exogenous antigen by dendritic cells induces potent antitumor T helper and CTL responses", Cancer Research, 61(1): 197-205 (2001).
You, Z. et al., "Targeting dentritic cells to enhance DNA vaccine potency", Cancer Research, vol. 61, pp. 3704-3711, May 1, 2001.
You, Z. et al., "Induction of vigorous helper and cytotoxic T cell as well as B cell responses by dentritic cells expressing a modified antigen targeting receptor-mediated internalization pathway", Journal of Immunology, 165:8, pp. 4581-4591, Oct. 15, 2001.
Feng, Z-H et al., Database Embase 'Online!, Database accession No. EMB-2003261340, "Construction and expression of chrimeid plasmid pHCV-IgFc", Elsevier Science Publishers and World Chinese Journal of Digestology, 11:6, pp. 697-700, Jun. 1, 2003.
Berlyn, et al., "Generation of CD4(+) and CD8(+) T lymphocyte responses by dendritic cells armed with PSA/anti-PSA (antigen/antibody) complexes," Clin. Immunol., 101(3):276-283 (2001).
Bonini et al., "Targeting antigen in mature dendritic cells for simultaneous stimulation of CD4+ and CD8+ T cells", Journal Immunology 166: 5250-5257, (2001).
Campton, et al. "Tumor antigen presentation by dermal antigen-presenting cells", J. Invest. Dermatol. 115: 57-61 (2000).
Chamow et al., Immunoadshesins: principles and applications, Tibtech 14: 52-59 (1996).
Chapman-Smith et al., "The enzyme biotinylation of proteins: a post-translational modification of exceptional specificity", TIBS, 24: 359-363 (1999).
Clarke, "Molecular virology of hepatitis C virus" J. Gen. Virol. 78: 2397-2410 (1997).
Coughlan et al. "Enhanced proliferation of CD4+ T cells induced by dendritic cells following antigen uptake in the presence of specific antibody", Vetrinary Immunology and Immunopathology 49: 321-330, 1996.
Deres, et al., "In vivo priming of virus-specific cytotoxic T lymphocytes with synthetic lipopeptide vaccine," Nature 342: 561-564 (1989).
Donnelly, et al. "DNA vaccines." Annu. Rev. Immunol. 15: 617-648 (1997).
Dwyer, M.A. et al., "Expression and characterization of a Dnase I-Fc fusion enzyme", Journal of Biological Chemistry: 274(14): 9738-9743 (1999).
Fanger, N.A. "Characterization of expression, cytokine regulation, and effector function of the high affnity IgG receptor FcγRI(CD64) expressed on human blood dendritic cells", Journal of Immunology 158: 3090-3098 (1997).
Fanger et al., "Type I (CD64) and Type II (CD32) Fcγ receptor-mediated phagocytosis by human blood dendritic cells", Journal of Immunology 157: 541-548 (1996).
Ferlazzo et al., "Dendritic cells generated either from CD34+ progenitor cells or from monocytes differ in their ability to activate antigen-specific CD8+ T cells", Journal of Immunology 163: 3597-3604 (1999).
Finkleman et al., "Dendritic cells can present antigen in vivo in a tolerogenic or immunogenic fashion", Journal of Immunology 157: 1406-1414 (1996).
Fong and Engleman "Dendritic cells in cancer immunotherapy." Annu. Rev. Immunol. 18: 245-273 (2000).
Fried et al., "Peginterferon alfa-2a plus ribavirin for chronic hepatitis C virus infection." N. Engl. J. Med. 347(13): 975-982 (2002).
Ganem, "Perspectives: Virology: The X files—one step closer to closure." Science 294: 2299-2300 (2001).

Grohmann et al., "CD40 litigation ablates the tolerogenic potential of lymphoid dendritic cells", Journal of Immunology 166: 277-283 (2001).
Guermonpres et al., "Antigen presentation and T cell stimulation by dendritic cells", Annual Review Immunology 20: 621-667 (2002).
Gust, et al., "Taxonomic classification of human hepatitis B virus," Intervirology 25:14-29 (1986).
Hartgers et al., "Toward a molecular understanding of dendritic cell immunobiology", Immunology Today 21(11): 542-545 (2000).
Hellström et al., "Significance of Pre-S2 Peptide of Hepatitis B Virus: Should it be in the Vaccine?", Prog. Med. Virol. 35: 76-106 (1998).
Henikoff and Henikoff, "Amino acid substitution matrices from protein blocks," PNAS 89:10915-10919 (1992).
Hilgers, et al. "Sulfolipo-cyclodextrin in squalane-in-water as a novel and safe vaccine adjuvant." Vaccine 17: 219-228 (1999).
Hochrein et al., "Differential production of IL-12, IGN-α and IFN-γ by mouse dendritic cell subsets", Journal of Immunology 166: 5448-5455 (2001).
Jenne et al., "Viral vectors for dendritic cell-based immunotherapy", Trends in Immunology 22(2): 102-107, 2001.
Jonuleit et al., "Dendritic cells as a tool to induce anergic and regulatory T cells", Trends in Immunology 22(7): 394-400 (2001).
Kane, "Global programme for control of hepatitis B infection", Vaccine 13(Supplement 1): S47-S49 (1995).
Kotenko et al. "Identification of the Functional Interleukin-22 (IL-22) Receptor Complex", Journal of Biological Chemistry 276(4): 2725-2732 (2002).
Kozak, "Adherence to the first-AUG rule when a second AUG codon follows closely upon the first," PNAS 92: 2662-2666 (1995).
Kozak, "An analysis of 5'-noncoding sequences from 699 vertebrate messenger RNAs," NAR 15(20): 8125-8132 (1987).
Kozak, "Context Effects and Inefficient Initiation at Non-AUG Codons in Eucaryotic Cell-Free Translation Systems," Mol. Cell. Biol., 9(11): 5073-5080 (1989).
Lai and Bennett "DNA vaccines." Crit. Rev. Immunol. 18: 449-484 (1998).
Larsson, et al. "Dendritic cells resurrect antigens from dead cells." Trends Immunol. 22(3): 141-148 (2001).
Lauer and Walker, "Medical Progress: Hepatitis C Virus Infection", N. Engl. J. Med. 345(1):41-52 (2001).
Laupéze, et al. "Differential expression of major histocompatibility complex class Ia, Ib, and II molecules on monocytes and monocyte-derived dendritic and macrophagic cells." Hum. Immunol. 60: 591-597 (1999).
Lei et al., "Structure-function analysis of human glucose-6-phosphatase, the enzyme deficient in glycogen storage disease type 1a," J. Biol. Chem. 270(20):11882-11886 (1995).
Lorenz et al., "Induction of Ani-Tumor Immunity Elicited yb Tumor Cells Expressing a Murine LFA-3 Analog via a Recombinant Vaccinia virus", Hum. Gene Ther. 10: 623-631 (1999).
Lorenz, et al. "Anti-tumor immunity elicited by a recombinant vaccinia virus expressing CD70 (CD27L)." Hum. Gene Ther. 10: 1095-1103 (1999).
Manns, et al., "Peginterferon alfa-2b plus ribavirin compared with interferon alfa-2b plus ribavirin for initial treatment of chronic hepatitis C: a randomised trial," Lancet 358:958-965 (2001).
Marion "Use of animal models to study hepatitis B virus." Prog. Med. Virol. 35:43-75 (1988).
Mason, et al. "Virus of Pekin Ducks with Structural and Biological Relatedness to Human Hepatitis B Virus." J. Virol. 36(3): 829-36 (1980).
Merad et al., "Differentiation of myeloid dendritic cells into CD8α-positive", Blood 96(5): 1865-1872 (2000).
Moore et al., "Interleukin-10 and the interleukin-10 receptor", Annual Review Immunology 19: 683-765 (2001).
Nagarajan et al., "Ligand binding and phagocytosis by CD16 (Fcγ receptor III) isoforms", Journal of Biological Chemistry 270(43): 25672-25770 (1995).
Neuhaus et al., "Multiple sclerosis: comparison of copolymer-1-reactive T cell lines from treated and untreated subjects reveals cytokine shift from T helper 1 to T helper 2 cells", PNAS 97(13): 7452-7457 (2000).

Newman, et al. "Uptake of poly(D,L-lactic-co-glycolic acid) microspheres by antigen-presenting cells in vivo," J. Biomed Mater Res. 603: 480-486 (2002).
Newman, et al. "Ovalbumin peptide encapsulated in poly(d/l lactic-co-glycolic acid) microspheres is capable of inducing a T helper type 1 immune response." J. Control Release 54: 49-59 (1998).
Newman, et al. "Cytoplasmic delivery of a macromolecular fluorescent probe by poly(d, l-lactic-co-glycolic acid) microspheres." J. Biomed Mater Res. 50: 591-597 (2000).
Novak et al., "Engagement of FcεRI on human monocytes induces the production of IL-10 and prevents their differnetation in dendritic cells", Journal of Immunology 167: 797-804 (2001).
Qin et al. "Fcγ receptor IIB on follicular dendritic cells regulates the B cell recall response", Journal of Immunology 164: 6268-6275 (2000).
Quarantino et al., "Fully competent dendritic cells as inducers of T cell anergy in autoimmunity", PNAS 97(20): 10911-10916 (2000).
Ramakrishna et al., "Mannose receptor targeting of tumor antigen pmel17 to human dendritic cells directs anti-melanoma T cell responses via multiple HLA molecules," J. Immunol. 172: 2845-2852 (2004).
Regnault et al., "Fcγ receptor-mediated induction of dendritic cell maturation and major histocompatibility complex Class 1-restricted antigen presentation after immune complex internalization", Journal Exp. Medicine 189(2): 371-380, (1999).
Roncarolo et al., "Differentation of T regulatory cells by immature dendritic cells", Journal Exp. Medicine 193(2): F5-F9 (2001).
Saito et. al., "Hepatitis C virus infection is associated with the development of hepatocellular carcinoma" PNAS USA 87: 6547-6549 (1990).
Schultz et al., "Duck Hepatitis B Virus: An Invaluable Model System for HBV Infection", Advances in Virus Research 63: 1-70 (2004).
Schuurhuis et al., "Antigen-antibody immune complexes empower dendritic cells to efficiently prime specific $CD8^+CTL$ responses in vivo", Journal of Immunology 168: 2240-2246, (2002).
Sprengel, et al. "Isolation and characterization of a hepatitis B virus endemic in herons." J. of Virol. 62(10): 3832-3839 (1988).
Steinman, et al. "Antigen capture, processing, and presentation by dendritic cells: recent cell biological studies." Hum. Immunol. 60(7): 562-567 (1999).
Summers, , et al. "A virus similar to human hepatitis B virus associated with hepatitis and hepatoma in woodchucks." Proc. Natl. Acad. Sci. USA 75(9): 4533-7 (1978).
Szoka, et al., "Comparative properties and methods of preparation of lipid vesicles (liposomes)," Ann. Rev. Biophys. Bioeng. 9:467-508 (1980).
Tan and Katze, "How hepatitis C virus counteracts the interferon response: the jury is still out on NS5A" Virology 284: 1-12 (2001).
Whitton et al., "The Regulation and Maturation of Antiviral Immune Responses", Advances in Virus Research, 63: 181-238 (2004).
Zhu et al., "MHC class 1-related neonatal Fc receptor for IgG is functionally expressed in monocytes, intestinal macrophages, and dendritic cells", Journal of Immunology 166: 3266-3276, (2001).
Zuckerman, "More than third of world's population has been infected with hepatitis B virus", BMJ 318(7192): 1213 (1999).
Adema, et al., "Migration of dendritic cell based cancer vaccines: ' in vivo veritas?," Current Opinion in Immunology, 2005, vol. 17, pp. 1-5.
Akiyama, et al., "Targeting apoptotic tumor cells to FcyR provides efficient and versatile vaccination against tumors by dendritic cells", J. Immunol., 2003, vol. 170, pp. 1641-1648.
Alter, et al., "Recovery, persistence and sequelae in hepatitis C virus infection: a perspective on long-term outcome", Semin. Liver Dis., 2000, vol. 20, pp. 17-35.
Alter, et al., "The Prevalence of Hepatitis C Virus Infection in the United States, 1988 through 1994" N. Eng. J. Med., 1999, vol. 341, pp. 556-562.
Andoniou, et al., "Interation between conventional dendritic cells and natural killer cells is integral to the activation of effective antiviral immunity", Nature Immunol. Online, 2005, vol. 6, No. 10, pp. 1011-1019.

Arribillaga, et al., "Enhancement of CD4 and CD8 immunity by anti-CD137 (4-1BB) monoclonal antibodies during hepatitis C vaccination with recombinant adenovirus", Vaccine, 2005, vol. 23, pp. 3493-3499.

Babiuk et al. "Electroporation improves the efficacy of DNA vaccines in large animals." Vaccine, 2002, 20: 3399-3408.

Babiuk et al., "Increased gene expression and inflammatory cell infiltration causedby electroporation are both important for improving the efficacy of DNA vaccines." J. Biotechnol, 2004, 110: 1-10.

Babiuk, et al., "Needle-free topical electroporation improves gene expression from plasmids administered in porcine skin", Molecular Therapy, 2003, vol. 8, pp. 992-998.

Bartenschlager, "Hepatitis C virus replicons: potential role for drug development", Nature Rev. Drug. Discov., 2002, vol. 1, pp. 911-916.

Bartenschlager, et al., "Nonstructural Protein 3 of the Hepatitis C Virus Encodes a Serine-Type Proteinase Required for Cleavage at the NS3/4 and NS4/5 Junctions", J. Virol., 1993, vol. 67, pp. 3835-3844.

Barth, et al., "Uptake and presentation of hepatitis C Virus-like particles by human dendritic cells", Blood, May 1, 2005, vol. 105, No. 9, pp. 3605-3614.

Batista, et al., "The two membrane isoforms of human IgE assemble into functionally distinct B cell antigen receptors", J. Exp. Med., 1996, vol. 184, pp. 2197-2206.

Baumert, et al., "Hepatitis C Virus Structural Proteins Assemble into Viruslike Particles in Insect Cells", Journal of Virology, 1998, vol. 72, No. 5, pp. 3827-3836.

Behrens, et al., "Identification and properties of the RNA-dependent RNA polymerase of Hepatitis C virus", EMBO, 1996, vol. 15, pp. 12-22.

Berzofsky, et al., "Progress on new vaccine strategies against chronic viral infections", The Journal of Clinical Investigation, Aug. 2004, vol. 114, No. 4, pp. 450-462.

Biochemistry 4th Ed., Lubert Stryer ed., W. H. Freeman and Co., 1995, pp. 18-23.

Björklunda, et al., "Characterization of recombinant human IgE-Fc fragments expressed in baculovirus-infected insect cells", Mol. Immunol., 2000, vol. 37, pp. 169-177.

Boruchov, et al., "Activating and inhibitory IgC Fc receptors on human DCs mediate opposing functions", The Journal of Clinical Investigation, Oct. 2005, vol. 115, No. 10, pp. 2914-2923.

Bouige, et al., "Molecular analysis of the modulatory factors of the response to HBsAg in mice as an approach to HBV vaccine enhancement", FEMS Immunology & Medical Microbiology, Jan. 1996, vol. 13, No. 1 p. 71-79.

Bowen, et al., "Adaptive immune responses in acute and chronic hepatitis C virus infection." Nature, 2005, vol. 436, pp. 946-952.

Brown, "Hepatitis C and Liver transplantation", Nature, 2005, vol. 436, No. 7053, pp. 973-978.

Cao, et al., "In Vivo Inhibition of Anti-Hepatitis B Virus Core Antigen (HBcAg) Immunoglobulin G Production by HBcAg-Specific CD4+ Th1-Type T-Cell Clones in a hu-PBL-NOD/SCID Mouse Model", Journal of Virology, Dec. 2001, vol. 75, No. 23, pp. 11449-11456.

Carroll, "The complement system in regulation of adaptive immunity", Nature Immunol., 2005, vol. 5, pp. 981-986.

Chisari, "Unscrambling hepatitis C virus-host interactions", Nature, Aug. 18, 2005, vol. 436, pp. 930-932.

Cooper, et al., "Analysis of a successful immune response against hepatitis C virus", Immunity, 1999, vol. 10, pp. 439-449.

De Francesco, et al., "Challenges and successes in developing new therapies for hepatitis C", Nature, 2005, vol. 436, pp. 953-960.

Delwaide, et al., "Evidence-based medicine: treatment of chronic hepatitis C. Liege Study Group on Viral Hepatitis", Rev. Med. Liege, 2000, vol. 55, pp. 337-340 (Abstract).

Diepolder, et al., "Possible mechanism involving T lymphocyte response to non-structural protein 3 in viral clearance in acute hepatitis C infection", Lancet, 1995, vol. 36, pp. 1006-1007.

Dodson, et al., "Prevention of de novo hepatitis B infection in recipients of hepatic allografts from anti-HBc positive donors", Transplantation, 1999, vol. 68, No. 7, pp. 1058-1061.

Dolganiuc, et al., "Hepatitis C Virus Core and Nonstructural Protein 3 Proteins Induce Pro- and Anti-inflammatory Cytokines and Inhibit Dendritic Cell Differentiation", J. Immunol., 2003, vol. 170, pp. 5615-5624.

Encke, et al., "Prophylactic and therapeutic vaccination with dendritic cells against hepatitis C virus infection", British Society for Immunology, Clinical and Experimental Immunology, 2005, vol. 142, pp. 362-369.

Ewen, et al., "A novel cytotoxicity assay to evaluate antigen-specific CTL responses using a colorimetric substrate for Granzyme B" J. Immunol. Meth., 2003, vol. 276, pp. 89-101.

Eyles, et al., "Stimulation of spleen cells in vitro by nanospheric particles containing antigen", Journal of Controlled Release, 2003, vol. 86, pp. 25-32.

Faith, et al., "Targeting the dendritic cell: The key to immunotherapy in cancer?", British Society for Immunology, Clinical and Experimental Immunology, 2005, vol. 139, pp. 395-397.

Feld, et al., "Mechanism of action of interferon and ribavirin in treatment of hepatitis C", Nature, 2005, vol. 436, pp. 967-972.

Fournillier, et al., "Primary and memory T cell responses induced by hepatitis C Virus multiepitope long peptides", Vaccine, 2006, vol. 24, pp. 3153-3164.

Gale, Jr, et al., "Evasion of intracellular host defence by hepatitis C virus", Nature, 2005, vol. 436, pp. 939-945.

Geijtenbeek, et al., "Self- and nonself-recognition by C-type lectins on dendritic cells", Annu. Rev. Immunol., 2004, vol. 22, pp. 33-54.

George et al. (2006) A new class of therapeutic vaccines for the treatment of chronic hepatitis B infections. In "Framing the Knowledge of Viral Hepatitis" Schinazi, R. F. Editor, 1HL Press USA, pp. 379-403.

George, et al. "Chimigen Vaccines: A novel class of therapeutic vaccines for the treatment of chronic viral infections." International Meeting of the Molecular Biology of Hepatitis B Viruses, Sep. 7-10, 2003, Centro Congressi Giovanni XXIII, Bergamo, Italy, 1 page.

George, et al., "A novel Class of Therapeutic Vaccines for the Treatment of Chronic Viral Infections: Evaluation in Ducks Chronically Infected with Duck Hepatitis B Virus (DHBV)", Hepdart 2003, Frontiers in Drug Development for Viral Hepatitis, Dec. 14-18, Kauai, Hawaii, USA., 1 page.

George, et al., "A new class of chimeric vaccines for the treatment of hepatitis C infections." 11th International Symposium on Hepatitis C and Related Viruses, Heidelberg, Germany, Oct. 3-7, 2004.

George, et al., "A New Class of Therapeutic Vaccines Produced in Insect Cells for the Treatment of Chronic Viral Infections", BioProcessing Journal, 2005, vol. 4, pp. 38-44.

George, et al., "Immunological Evaluation of a Novel Chimeric Therapeutic Vaccine for the Treatment of Chronic Hepatitis B Infections", International Meeting of the Molecular Biology of Hepatitis B Viruses, Woods Hole, MA, Oct. 24-27, 2004, 1 page.

Grakoui, et al., "HCV persistence and immune evasion in the absence of memory T cell help", Science, 2003, vol. 302, pp. 659-662.

Guyre, et al., "Colocalization of FcγRI-targeted antigen with class I MHC: implications for antigen processing", J. Immunol., 2001, vol. 166, pp. 2469-2478.

Hahn, "Subversion of immune responses by hepatitis C virus: 25 immunomodulatory strategies beyond evasion?", Curr. Opin. Immunol., 2003, vol. 15, pp. 443-449.

Hamann, et al., "Phenotypic and functional separation of memory and effector human CD8+ T cells", J. Exp. Med., 1997, vol. 186, p. 1407.

Hameed, et al., "Immunohistochemical identification of cytotoxic lymphocytes using human perforin monoclonal antibody" Am. J. Pathol., 1992, vol. 140, pp. 1025-1030.

Hewlett, et al., "The coated pit and macropinocytic pathways serve distinct endosome populations." J. Cell Biology, 1994, vol. 124, pp. 689-703.

Hijikkata, et al., "Gene mapping of the putative structural region of the hepatitis C virus genome by in vitro processing analysis", Proc. Natl. Acad. Sci. USA, 1991, vol. 88, pp. 5547-5551.

Hinrichsen, et al, "Short-term antiviral efficacy of BILN 2061, a hepatitis C 30 virus serine protease inhibitor, in hepatitis C genotype 1 patients", Gastroenterology, 2004, vol. 127, pp. 1347-1355.

Ho, et al., "The likelihood of aggregation during protein renaturation can be assessed using the second viral coefficient", Prot. Sci., 2003, vol. 12, pp. 708-716.

Hoofnagle, "Course and outcome of hepatitis C", Hepatology, 2002, vol. 36, pp. S21-S29.

Houghton, et al., "Prospects for a vaccine against the hepatitis C virus", Nature, Aug. 18, 2005, vol. 436, pp. 961-966.
Iwasaki, et al., "Toll-like receptor control of the adaptive immune responses", Nature Immunol., 2004, vol. 5, pp. 987-995.
Jefferis, "Glycosylation of Recombinant Antibody Therapeutics", Biotechnol. Prog., 2005, vol. 21, pp. 11-16.
Jilg, et al., "Novel hepatitis B vaccines", Vaccine, 1998, vol. 16, pp. s65-s68.
Koo et al. "Construction and expression of a bifunctional single-chain antibody against *Bacillus cereus* p6ores." Applied and Environmental Microbiology 1998, vol. 64, No. 7, pp. 2490-2496.
Kozlowski, et al., "Lactacystin inhibits cathepsin A activity in melanoma cell lines", Tumour Biol., 2001, vol. 22, No. 4, pp. 211-215.
Langhans, et al., "Cytotoxic Capacity of Hepatitis C Virus (HVC)-specific Lymphocytes After In Vitro Immunization with HCV -Derived Lipopeptides", Cytometry Part A, 2005, vol. 65A, pp. 59-68.
Lebensztein, et al., "Current knowledge on treatment of chronic hepatitis B in children", Med. Sci. Monit., 2000, vol. 6, No. 1, pp. 198-203.
Lechner, et al., "Analysis of successful immune responses in persons infected with hepatitis C virus.", J. Exp. Med., 2000, vol. 191, pp. 1499-1522.
Leyssen, et al., "Perspectives for the Treatment of Infections with Flaviviridae", Clinical Microbiology Reviews, Jan. 2000, vol. 13, No. 1, pp. 67-82.
Li, et al., "A novel HBV DNA vaccine based on T cell epitopes and its potential therapeutic effect in HBV transgenic mice", International Immunology, 2005, vol. 17, No. 10, pp. 1293-1302.
Liang, et al., "Pathogenesis, Natural History, Treatment, and Prevention of Hepatitis C", Annals of Internal Medicine, Feb. 15, 2000, vol. 132, No. 4, pp. 296-305.
Lin, et al, "In vitro resistance studies of hepatitis C virus serine protease inhibitors, VX-950 and BILN 2061: structural analysis indicates different resistance 5 mechanisms", J. Biol. Chem, 2004, vol. 279, pp. 17508-17514.
Lindenbach, et al, Complete Replication of hepatitis C Virus in culture, Science, 2005, vol. 309, pp. 623-626.
Lindenbach, et al., "Unravelling hepatitis C virus replication from genome to function", Nature, 2005, vol. 436, pp. 933-938.
Liu, et al., "Dendritic cell lineage, plasticity and cross-regulation", Nature immunology, 2001, vol. 2, No. 7, pp. 585-589).
Lizée, et al., "Tails of wonder: endocytic-sorting motifs key for exogenous antigen presentation" Trends Immunol., 2005, vol. 26, No. 3, pp. 141-149.
Lobe, et al, "Novel serine proteases encoded by two cytotoxic T lymphocyte-specific genes." Science , 1986, vol. 232, pp. 858-861.
Lohmann, et al., "Processing pathways of 15 the hepatitis C virus proteins", J. Hepatol., 1996, vol. 24, pp. 11-19.
Loirat, et al., "Multiepitopic HLA-A 0201-Restricted Immune Response Against Hepatitis B Surface Antigen After DNA-Based Immunization", The Journal of Immunology, 2000, vol. 165, No. 8, pp. 4748-4755.
Lu, et al, "Mutations conferring resistance to a potent hepatitis C virus serine protease inhibitors in vitro." Antimicrob Agents Chemother., 2004, vol. 48, pp. 2260-2266.
Lutsiak, et al., "Analysis of poly(D,L-lactic-co-glycolic acid) nanosphere uptake by human dendritic cells and macrophages in vitro", Pharmaceutical Research, Oct. 2002, vol. 19, No. 10, pp. 1480-1487 (Abstract only.
Maini, et al., "The role of virus-specific CD8(+) cells in liver damage and viral control during persistent hepatitis B virus infection" J. Exp. Med., 2000, vol. 191, pp. 1269-1280.
McGreal, et al., "Ligand recognition by antigen-presenting cell C-type lectin receptors", Current Opinion in Immunology, 2005, vol. 17, pp. 18-24.
McHutchison, et al., "Current therapy for hepatitis C: pegylated interferon and ribavirin",Clin. Liver Dis., 2003, vol. 7, pp. 149-161.
Mehta, et al, "Protection against persistence of hepatitis C", 2002, Lancet, 2002, vol. 359, pp. 1478-1483.
Mercer, et al, "Hepatitis C virus replication in mice with chimeric human livers", Nat. Med., 2001, vol. 7, pp. 927-933.
Michel, et al., "Therapeutic vaccination against chronic hepatitis B Virus infection", Journal of Clinical Virology, 2005, vol. 34, Suppl. 1, pp. S108-S114.
Middelberg, "Preparative protein refolding", Trends Biotech., 2002, vol. 20, pp. 437-443.
Mihailova, et al., "Recombinant virus-like particles as a carrier of B- and T-cell epitopes of hepatitis C Virus (HCV)", Vaccine, 2006, pp. 1-9.
Moll, et al., "Designed heterodimerizing leucine zippers with a range of pIs and stabilities up to 10-15 M.", Protein Science, 2001, vol. 10, pp. 649-655.
Morris, et al., "Incorporation of an Isoleucine Zipper Motif Enhances the Biiological Activity of Soluble CD40L (CD154)*", The Journal of Biological Chemistry, Jan. 1999, vol. 274, No. 1, pp. 418-422.
Nestle, et al., "Dendritic-cell-based therapeutic vaccination against cancer", Current Opinion in Immunlogy, 2005, vol. 17, pp. 1-7.
Pawlotsky, "Diagnostic tests for hepatitis", J. Hepatol., 1999, vol. 31(suppl), pp. 71-79.
Peng, et al., "Novel vaccines for the treatment of chronic HBV infection based on mycobacterial heat shock protein 70", Vaccine, 2006, vol. 24, pp. 887-896.
Penin et al. (2004) Structural Biology of hepatitis C virus.Hepatology 39: 5-19.
Polyak, et al., "Hepatitis C Virus Nonstructural 5A Protein Induces Interleukin-8, Leading to Partial Inhibition of the Interferon-Induced Antiviral Response", J. Virol., 2001, vol. 75, pp. 6095-6106.
Post, et al., "Clearance of Hepatitis C Viremia Associated with Cellular Immunity in the Absence of Seroconversion in the Hepatitis C Incidence and Transmission in Prisons Study Cohort", J. Infect. Dis., 2004, vol. 189, pp. 1846-1855.
Rehermann, et al., "Immunology of hepatitis B and hepatitis C virus infection", Nature Rev. Immunol., 2005, vol. 5, pp. 215-229.
Reiser, et al, "Antiviral efficacy of NS3-serine protease inhibitor BILN-2061 in patients with chronic genotype 2 and 3 hepatitis C", Hepatology, 2005, vol. 41, pp. 832-835.
Roque, et al., "Antibodies and Genetically Engineered Related Molecules: Production and Purification", Biotechnol. Prog., 2004, vol. 20, pp. 639-654.
Rozema, et al., "Artificial chaperone-assisted refolding of denatured-reduced lysozyme: Modulation of competition between renaturation and aggregation", Biochem., 1996, vol. 35, pp. 15760-15771.
Sarobe, et al., "Abnormal priming of CD4(+) T cells by dendritic cells expressing hepatitis C virus core and E1 proteins" J. Virol., 2002, vol. 76, pp. 5062-5070.
Sarobe, et al., "Hepatitis C virus structural proteins impair dendritic cell maturation and inhibit in vivo induction of cellular immune responses", J. Virol., 2002, vol. 77, pp. 10862-10871.
Schirmbeck, et al. "Ongoing murine T1 or T2 immune responses to the hepatitis B surface antigen are excluded from the liver that expresses transgene-encoded hepatitis B surface antigen", J. Immunol., Apr. 15, 2000, vol. 164, No. 8), pp. 4235-4243.
Seeff, "Natural history of chronic hepatitis C", Hepatology, 2002, vol. 36, pp. s35-s46.
Shoji, et al., "Internal Processing of Hepatitis C Virus NS3 Protein" Virology, 1999, vol. 254, pp. 315-323.
Shoukry, et al., "Cell-mediated immunity 15 and the outcome of hepatitis C virus infection", Ann. Rev. Microbiol, 2004, vol. 58, pp. 391-424.
Shoukry, et al., "Memory CD8+ T cells are required for protection from persistent hepatitis C virus infection", J. Exp. Med., 2003, vol. 197, pp. 1645-1655.
Spaeny-Dekking, et al., "Extracellular granzymes A and B in humans: detection of native species during CTL responses in vitro and in vivo", J. Immunol., 1988, vol. 160, p. 3610.
Strader, "Understudied populations with hepatitis C", Hepatology, 2002, vol. 36, pp. S226-S236.
Strader, et al., (2004) "Diagnosis, management, and treatment of hepatitis C", Hepatology, 2004, vol. 39, pp. 1147-1171.
Takeda, et al, "Toll-like receptors", Annu. Rev. Immunol., 2003, vol. 21, pp. 335-376.
Tarte, et al., "Dendritic cell-based vaccine: a promising 5 approach for cancer immunotherapy", Leukemia, 1999, vol. 13, pp. 653-663.

Taylor, et al., "Macrophage receptors and immune recognition", Annu. Rev. Immunol., 2005, vol. 23, pp. 901-944.

Taylor, et al., "The mannose receptor: linking homeostasis and immunity through sugar recognition", Trends in Immunology, Feb. 2005, vol. 26, No. 2, pp. 104-110.

Thimme, et al., "Determinants of viral clearance and persistence during acute hepatitis C virus infection", J. Exp. Med., 2002, vol. 194, pp. 1395-1406.

Thimme, et al., "Viral and immunological determinants of hepatitis C virus clearance, persistence, and disease", Proc. Natl. Acad. Sci. USA, 2001, vol. 99, pp. 15661-15668.

Trozzi, et al. "In vitro selection and characterization of hepatitis C virus serine protease variants resistant to an active-site peptide inhibitor", J. Virol., 2003, vol. 77, pp. 3669-3679.

Wakita, et al., 2005 "Production of infectious hepatitis C virus in tissue culture from a cloned viral genome", Nature Med., 2005, vol. 11, pp. 791-796.

Wang, et al., "Induction of hepatitis C virus-specific cytotoxic T and B cell responses by dendritic cells expressing a modified antigen targeting receptor." World J. Gastroenterol,2005; 11(4):557-560.

Wen, et al., "Antigen-antibody complex as therapeutic vaccine for viral hepatitis B", Int. Rev. Immunol., 1999, vol. 18, pp. 251-258.

Wen, et al., "Hepatitis B vaccine and anti-HBs complex as approach for vaccine therapy", The Lacent 1995, vol. 345, No. 8964, pp. 1575-1576.

Wetlaufer, et al., "Control of aggregation in protein refolding: A variety of surfactants promote renaturation of carbonice anhydrase II", Prot. Sci., 1995, vol. 4, pp. 1535-1543.

Wieland, et al., "Stealth and cunning: Hepatitis B and Hepatitis C viruses.", J. Virol., 2005, vol. 79, pp. 9369-9380.

Wild, et al., "Primary prevention of hepatocellular carcinoma in developing countries", Mutation Res., 2000, vol. 462, pp. 381-393.

Xu, et al, "Endoplasmic reticulum targeting sequence enhances HBV-specific cytotoxic T lympocytes induced by a CTL epitope-based DNA vaccine", Virology, 2005 vol. 334, pp. 255-263.

Yanagi, et al., "Transcripts from a single full-length cDNA clone of hepatitis C virus are infectious when directly transfected into the liver of a chimpanzee", Proc. Natl. Acad. Sci. USA, 1997, vol. 94, pp. 8738-8743.

Yotsuyanagi et al. "Prolonged Fecal Excretion of Hepatitis A Virus in Adult Patients With Hepatitis A as Determined by Polymerase Chain Reaction", Hepatology vol. 24, No. 1, 1996, pp. 10-13.

Yu, et al., "Priming with CpG-enriched plasmid and boosting with protein formulated with CpG oligodeoxynucleotides and Quil A induces strong cellular and humoral immune responses to hepatitis C virus NS3", J. Gen. Virol., 2004, vol. 85, pp. 1533-1543.

Zheng, et al., "Therapeutic efficacy of hepatitis B surface antigen-antibodies-recombinant ONA composite in HBsAg transgenic mice", Vaccine, Jul. 2001, vol. 19, No. 30, pp. 4219-4225.

Zhong, et al, 2005 "Robust hepatitis C infection in vitro", Proc. Natl. Acad. Sci. USA, 2005, vol. 102, pp. 9294-9299.

Zou, "Regulatory T cells, tumour immunity and immunotherapy", Nat Rev Immunol., Apr. 2006, vol. 6, pp. 295-307.

Altman, et al., "Insect Cells as Hosts for the Expression of Recombinant Glycoproteins." *Glycoconjugate Journal* 16: 109-123 (1999).

Apostolopoulos et al., "Aldehyde-mannan antigen complexes target the MHC class I antigen-presentation pathway." *Eur. J. Immunol.* 30:1714-1723 (2000).

Apostolopoulos and McKenzie, "Role of the mannose receptor in the immune response," *Curr. Mol. Med.* 1:469-474 (2001).

Ashkenazi et al., "Immunoadhesins as research tools and therapeutic agents", *Curr. Op Immunol.* 9: 195-200, (1997).

Banchereau, and Steinman "Dendritic cells and the control of immunity," *Nature* 392: 245-252 (1998).

Bartenschlager et al., "Novel Insights into Hepatitis C Virus Replication and Persistence", *Advances in Virus Research* 63: 71-180 (2004).

Beasley, "Hepatitis B Virus. The major etiology of hepatocellular carcinoma," *Cancer* 61(10): 1942-1956, (1988).

Purcell, "The Hepatitis C Virus: Overview," Hepatology, 1997, vol. 26(3), pp. 11S-14S.

Wines et al. "The IgG Fc Contains Distinct Fc Receptor (FcR) Binding Sites: The Leukocyte Receptors Fc{gamma}RI and Fc{gamma}RlIa Bind to a Region in the Fc Distinct from That Recognized by Neonatal FcR and Protein A," J. Immuno., 2000, vol. 164, pp. 5313-5318.

\* cited by examiner

N-terminus                                    C-terminus

```
1/1                                           31/11
GGC GCC ATG GAT CCG GAA TTC AAA GGC CTA CGT CGA CGA GCT CAA CTA GTC CGG CCG CAA
gly ala met asp pro glu phe lys gly leu arg arg arg ala gln leu val arg pro gln
61/21                                         91/31
GGC GGC GGA TCC GTG GAC AAG AAA ATT GTG CCC AGG GAT TGT GGT TGT AAG CCT TGC ATA
gly gly gly ser val asp lys lys ile val pro arg asp cys gly cys lys pro cys ile
121/41                                        151/51
TGT ACA GTC CCA GAA GTA TCA TCT GTC TTC ATC TTC CCC CCA AAG CCC AAG GAT GTG CTC
cys thr val pro glu val ser ser val phe ile phe pro pro lys pro lys asp val leu
181/61                                        211/71
ACC ATT ACT CTG ACT CCT AAG GTC ACG TGT GTT GTG GTA GAC ATC AGC AAG GAT GAT CCC
thr ile thr leu thr pro lys val thr cys val val val asp ile ser lys asp asp pro
241/81                                        271/91
GAG GTC CAG TTC AGC TGG TTT GTA GAT GAT GTG GAG GTG CAC ACA GCT CAG ACG CAA CCC
glu val gln phe ser trp phe val asp asp val glu val his thr ala gln thr gln pro
301/101                                       331/111
CGG GAG GAG CAG TTC AAC AGC ACT TTC CGC TCA GTC AGT GAA CTT CCC ATC ATG CAC CAG
arg glu glu gln phe asn ser thr phe arg ser val ser glu leu pro ile met his gln
361/121                                       391/131
GAC TGG CTC AAT GGC AAG GAG TTC AAA TGC AGG GTC AAC AGT GCA GCT TTC CCT GCC CCC
asp trp leu asn gly lys glu phe lys cys arg val asn ser ala ala phe pro ala pro
421/141                                       451/151
ATC GAG AAA ACC ATC TCC AAA ACC AAA GGC AGA CCG AAG GCT CCA CAG GTG TAC ACC ATT
ile glu lys thr ile ser lys thr lys gly arg pro lys ala pro gln val tyr thr ile
481/161                                       511/171
CCA CCT CCC AAG GAG CAG ATG GCC AAG GAT AAA GTC AGT CTG ACC TGC ATG ATA ACA GAC
pro pro pro lys glu gln met ala lys asp lys val ser leu thr cys met ile thr asp
541/181                                       571/191
TTC TTC CCT GAA GAC ATT ACT GTG GAG TGG CAG TGG AAT GGG CAG CCA GCG GAG AAC TAC
phe phe pro glu asp ile thr val glu trp gln trp asn gly gln pro ala glu asn tyr
601/201                                       631/211
AAG AAC ACT CAG CCC ATC ATG GAC ACA GAT GGC TCT TAC TTC GTC TAC AGC AAG CTC AAT
lys asn thr gln pro ile met asp thr asp gly ser tyr phe val tyr ser lys leu asn
661/221                                       691/231
GTG CAG AAG AGC AAC TGG GAG GCA GGA AAT ACT TTC ACC TGC TCT GTG TTA CAT GAG GGC
val gln lys ser asn trp glu ala gly asn thr phe thr cys ser val leu his glu gly
721/241                                       751/251
CTG CAC AAC CAC CAT ACT GAG AAG AGC CTC TCC CAC TCT CCT GGG CTG CAA AGC TTG TCG
leu his asn his his thr glu lys ser leu ser his ser pro gly leu gln ser leu ser
781/261
AGA AGT ACT AGA GGA TCA
arg ser thr arg gly ser
```

Figure 6

Figure 8. Nucleotide and Amino Acid Sequences of the ORF of HBV S1/S2 Protein in the Plasmid pFASTBACHTa-HBV S1/S2.

Fig 8A. DNA sequence of HBV S1/S2 Protein expression cassette

ATGTCGTACTACCATCACCATCACCATCACGATTACGATATCCCAACGACCGAAAACCT
GTATTTTCAGGGCGCCATGGATCCTATGAAAAAATGGTCATCAAAACCTCGCAAAGGCA
TGGGGACGAATCTTTCTGTTCCCAACCCTCTGGGATTCTTTCCCGATCATCAGTTGGAC
CCTGTATTCGGAGCCAACTCAAACAATCCAGATTGGACTTCAACCCCATCAAGGACCA
CTGGCCAGCAGCCAACCAGGTAGGAGTGGGAGCATTCGGGCCAGGGTTCACCCCTCCAC
ACGGCGGTGTTTTGGGGTGGAGCCCTCAGGCTCAGGGCATGTTGACCCCAGTGTCAACA
ATTCCTCCTCCTGCCTCCGCCAATCGGCAGTCAGGAAGGCAGCCTACTCCCATCTCTCC
ACCTCTAAGAGACAGTCATCCTCAGGCCATGCAGTGGAATTCCACTGCCTTCCACCAAG
CTCTGCAAGACCCCAGAGTCAGGGGTCTGTATTTTCCTGCTGGTGGCTCCAGTTCAGGA
ACAGTAAACCCTGCTCCGAATATTGCCTCTCACATCTCGTCAATCTCCGCGAGGACCGG
GGACCCTGTGACGAACTCGCGGCCGCTTTCGAATCTAGAGCCTGCAGTATCGAGGCATG
CGGTACCAAGCTTGTCGAGAAGTACTAGAGGATCA

Fig 8B. Amino Acid Sequence of HBV S1/S2 Protein (228 AA, 24.6 KDa, 684 bp.)

MSYYHHHHHHDYDIPTTENLYFQGAMDPMKKWSSKPRKGMGTNLSVPNPLGFFPDHQLD
PVFGANSNNPDWDFNPIKDHWPAANQVGVGAFGPGFTPPHGGVLGWSPQAQGMLTPVST
IPPPASANRQSGRQPTPISPPLRDSHPQAMQWNSTAFHQALQDPRVRGLYFPAGGSSSG
TVNPAPNIASHISSISARTGDPVTNSRPLSNLEPAVSRHAVPSLSRSTRGS

```
4050/1                                          4080/11
ATG TCG TAC TAC CAT CAC CAT CAC CAT CAC GAT TAC GAT ATC CCA ACG ACC GAA AAC CTG
 M   S   Y   Y   H   H   H   H   H   H   D   Y   D   I   P   T   T   E   N   L
4110/21                                         4140/31
TAT TTT CAG GGC GCC ATG GAT CCT ATG AAA AAA TGG TCA TCA AAA CCT CGC AAA GGC ATG
 Y   F   Q   G   A   M   D   P   M   K   K   W   S   S   K   P   R   K   G   M
4170/41                                         4200/51
GGG ACG AAT CTT TCT GTT CCC AAC CCT CTG GGA TTC TTT CCC GAT CAT CAG TTG GAC CCT
 G   T   N   L   S   V   P   N   P   L   G   F   F   P   D   H   Q   L   D   P
4230/61                                         4260/71
GTA TTC GGA GCC AAC TCA AAC AAT CCA GAT TGG GAC TTC AAC CCC ATC AAG GAC CAC TGG
 V   F   G   A   N   S   N   N   P   D   W   D   F   N   P   I   K   D   H   W
4290/81                                         4320/91
CCA GCA GCC AAC CAG GTA GGA GTG GGA GCA TTC GGG CCA GGG TTC ACC CCT CCA CAC GGC
 P   A   A   N   Q   V   G   V   G   A   F   G   P   G   F   T   P   P   H   G
4350/101                                        4380/111
GGT GTT TTG GGG TGG AGC CCT CAG GCT CAG GGC ATG TTG ACC CCA GTG TCA ACA ATT CCT
 G   V   L   G   W   S   P   Q   A   Q   G   M   L   T   P   V   S   T   I   P
4410/121                                        4440/131
CCT CCT GCC TCC GCC AAT CGG CAG TCA GGA AGG CAG CCT ACT CCC ATC TCT CCA CCT CTA
 P   P   A   S   A   N   R   Q   S   G   R   Q   P   T   P   I   S   P   P   L
4470/141                                        4500/151
ACA GAC AGT CAT CCT CAG GCC ATG CAG TGG AAT TCC ACT GCC TTC CAC CAA GCT CTG CAA
 R   D   S   H   P   Q   A   M   Q   W   N   S   T   A   F   H   Q   A   L   Q
4530/161                                        4560/171
GAC CCC AGA GTC AGG GGT CTG TAT TTT CCT GCT GGT GGC TCC AGT TCA GGA ACA GTA AAC
 D   P   R   V   R   G   L   Y   F   P   A   G   G   S   S   S   G   T   V   N
4590/181                                        4620/191
CCT GCT CCG AAT ATT GCC TCT CAC ATC TCG TCA ATC TCC GCG AGG ACC GGG GAC CCT GTG
 P   A   P   N   I   A   S   H   I   S   S   I   S   A   R   T   G   D   P   V
4650/201                                        4680/211
ACG AAC TCG CGG CCG CTT TCG AAT CTA GAG CCT GCA GTC TCG AGG CAT GCG GTA CCA AGC
 T   N   S   R   P   L   S   N   L   E   P   A   V   S   R   H   A   V   P   S
4710/221
TTC TCG AGA AGT ACT AGA GGA TCA TAA
 L   S   R   S   T   R   G   S   *
```

Figure 9

Figure 11. Nucleotide and Amino Acid Sequences of the ORF of HBV S1/S2-TBD Protein in the Plasmid pFASTBACHTaHBV S1/S2-TBD.

11.A. DNA sequence of HBV S1/S2-TBD Protein Expression Cassette

ATGTCGTACTACCATCACCATCACCATCACGATTACGATATCCCAACGACCGAAAACCT
GTATTTTCAGGGCGCCATGGATCCTATGAAAAAATGGTCATCAAAACCTCGCAAAGGCA
TGGGGACGAATCTTTCTGTTCCCAACCCTCTGGGATTCTTTCCCGATCATCAGTTGGAC
CCTGTATTCGGAGCCAACTCAAACAATCCAGATTGGGACTTCAACCCCATCAAGGACCA
CTGGCCAGCAGCCAACCAGGTAGGAGTGGGAGCATTCGGGCCAGGGTTCACCCCTCCAC
ACGGCGGTGTTTTGGGGTGGAGCCCTCAGGCTCAGGGCATGTTGACCCCAGTGTCAACA
ATTCCTCCTCCTGCCTCCGCCAATCGGCAGTCAGGAAGGCAGCCTACTCCCATCTCTCC
ACCTCTAAGAGACAGTCATCCTCAGGCCATGCAGTGGAATTCCACTGCCTTCCACCAAG
CTCTGCAAGACCCCAGAGTCAGGGGTCTGTATTTTCCTGCTGGTGGCTCCAGTTCAGGA
ACAGTAAACCCTGCTCCGAATATTGCCTCTCACATCTCGTCAATCTCCGCGAGGACCGG
GGACCCTGTGACGAACTCGCGGCCGCAAGGCGGCGGATCCGTGGACAAGAAAATTGTGC
CCAGGGATTGTGGTTGTAAGCCTTGCATATGTACAGTCCCAGAAGTATCATCTGTCTTC
ATCTTCCCCCCAAAGCCCAAGGATGTGCTCACCATTACTCTGACTCCTAAGGTCACGTG
TGTTGTGGTAGACATCAGCAAGGATGATCCCGAGGTCCAGTTCAGCTGGTTTGTAGATG
ATGTGGAGGTGCACACAGCTCAGACGCAACCCCGGGAGGAGCAGTTCAACAGCACTTTC
CGCTCAGTCAGTGAACTTCCCATCATGCACCAGGACTGGCTCAATGGCAAGGAGTTCAA
ATGCAGGGTCAACAGTGCAGCTTTCCCTGCCCCCATCGAGAAAACCATCTCCAAAACCA
AAGGCAGACCGAAGGCTCCACAGGTGTACACCATTCCACCTCCCAAGGAGCAGATGGCC
AAGGATAAAGTCAGTCTGACCTGCATGATAACAGACTTCTTCCCTGAAGACATTACTGT
GGAGTGGCAGTGGAATGGGCAGCCAGCGGAGAACTACAAGAACACTCAGCCCATCATGG
ACACAGATGGCTCTTACTTCGTCTACAGCAAGCTCAATGTGCAGAAGAGCAACTGGGAG
GCAGGAAATACTTTCACCTGCTCTGTGTTACATGAGGGCCTGCACAACCACCATACTGA
GAAGAGCCTCTCCCACTCTCCTGGGCTGCAAAGCTTGTCGAGAAGTACTAGAGGATCA

Fig. 11B. Amino Acid Sequence of HBV S1/S2-TBD Protein

(452 AA, 49.9 KDa, 1356 bp.)

MSYYHHHHHHDYDIPTTENLYFQGAMDPMKKWSSKPRKGMGTNLSVPNPLGFFPDHQLD
PVFGANSNNPDWDFNPIKDHWPAANQVGVGAFGPGFTPPHGGVLGWSPQAQGMLTPVST
IPPPASANRQSGRQPTPISPPLRDSHPQAMQWNSTAFHQALQDPRVRGLYFPAGGSSSG
TVNPAPNIASHISSISARTGDPVTNSRPQGGGSVDKKIVPRDCGCKPCICTVPEVSSVF
IFPPKPKDVLTITLTPKVTCVVVDISKDDPEVQFSWFVDDVEVHTAQTQPREEQFNSTF
RSVSELPIMHQDWLNGKEFKCRVNSAAFPAPIEKTISKTKGRPKAPQVYTIPPPKEQMA
KDKVSLTCMITDFFPEDITVEWQWNGQPAENYKNTQPIMDTDGSYFVYSKLNVQKSNWE
AGNTFTCSVLHEGLHNHHTEKSLSHSPGLQSLSRSTRGS

Figure 12. Nucleotide and Amino Acid Sequences of the ORF of
HBV S1/S2/S Protein in the Plasmid pFastBac HTa HBV S1/S2/S Fig 12A. DNA Sequence of HBV S1/S2/S Protein Expression
Cassette

```
ATG TCG TAC TAC CAT CAC CAT CAC CAT CAC GAT TAC GAT ATC CCA
ACG ACC GAA AAC CTG TAT TTT CAG GGC GCC ATG GAT CCT ATG GGA
GGT TGG TCA TCA A

Fig 12B. Amino Acid Sequence of HBV S1/S2/S Protein (454 AA, 49.9 KDa, 1365 bp.)

MSYYHHHHHHDYDIPTTENLYFQGAMDPMGGWSSKPRKGMGTNLSVPNPLGFFPDHQLDP
VFGANSNNPDWDFNPIKDHWPAANQVGVGAFGPGFTPPHGGVLGWSPQAQGMLTPVSTIP
PPASANRQSGRQPTPISPPLRDSHPQAMQWNSTAFHQALQDPRVRGLYFPAGGSSSGTVN
PAPNIASHISSISARTGDPVTNMENITSGFLGPLLVLQAGFFLLTRILTIPQSLDSWWTS
LNFLGGSPVCLGQNSQSPTSNHSPTSCPPICPGYRWMCLRRFIIFLFILLLCLIFLLVLL
DYQGMLPVCPLIPGSTTTSTGPCKTCTTPAQGNSMFPSCCCTKPTDGNCTCIPIPSSWAF
AKYLWEWASVRFSWLSLLVPFVQWFVGLSPTVWLSAIWMMWYWGPSLYSIVSPFIPLLPI
FFCLWVYISRPLSNLEPAVSRHAVPSLSRSTRGS

Figure 14. Nucleotide and Amino Acid Sequences of the ORF of

HBV Core-TBD Protein in the Plasmid pFASTBACHTa HBV Core-TBD.

Fig. 14A. DNA sequence of HBV Core-TBD Protein Expression Cassette

ATGTCGTACTACCATCACCATCACCATCACGATTACGATATCCCAACGACCGAAAACCT
GTATTTTCAGGGCGCCATGGACATTGACCCTTATAAAGAATTTGGAGCTACTGTGGAGT
TACTCTCGTTTTTGCCTTCTGACTTCTTTCCTTCCGTCAGAGATCTCCTANACACCGCC
TCGGCTCTGTATCGGGAAGCCTTAGAGTCTCCTGAGCATTGCTCACCTCACCATACCGC
ACTCAGGCAAGCCATTCTCTGCTGGGGGGAATTGATGACTCTAGCTACCTGGGTGGGTA
ATAATTTGGAAGATCCAGCATCCAGGGATCTAGTAGTCAATTATGTTAATACTAACATG
GGATTAAAGATCAGGCAACTCTTGTGGTTTCATATCTCTTGCCTTACTTTTGGAAGAGA
AACTGTACTTGAATATTTGGTCTCTTTCGGAGTGTGGATTCGCACTCCTCCAGCCTATA
GACCACCAAATGCCCCTATCTTATCAACACTTCCGGAAACTACTGTTGTTAGACGACGG
GACCGAGGCAGGTCCCCTAGAAGAAGAACTCCCTCGCCTCGCAGACGCAGATCTCAATC
GCCGCGTCGCAGAAGATCTCAATCTCGGGAATCTCAATGTTCGCGGCCGCAAGGCGGCG
GATCCGTGGACAAGAAAATTGTGCCCAGGGATTGTGGTTGTAAGCCTTGCATATGTACA
GTCCCAGAAGTATCATCTGTCTTCATCTTCCCCCCAAAGCCCAAGGATGTGCTCACCAT
TACTCTGACTCCTAAGGTCACGTGTGTTGTGGTAGACATCAGCAAGGATGATCCCGAGG
TCCAGTTCAGCTGNTTTGTAGATGATGTGNAGNTGCACACAGCTCAGACGCAACCCCGG
GAGGAGCAGTTCAACAGCACTTTCCGCTCAGTCAGTGAACTTCCCATCATGCACCAGGA
CTGGCTCAATGGCAAGGAGTTCAAATGCAGGGTCAACAGTGCAGCTTTCCCTGCCCCCA
TCGAGAAAACCATCTCCAAAACCAAAGGCAGACCGAAGGCTCCACAGGTGTACACCATT
CCACCTCCCAAGGAGCAGATGGCCAAGGATAAAGTCAGTCTGACCTGCATGATAACAGA
CTTCTTCCCTGAAGACATTACTGTGGAGTGGCAGTGGAATGGGCAGCCAGCGGAGAACT
ACAAGAACACTCAGCCCATCATGGACACAGATGGCTCTTACTTCGTCTACAGCAAGCTC
AATGTGCAGAAGAGCAACTGGGAGGCAGGAAATACTTTCACCTGCTCTGTGTTACATGA
GGGCCTGCACAACCACCATACTGAGAAGAGCCTCTCCCACTCTCCTGGGCTGCAAAGCT
TGTCGAGAAGTACTAGAGGATCA

Fig 14B Amino Acid Sequence of HBV Core-TBD Protein
(460 AA, 52.5 KDa, 1380 bp)

MSYYHHHHHHDYDIPTTENLYFQGAMDIDPYKEFGATVELLSFLPSDFFPSVRDLLDTA
SALYREALESPEHCSPHHTALRQAILCWGELMTLATWVGNNLEDPASRDLVVNYVNTNM
GLKIRQLLWFHISCLTFGRETVLEYLVSFGVWIRTPPAYRPPNAPILSTLPETTVVRRR
DRGRSPRRRTPSPRRRRSQSPRRRRSQSRESQCSRPQGGGSVDKKIVPRDCGCKPCICT
VPEVSSVFIPPPKPKDVLTITLTPKVTCVVVDISKDDPEVQFSWFVDDVEVHTAQTQPR
EEQFNSTFRSVSELPIMHQDWLNGKEFKCRVNSAAFPAPIEKTISKTKGRPKAPQVYTI
PPPKEQMAKDKVSLTCMITDFFPEDITVEWQWNGQPAENYKNTQPIMDTDGSYFVYSKL
NVQKSNWEAGNTFTCSVLHEGLHNHHTEKSLSHSPGLQSLSRSTRGS

Figure 15. Nucleotide and Amino Acid Sequences of the ORF of HBV

Core Protein in the Plasmid pFASTBACHTa-HBV Core.

Fig 15A.  DNA sequence of HBV Core Protein expression cassette

```
ATGTCGTACTACCATCACCATCACCATCACGATTACGATATCCCAACGACCGAAAACCT
GTATTTTCAGGGCGCCATGGACATTGACCCTTATAAAGAATTTGGAGCTACTGTGGAGT
TACTCTCGTTTTTGCCTTCTGACTTCTTTCCTTCCGTCAGAGATCTCCTAGACACCGCC
TCGGCTCTGTATCGGGAAGCCTTAGAGTCTCCTGAGCATTGCTCACCTCACCATACCGC
ACTCAGGCAAGCCATTCTCTGCTGGGGGGAATTGATGACTCTAGCTACCTGGGTGGGTA
ATAATTTGGAAGATCCAGCATCCAGGGATCTAGTAGTCAATTATGTTAATACTAACATG
GGATTAAAGATCAGGCAACTCTTGTGGTTTCATATCTCTTGCCTTACTTTTGGAAGAGA
AACTGTACTTGAATATTTGGTCTCTTTCGGAGTGTGGATTCGCACTCCTCCAGCCTATA
GACCACCAAATGCCCCTATCTTATCAACACTTCCGGAAACTACTGTTGTTAGACGACGG
GACCGAGGCAGGTCCCCTAGAAGAAGAACTCCCTCGCCTCGCAGACGCAGATCTCAATC
GCCGCGTCGCAGAAGATCTCAATCTCGGGAATCTCAATGTTCGCGGCCGCTTTCGAATC
TAGAGCCTGCAGTCTCGAGGCATGCGGTACCAAGCTTGTCGAGAAGTACTAGAGGATCA
```

Fig 15.B.  Amino Acid Sequence of HBV Core Protein

```
MSYYHHHHHHDYDIPTTENLYFQGAMDIDPYKEFGATVELLSFLPSDFFPSVRDLLDTA
SALYREALESPEHCSPHHTALRQAILCWGELMTLATWVGNNLEDPASRDLVVNYVNTNM
GLKIRQLLWFHISCLTFGRETVLEYLVSFGVWIRTPPAYRPPNAPILSTLPETTVVRRR
DRGRSPRRRTPSPRRRRSQSPRRRRSQSRESQCSRPLSNLEPAVSRHAVPSLSRSTRGS
```

Figure 17. Nucleotide and Amino Acid Sequences of the ORF of DHBV PreS-TBD Protein in the Plasmid pFastBac HTa dPreS-TBD Fig 17A. DNA Sequence of DHBV PreS-TBD Protein Expression Cassette

```
ATG TCG TAC TAC CAT CAC CAT CAC CAT CAC GAT TAC GAT ATC CCA
ACG ACC GAA AAC CTG TAT TTT CAG GGC GCC ATG GAT CCG GAA TTC
ATG GGG CAA CAT CCA GCA AAA TCA ATG GAC GTC AGA CGG ATA GAA
GGA GGA GAA ATA CTG TTA AAC CAA CTT GCC GGA AGG ATG ATC CCA
AAA GGG ACT TTG ACA TGG TCA GGC AAG TTT CCA ACA CTA GAT CAC
GTG TTA GAC CAT GTG CAA ACA ATG GAG GAG ATA AAC ACC CTC CAG
AAT CAG GGA GCT TGG CCT GCT GGG GCG GGA AGG AGA GTA GGA TTA
TCA AAT CCG ACT CCT CAA GAG ATT CCT CAG CCC CAG TGG ACT CCC
GAG GAA GAC CAA AAA GCA CGC GAA GCT TTT CGC CGT TAT CAA GAA
GAA AGA CCA CCG GAA ACC ACC ACC ATT CCT CCG TCT TCC CCT CCT
CAG TGG AAG CTA CAA CCC GGG GAC GAT CCA CTC CTG GGA AAT CAG
TCT CTC CTC GAG ACT CAT CCG CTA TAC CAG TCA GAA CCA GCG GTG
CCA GTG ATA AAA ACT CCC CCC TTG AAG AAG AAA ACG CGG CCG CAA
GGC GGC GGA TCC GTG GAC AAG AAA ATT GTG CCC AGG GAT TGT GGT
TGT AAG CCT TGC ATA TGT ACA GTC CCA GAA GTA TCA TCT GTC TTC
ATC TTC CCC CCA AAG CCC AAG GAT GTG CTC ACC ATT ACT CTG ACT
CCT AAG GTC ACG TGT GTT GTG GTA GAC ATC AGC AAG GAT GAT CCC
GAG GTC CAG TTC AGC TGG TTT GTA GAT GAT GTG GAG GTG CAC ACA
GCT CAG ACG CAA CCC CGG GAG GAG CAG TTC AAC AGC ACT TTC CGC
TCA GTC AGT GAA CTT CCC ATC ATG CAC CAG GAC TGG CTC AAT GGC
AAG GAG TTC AAA TGC AGG GTC AAC AGT GCA GCT TTC CCT GCC CCC
ATC GAG AAA ACC ATC TCC AAA ACC AAA GGC AGA CCG AAG GCT CCA
CAG GTG TAC ACC ATT CCA CCT CCC AAG GAG CAG ATG GCC AAG GAT
AAA GTC AGT CTG ACC TGC ATG ATA ACA GAC TTC TTC CCT GAA GAC
ATT ACT GTG GAG TGG CAG TGG AAT GGG CAG CCA GCG GAG AAC TAC
AAG AAC ACT CAG CCC ATC ATG GAC ACA GAT GGC TCT TAC TTC GTC
TAC AGC AAG CTC AAT GTG CAG AAG AGC AAC TGG GAG GCA GGA AAT
ACT TTC ACC TGC TCT GTG TTA CAT GAG GGC CTG CAC AAC CAC CAT
ACT GAG AAG AGC CTC TCC CAC TCT CCT GGG CTG CAA AGC TTG TCG
AGA AGT ACT AGA GGA TCA TAA
```

Fig 17B. Amino Acid Sequence of DHBV PreS-TBD Protein

(441 AA, 49.8 KDa, 1326 bp.)

```
MSYYHHHHHHDYDIPTTENLYFQGAMDPEFMGQHPAKSMDVRRIEGGEILLNQLAGRMIP
KGTLTWSGKFPTLDHVLDHVQTMEEINTLQNQGAWPAGAGRRVGLSNPTPQEIPQPQWTP
EEDQKAREAFRRYQEERPPETTTIPPSSPPQWKLQPGDDPLLGNQSLLETHPLYQSEPAV
PVIKTPPLKKKTRPQGGGSVDKKIVPRDCGCKPCICTVPEVSSVFIFPPKPKDVLTITLT
PKVTCVVVDISKDDPEVQFSWFVDDVEVHTAQTQPREEQFNSTFRSVSELPIMHQDWLNG
KEFKCRVNSAAFPAPIEKTISKTKGRPKAPQVYTIPPPKEQMAKDKVSLTCMITDFFPED
ITVEWQWNGQPAENYKNTQPIMDTDGSYFVYSKLNVQKSNWEAGNTFTCSVLHEGLHNHH
TEKSLSHSPGLQSLSRSTRGS
```

```
1/1                                      31/11
ATG TCG TAC TAC CAT CAC CAT CAC CAT CAC GAT TAC GAT ATC CCA ACG ACC GAA AAC CTG
 M   S   Y   Y   H   H   H   H   H   H   D   Y   D   I   P   T   T   E   N   L
61/21                                    91/31
TAT TTT CAG GGC GCC ATG GAT CCG GAA TTC ATG GGG CAA CAT CCA GCA AAA TCA ATG GAC
 Y   F   Q   G   A   M   D   P   E   F   M   G   Q   H   P   A   K   S   M   D
121/41                                   151/51
GTC AGA CGG ATA GAA GGA GGA GAA ATA CTG TTA AAC CAA CTT GCC GGA AGG ATG ATC CCA
 V   R   R   I   E   G   G   E   I   L   L   N   Q   L   A   G   R   M   I   P
181/61                                   211/71
AAA GGG ACT TTG ACA TGG TCA GGC AAG TTT CCA ACA CTA GAT CAC GTG TTA GAC CAT GTG
 K   G   T   L   T   W   S   G   K   F   P   T   L   D   H   V   L   D   H   V
241/81                                   271/91
CAA ACA ATG GAG GAG ATA AAC ACC CTC CAG AAT CAG GGA GCT TGG CCT GCT GGG GCG GGA
 Q   T   M   E   E   I   N   T   L   Q   N   Q   G   A   W   P   A   G   A   G
301/101                                  331/111
AGG AGA GTA GGA TTA TCA AAT CCG ACT CCT CAA GAG ATT CCT CAG CCC CAG TGG ACT CCC
 R   R   V   G   L   S   N   P   T   P   Q   E   I   P   Q   P   Q   W   T   P
361/121                                  391/131
GAG GAA GAC CAA AAA GCA CGC GAA GCT TTT CGC CGT TAT CAA GAA AGA CCA CCG GAA
 E   E   D   Q   K   A   R   E   A   F   R   R   Y   Q   E   R   P   P   E
421/141                                  451/152
ACC ACC ACC ATT CCT CCG TCT TCC CCT CCT CAG TGG AAG CTA CAA CCC GGG GAC GAT CCA
 T   T   T   I   P   P   S   S   P   P   Q   W   K   L   Q   P   G   D   D   P
481/161                                  511/171
CTC CTG GGA AAT CAG TCT CTC CTC GAG ACT CAT CCG CTA TAC CAG TCA GAA CCA GCG GTG
 L   L   G   N   Q   S   L   L   E   T   H   P   L   Y   Q   S   E   P   A   V
541/181                                  571/191
CCA GTG ATA AAA ACT CCC CCC TTG AAG AAG AAA ACG CGG CCG CTT TCG AAT CTA GAG CCT
 P   V   I   K   T   P   P   L   K   K   K   T   R   P   L   S   N   L   E   P
601/201                                  631/211
GCA GTC TCG AGG CAT GCG GTA CCA AGC TTG TCG AGA AGT ACT AGA GGA TCA TAA
 A   V   S   R   H   A   V   P   S   L   S   R   S   T   R   G   S   *
```

Figure 18

Figure 20. Nucleotide and Amino Acid Sequences of the ORF of DHBV PreS/S-TBD Protein in the Plasmid pFASTBACHTa-DHBV PreS/S-TBD.

Fig 20A. DNA sequence of DHBV PreS/S-TBD Protein expression cassette

ATGTCGTACTACCATCACCATCACCATCACGATTACGATATCCCAACGACCG
AAAACCTGTATTTTCAGGGCGCCATGGATCCGGAATTCATGGGGCAACATCC
AGCAAAATCAATGGACGTCAGACGGATAGAAGGAGGAGAAATACTGTTAAA
CCAACTTGCCGGAAGGATGATCCCAAAAGGGACTTTGACATGGTCAGGCAAG
TTTCCAACACTAGATCACGTGTTAGACCATGTGCAAACAATGGAGGAGATAA
ACACCCTCCAGAATCAGGGAGCTTGGCCTGCTGGGGCGGGAAGGAGAGTAG
GATTATCAAATCCGACTCCTCAAGAGATTCCTCAGCCCCAGTGGACTCCCGA
GGAAGAACAAAAAGCACGCGAAGCTTTTCGCCGTTATCAAGAAGAAAGACC
ACCGGAAACCACCACCATTCCTCCGTCTTCCCCTCCTCAGTGGAAGCTACAAC
CCGGGGACGATCCACTCCTGGGAAATCAGTCTCTCCTCGAGACTCATCCGCT
ATACCAGTCAGAACCAGCGGTGCCAGTGATAAAAACTCCCCCCTTGAAGAAG
AAAATGTCTGGTACCTTCGGGGGAATACTAGCTGGCCTAATCGGATTACTGG
TAAGCTTTTTCTTGTTGATAAAAATTCTAGAAATACTGAGGAGGCTAGATTGG
TGGTGGATTTCTCTCAGTTCTCCAAAGGGAAAAATGCAATGCGCTTTCCAAGA
TACTGGAGCCCAAATCTCTCCACATTACGTAGGATCTTGCCCGTGGGGATGCC
CAGGATTTCTTTGGACCTATCTCAGGCTTTTTATCATCTTCCTCTTAATCCTGC
TAGTAGCAGCAGGCTTGCTGTATCTGACGGACAACGGGTCTACTATTTTAGG
AAAGCTCCAATGGGCGTCGGTCTCAGCCCTTTTCTCCTCCATCTCTTCACTAC
TGCCCTCGGATCCGAAATCTCTCGTCGCTTTAACGTTTGGACTTTCACTTATAT
GGATGACTTCCTCCTCTGCCACCCAAACGCTCGTCACCTTAACGCAATTAGCC
ACGCTGTCTGCTCTTTTTTACAAGAGTTCGCGGCCGCAAGGCGGCGGATCCGT
GGACAAGAAAATTGTGCCCAGGGATTGTGGTTGTAAGCCTTGCATATGTACA
GTCCCAGAAGTATCATCTGTCTTCATCTTCCCCCCAAAGCCCAAGGATGTGCT
CACCATTACTCTGACTCCTAAGGTCACGTGTGTTGTGGTAGACATCAGCAAGG
ATGATCCCGAGGTCCAGTTCAGCTGGTTTGTAGATGATGTGGAGGTGCACAC
AGCTCAGACGCAACCCCGGGAGGAGCAGTTCAACAGCACTTTCCGCTCAGTC
AGTGAACTTCCCATCATGCACCAGGACTGGCTCAATGGCAAGGAGTTCAAAT
GCAGGGTCAACAGTGCAGCTTTCCCTGCCCCCATCGAGAAAACCATCTCCAA
AACCAAAGGCAGACCGAAGGCTCCACAGGTGTACACCATTCCACCTCCCAAG
GAGCAGATGGCCAAGGATAAAGTCAGTCTGACCTGCATGATAACAGACTTCT
TCCCTGAAGACATTACTGTGGAGTGGCAGTGGAATGGGCAGCCAGCGGAGAA
CTACAAGAACACTCAGCCCATCATGGACACAGATGGCTCTTACTTCGTCTAC
AGCAAGCTCAATGTGCAGAAGAGCAACTGGGAGGCAGGAAATACTTTCACCT
GCTCTGTGTTACATGAGGGCCTGCACAACCACCATACTGAGAAGAGCCTCTC
CCACTCTCCTGGGCTGCAAAGCTTGTCGAGAAGTACTAGAGGATCA

Fig 20B. Amino Acid Sequence of DHBV PreS/S-TBD Protein

(608 AA, 1824 bp, 68.0 KDa)

```
MSYYHHHHHHDYDIPTTENLYFQGAMDPEFMGQHPAKSMDVRRIEGGEILLNQLAGRMI
PKGTLTWSGKFPTLDHVLDHVQTMEEINTLQNQGAWPAGAGRRVGLSNPTPQEIPQPQW
TPEEEQKAREAFRRYQEERPPETTTIPPSSPPQWKLQPGDDPLLGNQSLLETHPLYQSE
PAVPVIKTPPLKKKMSGTFGGILAGLIGLLVSFFLLIKILEILRRLDWWWISLSSPKGK
MQCAFQDTGAQISPHYVGSCPWGCPGFLWTYLRLFIIFLLILLVAAGLLYLTDNGSTIL
GKLQWASVSALFSSISSLLPSDPKSLVALTFGLSLIWMTSSSATQTLVTLTQLATLSAL
FYKSSRPQGGGSVDKKIVPRDCGCKPCICTVPEVSSVFIFPPKPKDVLTITLTPKVTCV
VVDISKDDPEVQFSWFVDDVEVHTAQTQPREEQFNSTFRSVSELPIMHQDWLNGKEFKC
RVNSAAFPAPIEKTISKTKGRPKAPQVYTIPPPKEQMAKDKVSLTCMITDFFPEDITVE
WQWNGQPAENYKNTQPIMDTDGSYFVYSKLNVQKSNWEAGNTFTCSVLHEGLHNHHTEK
SLSHSPGLQSLSRSTRGS
```

Figure 21. Nucleotide and Amino Acid Sequences of the ORF ofDHBV PreS/S Protein in the Plasmid pFASTBACHTa-DHBV PreS/S.

Fig 21A. DNA sequence of DHBV PreS/S Protein expression cassette

ATGTCGTACTACCATCACCATCACCATCACGATTACGATATCCCAACGACCG
AAAACCTGTATTTTCAGGGCGCCATGGATCCGGAATTCATGGGGCAACATCC
AGCAAAATCAATGGACGTCAGACGGATAGAAGGAGGAGAAATACTGTTAAA
CCAACTTGCCGGAAGGATGATCCCAAAAGGGACTTTGACATGGTCAGGCAAG
TTTCCAACACTAGATCACGTGTTAGACCATGTGCAAACAATGGAGGAGATAA
ACACCCTCCAGAATCAGGGAGCTTGGCCTGCTGGGGCGGGAAGGAGAGTAG
GATTATCAAATCCGACTCCTCAAGAGATTCCTCAGCCCCAGTGGACTCCCGA
GGAAGACCAAAAAGCACGCGAAGCTTTTCGCCGTTATCAAGAAGAAAGACC
ACCGGAAACCACCACCATTCCTCCGTCTTCCCCTCCTCAGTGGAAGCTACAAC
CCGGGGACGATCCACTCCTGGGAAATCAGTCTCTCCTCGAGACTCATCCGCT
ATACCAGTCAGAACCAGCGGTGCCAGTGATAAAAACTCCCCCCTTGAAGAAG
AAAATGTCTGGTACCTTCGGGGGAATACTAGCTGGCCTAATCGGATTACTGG
TAAGCTTTTTCTTGTTGATAAAAATTCTAGAAATACTGAGGAGGCTAGATTGG
TGGTGGATTTCTCTCAGTTCTCCAAAGGGAAAAATGCAATGCGCTTTCCAAGA
TACTGGAGCCCAAATCTCTCCACATTACGTAGGATCTTGCCCGTGGGGATGCC
CAGGATTTCTTTGGACCTATCTCAGGCTTTTATCATCTTCCTCTTAATCCTGC
TAGTAGCAGCAGGCTTGCTGTATCTGACGGACAACGGGTCTACTATTTTAGG
AAAGCTCCAATGGGCGTCGGTCTCAGCCCTTTTCTCCTCCATCTCTTCACTAC
TGCCCTCGGATCCGAAATCTCTCGTCGCTTTAACGTTTGGACTTTCACTTATAT
GGATGACTTCCTCCTCTGCCACCCAAACGCTCGTCACCTTAACGCAATTAGCC
ACGCTGTCTGCTCTTTTTTACAAGAGTTCGCGGCCGCTTTCGAATCTAGAGCC
TGCAGTCTCGAGGCATGCGGTACCAAGCTTGTCGAGAAGTACTAGAGGATCA

Fig 21B. Amino Acid Sequence of DHBV PreS/S Protein (384 AA, 1152 bp, 42.7 KDa)

MSYYHHHHHHDYDIPTTENLYFQGAMDPEFMGQHPAKSMDVRRIEGGEILLNQ
LAGRMIPKGTLTWSGKFPTLDHVLDHVQTMEEINTLQNQGAWPAGAGRRVGLS
NPTPQEIPQPQWTPEEDQKAREAFRRYQEERPPETTIPPSSPPQWKLQPGDDPLL
GNQSLLETHPLYQSEPAVPVIKTPPLKKKMSGTFGGILAGLIGLLVSFFLLIKILEIL
RRLDWWWISLSSPKGKMQCAFQDTGAQISPHYVGSCPWGCPGFLWTYLRLFIIF
LLILLVAAGLLYLTDNGSTILGKLQWASVSALFSSISSLLPSDPKSLVALTFGLSLI
WMTSSSATQTLVTLTQLATLSALFYKSSRPLSNLEPAVSRHAVPSLSRSTRGS

Figure 23. Nucleotide and Amino Acid Sequences of the ORF of DHBV Core-TBD Protein in the Plasmid pFASTBACHTa-DHBV Core-TBD.

Fig 23A. DNA sequence of DHBV Core-TBD Protein expression cassette

ATGTCGTACTACCATCACCATCACCATCACGATTACGATATCCCAACGACCGAAAACCT
GTATTTTCAGGGCGCCATGGATATCAATGCTTCTAGAGCCTTAGCCAATGTGTATGATC
TACCAGATGATTTCTTTCCAAAAATAGATGATCTTGTTAGAGATGCTAAAGACGCTTTA
GAGCCTTATTGGAAATCAGATTCAATAAAGAAACATGTTTTGATTGCAACTCACTTTGT
GGATCTCATTGAAGACTTCTGGCAGACTACACAGGGCATGCATGAAATAGCCGAATCAT
TAAGAGCTGTTATACCTCCCACTACTACTCCTGTTCCACCGGGTTATCTTATTCAGCAC
GAGGAAGCTGAAGAGATACCTTTGGGAGATTTATTTAAACACCAAGAAGAAAGGATAGT
AAGTTTCCAACCCGACTATCCGATTACGGCTAGAATTCATGCTCATTTGAAAGCTTATG
CAAAAATTAACGAGGAATCACTGGATAGGGCTAGGAGATTGCTTTGGTGGCATTACAAC
TGTTTACTGTGGGGAGAAGCTCAAGTTACTAACTATATTTCTCGTTTGCGTACTTGGTT
GTCAACTCCTGAGAAATATAGAGGTAGAGATGCCCCGACCATTGAAGCAATCACTAGAC
CAATCCAGGTGGCTCAGGGAGGCAGAAAAACAACTACGGGTACTAGAAAACCTCGTGGA
CTCGAACCTAGAAGAAGAAAAGTTAAAACCACAGTTGTCTATGGGAGAAGACGTTCAAA
GTCCCGGGAAAGGAGAGCCCCTACACCCCAACGTGCGGGCTCCCCTCTCCCACGTAGTT
CGAGCAGCCACCATAGATCTCCCTCGCCTAGGAAATCGCGGCCGCAAGGCGGCGGATCC
GTGGACAAGAAAATTGTGCCCAGGGATTGTGGTTGTAAGCCTTGCATATGTACAGTCCC
AGAAGTATCATCTGTCTTCATCTTCCCCCCAAAGCCCAAGGATGTGCTCACCATTACTC
TGACTCCTAAGGTCACGTGTGTTGTGGTAGACATCAGCAAGGATGATCCCGAGGTCCAG
TTCAGCTGGTTTGTAGATGATGTGGAGGTGCACACAGCTCAGACGCAACCCCGGGAGGA
GCAGTTCAACAGCACTTTCCGCTCAGTCAGTGAACTTCCCATCATGCACCAGGACTGGC
TCAATGGCAAGGAGTTCAAATGCAGGGTCAACAGTGCAGCTTTCCCTGCCCCCATCGAG
AAAACCATCTCCAAAACCAAAGGCAGACCGAAGGCTCCACAGGTGTACACCATTCCACC
TCCCAAGGAGCAGATGGCCAAGGATAAAGTCAGTCTGACCTGCATGATAACAGACTTCT
TCCCTGAAGACATTACTGTGGAGTGGCAGTGGAATGGGCAGCCAGCGGAGAACTACAAG
AACACTCAGCCCATCATGGACACAGATGGCTCTTACTTCGTCTACAGCAAGCTCAATGT
GCAGAAGAGCAACTGGGAGGCAGGAAATACTTTCACCTGCTCTGTGTTACATGAGGGCC
TGCACAACCACCATACTGAGAAGAGCCTCTCCCACTCTCCTGGGCTGCAAAGCTTGTCG
AGAAGTACTAGAGGATCA

Fig 23B. Amino Acid Sequence of DHBV Core-TBD Protein (537 AA, 61.4 KDa, 1611 bp.)

MSYYHHHHHHDYDIPTTENLYFQGAMDINASRALANVYDLPDDFFPKIDDLVRDAKDAL
EPYWKSDSIKKHVLIATHFVDLIEDFWQTTQGMHEIAESLRAVIPPTTTPVPPGYLIQH
EEAEEIPLGDLFKHQEERIVSFQPDYPITARIHAHLKAYAKINEESLDRARRLLWWHYN
CLLWGEAQVTNYISRLRTWLSTPEKYRGRDAPTIEAITRPIQVAQGGRKTTTGTRKPRG
LEPRRRKVKTTVVYGRRRSKSRERRAPTPQRAGSPLPRSSSSHHRSPSPRKSRPQGGGS
VDKKIVPRDCGCKPCICTVPEVSSVFIFPPKPKDVLTITLTPKVTCVVVDISKDDPEVQ
FSWFVDDVEVHTAQTQPREEQFNSTFRSVSELPIMHQDWLNGKEFKCRVNSAAFPAPIE
KTISKTKGRPKAPQVYTIPPPKEQMAKDKVSLTCMITDFFPEDITVEWQWNGQPAENYK
NTQPIMDTDGSYFVYSKLNVQKSNWEAGNTFTCSVLHEGLHNHHTEKSLSHSPGLQSLS
RSTRGS

Figure 24. Nucleotide and Amino Acid Sequences of the ORF of DHBV- Core Protein in the Plasmid pFASTBACHTa-DHBV Core.

Fig 24A. DNA sequence of DHBV Core Protein expression cassette

```
ATGTCGTACTACCATCACCATCACCATCACGATTACGATATCCCAACGACCGAAAACCT
GTATTTTCAGGGCGCCATGGATATCAATGCTTCTAGAGCCTTAGCCAATGTGTATGATC
TACCAGATGATTTCTTTCCAAAAATAGATGATCTTGTTAGAGATGCTAAAGACGCTTTA
GAGCCTTATTGGAAATCAGATTCAATAAAGAAACATGTTTTGATTGCAACTCACTTTGT
GGATCTCATTGAAGACTTCTGGCAGACTACACAGGGCATGCATGAAATAGCCGAATCAT
TAAGAGCTGTTATACCTCCCACTACTACTCCTGTTCCACCGGGTTATCTTATTCAGCAC
GAGGAAGCTGAAGAGATACCTTTGGGAGATTTATTTAAACACCAAGAAGAAAGGATAGT
AAGTTTCCAACCCGACTATCCGATTACGGCTAGAATTCATGCTCATTTGAAAGCTTATG
CAAAAATTAACGAGGAATCACTGGATAGGGCTAGGAGATTGCTTTGGTGGCATTACAAC
TGTTTACTGTGGGGAGAAGCTCAAGTTACTAACTATATTTCTCGTTTGCGTACTTGGTT
GTCAACTCCTGAGAAATATAGAGGTAGAGATGCCCCGACCATTGAAGCAATCACTAGAC
CAATCCAGGTGGCTCAGGGAGGCAGAAAAACAACTACGGGTACTAGAAAACCTCGTGGA
CTCGAACCTAGAAGAAGAAAAGTTAAAACCACAGTTGTCTATGGGAGAAGACGTTCAAA
GTCCCGGGAAAGGAGAGCCCCTACACCCCAACGTGCGGGCTCCCCTCTCCCACGTAGTT
CGAGCAGCCACCATAGATCTCCCTCGCCTAGGAAATCGCGGCCGCTTTCGAATCTAGAG
CCTGCAGTCTCGAGGCATGCGGTACCAAGCTTGTCGAGAAGTACTAGAGGATCA
```

Fig 24B. Amino Acid Sequence of DHBV Core Protein (313 AA, 36.1 KDa, 939 bp.)

```
MSYYHHHHHHDYDIPTTENLYFQGAMDINASRALANVYDLPDDFFPKIDDLVRDAKDAL
EPYWKSDSIKKHVLIATHFVDLIEDFWQTTQGMHEIAESLRAVIPPTTTPVPPGYLIQH
EEAEEIPLGDLFKHQEERIVSFQPDYPITARIHAHLKAYAKINEESLDRARRLLWWHYN
CLLWGEAQVTNYISRLRTWLSTPEKYRGRDAPTIEAITRPIQVAQGGRKTTTGTRKPRG
LEPRRRKVKTTVVYGRRRSKSRERRAPTPQRAGSPLPRSSSSHHRSPSPRKSRPLSNLE
PAVSRHAVPSLSRSTRGS
```

DC maturition with HepaVaxx B

Time Course of Expression of Antigen Binding Receptors on Maturing DCS

Figure 32. Nucleotide and Amino Acid Sequences of the ORF of TBD Protein in the Plasmid pFASTBACHTA-TBD.

Figure 32 A. DNA sequence of TBD Protein expression cassette

ATGTCGTACTACCATCACCATCACCATCACGATTACGATATCCCAACGACCG
AAAACCTGTATTTTCAGGGCGCCATGGATCCGGAATTCAAAGGCCTACGTC
GACGAGCTCAACTAGTGCGGCCGCAAGGCGGCGGATCCGTGGACAAGAAA
ATTGTGCCCAGGGATTGTGGTTGTAAGCCTTGCATATGTACAGTCCCAGAA
GTATCATCTGTCTTCATCTTCCCCCCAAAGCCCAAGGATGTGCTCACCATTA
CTCTGACTCCTAAGGTCACGTGTGTTGTGGTAGACATCAGCAAGGATGATC
CCGAGGTCCAGTTCAGCTGGTTTGTAGATGATGTGGAGGTGCACACAGCTC
AGACGCAACCCCGGGAGGAGCAGTTCAACAGCACTTTCCGCTCAGTCAGT
GAACTTCCCATCATGCACCAGGACTGGCTCAATGGCAAGGAGTTCAAATGC
AGGGTCAACAGTGCAGCTTTCCCTGCCCCATCGAGAAAACCATCTCCAAA
ACCAAAGGCAGACCGAAGGCTCCACAGGTGTACACCATTCCACCTCCCAAG
GAGCAGATGGCCAAGGATAAAGTCAGTCTGACCTGCATGATAACAGACTTC
TTCCCTGAAGACATTACTGTGGAGTGGCAGTGGAATGGGCAGCCAGCGGA
GAACTACAAGAACACTCAGCCCATCATGGACACAGATGGCTCTTACTTCGTC
TACAGCAAGCTCAATGTGCAGAAGAGCAACTGGGAGGCAGGAAATACTTTC
ACCTGCTCTGTGTTACATGAGGGCCTGCACAACCACCATACTGAGAAGAGC
CTCTCCCACTCTCCTGGGCTGCAAAGCTTGTCGAGAAGTACTAGAGGATCA

Figure 32B Amino Acid Sequence of TBD Protein (289 AA, 32.9 KDa, 867 bp.)

YHHHHHHDYDIPTTENLYFQGAMDPEFKGLRRRAQLVRPQGGGSVDKKIVPR
DCGCKPCICTVPEVSSVFIFPPKPKDVLTITLTPKVTCVVVDISKDDPEVQFSWF
VDDVEVHTAQTQPREEQFNSTFRSVSELPIMHQDWLNGKEFKCRVNSAAFPA
PIEKTISKTKGRPKAPQVYTIPPPKEQMAKDKVSLTCMITDFFPEDITVEWQWNG
QPAENYKNTQPIMDTDGSYFVYSKLNVQKSNWEAGNTFTCSVLHEGLHNHHT
EKSLSHSPGLQSLSRSTRGS

Figure 33. Nucleotide and Amino Acid Sequences of the ORF of

HBV S1/S2-TBD Protein in the Plasmid pFASTBACHTaHBV S1/S2-TBD.

33A. DNA sequence of HBV S1/S2-TBD Protein Expression Cassette

```
ATGTCGTACTACCATCACCATCACCATCACGATTACGATATCCCAACGACCGAAAACCT
GTATTTTCAGGGCGCCATGGATCCTATGAAAAAATGGTCATCAAAACCTCGCAAAGGCA
TGGGGACGAATCTTTCTGTTCCCAACCCTCTGGGATTCTTTCCCGATCATCAGTTGGAC
CCTGTATTCGGAGCCAACTCAAACAATCCAGATTGGGACTTCAACCCCATCAAGGACCA
CTGGCCAGCAGCCAACCAGGTAGGAGTGGGAGCATTCGGGCCAGGGTTCACCCCTCCAC
ACGGCGGTGTTTTGGGGTGGAGCCCTCAGGCTCAGGGCATGTTGACCCCAGTGTCAACA
ATTCCTCCTCCTGCCTCCGCCAATCGGCAGTCAGGAAGGCAGCCTACTCCCATCTCTCC
ACCTCTAAGAGACAGTCATCCTCAGGCCATGCAGTGGAATTCCACTGCCTTCCACCAAG
CTCTGCAAGACCCCAGAGTCAGGGGTCTGTATTTTCCTGCTGGTGGCTCCAGTTCAGGA
ACAGTAAACCCTGCTCCGAATATTGCCTCTCACATCTCGTCAATCTCCGCGAGGACCGG
GGACCCTGTGACGAACTCGCGGCCGCAAGGCGGCGGATCCGTGGACAAGAAAATTGTGC
CCAGGGATTGTGGTTGTAAGCCTTGCATATGTACAGTCCCAGAAGTATCATCTGTCTTC
ATCTTCCCCCCAAAGCCCAAGGATGTGCTCACCATTACTCTGACTCCTAAGGTCACGTG
TGTTGTGGTAGACATCAGCAAGGATGATCCCGAGGTCCAGTTCAGCTGGTTTGTAGATG
ATGTGGAGGTGCACACAGCTCAGACGCAACCCCGGGAGGAGCAGTTCAACAGCACTTTC
CGCTCAGTCAGTGAACTTCCCATCATGCACCAGGACTGGCTCAATGGCAAGGAGTTCAA
ATGCAGGGTCAACAGTGCAGCTTTCCCTGCCCCCATCGAGAAAACCATCTCCAAAACCA
AAGGCAGACCGAAGGCTCCACAGGTGTACACCATTCCACCTCCCAAGGAGCAGATGGCC
AAGGATAAAGTCAGTCTGACCTGCATGATAACAGACTTCTTCCCTGAAGACATTACTGT
GGAGTGGCAGTGGAATGGGCAGCCAGCGGAGAACTACAAGAACACTCAGCCCATCATGG
ACACAGATGGCTCTTACTTCGTCTACAGCAAGCTCAATGTGCAGAAGAGCAACTGGGAG
GCAGGAAATACTTTCACCTGCTCTGTGTTACATGAGGGCCTGCACAACCACCATACTGA
GAAGAGCCTCTCCCACTCTCCTGGGCTGCAAAGCTTGTCGAGAAGTACTAGAGGATCA
```

Fig. 33B. Amino Acid Sequence of HBV S1/S2-TBD Protein (452 AA, 49.9 KDa, 1356 bp.)

```
MSYYHHHHHHDYDIPTTENLYFQGAMDPMKKWSSKPRKGMGTNLSVPNPLGFFPDHQLD
PVFGANSNNPDWDFNPIKDHWPAANQVGVGAFGPGFTPPHGGVLGWSPQAQGMLTPVST
IPPPASANRQSGRQPTPISPPLRDSHPQAMQWNSTAFHQALQDPRVRGLYFPAGGSSSG
TVNPAPNIASHISSISARTGDPVTNSRPQGGGSVDKKIVPRDCGCKPCICTVPEVSSVF
IFPPKPKDVLTITLTPKVTCVVVDISKDDPEVQFSWFVDDVEVHTAQTQPREEQFNSTF
RSVSELPIMHQDWLNGKEFKCRVNSAAFPAPIEKTISKTKGRPKAPQVYTIPPPKEQMA
KDKVSLTCMITDFFPEDITVEWQWNGQPAENYKNTQPIMDTDGSYFVYSKLNVQKSNWE
AGNTFTCSVLHEGLHNHHTEKSLSHSPGLQSLSRSTRGS
```

Figure 34: Comparison of the Binding of S1/S2-TBD, IgG1 and IgG2 as a Function of Time Figure 35 :Comparison of S1/S2-TBD, IgG2a and IgG1 Binding to Maturing DCs on Day 1

S1/S2-TBD murine IgG2a murine IgG1

F(ab')$_2$ anti-murine IgG

Relative fluorescence

Figure 36: Comparison of S1/S2-TBD IgG2a and IgG1 Binding to Maturing DCs on Day 4
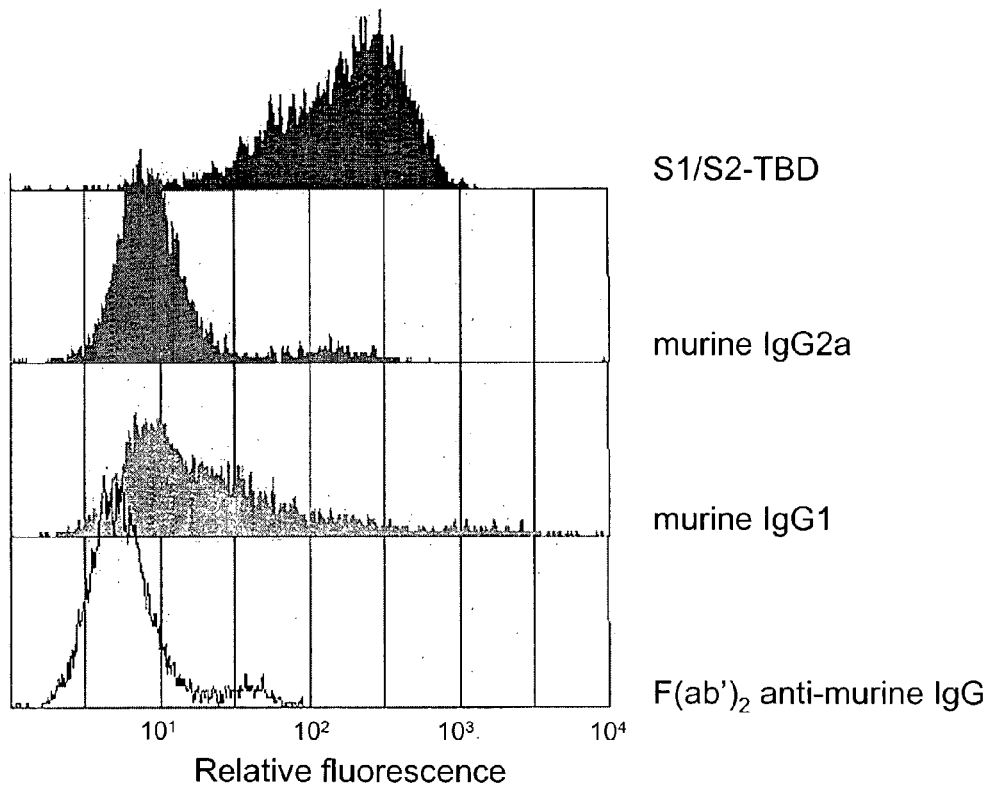
Figure 37: Comparison of the Uptake of S1/S2-TBD, IgG1 and IgG2 as a Function of Concentration
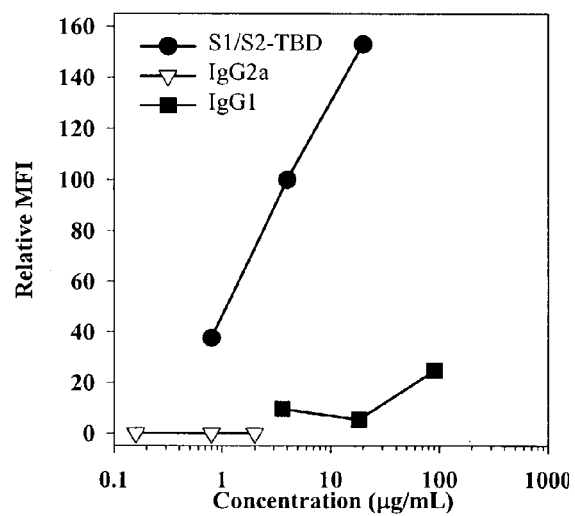

Figure 38: Correlation of S1/S2-TBD Binding to CD32 and CD206 Expression on DC

Figure 39. The binding of S1/S2-TBD Binding to CD32 and CD206 on DCs is abolished by anti-Fc Mab.

Figure 40. Glycosylation of S1/S2 antigen increases the uptake via CD206 receptor Figure 41: Intracellular IFNγ Positive T Cells after Antigen Presentation by DCs Loaded with S1/S2-TBD or its Components
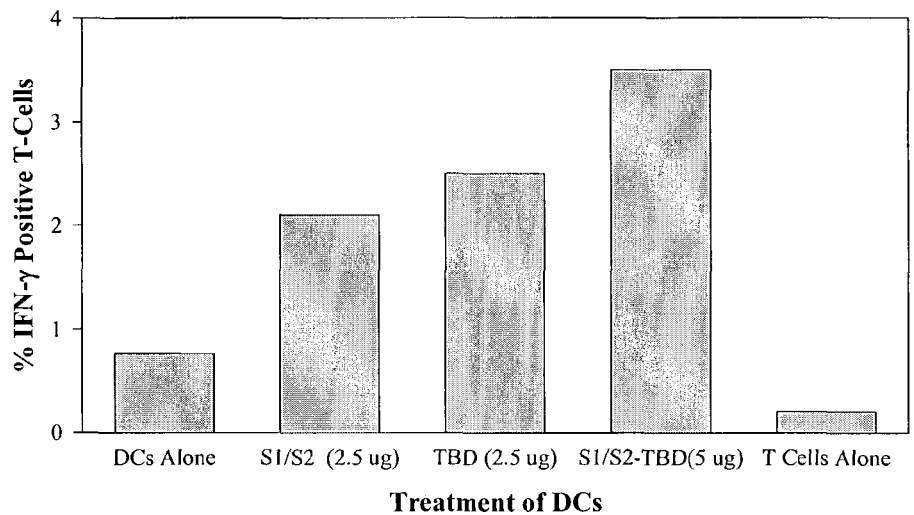
Figure 42: Secretion of IFNγ By T Cells After Antigen Presentation by DCs Loaded with S1/S2-TBD or Its Components
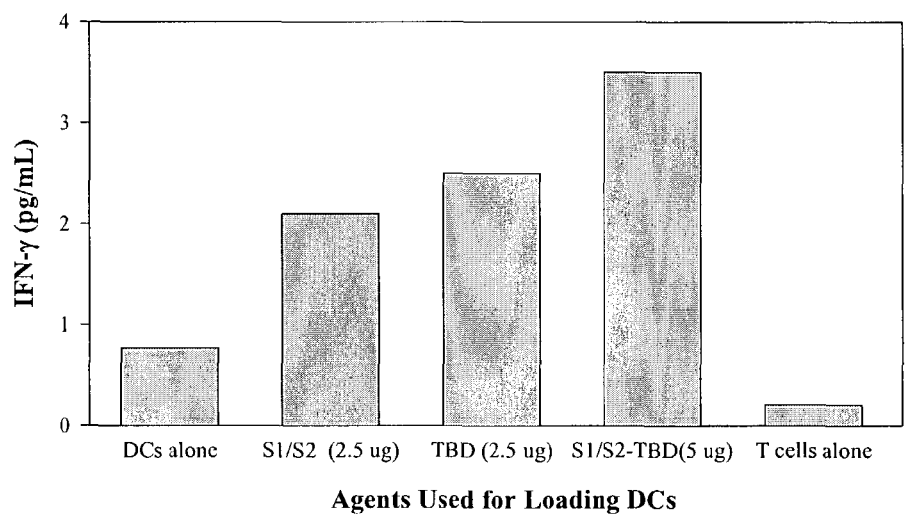

Figure 43: Intracellular IFNγ Positive T Cells as a Function of S1/S2-TBD Concentration
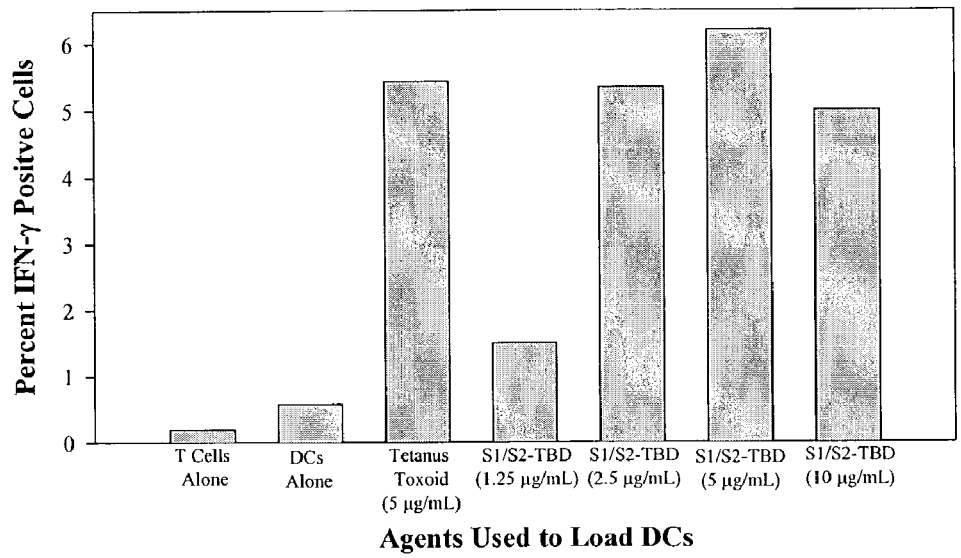
Figure 44: IFNγ Secretion by T Cells as Figure 45: Effect of Glycosylation on Intracellular IFNγ Production in T Cells
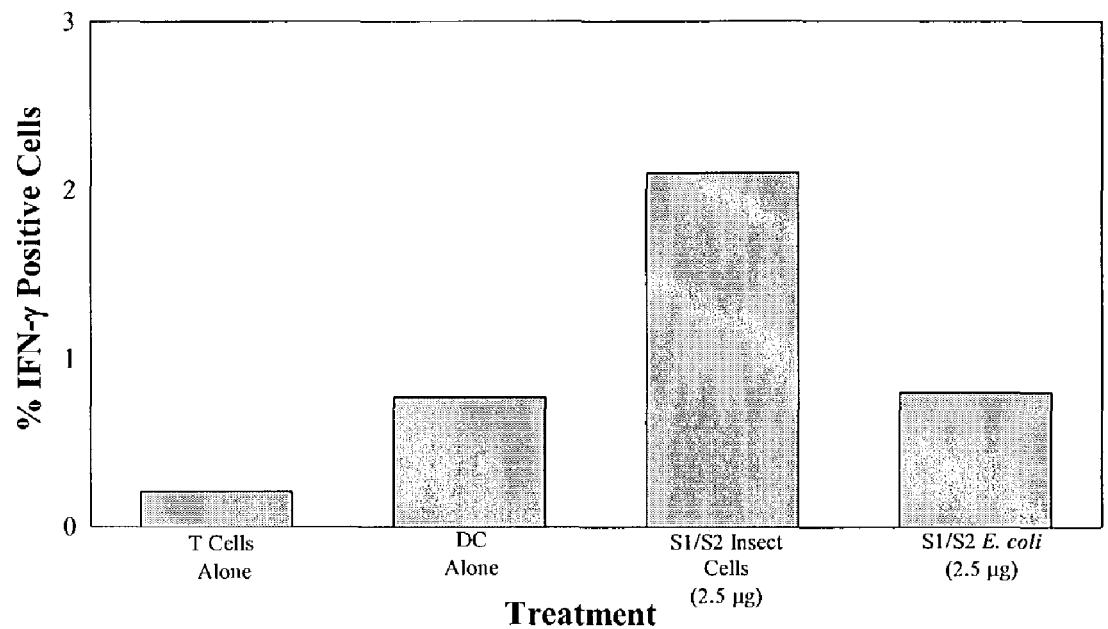
Figure 46: Effect of Glycosylation on IFNγ Secretion by T Cells
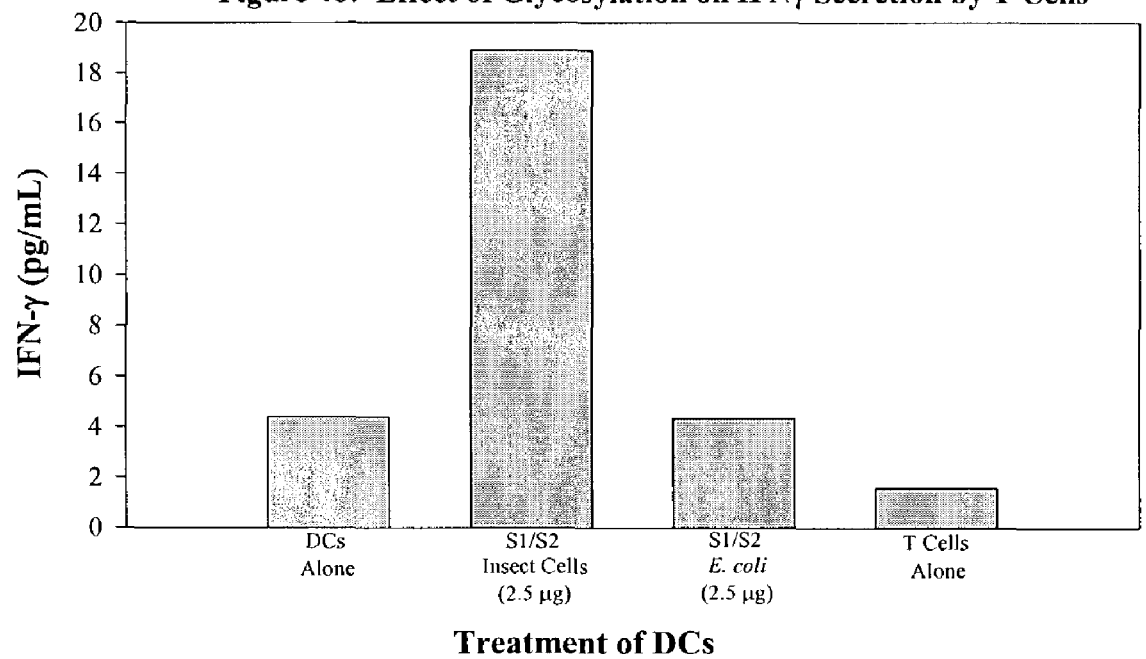

Figure 47. Nucleotide and Amino Acid Sequences of the ORF of HCV Core (1-191) Protein in the Plasmid pFASTBACHTa-HCV Core(1-191).

Fig 47A. DNA sequence of HCV Core(1-191) Protein expression cassette

ATG TCG TAC TAC CAT CAC CAT CAC CAT CAC GAT TAC GAT ATC CCA
ACG ACC GAA AAC CTG TAT TTT CAG GGC GCC ATG GAT CCG GAA TTC
ATG AGC ACG AAT CCT AAA CCT CAA AGA AAA ACC AAA CGT AAC ACC
AAC CGT CGC CCA CAG GAC GTC AAG TTC CCG GGT GGC GGT CAG ATC
GTT GGT GGA GTT TAC TTG TTG CCG CGC AGG GGC CCT AGA TTG GGT
GTG CGC GCG ACG AGG AAG ACT TCC GAG CGG TCG CAA CCT CGA
GGT AGA CGT CAG CCT ATC CCC AAG GCA CGT CGG CCC GAG GGC
AGG ACC TGG GCT CAG CCC GGG TAC CCT TGG CCC CTC TAT GGC AAT
GAG GGT TGC GGG TGG GCG GGA TGG CTC CTG TCT CCC CGT GGC
TCT CGG CCT AGC TGG GGC CCC ACA GAC CCC CGG CGT AGG TCG
CGC AAT TTG GGT AAG GTC ATC GAT ACC CTT ACG TGC GGC TTC GCC
GAC CTC ATG GGG TAC ATA CCG CTC GTC GGC GCC CCT CTT GGA GGC
GCT GCC AGG GCC CTG GCG CAT GGC GTC CGG GTT CTG GAA GAC
GGC GTG AAC TAT GCA ACA GGG AAC CTT CCT GGT TGC TCT TTC TCT
ATC TTC CTT CTG GCC CTG CTC TCT TGC CTG ACT GTG CCC GCT TCA
GCC GGA CTA GTG CGG CCG CTT TCG AAT CTA GAG CCT GCA GTC TCG
AGG CAT GCG GTA CCA AGC TTG TCG AGA AGT ACT AGA GGA TCA TAA

Fig 47B. Amino Acid Sequence of HCV Core(1-191) Protein

M S Y Y H H H H H H D Y D I P T T E N L Y F Q G A
M D P E F M S T N P K P Q R K T K R N T N R R P Q
D V K F P G G G Q I V G G V Y L L P R R G P R L G V
R A T R K T S E R S Q P R G R R Q P I P K A R R P E
G R T W A Q P G Y P W P L Y G N E G C G W A G W L
L S P R G S R P S W G P T D P R R R S R N L G K V I
D T L T C G F A D L M G Y I P L V G A P L G G A A
R A L A H G V R V L E D G V N Y A T G N L P G C S
F S I F L L A L L S C L T V P A S A G L V R P L S N
L E P A V S R H A V P S L S R S T R G S

Figure 48. Nucleotide and Amino Acid Sequences of the ORF of HCV Core (1-191)-TBD Protein in the Plasmid pFASTBACHTa-HCV Core(1-191)-TBD.

Fig 48A. DNA sequence of HCV Core-TBD Protein expression cassette

ATG TCG TAC TAC CAT CAC CAT CAC CAT CAC GAT TAC GAT ATC CCA
ACG ACC GAA AAC CTG TAT TTT CAG GGC GCC ATG GAT CCG GAA TTC
ATG AGC ACG AAT CCT AAA CCT CAA AGA AAA ACC AAA CGT AAC ACC
AAC CGT CGC CCA CAG GAC GTC AAG TTC CCG GGT GGC GGT CAG ATC
GTT GGT GGA GTT TAC TTG TTG CCG CGC AGG GGC CCT AGA TTG GGT
GTG CGC GCG ACG AGG AAG ACT TCC GAG CGG TCG CAA CCT CGA
GGT AGA CGT CAG CCT ATC CCC AAG GCA CGT CGG CCC GAG GGC
AGG ACC TGG GCT CAG CCC GGG TAC CCT TGG CCC CTC TAT GGC AAT
GAG GGT
TGC GGG TGG GCG GGA TGG CTC CTG TCT CCC CGT GGC TCT CGG
CCT AGC TGG GGC CCC ACA GAC CCC CGG CGT AGG TCG CGC AAT
TTG GGT AAG GTC ATC GAT ACC CTT ACG TGC GGC TTC GCC GAC CTC
ATG GGG TAC ATA CCG CTC GTC GGC GCC CCT CTT GGA GGC GCT GCC
AGG GCC
CTG GCG CAT GGC GTC CGG GTT CTG GAA GAC GGC GTG AAC TAT GCA
ACA GGG AAC CTT CCT GGT TGC TCT TTC TCT ATC TTC CTT CTG GCC
CTG CTC TCT TGC CTG ACT GTG CCC GCT TCA GCC GGA CTA GTG CGG
CCG CAA GGC GGC GGA TCC GTG GAC AAG AAA ATT GTG CCC AGG GAT
TGT GGT TGT AAG CCT TGC ATA TGT ACA GTC CCA GAA GTA TCA TCT
GTC TTC ATC TTC CCC CCA AAG CCC AAG GAT GTG CTC ACC ATT ACT
CTG ACT CCT AAG GTC ACG TGT GTT GTG GTA GAC ATC AGC AAG GAT
GAT CCC GAG GTC CAG TTC AGC TGG TTT GTA GAT GAT GTG GAG GTG
CAC ACA GCT CAG ACG CAA CCC CGG GAG GAG CAG TTC AAC AGC ACT
TTC CGC TCA GTC AGT GAA CTT CCC ATC ATG CAC CAG GAC TGG CTC
AAT GGC AAG GAG TTC AAA TGC AGG GTC AAC AGT GCA GCT TTC CCT
GCC CCC ATC GAG AAA ACC ATC TCC AAA ACC AAA GGC AGA CCG AAG
GCT CCA CAG GTG TAC ACC ATT CCA CCT CCC AAG GAG CAG ATG GCC
AAG GAT AAA GTC AGT CTG ACC TGC ATG ATA ACA GAC TTC TTC CCT
GAA GAC ATT ACT GTG GAG TGG CAG TGG AAT GGG CAG CCA GCG
GAG AAC TAC AAG AAC ACT CAG CCC ATC ATG GAC ACA GAT GGC TCT
TAC TTC GTC TAC AGC AAG CTC AAT GTG CAG AAG AGC AAC TGG GAG
GCA GGA AAT ACT TTC ACC TGC TCT GTG TTA CAT GAG GGC CTG CAC
AAC CAC CAT ACT GAG AAG AGC CTC TCC CAC TCT CCT GGG CTG CAA
AGC TTG TCG AGA AGT ACT AGA GGA TCA TAA

Fig 48B. Amino Acid Sequence of HCV Core(1-191)-TBD Protein

```
M S Y Y H H H H H H D Y D I P T T E N L Y F Q G
A M D P E F M S T N P K P Q R K T K R N T N R R
P Q D V K F P G G G Q I V G G V Y L L P R R G P
R L G V R A T R K T S E R S Q P R G R R Q P I P
K A R R P E G R T W A Q P G Y P W P L Y G N E
G C G W A G W L L S P R G S R P S W G P T D P
R R R S R N L G K V I D T L T C G F A D L M G Y
I P L V G A P L G G A A R A L A H G V R V L E D
G V N Y A T G N L P G C S F S I F L L A L L S C
L T V P A S A G L V R P Q G G G S V D K K I V P
R D C G C K P C I C T V P E V S S V F I F P P K
P K D V L T I T L T P K V T C V V V D I S K D D P
E V Q F S W F V D D V E V H T A Q T Q P R E E Q
F N S T F R S V S E L P I M H Q D W L N G K E F
K C R V N S A A F P A P I E K T I S K T K G R P
K A P Q V Y T I P P P K E Q M A K D K V S L T C
M I T D F F P E D I T V E W Q W N G Q P A E N Y
K N T Q P I M D T D G S Y F V Y S K L N V Q K S
N W E A G N T F T C S V L H E G L H N H H T E K
S L S H S P G L Q S L S R S T R G S
```

Figure 49. Nucleotide and Amino Acid Sequences of the ORF of HCV Core (1-177) Protein in the Plasmid pFASTBACHTa-HCV Core(1-177).

Fig 49A. DNA sequence of HCV Core(1-177) Protein expression cassette

ATG TCG TAC TAC CAT CAC CAT CAC CAT CAC GAT TAC GAT ATC CCA
ACG ACC GAA AAC CTG TAT TTT CAG GGC GCC ATG GAT CCG gaa ttc ATG
AGC ACG AAT CCT AAA CCT CAA AGA AAA ACC AAA CGT AAC ACC AAC
CGT CGC CCA CAG GAC GTC AAG TTC CCG GGT GGC GGT CAG ATC GTT
GGT GGA GTT TAC TTG TTG CCG CGC AGG GGC CCT AGA TTG GGT GTG
CGC GCG ACG AGG AAG ACT TCC GAG CGG TCG CAA CCT CGA GGT AGA
CGT CAG CCT ATC CCC AAG GCA CGT CGG CCC GAG GGC AGG ACC TGG
GCT CAG CCC GGG TAC CCT TGG CCC CTC TAT GGC AAT GAG GGT TGC
GGG TGG GCG GGA TGG CTC CTG TCT CCC CGT GGC TCT CGG CCT AGC
TGG GGC CCC ACA GACGCC GAC CTC ATG GGG TAC ATA CCG CTC GTC
GGC GCC CCT CTT GGA GGC GCT GCC AGG GCC CTG GCG CAT GGC GTC
CGG GTT CTG GAA GAC GGC GTG AAC TAT GCA ACA GGG AAC CTT CCT
GGT TGC TCT TTC TCT ATC TTC gga cta gtG CGG CCG CTT TCG AAT CTA GAG
CCT GCA GTC TCG AGG CAT GCG GTA CCA AGC TTG TCG AGA AGT ACT
AGA GGA TCA TAA Fig 49B. Amino Acid Sequence of HCV Core(1-177) Protein M S Y Y H H H H H H D Y D I P T T E N L Y F Q G
A M D P E F M S T N P K P Q R K T K R N T N R R
P Q D V K F P G G G Q I V G G V Y L L P R R G P
R L G V R A T R K T S E R S Q P R G R R Q P I P
K A R R P E G R T W A Q P G Y P W P L Y G N E
G C G W A G W L L S P R G S R P S W G P T D P
R R R S R N L G K V I D T L T C G F A D L M G Y
I P L V G A P L G G A A R A L A H G V R V L E D
G V N Y A T G N L P G C S F S I F G L V R P L S
N L E P A V S R H A V P S L S R S T R G S Figure 50. Nucleotide and Amino Acid Sequences of the ORF of HCV Core (1-177)-TBD Protein in the Plasmid pFASTBACHTa-HCV Core(1-177)-TBD.

Fig 50A. DNA sequence of HCV Core(1-177)-TBD Protein expression cassette

ATG TCG TAC TAC CAT CAC CAT CAC CAT CAC GAT TAC GAT ATC CCA
ACG ACC GAA AAC CTG TAT TTT CAG GGC GCC ATG GAT CCG gaa ttc
ATG AGC ACG AAT CCT AAA CCT CAA AGA AAA ACC AAA CGT AAC ACC
AAC CGT CGC CCA CAG GAC GTC AAG TTC CCG GGT GGC GGT CAG ATC
GTT GGT GGA GTT TAC TTG TTG CCG CGC AGG GGC CCT AGA TTG GGT
GTG CGC GCG ACG AGG AAG ACT TCC GAG CGG TCG CAA CCT CGA
GGT AGA CGT CAG CCT ATC CCC AAG GCA CGT CGG CCC GAG GGC
AGG ACC TGG GCT CAG CCC GGG TAC CCT TGG CCC CTC TAT GGC AAT
GAG GGT TGC GGG TGG GCG GGA TGG CTC CTG TCT CCC CGT GGC
TCT CGG CCT AGC TGG GGC CCC ACA GAC CCC CGG CGT AGG TCG
CGC AAT TTG GGT AAG GTC ATC GAT ACC CTT ACG TGC GGC TTC GCC
GAC CTC ATG GGG TAC ATA CCG CTC GTC GGC GCC CCT CTT GGA GGC
GCT GCC AGG GCC CTG GCG CAT GGC GTC CGG GTT CTG GAA GAC
GGC GTG AAC TAT GCA ACA GGG AAC CTT CCT GGT TGC TCT TTC TCT
ATC TTC gga cta gtG CGG CCG CAA GGC GGC GGA TCC GTG GAC AAG
AAA ATT GTG CCC AGG GAT TGT GGT TGT AAG CCT TGC ATA TGT ACA
GTC CCA GAA GTA TCA TCT GTC TTC ATC TTC CCC CCA AAG CCC AAG
GAT GTG CTC ACC ATT ACT CTG ACT CCT AAG GTC ACG TGT GTT GTG
GTA GAC ATC AGC AAG GAT GAT CCC GAG GTC CAG TTC AGC TGG TTT
GTA GAT GAT GTG GAG GTG CAC ACA GCT CAG ACG CAA CCC CGG GAG
GAG CAG TTC AAC AGC ACT TTC CGC TCA GTC AGT GAA CTT CCC ATC
ATG CAC CAG GAC TGG CTC AAT GGC AAG GAG TTC AAA TGC AGG GTC
AAC AGT GCA GCT TTC CCT GCC CCC ATC GAG AAA ACC ATC TCC AAA
ACC AAA GGC AGA CCG AAG GCT CCA CAG GTG TAC ACC ATT CCA CCT
CCC AAG GAG CAG ATG GCC AAG GAT AAA GTC AGT CTG ACC TGC ATG
ATA ACA GAC TTC TTC CCT GAA GAC ATT ACT GTG GAG TGG CAG TGG
AAT GGG CAG CCA GCG GAG AAC TAC AAG AAC ACT CAG CCC ATC ATG
GAC ACA GAT GGC TCT TAC TTC GTC TAC AGC AAG CTC AAT GTG CAG
AAG AGC AAC TGG GAG GCA GGA AAT ACT TTC ACC TGC TCT GTG TTA
CAT GAG GGC CTG CAC AAC CAC CAT ACT GAG AAG AGC CTC TCC CAC
TCT CCT GGG CTG CAA AGC TTG TCG AGA AGT ACT AGA GGA TCA TAA

Fig 50B. Amino Acid Sequence of HCV Core(1-177)-TBD Protein

```
M S Y Y H H H H H H D Y D I P T T E N L Y F Q G
A M D P E F M S T N P K P Q R K T K R N T N R R
P Q D V K F P G G G Q I V G G V Y L L P R R G P
R L G V R A T R K T S E R S Q P R G R R Q P I P
K A R R P E G R T W A Q P G Y P W P L Y G N E
G C G W A G W L L S P R G S R P S W G P T D P
R R R S R N L G K V I D T L T C G F A D L M G Y
I P L V G A P L G G A A R A L A H G V R V L E D
G V N Y A T G N L P G C S F S I F G L V R P Q G
G G S V D K K I V P R D C G C K P C I C T V P E
V S S V F I F P P K P K D V L T I T L T P K V T C
V V V D I S K D D P E V Q F S W F V D D V E V H
T A Q T Q P R E E Q F N S T F R S V S E L P I M
H Q D W L N G K E F K C R V N S A A F P A P I E
K T I S K T K G R P K A P Q V Y T I P P P K E Q
M A K D K V S L T C M I T D F F P E D I T V E W
Q W N G Q P A E N Y K N T Q P I M D T D G S Y F
V Y S K L N V Q K S N W E A G N T F T C S V L H
E G L H N H H T E K S L S H S P G L Q S L S R S
T R G S
```

Figure 51. Nucleotide and Amino Acid Sequences of the ORF of HCV NS5A Protein in the Plasmid pFASTBACHTa-HCV NS5A

Fig 51A. DNA sequence of HCV NS5A Protein expression cassette

ATG TCG TAC TAC CAT CAC CAT CAC CAT CAC GAT TAC GAT ATC CCA
ACG ACC GAA AAC CTG TAT TTT CAG GGC GCC ATG GAT CCG GAA TTC
TCC GGT TCC TGG CTA AGG GAC ATC TGG GAC TGG ATA TGC GAG GTG
CTG AGC GAC TTT AAG ACC TGG CTG AAA GCC AAG CTC ATG CCA CAA
CTG CCT GGG ATT CCC TTT GTG TCC TGC CAG CGC GGG TAT AGG GGG
GTC TGG CGA GGA GAC GGC ATT ATG CAC ACT CGC TGC CAC TGT GGA
GCT GAG ATC ACT GGA CAT GTC AAA AAC GGG ACG ATG AGG ATC GTC
GGT CCT AGG ACC TGC AGG AAC ATG TGG AGT GGG ACG TTC CCC ATT
AAC GCC TAC ACC ACG GGC CCT GT ACT CCC CTT CCT GCG CCG AAC
TAT AAG TTC GCG CTG TGG AGG GTG TCT GCA GAG GAA TAC GTG GAG
ATA AGG CGG GTG GGG GAC TTC CAC TAC GTA TCG GGT ATG ACT ACT
GAC AAT CTT AAA TGC CCG TGC CAG ATC CCA TCG CCC GAA TTT TTC
ACA GAA TTG GAC GGG GTG CGC CTA CAC AGG TTT GCG CCC CCT TGC
AAG CCC TTG CTG CGG GAG GAG GTA TCA TTC AGA GTA GGA CTC CAC
GAG TAC CCG GTG GGG TCG CAA TTA CCT TGC GAG CCC GAA CCG GAC
GTA GCC GTG TTG ACG TCC ATG CTC ACT GAT CCC TCC CAT ATA ACA
GCA GAG GCG GCC GGG AGA AGG TTG GCG AGA GGG TCA CCC CCT
TCT ATG GCC AGC TCC TCG GCT AGC AGC TG TCC GCT CCA TCT CTC
AAG GCA ACT TGC ACC GCC AAC CAT GAC TCC CCT GAC GCC GAG CTC
ATA GAG GCT AAC CTC CTG TGG AGG CAG GAG ATG GGC GGC AAC ATC
ACC
AGG GTT GAG TCA GAG AAC AAA GTG GTG ATT CTG GAC TCC TTC GAT
CCG CTT GTG GCA GAG GAG GAT GAG CGG GAG GTC TCC GTA CCT
GCA GAA ATT CTG CGG AAG TCT CGG AGA TTC GCC CGG GCC CTG CCC
GTC TGG GCG CGG CCG GAC TAC AAC CCC CCG CTA GTA GAG ACG
TGG AAA
AAG CCT GAC TAC GAA CCA CCT GTG GTC CAT GGC TGC CCG CTA CCA
CCT CCA CGG TCC CCT CCT GTG CCT CCG CCT CGG AAA AAG CGT ACG
GTG GTC CTC ACC GAA TCA ACC TA TCT ACT GCC TTG GCC GAG CTT
GCC ACC AAA AGT TTT GGC AGC TCC TCA ACT TCC GGC ATT ACG GGC
GAC AAT ACG ACA ACA TCC TCT GAG CCC GCC CCT TCT GGC TGC CCC
CCC GAC TCC GAC GTT GAG TCC TAT TCT TCC ATG CCC CCC CTG GAG
GGG GAG CCT GGG GAT CCG GAT CTC AGC GAC GGG TCA TGG TCG
ACG TCA GT AGT GGG GCC GAC ACG GAA GAT GTC GTG TGC GGA CTA
GTG
CGG CCG CTT TCG AAT CTA GAG CCT GCA GTC TCG AGG CAT GCG GTA
CCA AGC TTG TCG AGA AGT ACT AGA GGA TCA TAA

Fig 51B. Amino Acid Sequence of HCV NS5A Protein

M S Y Y H H H H H H D Y D I P T T E N L Y F Q G A
M D P E F S G S W L R D I W D W I C E V L S D F K T
W L K A K L M P Q L P G I P F V S C Q R G Y R G V
W R G D G I M H T R C H C G A E I T G H V K N G T
M R I V G P R T C R N M W S G T F P I N A Y T T G P
C T P L P A P N Y K F A L W R V S A E E Y V E I R R
V G D F H Y V S G M T T D N L K C P C Q I P S P E F
F T E L D G V R L H R F A P P C K P L L R E E V S F
R V G L H E Y P V G S Q L P C E P E P D V A V L T S
M L T D P S H I T A E A A G R R L A R G S P P S M A
S S S A S Q L S A P S L K A T C T A N H D S P D A E
L I E A N L L W R Q E M G G N I T R V E S E N K V V
I L D S F D P L V A E E D E R E V S V P A E I L R K
S R R F A R A L P V W A R P D Y N P P L V E T W K
K P D Y E P P V V H G C P L P P P R S P P V P P P R
K K R T V V L T E S T L S T A L A E L A T K S F G S
S S T S G I T G D N T T T S S E P A P S G C P P D S
D V E S Y S S M P P L E G E P G D P D L S D G S W S
T V S S G A D T E D V V C G L V R P L S N L E P A V
S R H A V P S L S R S T R G S

Figure 52. Nucleotide and Amino Acid Sequences of the ORF of HCV NS5A-TBD Protein in the Plasmid pFASTBACHTa-HCV NS5A-TBD

Fig 52A. DNA sequence of HCV NS5A-TBD Protein expression cassette

ATG TCG TAC TAC CAT CAC CAT CAC CAT CAC GAT TAC GAT ATC CCA
ACG ACC GAA AAC CTG TAT TTT CAG GGC GCC ATG GAT CCG GAA TTC
TCC GGT TCC TGG CTA AGG GAC ATC TGG GAC TGG ATA TGC GAG GTG
CTG AGC GAC TTT AAG ACC TGG CTG AAA GCC AAG CTC ATG CCA CAA
CTG CCT GGG ATT CCC TTT GTG TCC TGC CAG CGC GGG TAT AGG GGG
GTC TGG CGA GGA GAC GGC ATT ATG CAC ACT CGC TGC CAC TGT GGA
GCT GAG ATC ACT GGA CAT GTC AAA AAC GGG ACG ATG AGG ATC GTC
GGT CCT AGG ACC TGC AGG AAC ATG TGG AGT GGG ACG TTC CCC ATT
AAC GCC TAC ACC ACG GGC CCC TGT ACT CCC CTT CCT GCG CCG AAC
TAT AAG TTC GCG CTG TGG AGG GTG TCT GCA GAG GAA TAC GTG GAG
ATA AGG CGG GTG GGG GAC TTC CAC TAC GTA TCG GGT ATG ACT ACT
GAC AAT CTT AAA TGC CCG TGC CAG ATC CCA TCG CCC GAA TTT TTC
ACA GAA TTG GAC GGG GTG CGC CTA CAC AGG TTT GCG CCC CCT TGC
AAG CCC TTG CTG CGG GAG GAG GTA TCA TTC AGA GTA GGA CTC CAC
GAG TAC CCG GTG GGG TCG CAA TTA CCT TGC GAG CCC GAA CCG GAC
GTA GCC GTG TTG ACG TCC ATG CTC ACT GAT CCC TCC CAT ATA ACA
GCA GAG GCG GCC GGG AGA AGG TTG GCG AGA GGG TCA CCC CCT
TCT ATG GCC AGC TCC TCG CTA GCC AGC TGT CCG CTC CA TCT CTC
AAG GCA ACT TGC ACC GCC AAC CAT GAC TCC CCT GAC GCC GAG CTC
ATA GAG CTA ACC TGT GG AGG CAG GAG ATG GGC GGC AAC ATC
ACC
AGG GTT GAG TCA GAG AAC AAA GTG GTG ATT CTG GAC TCC TTC GAT
CCG CTT GTG GCA GAG GAG GAT GAG CGG GAG GTC TCC GTA CCT
GCA GAA ATT CTG CGG AAG TCT CGG AGA TTC GCC CGG GCC CTG CCC
GTC TGG GCG CGG CCG GAC TAC AAC CCC CCG CTA GTA GAG ACG
TGG AAA
AAG CCT GAC TAC GAA CCA CCT GTG GTC CAT GGC TGC CCG CTA CCA
CCT CCA CGG TCC CCT CCT GTG CCT CCG CCT CGG AAA AAG CGT ACG
GTG GTC CTC ACC GAA TCA ACC CTA TCT ACT GCC TTG GCC GAG CTT
GCC ACC AAA AGT TTT GGC AGC TCC TCA ACT TCC GGC ATT ACG GGC
GAC AAT ACG ACA ACA TCC TCT GAG CCC GCC CCT TCT GGC TGC CCC
CCC GAC TCC GAC GTT GAG TCC TAT TCT TCC ATG CCC CCC CTG GAG
GGG GAG CCT GGG GAT CCG GAT CTC AGC GAC GGG TCA TGG TCG
ACG TCA GTA GT GGG GCC GAC ACG GAA GAT GTC GTG TGC GGA CTA
GTG
CGG CCG CAA GGC GGC GGA TCC GTG GAC AAG AAA ATT GTG CCC
AGG GAT TGT GGT TGT AAG CCT TGC ATA TGT ACA GTC CCA GAA GTA
TCA TCT GTC TTC ATC TTC CCC CCA AAG CCC AAG GAT GTG CTC ACC
ATT ACT CTG ACT CCT AAG GTC ACG TGT GTT GTG GTA GAC ATC AGC
AAG GAT GAT CCC GAG GTC CAG TTC AGC TGG TTT GTA GAT GAT GTG
GAG GTG CAC ACA GCT CAG ACG CAA CCC CGG GAG GAG CAG TTC

AAC AGC ACT TTC CGC TCA GTC AGT GAA CTT CCC ATC ATG CAC CAG
GAC TGG CTC AAT GGC AAG GAG TTC AAA TGC AGG GTC AAC AGT GCA
GCT TTC CCT GCC CCC ATC GAG AAA ACC ATC TCC AAA ACC AAA GGC
AGA CCG AAG GCT CCA CAG GTG TAC ACC ATT CCA CCT CCC AAG GAG
CAG ATG GCC AAG GAT AAA GTC AGT CTG ACC TGC ATG ATA ACA GAC
TTC TTC CCT GAA GAC ATT ACT GTG GAG TGG CAG TGG AAT GGG CAG
CCA GCG GAG AAC TAC AAG AAC ACT CAG CCC ATC ATG GAC ACA GAT
GGC TCT TAC TTC GTC TAC AGC AAG CTC AAT GTG CAG AAG AGC AAC
TGG GAG GCA GGA AAT ACT TTC ACC TGC TCT GTG TTA CAT GAG GGC
CTG CAC AAC CAC CAT ACT GAG AAG AGC CTC TCC CAC TCT CCT GGG
CTG CAA AGC TTG TCG AGA AGT ACT AGA GGA TCA TAA

Fig. 52B. Amino Acid Sequence of HCV NS5A-TBD Protein

```
M S Y Y H H H H H H D Y D I P T T E N L Y F Q G
A M D P E F S G S W L R D I W D W I C E V L S D
F K T W L K A K L M P Q L P G I P F V S C Q R G
Y R G V W R G D G I M H T R C H C G A E I T G H
V K N G T M R I V G P R T C R N M W S G T F P I
N A Y T T G P C T P L P A P N Y K F A L W R V S
A E E Y V E I R R V G D F H Y V S G M T T D N L
K C P C Q I P S P E F F T E L D G V R L H R F A
P P C K P L L R E E V S F R V G L H E Y P V G S
Q L P C E P E P D V A V L T S M L T D P S H I T
A E A A G R R L A R G S P P S M A S S S A S Q L
S A P S L K A T C T A N H D S P D A E L I E A N
L L W R Q E M G G N I T R V E S E N K V V I L D
S F D P L V A E E D E R E V S V P A E I L R K S
R R F A R A L P V W A R P D Y N P P L V E T W K
K P D Y E P P V V H G C P L P P P R S P P V P P
P R K K R T V V L T E S T L S T A L A E L A T K
S F G S S S T S G I T G D N T T T S S E P A P S
G C P P D S D V E S Y S S M P P L E G E P G D P
D L S D G S W S T V S S G A D T E D V V C G L V
R P Q G G G S V D K K I V P R D C G C K P C I C
T V P E V S S V F I F P P K P K D V L T I T L T P
K V T C V V V D I S K D D P E V Q F S W F V D D
V E V H T A Q T Q P R E E Q F N S T F R S V S E
L P I M H Q D W L N G K E F K C R V N S A A F P
A P I E K T I S K T K G R P K A P Q V Y T I P P P
K E Q M A K D K V S L T C M I T D F F P E D I T
V E W Q W N G Q P A E N Y K N T Q P I M D T D
G S Y F V Y S K L N V Q K S N W E A G N T F T C
S V L H E G L H N H H T E K S L S H S P G L Q S
L S R S T R G S
```

Figure 53. Nucleotide and Amino Acid Sequences of the ORF of HCV E1 Protein in the Plasmid pFASTBACHTa-HCV E1

Fig. 53A. DNA sequence of HCV E1 Protein expression cassette

ATG TCG TAC TAC CAT CAC CAT CAC CAT CAC GAT TAC GAT ATC CCA
ACG ACC GAA AAC CTG TAT TTT CAG GGC GCC ATG GAT CCG GAA TTC
TAC CAA GTG CGC AAT TCC TCG GGG CTT TAC CAT GTC ACC AAT GAT
TGC CCT AAC TCG AGT ATT GTG TAC GAG GCG GCC GAT GCC ATC CTG
CAC ACT CCG GGG TGT GTC CCT TGC GTT CGC GAG GGT AAC GCC TCG
AGG TGT TGG GTG GCG GTG ACC CCC ACG GTG GCC ACC AGG GAC
GGC AAA CTC CCC ACA ACG CAG CTT CGA CGT CAT ATC GAT CTG CTT
GTC GGG AGC GCC ACC CTC TGC TCG GCC CTC TAC GTG GGG GAC
CTG TGC
GGG TCT GTC TTT CTT GTT GGT CAA CTG TTT ACC TTC TCT CCC AGG
CGC CAC TGG ACG ACG CAA GAC TGC AAT TGT TCT ATC TAT CCC GGC
CAT ATA ACG GGT CAT CGC ATG GCA TGG GAT ATG ATG ATG AAC TGG
TCC CCT ACG GCA GCG TTG GTG GTA GCT CAG CTG CTC CGG ATC CCA
CAA GCC ATC ATG GAC ATG ATC GCT GGT GCT CAC TGG GGA GTC CTG
GCG GGC ATA GCG TAT TTC TCC ATG GTG GGG AAC TGG GCG AAG GTC
CTG GTA GTG CTG CTG CTA TTT GCC GGC GTC GAC GCG GAA GGA CTA
GTG CGG CCG CTT TCG AAT CTA GAG CCT GCA GTC TCG AGG CAT GCG
GTA CCA AGC TTG TCG AGA AGT ACT AGA GGA TCA TAA

Fig 53B. Amino Acid Sequence of HCV E1 Protein

M S Y Y H H H H H H D Y D I P T T E N L Y F Q G
A M D P E F Y Q V R N S S G L Y H V T N D C P N
S S I V Y E A A D A I L H T P G C V P C V R E G
N A S R C W V A V T P T V A T R D G K L P T T Q
L R R H I D L L V G S A T L C S A L Y V G D L C
G S V F L V G Q L F T F S P R R H W T T Q D C N
C S I Y P G H I T G H R M A W D M M M N W S P
T A A L V V A Q L L R I P Q A I M D M I A G A H
W G V L A G I A Y F S M V G N W A K V L V V L L
L F A G V D A E G L V R P L S N L E P A V S R H
A V P S L S R S T R G S

Figure 54. Nucleotide and Amino Acid Sequences of the ORF of HCV E1-TBD Protein in the Plasmid pFASTBACHTa-HCV E1-TBD Fig. 54A. DNA sequence of HCV E1-TBD Protein expression cassette ATG TCG TAC TAC CAT CAC CAT CAC CAT CAC GAT TAC GAT ATC CCA
ACG ACC GAA AAC CTG TAT TTT CAG GGC GCC ATG GAT CCG GAA TTC
TAC CAA GTG CGC AAT TCC TCG GGC TT TAC CAT GTC ACC AAT GAT
TGC CCT AAC TCG AGT ATT GTG TAC GAG GCG GCC GAT GCC ATC CTG
CAC ACT CCG GGG TGT GTC CCT TGC GTT CGC GAG GGT AAC GCC TCG
AGG TGT TGG GTG GCG GTG ACC CCC ACG GTG GCC ACC AGG GAC
GGC AAA CTC CCC ACA ACG CAG CTT CGA CGT CAT ATC GAT CTG CTT
GTC GGG AGC GCC ACC CTC TGC TCG GCC CTC TAC GTG GGG GAC
CTG TGC
GGG TCT GTC TTT CTT GTT GGT CAA CTG TTT ACC TTC TCT CCC AGG
CGC CAC TGG ACG ACG CAA GAC TGC AAT TGT TCT ATC TAT CCC GGC
CAT ATA ACG GGT CAT CGC ATG GCA TGG GAT ATG ATG ATG AAC TGG
TCC CCT ACG GCA GCG TTG GTG GTA GCT CAG CTG CTC CGG ATC CCA
CAA GCC ATC ATG GAC ATG ATC GCT GGT GCT CAC TGG GGA GTC CTG
GCG GGC ATA GCG TAT TTC TCC ATG GTG GGG AAC TGG GCG AAG GTC
CTG GTA GTG CTG CTG CTA TTT GCC GGC GTC GAC GCG GAA GGA CTA
GTG CGG CCG CAA GGC GGC GGA TCC GTG GAC AAG AAA ATT GTG
CCC
AGG GAT TGT GGT TGT AAG CCT TGC ATA TGT ACA GTC CCA GAA GTA
TCA TCT GTC TTC ATC TTC CCC CCA AAG CCC AAG GAT GTG CTC ACC
ATT ACT CTG ACT CCT AAG GTC ACG TGT GTT GTG GTA GAC ATC AGC
AAG GAT GAT CCC GAG GTC CAG TTC AGC TGG TTT GTA GAT GAT GTG
GAG GTG CAC ACA GCT CAG ACG CAA CCC CGG GAG GAG CAG TTC
AAC AGC ACT TTC CGC TCA GTC AGT GAA CTT CCC ATC ATG CAC CAG
GAC TGG CTC AAT GGC AAG GAG TTC AAA TGC AGG GTC AAC AGT GCA
GCT TTC CCT GCC CCC ATC GAG AAA ACC ATC TCC AAA ACC AAA GGC
AGA CCG AAG GCT CCA CAG GTG TAC ACC ATT CCA CCT CCC AAG GAG
CAG ATG GCC AAG GAT AAA GTC AGT CTG ACC TGC ATG ATA ACA GAC
TTC TTC CCT GAA GAC ATT ACT GTG GAG TGG CAG TGG AAT GGG CAG
CCA GCG GAG AAC TAC AAG AAC ACT CAG CCC ATC ATG GAC ACA GAT
GGC
TCT TAC TTC GTC TAC AGC AAG CTC AAT GTG CAG AAG AGC AAC TGG
GAG GCA GGA AAT ACT TTC ACC TGC TCT GTG TTA CAT GAG GGC CTG
CAC AAC CAC CAT ACT GAG AAG AGC CTC TCC CAC TCT CCT GGG CTG
CAA AGC TTG TCG AGA AGT ACT AGA GGA TCA TAA

Fig 54B. Amino Acid Sequence of HCV E1-TBD Protein

```
M S Y Y H H H H H H D Y D I P T T E N L Y F Q G
A M D P E F Y Q V R N S S G L Y H V T N D C P N
S S I V Y E A A D A I L H T P G C V P C V R E G
N A S R C W V A V T P T V A T R D G K L P T T Q
L R R H I D L L V G S A T L C S A L Y V G D L C
G S V F L V G Q L F T F S P R R H W T T Q D C N
C S I Y P G H I T G H R M A W D M M M N W S P
T A A L V V A Q L L R I P Q A I M D M I A G A H
W G V L A G I A Y F S M V G N W A K V L V V L L
L F A G V D A E G L V R P Q G G G S V D K K I V
P R D C G C K P C I C T V P E V S S V F I F P P
K P K D V L T I T L T P K V T C V V V D I S K D D
P E V Q F S W F V D D V E V H T A Q T Q P R E E
Q F N S T F R S V S E L P I M H Q D W L N G K E
F K C R V N S A A F P A P I E K T I S K T K G R
P K A P Q V Y T I P P P K E Q M A K D K V S L T
C M I T D F F P E D I T V E W Q W N G Q P A E N
Y K N T Q P I M D T D G S Y F V Y S K L N V Q K
S N W E A G N T F T C S V L H E G L H N H H T E
K S L S H S P G L Q S L S R S T R G S
```

Figure 55. Nucleotide and Amino Acid Sequences of the ORF of HCV E 2 Protein in the Plasmid pFASTBACHTa-HCV E2

Fig. 55A. DNA sequence of HCV E 2 Protein expression cassette

ATG TCG TAC TAC CAT CAC CAT CAC CAT CAC GAT TAC GAT ATC CCA
ACG ACC GAA AAC CTG TAT TTT CAG GGC GCC ATG GAT CCG GAA TTC
ACC CAC GTC ACC GGG GGA AAT GCC GGC CGC ACC ACG GCT GGG
CTT GTT GGT CTC CTT ACA CCA GGC GCC AAG CAG AAC ATC CAA CTG
ATC
AAC ACC AAC GGC AGT TGG CAC ATC AAT AGC ACG GCC TTG AAT TGC
AAT GAA AGC CTT AAC ACC GGC TGG TTA GCA GGG CTC TTC TAT CAA
CAC AAA TTC AAC TCT TCA GGC TGT CCT GAG AGG TTG GCC AGC TGC
CGA CGC CTT ACC GAT TTT GCC CAG GGC TGG GGT CCT ATC AGT TAT
GCC AAC GGA AGC GGC CTC GAC GAA CGC CCC TAC TGC TGG CAC TAC
CCT CCA AGA CCT TGT GGC ATT GTG CCC GCA AAG AGC GTG TGT GGC
CCG GTA TAT TGC TTC ACT CCC AGC CCC GTG GTG GTG GGA ACG ACC
GAC AGG TCG GGC GCG CCT ACC TAC AGC TGG GGT GCA AAT GAT ACG
GAT GTC TTC GTC CTT AAC AAC ACC AGG CCA CCG CTG GGC AAT TGG
TTC GGT TGT ACC TGG ATG AAC TCA ACT GGA TTC ACC AAA GTG TGC
GGA GCG CCC CCT TGT GTC ATC GGA GGG GTG GGC AAC AAC ACC TTG
CTC TGC CCC ACT GAT TGC TTC CGC AAA CAT CCG GAA GCC ACA TAC
TCT CGG TGC GGC TCC GGT CCC TGG ATT ACA CCC AGG TGC ATG GTC
GAC TAC CCG TAT AGG CTT TGG CAC TAT CCT TGT ACC ATC AAT TAC
ACC ATA TTC AAA GTC AGG ATG TAC GTG GGA GGG TCG AGC ACA GG
CTG GAA GCG GCC TGC AAC TGG ACG CGG GGC GAA CGC TGT GAT
CTG
GAA GAC AGG GAC AGG TCC GAG CTC AGC CCG TTG CTG CTG TCC ACC
ACA CAG TGG CAG GTC CTT CCG TGT TCT TCA CGA CCT GCC AGC
TTG TCC ACC GGC CTC ATC CAC CTC CAC CAG AAC ATT GTG GAC GTG
CAG TAC TTG TAC GGG GTA GGG TCA AGC ATC GCG TCC TGG GCC ATT
AAG TGG GAG TAC GTC GTT CTC CTG TTC CTT CTG CTT GCA GAC GCG
CGC GTC TGC TCC TGC TTG TGG ATG ATG TTA CTC ATA TCC CAA GCG
GAG GCG GCT GGA CTA GTG CGG CCG CTT TCG AAT CTA GAG CCT GCA
GTC TCG AGG CAT GCG GTA CCA AGC TTG TCG AGA AGT ACT AGA GGA
TCA TAA

Fig 55B. Amino Acid Sequence of HCV E 2 Protein

```
M S Y Y H H H H H H D Y D I P T T E N L Y F Q G
A M D P E F T H V T G G N A G R T T A G L V G L
L T P G A K Q N I Q L I N T N G S W H I N S T A
L N C N E S L N T G W L A G L F Y Q H K F N S S
G C P E R L A S C R R L T D F A Q G W G P I S Y
A N G S G L D E R P Y C W H Y P P R P C G I V P
A K S V C G P V Y C F T P S P V V V G T T D R S
G A P T Y S W G A N D T D V F V L N N T R P P L
G N W F G C T W M N S T G F T K V C G A P P C
V I G G V G N N T L L C P T D C F R K H P E A T
Y S R C G S G P W I T P R C M V D Y P Y R L W H
Y P C T I N Y T I F K V R M Y V G G V E H R L E
A A C N W T R G E R C D L E D R D R S E L S P L
L L S T T Q W Q V L P C S F T T L P A L S T G L I
H L H Q N I V D V Q Y L Y G V G S S I A S W A I
K W E Y V V L L F L L L A D A R V C S C L W M M
L L I S Q A E A A G L V R P L S N L E P A V S R
H A V P S L S R S T R G S
```

Figure 56. Nucleotide and Amino Acid Sequences of the ORF of HCV E2-TBD Protein in the Plasmid pFASTBACHTa-HCV E2-TBD

Fig 56A. DNA sequence of HCV E 2-TBD Protein expression cassette

ATG TCG TAC TAC CAT CAC CAT CAC CAT CAC GAT TAC GAT ATC CCA
ACG ACC GAA AAC CTG TAT TTT CAG GGC GCC ATG GAT CCG GAA TTC
ACC CAC GTC ACC GGG GGA AAT GCC GGC CGC ACC ACG GCT GGG
CTT GTT GGT CTC CTT ACA CCA GGC GCC AAG CAG AAC ATC CAA CTG
ATC
AAC ACC AAC GGC AGT TGG CAC ATC AAT AGC ACG GCC TTG AAT TGC
AAT GAA AGC CTT AAC ACC GGC TGG TTA GCA GGG CTC TTC TAT CAA
CAC AAA TTC AAC TCT TCA GGC TGT CCT GAG AGG TTG GCC AGC TGC
CGA CGC CTT ACC GAT TTT GCC CAG GGC TGG GGT CCT ATC AGT TAT
GCC AAC GGA AGC GGC CTC GAC GAA CGC CCC TAC TGC TGG CAC TAC
CCT CCA AGA CCT TGT GGC ATT GTG CCC GCA AAG AGC GTG TGT GGC
CCG GTA TAT TGC TTC ACT CCC AGC CCC GTG GTG GTG GGA ACG ACC
GAC AGG TCG GGC GCG CCT ACC TAC AGC TGG GGT GCA AAT GAT ACG
GAT GTC TTC GTC CTT AAC AAC ACC AGG CCA CCG CTG GCA AAT TGG
TTC GGT TGT ACC TGG ATG AAC TCA ACT GGA TTC ACC AAA GTG TGC
GGA GCG CCC CCT TGT GTC ATC GGA GGG GTG GGC AAC AAC ACC TTG
CTC TGC CCC ACT GAT TGC TTC CGC AAA CAT CCG GAA GCC ACA TAC
TCT CGG TGC GGC TCC GGT CCC TGG ATT ACA CCC AGG TGC ATG GTC
GAC TAC CCG TAT AGG CTT TGG CAC TAT CCT TGT ACC ATC AAT TAC
ACC ATA TTC AAA GTC AGG ATG TAC GTG GGA GGG GTC GAG CAC AGG
CTG GAA GCG GCC TGC AAC TGG ACG CGG GGC GAA CGC TGT GAT
CTG
GAA GAC AGG GAC AGG TCC GAG CTC AGC CCG TTG CTG CTG TCC ACC
ACA CAG TGG CAG GTC CTT CCG TGT TCT TTC ACG ACC TGC CAG CC
TTG TCC ACC GGC CTC ATC CAC CTC CAC CAG AAC ATT GTG GAC GTG
CAG TAC TTG TAC GGG GTA GGG TCA AGC ATC GCG TCC TGG GCC ATT
AAG TGG GAG TAC GTC GTT CTC CTG TTC CTT CTG CTT GCA GAC GCG
CGC GTC TGC TCC TGC TTG TGG ATG ATG TTA CTC ATA TCC CAA GCG
GAG GCG GCT GGA CTA GTG CGG CCG CAA GGC GGC GGA TCC GTG
GAC AAG AAA ATT GTG CCC AGG GAT TGT GGT TGT AAG CCT TGC ATA
TGT
ACA GTC CCA GAA GTA TCA TCT GTC TTC ATC TTC CCC CCA AAG CCC
AAG GAT GTG CTC ACC ATT ACT CTG ACT CCT AAG GTC ACG TGT GTT
GTG GTA GAC ATC AGC AAG GAT GAT CCC GAG GTC CAG TTC AGC TGG
TTT GTA GAT GAT GTG GAG GTG CAC ACA GCT CAG ACG CAA CCC CGG
GAG GAG CAG TTC AAC AGC ACT TTC CGC TCA GTC AGT GAA CTT CCC
ATC ATG CAC CAG GAC TGG CTC AAT GGC AAG GAG TTC AAA TGC AGG
GTC AAC AGT GCA GCT TTC CCT GCC CCC ATC GAG AAA ACC ATC TCC
AAA ACC AAA GGC AGA CCG AAG GCT CCA CAG GTG TAC ACC ATT CCA
CCT CCC AAG GAG CAG ATG GCC AAG GAT AAA GTC AGT CTG ACC

TGCATG ATA ACA GAC TTC TTC CCT GAA GAC ATT ACT GTG GAG TGG
CAG TGG AAT GGG CAG CCA GCG GAG AAC TAC AAG AAC ACT CAG CCC
ATC ATG GAC ACA GAT GGC TCT TAC TTC GTC TAC AGC AAG CTC AAT
GTG CAG AAG AGC AAC TGG GAG GCA GGA AAT ACT TTC ACC TGC TCT
GTG TTA CAT GAG GGC CTG CAC AAC CAC CAT ACT GAG AAG AGC CTC
TCC CAC TCT CCT GGG CTG CAA AGC TTG TCG AGA AGT ACT AGA GGA
TCA TAA

Fig 56B. Amino Acid Sequence of HCV E 2-TBD Protein

M S Y Y H H H H H H D Y D I P T T E N L Y F Q G
A M D P E F T H V T G G N A G R T T A G L V G L
L T P G A K Q N I Q L I N T N G S W H I N S T A
L N C N E S L N T G W L A G L F Y Q H K F N S S
G C P E R L A S C R R L T D F A Q G W G P I S Y
A N G S G L D E R P Y C W H Y P P R P C G I V P
A K S V C G P V Y C F T P S P V V G T T D R S
G A P T Y S W G A N D T D V F V L N N T R P P L
G N W F G C T W M N S T G F T K V C G A P P C
V I G G V G N N T L L C P T D C F R K H P E A T
Y S R C G S G P W I T P R C M V D Y P Y R L W H
Y P C T I N Y T I F K V R M Y V G G V E H R L E
A A C N W T R G E R C D L E D R D R S E L S P L
L L S T T Q W Q V L P C S F T T L P A L S T G L I
H L H Q N I V D V Q Y L Y G V G S S I A S W A I
K W E Y V V L L F L L L A D A R V C S C L W M M
L L I S Q A E A A G L V R P Q G G G S V D K K I
V P R D C G C K P C I C T V P E V S S V F I F P
P K P K D V L T I T L T P K V T C V V V D I S K D
D P E V Q F S W F V D D V E V H T A Q T Q P R E
E Q F N S T F R S V S E L P I M H Q D W L N G K
E F K C R V N S A A F P A P I E K T I S K T K G
R P K A P Q V Y T I P P P K E Q M A K D K V S L
T C M I T D F F P E D I T V E W Q W N G Q P A E
N Y K N T Q P I M D T D G S Y F V Y S K L N V Q
K S N W E A G N T F T C S V L H E G L H N H H T
E K S L S H S P G L Q S L S R S T R G S

Figure 57. Nucleotide and Amino Acid Sequences of the ORF of HCV E1/E2 Protein in the Plasmid pFASTBACHTa-HCVE1/E2

Fig 57A. DNA sequence of HCV E1/E2 Protein expression cassette

ATG TCG TAC TAC CAT CAC CAT CAC CAT CAC GAT TAC GAT ATC CCA
ACG ACC GAA AAC CTG TAT TTT CAG GGC GCC ATG GAT CCG GAA TTC
TAC CAA GTG CGC AAT TCC TCG GGG CTT TAC CAT GTC ACC AAT GAT
TGC CCT AAC TCG AGT ATT GTG TAC GAG GCG GCC GAT GCC ATC CTG
CAC ACT CCG GGG TGT GTC CCT TGC GTT CGC GAG GGT AAC GCC TCG
AGG TGT TGG GTG GCG GTG ACC CCC ACG GTG GCC ACC AGG GAC
GGC AAA CTC CCC ACA ACG CAG CTT CGA CGT CAT ATC GAT CTG CTT
GTC GGG AGC GCC ACC CTC TGC TCG GCC CTC TAC GTG GGG GAC
CTG TGC
GGG TCT GTC TTT CTT GTT GGT CAA CTG TTT ACC TTC TCT CCC AGG
CGC CAC TGG ACG ACG CAA GAC TGC AAT TGT TCT ATC TAT CCC GGC
CAT ATA ACG GGT CAT CGC ATG GCA TGG GAT ATG ATG ATG AAC TGG
TCC CCT ACG GCA GCG TTG GTG GTA GCT CAG CTG CTC CGG ATC CCA
CAA GCC ATC ATG GAC ATG ATC GCT GGT GCT CAC TGG GGA GTC CTG
GCG GGC ATA GCG TAT TTC TCC ATG GTG GGG AAC TGG GCG AAG GTC
CTG GTA GTG CTG CTG CTA TTT GCC GGC GTC GAC GCG GAA ACC CAC
GTC ACC GGG GGA AAT GCC GGC CGC ACC ACG GCT GGG CTT GTT
GGT
CTC CTT ACA CCA GGC GCC AAG CAG AAC ATC CAA CTG ATC AAC ACC
AAC GGC AGT TGG CAC ATC AAT AGC ACG GCC TTG AAT TGC AAT GAA
AGC CTT AAC ACC GGC TGG TTA GCA GGG CTC TTC TAT CAA CAC AAA
TTC AAC TCT TCA GGC TGT CCT GAG AGG TTG GCC AGC TGC CGA CGC
CTT ACC GAT TTT GCC CAG GGC TGG GGT CCT ATC AGT TAT GCC AAC
GGA AGC GGC CTC GAC GAA CGC CCC TAC TGC TGG CAC TAC CCT CCA
AGA CCT TGT GGC ATT GTG CCC GCA AAG AGC GTG TGT GGC CCG GTA
TAT TGC TTC ACT CCC AGC CCC GTG GTG GTG GGA ACG ACC GAC AGG
TCG GGC GCG CCT ACC TAC AGC TGG GGT GCA AAT GAT ACG GAT GTC
TTC GTC CTT AAC AAC ACC AGG CCA CCG CTG GGC AAT TGG TTC GGT
TGT ACC TGG ATG AAC TCA ACT GGA TTC ACC AAA GTG TGC GGA GCG
CCC CCT TGT GTC ATC GGA GGG GTG GGC AAC AAC ACC TTG CTC TGC
CCC ACT GAT TGC TTC CGC AAA CAT CCG GAA GCC ACA TAC TCT CGG
TGC GGC TCC GGT CCC TGG ATT ACA CCC AGG TGC ATG GTC GAC TAC
CCG TAT AGG CTT TGG CAC TAT CCT TGT ACC ATC AAT TAC ACC ATA
TTC AAA GTC AGG ATG TAC GTG GGA GGG TCG AGC ACA GGC TGA A
GCG GCC TGC AAC TGG ACG CGG GGC GAA CGC TGT GAT CTG GAA
GAC AGG GAC AGG TCC GAG CTC AGC CCG TTG CTG CTG TCC ACC ACA
CAG TGG CAG GTC CTT CCG TGT TCT TTC ACG ACC CTG CCA GCC TTG
TCC ACC GGC CTC ATC CAC CTC CAC CAG AAC ATT GTG GAC GTG CAG

```
TAC TTG TAC GGG GTA GGG TCA AGC ATC GCG TCC TGG GCC ATT AAG
TGG GAG TAC GTC GTT CTC CTG TTC CTT CTG CTT GCA GAC GCG CGC
GTC TGC TCC TGC TTG TGG ATG ATG TTA CTC ATA TCC CAA GCG GAG
GCG GCT GGA CTA GTG CGG CCG CTT TCG AAT CTA GAG CCT GCA GTC
TCG AGG CAT GCG GTA CCA AGC TTG TCG AGA AGT ACT AGA GGA TCA
TAA
```

Fig 57B. Amino Acid Sequence of HCV E1/E2 Protein

```
M S Y Y H H H H H H D Y D I P T T E N L Y F Q G
A M D P E F Y Q V R N S S G L Y H V T N D C P N
S S I V Y E A A D A I L H T P G C V P C V R E G
N A S R C W V A V T P T V A T R D G K L P T T Q
L R R H I D L L V G S A T L C S A L Y V G D L C
G S V F L V G Q L F T F S P R R H W T T Q D C N
C S I Y P G H I T G H R M A W D M M M N W S P
T A A L V V A Q L L R I P Q A I M D M I A G A H
W G V L A G I A Y F S M V G N W A K V L V V L L
L F A G V D A E T H V T G G N A G R T T A G L V
G L L T P G A K Q N I Q L I N T N G S W H I N S
T A L N C N E S L N T G W L A G L F Y Q H K F N
S S G C P E R L A S C R R L T D F A Q G W G P I
S Y A N G S G L D E R P Y C W H Y P P R P C G I
V P A K S V C G P V Y C F T P S P V V V G T T D
R S G A P T Y S W G A N D T D V F V L N N T R P
P L G N W F G C T W M N S T G F T K V C G A P
P C V I G G V G N N T L L C P T D C F R K H P E
A T Y S R C G S G P W I T P R C M V D Y P Y R L
W H Y P C T I N Y T I F K V R M Y V G G V E H R
L E A A C N W T R G E R C D L E D R D R S E L S
P L L L S T T Q W Q V L P C S F T T L P A L S T
G L I H L H Q N I V D V Q Y L Y G V G S S I A S
W A I K W E Y V V L L F L L L A D A R V C S C L
W M M L L I S Q A E A A G L V R P L S N L E P A
V S R H A V P S L S R S T R G S
```

Figure 58. Nucleotide and Amino Acid Sequences of the ORF of HCVE1/ E2-TBD Protein in the Plasmid pFASTBACHTa-HCVE1/ E2-TBD Fig 58A. DNA sequence of HCV E1/E2-TBD Protein expression cassette ATG TCG TAC TAC CAT CAC CAT CAC CAT CAC GAT TAC GAT ATC CCA
ACG ACC GAA AAC CTG TAT TTT CAG GGC GCC ATG GAT CCG GAA TTC
TAC CAA GTG CGC AAT TCC TCG GGG CTT TAC CAT GTC ACC AAT GAT
TGC CCT AAC TCG AGT ATT GTG TAC GAG GCG GCC GAT GCC ATC CTG
CAC ACT CCG GGG TGT GTC CCT TGC GTT CGC GAG GGT AAC GCC TCG
AGG TGT TGG GTG GCG GTG ACC CCC ACG GTG GCC ACC AGG GAC
GGC AAA CTC CCC ACA ACG CAG CTT CGA CGT CAT ATC GAT CTG CTT
GTC GGG AGC GCC ACC CTC TGC TCG GCC CTC TAC GTG GGG GAC
CTG TGC
GGG TCT GTC TTT CTT GTT GGT CAA CTG TTT ACC TTC TCT CCC AGG
CGC CAC TGG ACG ACG CAA GAC TGC AAT TGT TCT ATC TAT CCC GGC
CAT ATA ACG GGT CAT CGC ATG GCA TGG GAT ATG ATG ATG AAC TGG
TCC CCT ACG GCA GCG TTG GTG GTA GCT CAG CTG CTC CGG ATC CCA
CAA GCC ATC ATG GAC ATG ATC GCT GGT GCT CAC TGG GGA GTC CTG
GCG GGC ATA GCG TAT TTC TCC ATG GTG GGG AAC TGG GCG AAG GTC
CTG GTA GTG CTG CTG CTA TTT GCC GGC GTC GAC GCG GAA ACC CAC
GTC ACC GGG GGA AAT GCC GGC CGC ACC ACG GCT GGG CTT GTT
GGT CTC CTT ACA CCA GGC GCC AAG CAG AAC ATC CAA CTG ATC AAC
ACC AAC GGC AGT TGG CAC ATC AAT AGC ACG GCC TTG AAT TGC AAT
GAA AGC CTT AAC ACC GGC TGG TTA GCA GGG CTC TTC TAT CAA CAC
AAA TTC AAC TCT TCA GGC TGT CCT GAG AGG TTG GCC AGC TGC CGA
CGC CTT ACC GAT TTT GCC CAG GGC TGG GGT CCT ATC AGT TAT GCC
AAC GGA AGC GGC CTC GAC GAA CGC CCC TAC TGC TGG CAC TAC CCT
CCA AGA CCT TGT GGC ATT GTG CCC GCA AAG AGC GTG TGT GGC CCG
GTA TAT TGC TTC ACT CCC AGC CCC GTG GTG GTG GGA ACG ACC GAC
AGG TCG GGC GCG CCT ACC TAC AGC TGG GGT GCA AAT GAT ACG GAT
GTC TTC GTC CTT AAC AAC ACC AGG CCA CCG CTG GCA ATT GGT TC
GGT TGT ACC TGG ATG AAC TCA ACT GGA TTC ACC AAA GTG TGC GGA
GCG CCC CCT TGT GTC ATC GGA GGG GTG GGC AAC AAC ACC TTG CTC
TGC CCC ACT GAT TGC TTC CGC AAA CAT CCG GAA GCC ACA TAC TCT
CGG TGC GGC TCC GGT CCC TGG ATT ACA CCC AGG TGC ATG GTC GAC
TAC CCG TAT AGG CTT TGG CAC TAT CCT TGT ACC ATC AAT TAC ACC
ATA TTC
AAA GTC AGG ATG TAC GTG GGA GGG GTC GAG CAC AGG CTG GAA
GCG GCC TGC AAC TGG ACG CGG GGC GAA CGC TGT GAT CTG GAA
GAC AGG GAC AGG TCC GAG CTC AGC CCG TTG CTG CTG TCC ACC ACA
CAG TGG CAG GTC CTT CCG TGT TCT TTC ACG ACC TGC CAG CCT TG

```
TCC ACC GGC CTC ATC CAC CTC CAC CAG AAC ATT GTG GAC GTG CAG
TAC
TTG TAC GGG GTA GGG TCA AGC ATC GCG TCC TGG GCC ATT AAG TGG
GAG TAC GTC GTT CTC CTG TTC CTT CTG CTT GCA GAC GCG CGC GTC
TGC TCC TGC TTG TGG ATG ATG TTA CTC ATA TCC AAG CGA GAG GCG
GCT GGA CTA GTG CGG CCG CAA GGC GGC GGA TCC GTG GAC AAG
AAA
ATT GTG CCC AGG GAT TGT GGT TGT AAG CCT TGC ATA TGT ACA GTC
CCA GAA GTA TCA TCT GTC TTC ATC TTC CCC CCA AAG CCC AAG GAT
GTG CTC ACC ATT ACT CTG ACT CCT AAG GTC ACG TGT GTT GTG GTA
GAC ATC AGC AAG GAT GAT CCC GAG GTC CAG TTC AGC TGG TTT GTA
GAT GAT GTG GAG GTG CAC ACA GCT CAG ACG CAA CCC CGG GAG
GAG CAG TTC AAC AGC ACT TTC CGC TCA GTC AGT GAA CTT CCC ATC
ATG CAC CAG GAC TGG CTC AAT GGC AAG GAG TTC AAA TGC AGG GTC
AAC AGT GCA GCT TTC CCT GCC CCC ATC GAG AAA ACC ATC TCC AAA
ACC
AAA GGC AGA CCG AAG GCT CCA CAG GTG TAC ACC ATT CCA CCT CCC
AAG GAG CAG ATG GCC AAG GAT AAA GTC AGT CTG ACC TGC ATG ATA
ACA GAC TTC TTC CCT GAA GAC ATT ACT GTG GAG TGG CAG TGG AAT
GGG CAG CCA GCG GAG AAC TAC AAG AAC ACT CAG CCC ATC ATG GAC
ACA GAT GGC TCT TAC TTC GTC TAC AGC AAG CTC AAT GTG CAG AAG
AGC AAC TGG GAG GCA GGA AAT ACT TTC ACC TGC TCT GTG TTA CAT
GAG GGC CTG CAC AAC CAC CAT ACT GAG AAG AGC CTC TCC CAC TCT
CCT GGG CTG CAA AGC TTG TCG AGA AGT ACT AGA GGA TCA TAA
```

Fig 58B. Amino Acid Sequence of HCV E1/E2-TBD Protein

```
M S Y Y H H H H H H D Y D I

SEQUENCE LISTING

```
<160> NUMBER OF SEQ ID NOS: 76

<210> SEQ ID NO 1
<211> LENGTH: 55
<212> TYPE: DNA
<213> ORGANISM: artificial sequence
<220> FEATURE:
<223> OTHER INFORMATION: primer sequence

<400> SEQUENCE: 1
tgtcattctg cggccgcaag gcggcgggat ccgtggacaa gaaaattgtg ccagg          55

<210> SEQ ID NO 2
<211> LENGTH: 27
<212> TYPE: DNA
<213> ORGANISM: artificial sequence
<220> FEATURE:
<223> OTHER INFORMATION: primer sequence

<400> SEQUENCE: 2
acgaatcaag ctttgcagcc caggaga                                         27

<210> SEQ ID NO 3
<211> LENGTH: 21
<212> TYPE: DNA
<213> ORGANISM: artificial sequence
<220> FEATURE:
<223> OTHER INFORMATION: primer sequence

<400> SEQUENCE: 3
tattccggat tattcatacc g                                               21

<210> SEQ ID NO 4
<211> LENGTH: 20
<212> TYPE: DNA
<213> ORGANISM: artificial sequence
<220> FEATURE:
<223> OTHER INFORMATION: primer sequence

<400> SEQUENCE: 4
ctctacaaat gtggtatggc                                                 20
```

```
<210> SEQ ID NO 5
<211> LENGTH: 18
<212> TYPE: DNA
<213> ORGANISM: artificial sequence
<220> FEATURE:
<223> OTHER INFORMATION: primer sequence

<400> SEQUENCE: 5
ggatcctgta cgatgacg                                                       18

<210> SEQ ID NO 6
<211> LENGTH: 39
<212> TYPE: DNA
<213> ORGANISM: artificial sequence
<220> FEATURE:
<223> OTHER INFORMATION: primer sequence

<400> SEQUENCE: 6
agtcattctg cggccgcgag ttcgtcacag ggtccccgg                                 39

<210> SEQ ID NO 7
<211> LENGTH: 34
<212> TYPE: DNA
<213> ORGANISM: artificial sequence
<220> FEATURE:
<223> OTHER INFORMATION: primer sequence

<400> SEQUENCE: 7
gataaggatc ctatgggagg ttggtcatca aaac                                     34

<210> SEQ ID NO 8
<211> LENGTH: 40
<212> TYPE: DNA
<213> ORGANISM: artificial sequence
<220> FEATURE:
<223> OTHER INFORMATION: primer sequence

<400> SEQUENCE: 8
gtcatactgc ggccgcgaaa tgtataccca gagacaaaag                               40

<210> SEQ ID NO 9
<211> LENGTH: 21
<212> TYPE: DNA
<213> ORGANISM: artificial sequence
<220> FEATURE:
<223> OTHER INFORMATION: primer sequence

<400> SEQUENCE: 9
tattccggat tattcatacc g                                                   21

<210> SEQ ID NO 10
<211> LENGTH: 40
<212> TYPE: DNA
<213> ORGANISM: artificial sequence
<220> FEATURE:
<223> OTHER INFORMATION: primer sequence

<400> SEQUENCE: 10
tgtcattcag cggccgcgaa ctcttgtaaa aaagagcaga                               40

<210> SEQ ID NO 11
<211> LENGTH: 33
<212> TYPE: DNA
<213> ORGANISM: artificial sequence
<220> FEATURE:
<223> OTHER INFORMATION: primer sequence
```

```
<400> SEQUENCE: 11
tgcgctacca tggatatcaa tgcttctaga gcc                                    33

<210> SEQ ID NO 12
<211> LENGTH: 43
<212> TYPE: DNA
<213> ORGANISM: artificial sequence
<220> FEATURE:
<223> OTHER INFORMATION: primer sequence

<400> SEQUENCE: 12
tgtcattctg cggccgcgat ttcctaggcg agggagatct atg                         43

<210> SEQ ID NO 13
<211> LENGTH: 27
<212> TYPE: DNA
<213> ORGANISM: artificial sequence
<220> FEATURE:
<223> OTHER INFORMATION: primer sequence

<400> SEQUENCE: 13
cggaattcat gagcacgaat cctaaac                                           27

<210> SEQ ID NO 14
<211> LENGTH: 38
<212> TYPE: DNA
<213> ORGANISM: artificial sequence
<220> FEATURE:
<223> OTHER INFORMATION: primer sequence

<400> SEQUENCE: 14
ggactagtcc ggctgaagcg ggcacagtca ggcaagag                               38

<210> SEQ ID NO 15
<211> LENGTH: 27
<212> TYPE: DNA
<213> ORGANISM: artificial sequence
<220> FEATURE:
<223> OTHER INFORMATION: primer sequence

<400> SEQUENCE: 15
cggaattcat gagcacgaat cctaaac                                           27

<210> SEQ ID NO 16
<211> LENGTH: 27
<212> TYPE: DNA
<213> ORGANISM: artificial sequence
<220> FEATURE:
<223> OTHER INFORMATION: primer sequence

<400> SEQUENCE: 16
ggactagtcc gaagatagag aaagagc                                           27

<210> SEQ ID NO 17
<211> LENGTH: 27
<212> TYPE: DNA
<213> ORGANISM: artificial sequence
<220> FEATURE:
<223> OTHER INFORMATION: primer sequence

<400> SEQUENCE: 17
ccggaattct ccggttcctg gctaagg                                           27

<210> SEQ ID NO 18
<211> LENGTH: 28
<212> TYPE: DNA
```

```
<213> ORGANISM: artificial sequence
<220> FEATURE:
<223> OTHER INFORMATION: primer sequence

<400> SEQUENCE: 18
ggactagtcc gcacacgaca tcttccgt                                      28

<210> SEQ ID NO 19
<211> LENGTH: 28
<212> TYPE: DNA
<213> ORGANISM: artificial sequence
<220> FEATURE:
<223> OTHER INFORMATION: primer sequence

<400> SEQUENCE: 19
ccggaattct accaagtgcg caattcct                                      28

<210> SEQ ID NO 20
<211> LENGTH: 32
<212> TYPE: DNA
<213> ORGANISM: artificial sequence
<220> FEATURE:
<223> OTHER INFORMATION: primer sequence

<400> SEQUENCE: 20
ggactagtcc ttccgcgtcg acgccggcaa at                                 32

<210> SEQ ID NO 21
<211> LENGTH: 32
<212> TYPE: DNA
<213> ORGANISM: artificial sequence
<220> FEATURE:
<223> OTHER INFORMATION: primer sequence

<400> SEQUENCE: 21
gcggaattca cccacgtcac cgggggaaat gc                                 32

<210> SEQ ID NO 22
<211> LENGTH: 35
<212> TYPE: DNA
<213> ORGANISM: artificial sequence
<220> FEATURE:
<223> OTHER INFORMATION: primer sequence

<400> SEQUENCE: 22
ggactagtcc agccgcctcc gcttgggata tgagt                              35

<210> SEQ ID NO 23
<211> LENGTH: 28
<212> TYPE: DNA
<213> ORGANISM: artificial sequence
<220> FEATURE:
<223> OTHER INFORMATION: HCV E2 antigen primer

<400> SEQUENCE: 23
ccggaattct accaagtgcg caattcct                                      28

<210> SEQ ID NO 24
<211> LENGTH: 35
<212> TYPE: DNA
<213> ORGANISM: Artificial
<220> FEATURE:
<223> OTHER INFORMATION: HCV E1/E2 3' primer

<400> SEQUENCE: 24
ggactagtcc agccgcctcc gcttgggata tgagt                              35
```

```
<210> SEQ ID NO 25
<211> LENGTH: 32
<212> TYPE: DNA
<213> ORGANISM: artificial sequence
<220> FEATURE:
<223> OTHER INFORMATION: primer sequence

<400> SEQUENCE: 25
tgcgctacca tggacattga ccccttataa ag                                 32

<210> SEQ ID NO 26
<211> LENGTH: 42
<212> TYPE: DNA
<213> ORGANISM: artificial sequence
<220> FEATURE:
<223> OTHER INFORMATION: primer sequence

<400> SEQUENCE: 26
tgtcattctg cggccgcgaa cattgagatt cccgagattg ag                      42

<210> SEQ ID NO 27
<211> LENGTH: 40
<212> TYPE: DNA
<213> ORGANISM: artificial sequence
<220> FEATURE:
<223> OTHER INFORMATION: primer sequence

<400> SEQUENCE: 27
tgtcattctg cggccgcgtt ttcttcttca agggggagt                          40

<210> SEQ ID NO 28
<211> LENGTH: 8
<212> TYPE: PRT
<213> ORGANISM: Artificial
<220> FEATURE:
<223> OTHER INFORMATION: linker peptide

<400> SEQUENCE: 28

Ser Arg Pro Gln Gly Gly Gly Ser
1               5

<210> SEQ ID NO 29
<211> LENGTH: 867
<212> TYPE: DNA
<213> ORGANISM: Mus musculus
<220> FEATURE:
<221> NAME/KEY: CDS
<222> LOCATION: (1)..(867)

<400> SEQUENCE: 29 atg tcg tac tac cat cac cat cac cat cac gat tac gat atc cca acg        48
Met Ser Tyr Tyr His His His His His His Asp Tyr Asp Ile Pro Thr
1               5                   10                  15 acc gaa aac ctg tat ttt cag ggc gcc atg gat ccg gaa ttc aaa ggc        96
Thr Glu Asn Leu Tyr Phe Gln Gly Ala Met Asp Pro Glu Phe Lys Gly
                20                  25                  30 cta cgt cga cga gct caa cta gtg cgg ccg caa ggc ggc gga tcc gtg       144
Leu Arg Arg Arg Ala Gln Leu Val Arg Pro Gln Gly Gly Gly Ser Val
            35                  40                  45 gac aag aaa att gtg ccc agg gat tgt ggt tgt aag cct tgc ata tgt       192
Asp Lys Lys Ile Val Pro Arg Asp Cys Gly Cys Lys Pro Cys Ile Cys
        50                  55                  60 aca gtc cca gaa gta tca tct gtc ttc atc ttc ccc cca aag ccc aag       240
Thr Val Pro Glu Val Ser Ser Val Phe Ile Phe Pro Pro Lys Pro Lys
65                  70                  75                  80
```

```
gat gtg ctc acc att act ctg act cct aag gtc acg tgt gtt gtg gta      288
Asp Val Leu Thr Ile Thr Leu Thr Pro Lys Val Thr Cys Val Val Val
                85                  90                  95 gac atc agc aag gat gat ccc gag gtc cag ttc agc tgg ttt gta gat      336
Asp Ile Ser Lys Asp Asp Pro Glu Val Gln Phe Ser Trp Phe Val Asp
            100                 105                 110 gat gtg gag gtg cac aca gct cag acg caa ccc cgg gag gag cag ttc      384
Asp Val Glu Val His Thr Ala Gln Thr Gln Pro Arg Glu Glu Gln Phe
        115                 120                 125 aac agc act ttc cgc tca gtc agt gaa ctt ccc atc atg cac cag gac      432
Asn Ser Thr Phe Arg Ser Val Ser Glu Leu Pro Ile Met His Gln Asp
    130                 135                 140 tgg ctc aat ggc aag gag ttc aaa tgc agg gtc aac agt gca gct ttc      480
Trp Leu Asn Gly Lys Glu Phe Lys Cys Arg Val Asn Ser Ala Ala Phe
145                 150                 155                 160 cct gcc ccc atc gag aaa acc atc tcc aaa acc aaa ggc aga ccg aag      528
Pro Ala Pro Ile Glu Lys Thr Ile Ser Lys Thr Lys Gly Arg Pro Lys
                165                 170                 175 gct cca cag gtg tac acc att cca cct ccc aag gag cag atg gcc aag      576
Ala Pro Gln Val Tyr Thr Ile Pro Pro Pro Lys Glu Gln Met Ala Lys
            180                 185                 190 gat aaa gtc agt ctg acc tgc atg ata aca gac ttc ttc cct gaa gac      624
Asp Lys Val Ser Leu Thr Cys Met Ile Thr Asp Phe Phe Pro Glu Asp
        195                 200                 205 att act gtg gag tgg cag tgg aat ggg cag cca gcg gag aac tac aag      672
Ile Thr Val Glu Trp Gln Trp Asn Gly Gln Pro Ala Glu Asn Tyr Lys
    210                 215                 220 aac act cag ccc atc atg gac aca gat ggc tct tac ttc gtc tac agc      720
Asn Thr Gln Pro Ile Met Asp Thr Asp Gly Ser Tyr Phe Val Tyr Ser
225                 230                 235                 240 aag ctc aat gtg cag aag agc aac tgg gag gca gga aat act ttc acc      768
Lys Leu Asn Val Gln Lys Ser Asn Trp Glu Ala Gly Asn Thr Phe Thr
                245                 250                 255 tgc tct gtg tta cat gag ggc ctg cac aac cac cat act gag aag agc      816
Cys Ser Val Leu His Glu Gly Leu His Asn His His Thr Glu Lys Ser
            260                 265                 270 ctc tcc cac tct cct ggg ctg caa agc ttg tcg aga agt act aga gga      864
Leu Ser His Ser Pro Gly Leu Gln Ser Leu Ser Arg Ser Thr Arg Gly
        275                 280                 285 tca                                                                  867
Ser

<210> SEQ ID NO 30
<211> LENGTH: 289
<212> TYPE: PRT
<213> ORGANISM: Mus musculus

<400> SEQUENCE: 30

Met Ser Tyr Tyr His His His His His His Asp Tyr Asp Ile Pro Thr
1               5                   10                  15

Thr Glu Asn Leu Tyr Phe Gln Gly Ala Met Asp Pro Glu Phe Lys Gly
            20                  25                  30

Leu Arg Arg Arg Ala Gln Leu Val Arg Pro Gln Gly Gly Gly Ser Val
        35                  40                  45

Asp Lys Lys Ile Val Pro Arg Asp Cys Gly Cys Lys Pro Cys Ile Cys
    50                  55                  60

Thr Val Pro Glu Val Ser Ser Val Phe Ile Phe Pro Pro Lys Pro Lys
65                  70                  75                  80

Asp Val Leu Thr Ile Thr Leu Thr Pro Lys Val Thr Cys Val Val Val
                85                  90                  95
```

```
Asp Ile Ser Lys Asp Asp Pro Glu Val Gln Phe Ser Trp Phe Val Asp
            100                 105                 110

Asp Val Glu Val His Thr Ala Gln Thr Gln Pro Arg Glu Glu Gln Phe
        115                 120                 125

Asn Ser Thr Phe Arg Ser Val Ser Glu Leu Pro Ile Met His Gln Asp
    130                 135                 140

Trp Leu Asn Gly Lys Glu Phe Lys Cys Arg Val Asn Ser Ala Ala Phe
145                 150                 155                 160

Pro Ala Pro Ile Glu Lys Thr Ile Ser Lys Thr Lys Gly Arg Pro Lys
                165                 170                 175

Ala Pro Gln Val Tyr Thr Ile Pro Pro Lys Glu Gln Met Ala Lys
            180                 185                 190

Asp Lys Val Ser Leu Thr Cys Met Ile Thr Asp Phe Phe Pro Glu Asp
        195                 200                 205

Ile Thr Val Glu Trp Gln Trp Asn Gly Gln Pro Ala Glu Asn Tyr Lys
    210                 215                 220

Asn Thr Gln Pro Ile Met Asp Thr Asp Gly Ser Tyr Phe Val Tyr Ser
225                 230                 235                 240

Lys Leu Asn Val Gln Lys Ser Asn Trp Glu Ala Gly Asn Thr Phe Thr
                245                 250                 255

Cys Ser Val Leu His Glu Gly Leu His Asn His His Thr Glu Lys Ser
            260                 265                 270

Leu Ser His Ser Pro Gly Leu Gln Ser Leu Ser Arg Ser Thr Arg Gly
        275                 280                 285

Ser

<210> SEQ ID NO 31
<211> LENGTH: 1356
<212> TYPE: DNA
<213> ORGANISM: Artificial
<220> FEATURE:
<223> OTHER INFORMATION: HBV plus TBD
<220> FEATURE:
<221> NAME/KEY: CDS
<222> LOCATION: (1)..(1356)

<400> SEQUENCE: 31 atg tcg tac tac cat cac cat cac cat cac gat tac gat atc cca acg    48
Met Ser Tyr Tyr His His His His His His Asp Tyr Asp Ile Pro Thr
1               5                   10                  15 acc gaa aac ctg tat ttt cag ggc gcc atg gat cct atg aaa aaa tgg    96
Thr Glu Asn Leu Tyr Phe Gln Gly Ala Met Asp Pro Met Lys Lys Trp
            20                  25                  30 tca tca aaa cct cgc aaa ggc atg ggg acg aat ctt tct gtt ccc aac   144
Ser Ser Lys Pro Arg Lys Gly Met Gly Thr Asn Leu Ser Val Pro Asn
        35                  40                  45 cct ctg gga ttc ttt ccc gat cat cag ttg gac cct gta ttc gga gcc   192
Pro Leu Gly Phe Phe Pro Asp His Gln Leu Asp Pro Val Phe Gly Ala
    50                  55                  60 aac tca aac aat cca gat tgg gac ttc aac ccc atc aag gac cac tgg   240
Asn Ser Asn Asn Pro Asp Trp Asp Phe Asn Pro Ile Lys Asp His Trp
65                  70                  75                  80 cca gca gcc aac cag gta gga gtg gga gca ttc ggg cca ggg ttc acc   288
Pro Ala Ala Asn Gln Val Gly Val Gly Ala Phe Gly Pro Gly Phe Thr
                85                  90                  95 cct cca cac ggc ggt gtt ttg ggg tgg agc cct cag gct cag ggc atg   336
Pro Pro His Gly Gly Val Leu Gly Trp Ser Pro Gln Ala Gln Gly Met
            100                 105                 110
```

```
                                                          -continued ttg acc cca gtg tca aca att cct cct cct gcc tcc gcc aat cgg cag     384
Leu Thr Pro Val Ser Thr Ile Pro Pro Pro Ala Ser Ala Asn Arg Gln
        115                 120                 125 tca gga agg cag cct act ccc atc tct cca cct cta aga gac agt cat     432
Ser Gly Arg Gln Pro Thr Pro Ile Ser Pro Pro Leu Arg Asp Ser His
130                 135                 140 cct cag gcc atg cag tgg aat tcc act gcc ttc cac caa gct ctg caa     480
Pro Gln Ala Met Gln Trp Asn Ser Thr Ala Phe His Gln Ala Leu Gln
145                 150                 155                 160 gac ccc aga gtc agg ggt ctg tat ttt cct gct ggt ggc tcc agt tca     528
Asp Pro Arg Val Arg Gly Leu Tyr Phe Pro Ala Gly Gly Ser Ser Ser
                165                 170                 175 gga aca gta aac cct gct ccg aat att gcc tct cac atc tcg tca atc     576
Gly Thr Val Asn Pro Ala Pro Asn Ile Ala Ser His Ile Ser Ser Ile
        180                 185                 190 tcc gcg agg acc ggg gac cct gtg acg aac tcg cgg ccg caa ggc ggc     624
Ser Ala Arg Thr Gly Asp Pro Val Thr Asn Ser Arg Pro Gln Gly Gly
                195                 200                 205 gga tcc gtg gac aag aaa att gtg ccc agg gat tgt ggt tgt aag cct     672
Gly Ser Val Asp Lys Lys Ile Val Pro Arg Asp Cys Gly Cys Lys Pro
210                 215                 220 tgc ata tgt aca gtc cca gaa gta tca tct gtc ttc atc ttc ccc cca     720
Cys Ile Cys Thr Val Pro Glu Val Ser Ser Val Phe Ile Phe Pro Pro
225                 230                 235                 240 aag ccc aag gat gtg ctc acc att act ctg act cct aag gtc acg tgt     768
Lys Pro Lys Asp Val Leu Thr Ile Thr Leu Thr Pro Lys Val Thr Cys
                245                 250                 255 gtt gtg gta gac atc agc aag gat gat ccc gag gtc cag ttc agc tgg     816
Val Val Val Asp Ile Ser Lys Asp Asp Pro Glu Val Gln Phe Ser Trp
                260                 265                 270 ttt gta gat gat gtg gag gtg cac aca gct cag acg caa ccc cgg gag     864
Phe Val Asp Asp Val Glu Val His Thr Ala Gln Thr Gln Pro Arg Glu
            275                 280                 285 gag cag ttc aac agc act ttc cgc tca gtc agt gaa ctt ccc atc atg     912
Glu Gln Phe Asn Ser Thr Phe Arg Ser Val Ser Glu Leu Pro Ile Met
        290                 295                 300 cac cag gac tgg ctc aat ggc aag gag ttc aaa tgc agg gtc aac agt     960
His Gln Asp Trp Leu Asn Gly Lys Glu Phe Lys Cys Arg Val Asn Ser
305                 310                 315                 320 gca gct ttc cct gcc ccc atc gag aaa acc atc tcc aaa acc aaa ggc    1008
Ala Ala Phe Pro Ala Pro Ile Glu Lys Thr Ile Ser Lys Thr Lys Gly
                325                 330                 335 aga ccg aag gct cca cag gtg tac acc att cca cct ccc aag gag cag    1056
Arg Pro Lys Ala Pro Gln Val Tyr Thr Ile Pro Pro Pro Lys Glu Gln
                340                 345                 350 atg gcc aag gat aaa gtc agt ctg acc tgc atg ata aca gac ttc ttc    1104
Met Ala Lys Asp Lys Val Ser Leu Thr Cys Met Ile Thr Asp Phe Phe
                355                 360                 365 cct gaa gac att act gtg gag tgg cag tgg aat ggg cag cca gcg gag    1152
Pro Glu Asp Ile Thr Val Glu Trp Gln Trp Asn Gly Gln Pro Ala Glu
        370                 375                 380 aac tac aag aac act cag ccc atc atg gac aca gat ggc tct tac ttc    1200
Asn Tyr Lys Asn Thr Gln Pro Ile Met Asp Thr Asp Gly Ser Tyr Phe
385                 390                 395                 400 gtc tac agc aag ctc aat gtg cag aag agc aac tgg gag gca gga aat    1248
Val Tyr Ser Lys Leu Asn Val Gln Lys Ser Asn Trp Glu Ala Gly Asn
                405                 410                 415 act ttc acc tgc tct gtg tta cat gag ggc ctg cac aac cac cat act    1296
Thr Phe Thr Cys Ser Val Leu His Glu Gly Leu His Asn His His Thr
            420                 425                 430
```

-continued

```
gag aag agc ctc tcc cac tct cct ggg ctg caa agc ttg tcg aga agt      1344
Glu Lys Ser Leu Ser His Ser Pro Gly Leu Gln Ser Leu Ser Arg Ser
    435                 440                 445 act aga gga tca                                                       1356
Thr Arg Gly Ser
    450

<210> SEQ ID NO 32
<211> LENGTH: 452
<212> TYPE: PRT
<213> ORGANISM: Artificial
<220> FEATURE:
<223> OTHER INFORMATION: Synthetic Construct

<400> SEQUENCE: 32

Met Ser Tyr Tyr His His His His His His Asp Tyr Asp Ile Pro Thr
1               5                   10                  15

Thr Glu Asn Leu Tyr Phe Gln Gly Ala Met Asp Pro Met Lys Lys Trp
            20                  25                  30

Ser Ser Lys Pro Arg Lys Gly Met Gly Thr Asn Leu Ser Val Pro Asn
        35                  40                  45

Pro Leu Gly Phe Phe Pro Asp His Gln Leu Asp Pro Val Phe Gly Ala
    50                  55                  60

Asn Ser Asn Asn Pro Asp Trp Asp Phe Asn Pro Ile Lys Asp His Trp
65                  70                  75                  80

Pro Ala Ala Asn Gln Val Gly Val Gly Ala Phe Gly Pro Gly Phe Thr
                85                  90                  95

Pro Pro His Gly Gly Val Leu Gly Trp Ser Pro Gln Ala Gln Gly Met
            100                 105                 110

Leu Thr Pro Val Ser Thr Ile Pro Pro Ala Ser Ala Asn Arg Gln
        115                 120                 125

Ser Gly Arg Gln Pro Thr Pro Ile Ser Pro Pro Leu Arg Asp Ser His
    130                 135                 140

Pro Gln Ala Met Gln Trp Asn Ser Thr Ala Phe His Gln Ala Leu Gln
145                 150                 155                 160

Asp Pro Arg Val Arg Gly Leu Tyr Phe Pro Ala Gly Gly Ser Ser Ser
                165                 170                 175

Gly Thr Val Asn Pro Ala Pro Asn Ile Ala Ser His Ile Ser Ser Ile
            180                 185                 190

Ser Ala Arg Thr Gly Asp Pro Val Thr Asn Ser Arg Pro Gln Gly Gly
        195                 200                 205

Gly Ser Val Asp Lys Lys Ile Val Pro Arg Asp Cys Gly Cys Lys Pro
    210                 215                 220

Cys Ile Cys Thr Val Pro Glu Val Ser Ser Val Phe Ile Phe Pro Pro
225                 230                 235                 240

Lys Pro Lys Asp Val Leu Thr Ile Thr Leu Thr Pro Lys Val Thr Cys
                245                 250                 255

Val Val Val Asp Ile Ser Lys Asp Asp Pro Glu Val Gln Phe Ser Trp
            260                 265                 270

Phe Val Asp Asp Val Glu Val His Thr Ala Gln Thr Gln Pro Arg Glu
        275                 280                 285

Glu Gln Phe Asn Ser Thr Phe Arg Ser Val Ser Glu Leu Pro Ile Met
    290                 295                 300

His Gln Asp Trp Leu Asn Gly Lys Glu Phe Lys Cys Arg Val Asn Ser
305                 310                 315                 320

Ala Ala Phe Pro Ala Pro Ile Glu Lys Thr Ile Ser Lys Thr Lys Gly
                325                 330                 335
```

```
Arg Pro Lys Ala Pro Gln Val Tyr Thr Ile Pro Pro Lys Glu Gln
            340                 345                 350

Met Ala Lys Asp Lys Val Ser Leu Thr Cys Met Ile Thr Asp Phe Phe
        355                 360                 365

Pro Glu Asp Ile Thr Val Glu Trp Gln Trp Asn Gly Gln Pro Ala Glu
    370                 375                 380

Asn Tyr Lys Asn Thr Gln Pro Ile Met Asp Thr Asp Gly Ser Tyr Phe
385                 390                 395                 400

Val Tyr Ser Lys Leu Asn Val Gln Lys Ser Asn Trp Glu Ala Gly Asn
                405                 410                 415

Thr Phe Thr Cys Ser Val Leu His Glu Gly Leu His Asn His His Thr
            420                 425                 430

Glu Lys Ser Leu Ser His Ser Pro Gly Leu Gln Ser Leu Ser Arg Ser
        435                 440                 445

Thr Arg Gly Ser
    450

<210> SEQ ID NO 33
<211> LENGTH: 687
<212> TYPE: DNA
<213> ORGANISM: Hepatitis B virus
<220> FEATURE:
<221> NAME/KEY: CDS
<222> LOCATION: (1)..(687)

<400> SEQUENCE: 33 atg tcg tac tac cat cac cat cac cat cac gat tac gat atc cca acg      48
Met Ser Tyr Tyr His His His His His His Asp Tyr Asp Ile Pro Thr
1               5                   10                  15 acc gaa aac ctg tat ttt cag ggc gcc atg gat cct atg aaa aaa tgg     96
Thr Glu Asn Leu Tyr Phe Gln Gly Ala Met Asp Pro Met Lys Lys Trp
            20                  25                  30 tca tca aaa cct cgc aaa ggc atg ggg acg aat ctt tct gtt ccc aac     144
Ser Ser Lys Pro Arg Lys Gly Met Gly Thr Asn Leu Ser Val Pro Asn
        35                  40                  45 cct ctg gga ttc ttt ccc gat cat cag ttg gac cct gta ttc gga gcc     192
Pro Leu Gly Phe Phe Pro Asp His Gln Leu Asp Pro Val Phe Gly Ala
    50                  55                  60 aac tca aac aat cca gat tgg gac ttc aac ccc atc aag gac cac tgg     240
Asn Ser Asn Asn Pro Asp Trp Asp Phe Asn Pro Ile Lys Asp His Trp
65                  70                  75                  80 cca gca gcc aac cag gta gga gtg gga gca ttc ggg cca ggg ttc acc     288
Pro Ala Ala Asn Gln Val Gly Val Gly Ala Phe Gly Pro Gly Phe Thr
                85                  90                  95 cct cca cac ggc ggt gtt ttg ggg tgg agc cct cag gct cag ggc atg     336
Pro Pro His Gly Gly Val Leu Gly Trp Ser Pro Gln Ala Gln Gly Met
            100                 105                 110 ttg acc cca gtg tca aca att cct cct cct gcc tcc gcc aat cgg cag     384
Leu Thr Pro Val Ser Thr Ile Pro Pro Pro Ala Ser Ala Asn Arg Gln
        115                 120                 125 tca gga agg cag cct act ccc atc tct cca cct cta aga gac agt cat     432
Ser Gly Arg Gln Pro Thr Pro Ile Ser Pro Pro Leu Arg Asp Ser His
    130                 135                 140 cct cag gcc atg cag tgg aat tcc act gcc ttc cac caa gct ctg caa     480
Pro Gln Ala Met Gln Trp Asn Ser Thr Ala Phe His Gln Ala Leu Gln
145                 150                 155                 160 gac ccc aga gtc agg ggt ctg tat ttt cct gct ggt ggc tcc agt tca     528
Asp Pro Arg Val Arg Gly Leu Tyr Phe Pro Ala Gly Gly Ser Ser Ser
                165                 170                 175
```

```
gga aca gta aac cct gct ccg aat att gcc tct cac atc tcg tca atc    576
Gly Thr Val Asn Pro Ala Pro Asn Ile Ala Ser His Ile Ser Ser Ile
            180                 185                 190 tcc gcg agg acc ggg gac cct gtg acg aac tcg cgg ccg ctt tcg aat    624
Ser Ala Arg Thr Gly Asp Pro Val Thr Asn Ser Arg Pro Leu Ser Asn
        195                 200                 205 cta gag cct gca gta tcg agg cat gcg gta cca agc ttg tcg aga agt    672
Leu Glu Pro Ala Val Ser Arg His Ala Val Pro Ser Leu Ser Arg Ser
210                 215                 220 act aga gga tca taa                                                687
Thr Arg Gly Ser
225

<210> SEQ ID NO 34
<211> LENGTH: 228
<212> TYPE: PRT
<213> ORGANISM: Hepatitis B virus

<400> SEQUENCE: 34

Met Ser Tyr Tyr His His His His Asp Tyr Asp Ile Pro Thr
1               5                   10                  15

Thr Glu Asn Leu Tyr Phe Gln Gly Ala Met Asp Pro Met Lys Lys Trp
            20                  25                  30

Ser Ser Lys Pro Arg Lys Gly Met Gly Thr Asn Leu Ser Val Pro Asn
        35                  40                  45

Pro Leu Gly Phe Phe Pro Asp His Gln Leu Asp Pro Val Phe Gly Ala
    50                  55                  60

Asn Ser Asn Asn Pro Asp Trp Asp Phe Asn Pro Ile Lys Asp His Trp
65                  70                  75                  80

Pro Ala Ala Asn Gln Val Gly Val Gly Ala Phe Gly Pro Gly Phe Thr
                85                  90                  95

Pro Pro His Gly Gly Val Leu Gly Trp Ser Pro Gln Ala Gln Gly Met
            100                 105                 110

Leu Thr Pro Val Ser Thr Ile Pro Pro Pro Ala Ser Ala Asn Arg Gln
        115                 120                 125

Ser Gly Arg Gln Pro Thr Pro Ile Ser Pro Pro Leu Arg Asp Ser His
    130                 135                 140

Pro Gln Ala Met Gln Trp Asn Ser Thr Ala Phe His Gln Ala Leu Gln
145                 150                 155                 160

Asp Pro Arg Val Arg Gly Leu Tyr Phe Pro Ala Gly Gly Ser Ser Ser
                165                 170                 175

Gly Thr Val Asn Pro Ala Pro Asn Ile Ala Ser His Ile Ser Ser Ile
            180                 185                 190

Ser Ala Arg Thr Gly Asp Pro Val Thr Asn Ser Arg Pro Leu Ser Asn
        195                 200                 205

Leu Glu Pro Ala Val Ser Arg His Ala Val Pro Ser Leu Ser Arg Ser
    210                 215                 220

Thr Arg Gly Ser
225

<210> SEQ ID NO 35
<211> LENGTH: 1365
<212> TYPE: DNA
<213> ORGANISM: Hepatitis B virus
<220> FEATURE:
<221> NAME/KEY: CDS
<222> LOCATION: (1)..(1365)

<400> SEQUENCE: 35
```

```
atg tcg tac tac cat cac cat cac cat cac gat tac gat atc cca acg    48
Met Ser Tyr Tyr His His His His His His Asp Tyr Asp Ile Pro Thr
1               5                   10                  15 acc gaa aac ctg tat ttt cag ggc gcc atg gat cct atg gga ggt tgg    96
Thr Glu Asn Leu Tyr Phe Gln Gly Ala Met Asp Pro Met Gly Gly Trp
            20                  25                  30 tca tca aaa cct cgc aaa ggc atg ggg acg aat ctt tct gtt ccc aac   144
Ser Ser Lys Pro Arg Lys Gly Met Gly Thr Asn Leu Ser Val Pro Asn
        35                  40                  45 cct ctg gga ttc ttt ccc gat cat cag ttg gac cct gta ttc gga gcc   192
Pro Leu Gly Phe Phe Pro Asp His Gln Leu Asp Pro Val Phe Gly Ala
    50                  55                  60 aac tca aac aat cca gat tgg gac ttc aac ccc atc aag gac cac tgg   240
Asn Ser Asn Asn Pro Asp Trp Asp Phe Asn Pro Ile Lys Asp His Trp
65                  70                  75                  80 cca gca gcc aac cag gta gga gtg gga gca ttc ggg cca ggg ttc acc   288
Pro Ala Ala Asn Gln Val Gly Val Gly Ala Phe Gly Pro Gly Phe Thr
                85                  90                  95 cct cca cac ggc ggt gtt ttg ggg tgg agc cct cag gct cag ggc atg   336
Pro Pro His Gly Gly Val Leu Gly Trp Ser Pro Gln Ala Gln Gly Met
            100                 105                 110 ttg acc cca gtg tca aca att cct cct cct gcc tcc gcc aat cgg cag   384
Leu Thr Pro Val Ser Thr Ile Pro Pro Pro Ala Ser Ala Asn Arg Gln
        115                 120                 125 tca gga agg cag cct act ccc atc tct cca cct cta aga gac agt cat   432
Ser Gly Arg Gln Pro Thr Pro Ile Ser Pro Pro Leu Arg Asp Ser His
    130                 135                 140 cct cag gcc atg cag tgg aat tcc act gcc ttc cac caa gct ctg caa   480
Pro Gln Ala Met Gln Trp Asn Ser Thr Ala Phe His Gln Ala Leu Gln
145                 150                 155                 160 gac ccc aga gtc agg ggt ctg tat ttt cct gct ggt ggc tcc agt tca   528
Asp Pro Arg Val Arg Gly Leu Tyr Phe Pro Ala Gly Gly Ser Ser Ser
                165                 170                 175 gga aca gta aac cct gct ccg aat att gcc tct cac atc tcg tca atc   576
Gly Thr Val Asn Pro Ala Pro Asn Ile Ala Ser His Ile Ser Ser Ile
            180                 185                 190 tcc gcg agg act ggg gac cct gtg acg aac atg gag aac atc aca tca   624
Ser Ala Arg Thr Gly Asp Pro Val Thr Asn Met Glu Asn Ile Thr Ser
        195                 200                 205 gga ttc cta gga ccc ctc ctc gtg tta cag gcg ggg ttt ttc ttg ttg   672
Gly Phe Leu Gly Pro Leu Leu Val Leu Gln Ala Gly Phe Phe Leu Leu
    210                 215                 220 aca aga atc ctc aca ata ccg cag agt cta gac tcg tgg tgg act tct   720
Thr Arg Ile Leu Thr Ile Pro Gln Ser Leu Asp Ser Trp Trp Thr Ser
225                 230                 235                 240 ctc aat ttt cta ggg gga tca ccc gtg tgt ctt ggc caa aat tcg cag   768
Leu Asn Phe Leu Gly Gly Ser Pro Val Cys Leu Gly Gln Asn Ser Gln
                245                 250                 255 tcc cca acc tcc aat cac tca cca acc tcc tgt cct cca att tgt cct   816
Ser Pro Thr Ser Asn His Ser Pro Thr Ser Cys Pro Pro Ile Cys Pro
            260                 265                 270 ggt tat cgc tgg atg tgt ctg cgg cgt ttt atc ata ttc ctc ttc atc   864
Gly Tyr Arg Trp Met Cys Leu Arg Arg Phe Ile Ile Phe Leu Phe Ile
        275                 280                 285 ctg ctg cta tgc ctc atc ttc tta ttg gtt ctt ctg gat tat caa ggt   912
Leu Leu Leu Cys Leu Ile Phe Leu Leu Val Leu Leu Asp Tyr Gln Gly
    290                 295                 300 atg ttg ccc gtt tgt cct cta att cca gga tca aca aca acc agt acg   960
Met Leu Pro Val Cys Pro Leu Ile Pro Gly Ser Thr Thr Thr Ser Thr
305                 310                 315                 320
```

```
gga cca tgc aaa acc tgc acg act cct gct caa ggc aac tct atg ttt    1008
Gly Pro Cys Lys Thr Cys Thr Thr Pro Ala Gln Gly Asn Ser Met Phe
            325                 330                 335 ccc tca tgt tgc tgt aca aaa cct acg gat gga aat tgc acc tgt att    1056
Pro Ser Cys Cys Cys Thr Lys Pro Thr Asp Gly Asn Cys Thr Cys Ile
        340                 345                 350 ccc atc cca tcg tct tgg gct ttc gca aaa tac cta tgg gag tgg gcc    1104
Pro Ile Pro Ser Ser Trp Ala Phe Ala Lys Tyr Leu Trp Glu Trp Ala
            355                 360                 365 tca gtc cgt ttc tct tgg ctc agt tta cta gtg cca ttt gtt cag tgg    1152
Ser Val Arg Phe Ser Trp Leu Ser Leu Leu Val Pro Phe Val Gln Trp
        370                 375                 380 ttc gta ggg ctt tcc ccc act gtt tgg ctt tca gct ata tgg atg atg    1200
Phe Val Gly Leu Ser Pro Thr Val Trp Leu Ser Ala Ile Trp Met Met
385                 390                 395                 400 tgg tat tgg ggg cca agt ctg tac agc atc gtg agt ccc ttt ata ccg    1248
Trp Tyr Trp Gly Pro Ser Leu Tyr Ser Ile Val Ser Pro Phe Ile Pro
                405                 410                 415 ctg tta cca att ttc ttt tgt ctc tgg gta tac att tcg cgg ccg ctt    1296
Leu Leu Pro Ile Phe Phe Cys Leu Trp Val Tyr Ile Ser Arg Pro Leu
            420                 425                 430 tcg aat cta gag cct gca gtc tcg agg cat gcg gta cca agc ttg tcg    1344
Ser Asn Leu Glu Pro Ala Val Ser Arg His Ala Val Pro Ser Leu Ser
        435                 440                 445 aga agt act aga gga tca taa                                        1365
Arg Ser Thr Arg Gly Ser
    450
```

<210> SEQ ID NO 36
<211> LENGTH: 454
<212> TYPE: PRT
<213> ORGANISM: Hepatitis B virus

<400> SEQUENCE: 36

```
Met Ser Tyr Tyr His His His His His Asp Tyr Asp Ile Pro Thr
1               5                   10                  15

Thr Glu Asn Leu Tyr Phe Gln Gly Ala Met Asp Pro Met Gly Gly Trp
            20                  25                  30

Ser Ser Lys Pro Arg Lys Gly Met Gly Thr Asn Leu Ser Val Pro Asn
        35                  40                  45

Pro Leu Gly Phe Phe Pro Asp His Gln Leu Asp Pro Val Phe Gly Ala
    50                  55                  60

Asn Ser Asn Asn Pro Asp Trp Asp Phe Asn Pro Ile Lys Asp His Trp
65                  70                  75                  80

Pro Ala Ala Asn Gln Val Gly Val Gly Ala Phe Gly Pro Gly Phe Thr
                85                  90                  95

Pro Pro His Gly Gly Val Leu Gly Trp Ser Pro Gln Ala Gln Gly Met
            100                 105                 110

Leu Thr Pro Val Ser Thr Ile Pro Pro Ala Ser Ala Asn Arg Gln
        115                 120                 125

Ser Gly Arg Gln Pro Thr Pro Ile Ser Pro Pro Leu Arg Asp Ser His
    130                 135                 140

Pro Gln Ala Met Gln Trp Asn Ser Thr Ala Phe His Gln Ala Leu Gln
145                 150                 155                 160

Asp Pro Arg Val Arg Gly Leu Tyr Phe Pro Ala Gly Gly Ser Ser Ser
                165                 170                 175

Gly Thr Val Asn Pro Ala Pro Asn Ile Ala Ser His Ile Ser Ser Ile
            180                 185                 190
```

-continued

```
Ser Ala Arg Thr Gly Asp Pro Val Thr Asn Met Glu Asn Ile Thr Ser
        195                 200                 205

Gly Phe Leu Gly Pro Leu Leu Val Leu Gln Ala Gly Phe Phe Leu Leu
    210                 215                 220

Thr Arg Ile Leu Thr Ile Pro Gln Ser Leu Asp Ser Trp Trp Thr Ser
225                 230                 235                 240

Leu Asn Phe Leu Gly Gly Ser Pro Val Cys Leu Gly Gln Asn Ser Gln
                245                 250                 255

Ser Pro Thr Ser Asn His Ser Pro Thr Ser Cys Pro Pro Ile Cys Pro
            260                 265                 270

Gly Tyr Arg Trp Met Cys Leu Arg Arg Phe Ile Ile Phe Leu Phe Ile
        275                 280                 285

Leu Leu Leu Cys Leu Ile Phe Leu Leu Val Leu Leu Asp Tyr Gln Gly
    290                 295                 300

Met Leu Pro Val Cys Pro Leu Ile Pro Gly Ser Thr Thr Thr Ser Thr
305                 310                 315                 320

Gly Pro Cys Lys Thr Cys Thr Thr Pro Ala Gln Gly Asn Ser Met Phe
                325                 330                 335

Pro Ser Cys Cys Cys Thr Lys Pro Thr Asp Gly Asn Cys Thr Cys Ile
            340                 345                 350

Pro Ile Pro Ser Ser Trp Ala Phe Ala Lys Tyr Leu Trp Glu Trp Ala
        355                 360                 365

Ser Val Arg Phe Ser Trp Leu Ser Leu Leu Val Pro Phe Val Gln Trp
    370                 375                 380

Phe Val Gly Leu Ser Pro Thr Val Trp Leu Ser Ala Ile Trp Met Met
385                 390                 395                 400

Trp Tyr Trp Gly Pro Ser Leu Tyr Ser Ile Val Ser Pro Phe Ile Pro
                405                 410                 415

Leu Leu Pro Ile Phe Phe Cys Leu Trp Val Tyr Ile Ser Arg Pro Leu
            420                 425                 430

Ser Asn Leu Glu Pro Ala Val Ser Arg His Ala Val Pro Ser Leu Ser
        435                 440                 445

Arg Ser Thr Arg Gly Ser
    450
```

<210> SEQ ID NO 37
<211> LENGTH: 1380
<212> TYPE: DNA
<213> ORGANISM: Artificial
<220> FEATURE:
<223> OTHER INFORMATION: Hepatitis B virus plus murine
<220> FEATURE:
<221> NAME/KEY: CDS
<222> LOCATION: (1)..(1380)

<400> SEQUENCE: 37

```
atg tcg tac tac cat cac cat cac cat cac gat tac gat atc cca acg     48
Met Ser Tyr Tyr His His His His His His Asp Tyr Asp Ile Pro Thr
1               5                   10                  15 acc gaa aac ctg tat ttt cag ggc gcc atg gac att gac cct tat aaa     96
Thr Glu Asn Leu Tyr Phe Gln Gly Ala Met Asp Ile Asp Pro Tyr Lys
            20                  25                  30 gaa ttt gga gct act gtg gag tta ctc tcg ttt ttg cct tct gac ttc    144
Glu Phe Gly Ala Thr Val Glu Leu Leu Ser Phe Leu Pro Ser Asp Phe
        35                  40                  45 ttt cct tcc gtc aga gat ctc cta gac acc gcc tcg gct ctg tat cgg    192
Phe Pro Ser Val Arg Asp Leu Leu Asp Thr Ala Ser Ala Leu Tyr Arg
    50                  55                  60
```

```
gaa gcc tta gag tct cct gag cat tgc tca cct cac cat acc gca ctc      240
Glu Ala Leu Glu Ser Pro Glu His Cys Ser Pro His His Thr Ala Leu
 65                  70                  75                  80 agg caa gcc att ctc tgc tgg ggg gaa ttg atg act cta gct acc tgg      288
Arg Gln Ala Ile Leu Cys Trp Gly Glu Leu Met Thr Leu Ala Thr Trp
                 85                  90                  95 gtg ggt aat aat ttg gaa gat cca gca tcc agg gat cta gta gtc aat      336
Val Gly Asn Asn Leu Glu Asp Pro Ala Ser Arg Asp Leu Val Val Asn
100                 105                 110 tat gtt aat act aac atg gga tta aag atc agg caa ctc ttg tgg ttt      384
Tyr Val Asn Thr Asn Met Gly Leu Lys Ile Arg Gln Leu Leu Trp Phe
            115                 120                 125 cat atc tct tgc ctt act ttt gga aga gaa act gta ctt gaa tat ttg      432
His Ile Ser Cys Leu Thr Phe Gly Arg Glu Thr Val Leu Glu Tyr Leu
130                 135                 140 gtc tct ttc gga gtg tgg att cgc act cct cca gcc tat aga cca cca      480
Val Ser Phe Gly Val Trp Ile Arg Thr Pro Pro Ala Tyr Arg Pro Pro
145                 150                 155                 160 aat gcc cct atc tta tca aca ctt ccg gaa act act gtt gtt aga cga      528
Asn Ala Pro Ile Leu Ser Thr Leu Pro Glu Thr Thr Val Val Arg Arg
                165                 170                 175 cgg gac cga ggc agg tcc cct aga aga aga act ccc tcg cct cgc aga      576
Arg Asp Arg Gly Arg Ser Pro Arg Arg Arg Thr Pro Ser Pro Arg Arg
            180                 185                 190 cgc aga tct caa tcg ccg cgt cgc aga aga tct caa tct cgg gaa tct      624
Arg Arg Ser Gln Ser Pro Arg Arg Arg Ser Gln Ser Arg Glu Ser
        195                 200                 205 caa tgt tcg cgg ccg caa ggc ggc gga tcc gtg gac aag aaa att gtg      672
Gln Cys Ser Arg Pro Gln Gly Gly Gly Ser Val Asp Lys Lys Ile Val
210                 215                 220 ccc agg gat tgt ggt tgt aag cct tgc ata tgt aca gtc cca gaa gta      720
Pro Arg Asp Cys Gly Cys Lys Pro Cys Ile Cys Thr Val Pro Glu Val
225                 230                 235                 240 tca tct gtc ttc atc ttc ccc cca aag ccc aag gat gtg ctc acc att      768
Ser Ser Val Phe Ile Phe Pro Pro Lys Pro Lys Asp Val Leu Thr Ile
                245                 250                 255 act ctg act cct aag gtc acg tgt gtt gtg gta gac atc agc aag gat      816
Thr Leu Thr Pro Lys Val Thr Cys Val Val Val Asp Ile Ser Lys Asp
            260                 265                 270 gat ccc gag gtc cag ttc agc tgg ttt gta gat gat gtg gag gtg cac      864
Asp Pro Glu Val Gln Phe Ser Trp Phe Val Asp Asp Val Glu Val His
        275                 280                 285 aca gct cag acg caa ccc cgg gag gag cag ttc aac agc act ttc cgc      912
Thr Ala Gln Thr Gln Pro Arg Glu Glu Gln Phe Asn Ser Thr Phe Arg
290                 295                 300 tca gtc agt gaa ctt ccc atc atg cac cag gac tgg ctc aat ggc aag      960
Ser Val Ser Glu Leu Pro Ile Met His Gln Asp Trp Leu Asn Gly Lys
305                 310                 315                 320 gag ttc aaa tgc agg gtc aac agt gca gct ttc cct gcc ccc atc gag     1008
Glu Phe Lys Cys Arg Val Asn Ser Ala Ala Phe Pro Ala Pro Ile Glu
                325                 330                 335 aaa acc atc tcc aaa acc aaa ggc aga ccg aag gct cca cag gtg tac     1056
Lys Thr Ile Ser Lys Thr Lys Gly Arg Pro Lys Ala Pro Gln Val Tyr
            340                 345                 350 acc att cca cct ccc aag gag cag atg gcc aag gat aaa gtc agt ctg     1104
Thr Ile Pro Pro Pro Lys Glu Gln Met Ala Lys Asp Lys Val Ser Leu
        355                 360                 365 acc tgc atg ata aca gac ttc ttc cct gaa gac att act gtg gag tgg     1152
Thr Cys Met Ile Thr Asp Phe Phe Pro Glu Asp Ile Thr Val Glu Trp
370                 375                 380
```

```
cag tgg aat ggg cag cca gcg gag aac tac aag aac act cag ccc atc    1200
Gln Trp Asn Gly Gln Pro Ala Glu Asn Tyr Lys Asn Thr Gln Pro Ile
385                 390                 395                 400 atg gac aca gat ggc tct tac ttc gtc tac agc aag ctc aat gtg cag    1248
Met Asp Thr Asp Gly Ser Tyr Phe Val Tyr Ser Lys Leu Asn Val Gln
                405                 410                 415 aag agc aac tgg gag gca gga aat act ttc acc tgc tct gtg tta cat    1296
Lys Ser Asn Trp Glu Ala Gly Asn Thr Phe Thr Cys Ser Val Leu His
            420                 425                 430 gag ggc ctg cac aac cac cat act gag aag agc ctc tcc cac tct cct    1344
Glu Gly Leu His Asn His His Thr Glu Lys Ser Leu Ser His Ser Pro
        435                 440                 445 ggg ctg caa agc ttg tcg aga agt act aga gga tca                    1380
Gly Leu Gln Ser Leu Ser Arg Ser Thr Arg Gly Ser
    450                 455                 460

<210> SEQ ID NO 38
<211> LENGTH: 460
<212> TYPE: PRT
<213> ORGANISM: Artificial
<220> FEATURE:
<223> OTHER INFORMATION: Synthetic Construct

<400> SEQUENCE: 38

Met Ser Tyr Tyr His His His His His His Asp Tyr Asp Ile Pro Thr
1               5                   10                  15

Thr Glu Asn Leu Tyr Phe Gln Gly Ala Met Asp Ile Asp Pro Tyr Lys
            20                  25                  30

Glu Phe Gly Ala Thr Val Glu Leu Leu Ser Phe Leu Pro Ser Asp Phe
        35                  40                  45

Phe Pro Ser Val Arg Asp Leu Leu Asp Thr Ala Ser Ala Leu Tyr Arg
    50                  55                  60

Glu Ala Leu Glu Ser Pro Glu His Cys Ser Pro His His Thr Ala Leu
65                  70                  75                  80

Arg Gln Ala Ile Leu Cys Trp Gly Glu Leu Met Thr Leu Ala Thr Trp
                85                  90                  95

Val Gly Asn Asn Leu Glu Asp Pro Ala Ser Arg Asp Leu Val Val Asn
            100                 105                 110

Tyr Val Asn Thr Asn Met Gly Leu Lys Ile Arg Gln Leu Leu Trp Phe
        115                 120                 125

His Ile Ser Cys Leu Thr Phe Gly Arg Glu Thr Val Leu Glu Tyr Leu
    130                 135                 140

Val Ser Phe Gly Val Trp Ile Arg Thr Pro Pro Ala Tyr Arg Pro Pro
145                 150                 155                 160

Asn Ala Pro Ile Leu Ser Thr Leu Pro Glu Thr Thr Val Val Arg Arg
                165                 170                 175

Arg Asp Arg Gly Arg Ser Pro Arg Arg Arg Thr Pro Ser Pro Arg Arg
            180                 185                 190

Arg Arg Ser Gln Ser Pro Arg Arg Arg Arg Ser Gln Ser Arg Glu Ser
        195                 200                 205

Gln Cys Ser Arg Pro Gln Gly Gly Gly Ser Val Asp Lys Lys Ile Val
    210                 215                 220

Pro Arg Asp Cys Gly Cys Lys Pro Cys Ile Cys Thr Val Pro Glu Val
225                 230                 235                 240

Ser Ser Val Phe Ile Phe Pro Pro Lys Pro Lys Asp Val Leu Thr Ile
                245                 250                 255

Thr Leu Thr Pro Lys Val Thr Cys Val Val Val Asp Ile Ser Lys Asp
            260                 265                 270
```

```
Asp Pro Glu Val Gln Phe Ser Trp Phe Val Asp Asp Val Glu Val His
        275                 280                 285
Thr Ala Gln Thr Gln Pro Arg Glu Glu Gln Phe Asn Ser Thr Phe Arg
    290                 295                 300
Ser Val Ser Glu Leu Pro Ile Met His Gln Asp Trp Leu Asn Gly Lys
305                 310                 315                 320
Glu Phe Lys Cys Arg Val Asn Ser Ala Ala Phe Pro Ala Pro Ile Glu
                325                 330                 335
Lys Thr Ile Ser Lys Thr Lys Gly Arg Pro Lys Ala Pro Gln Val Tyr
            340                 345                 350
Thr Ile Pro Pro Pro Lys Glu Gln Met Ala Lys Asp Lys Val Ser Leu
        355                 360                 365
Thr Cys Met Ile Thr Asp Phe Phe Pro Glu Asp Ile Thr Val Glu Trp
    370                 375                 380
Gln Trp Asn Gly Gln Pro Ala Glu Asn Tyr Lys Asn Thr Gln Pro Ile
385                 390                 395                 400
Met Asp Thr Asp Gly Ser Tyr Phe Val Tyr Ser Lys Leu Asn Val Gln
                405                 410                 415
Lys Ser Asn Trp Glu Ala Gly Asn Thr Phe Thr Cys Ser Val Leu His
            420                 425                 430
Glu Gly Leu His Asn His His Thr Glu Lys Ser Leu Ser His Ser Pro
        435                 440                 445
Gly Leu Gln Ser Leu Ser Arg Ser Thr Arg Gly Ser
    450                 455                 460

<210> SEQ ID NO 39
<211> LENGTH: 708
<212> TYPE: DNA
<213> ORGANISM: Hepatitis B virus
<220> FEATURE:
<221> NAME/KEY: CDS
<222> LOCATION: (1)..(708)

<400> SEQUENCE: 39 atg tcg tac tac cat cac cat cac cac gat tac gat atc cca acg      48
Met Ser Tyr Tyr His His His His His Asp Tyr Asp Ile Pro Thr
1               5                   10                  15 acc gaa aac ctg tat ttt cag ggc gcc atg gac att gac cct tat aaa  96
Thr Glu Asn Leu Tyr Phe Gln Gly Ala Met Asp Ile Asp Pro Tyr Lys
            20                  25                  30 gaa ttt gga gct act gtg gag tta ctc tcg ttt ttg cct tct gac ttc  144
Glu Phe Gly Ala Thr Val Glu Leu Leu Ser Phe Leu Pro Ser Asp Phe
        35                  40                  45 ttt cct tcc gtc aga gat ctc cta gac acc gcc tcg gct ctg tat cgg  192
Phe Pro Ser Val Arg Asp Leu Leu Asp Thr Ala Ser Ala Leu Tyr Arg
    50                  55                  60 gaa gcc tta gag tct cct gag cat tgc tca cct cac cat acc gca ctc  240
Glu Ala Leu Glu Ser Pro Glu His Cys Ser Pro His His Thr Ala Leu
65                  70                  75                  80 agg caa gcc att ctc tgc tgg ggg gaa ttg atg act cta gct acc tgg  288
Arg Gln Ala Ile Leu Cys Trp Gly Glu Leu Met Thr Leu Ala Thr Trp
                85                  90                  95 gtg ggt aat aat ttg gaa gat cca gca tcc agg gat cta gta gtc aat  336
Val Gly Asn Asn Leu Glu Asp Pro Ala Ser Arg Asp Leu Val Val Asn
            100                 105                 110 tat gtt aat act aac atg gga tta aag atc agg caa ctc ttg tgg ttt  384
Tyr Val Asn Thr Asn Met Gly Leu Lys Ile Arg Gln Leu Leu Trp Phe
        115                 120                 125
```

```
cat atc tct tgc ctt act ttt gga aga gaa act gta ctt gaa tat ttg      432
His Ile Ser Cys Leu Thr Phe Gly Arg Glu Thr Val Leu Glu Tyr Leu
    130                 135                 140 gtc tct ttc gga gtg tgg att cgc act cct cca gcc tat aga cca cca      480
Val Ser Phe Gly Val Trp Ile Arg Thr Pro Pro Ala Tyr Arg Pro Pro
145                 150                 155                 160 aat gcc cct atc tta tca aca ctt ccg gaa act act gtt gtt aga cga      528
Asn Ala Pro Ile Leu Ser Thr Leu Pro Glu Thr Thr Val Val Arg Arg
                165                 170                 175 cgg gac cga ggc agg tcc cct aga aga aga act ccc tcg cct cgc aga      576
Arg Asp Arg Gly Arg Ser Pro Arg Arg Arg Thr Pro Ser Pro Arg Arg
            180                 185                 190 cgc aga tct caa tcg ccg cgt cgc aga aga tct caa tct cgg gaa tct      624
Arg Arg Ser Gln Ser Pro Arg Arg Arg Ser Gln Ser Arg Glu Ser
        195                 200                 205 caa tgt tcg cgg ccg ctt tcg aat cta gag cct gca gtc tcg agg cat      672
Gln Cys Ser Arg Pro Leu Ser Asn Leu Glu Pro Ala Val Ser Arg His
    210                 215                 220 gcg gta cca agc ttg tcg aga agt act aga gga tca                      708
Ala Val Pro Ser Leu Ser Arg Ser Thr Arg Gly Ser
225                 230                 235

<210> SEQ ID NO 40
<211> LENGTH: 236
<212> TYPE: PRT
<213> ORGANISM: Hepatitis B virus

<400> SEQUENCE: 40

Met Ser Tyr Tyr His His His His His Asp Tyr Asp Ile Pro Thr
1               5                   10                  15

Thr Glu Asn Leu Tyr Phe Gln Gly Ala Met Asp Ile Asp Pro Tyr Lys
                20                  25                  30

Glu Phe Gly Ala Thr Val Glu Leu Leu Ser Phe Leu Pro Ser Asp Phe
            35                  40                  45

Phe Pro Ser Val Arg Asp Leu Leu Asp Thr Ala Ser Ala Leu Tyr Arg
        50                  55                  60

Glu Ala Leu Glu Ser Pro Glu His Cys Ser Pro His His Thr Ala Leu
65                  70                  75                  80

Arg Gln Ala Ile Leu Cys Trp Gly Glu Leu Met Thr Leu Ala Thr Trp
                85                  90                  95

Val Gly Asn Asn Leu Glu Asp Pro Ala Ser Arg Asp Leu Val Val Asn
            100                 105                 110

Tyr Val Asn Thr Asn Met Gly Leu Lys Ile Arg Gln Leu Leu Trp Phe
        115                 120                 125

His Ile Ser Cys Leu Thr Phe Gly Arg Glu Thr Val Leu Glu Tyr Leu
    130                 135                 140

Val Ser Phe Gly Val Trp Ile Arg Thr Pro Pro Ala Tyr Arg Pro Pro
145                 150                 155                 160

Asn Ala Pro Ile Leu Ser Thr Leu Pro Glu Thr Thr Val Val Arg Arg
                165                 170                 175

Arg Asp Arg Gly Arg Ser Pro Arg Arg Arg Thr Pro Ser Pro Arg Arg
            180                 185                 190

Arg Arg Ser Gln Ser Pro Arg Arg Arg Ser Gln Ser Arg Glu Ser
        195                 200                 205

Gln Cys Ser Arg Pro Leu Ser Asn Leu Glu Pro Ala Val Ser Arg His
    210                 215                 220

Ala Val Pro Ser Leu Ser Arg Ser Thr Arg Gly Ser
225                 230                 235
```

<210> SEQ ID NO 41
<211> LENGTH: 1326
<212> TYPE: DNA
<213> ORGANISM: Artificial
<220> FEATURE:
<223> OTHER INFORMATION: Duck hepatitis B virus plus murine
<220> FEATURE:
<221> NAME/KEY: CDS
<222> LOCATION: (1)..(1326)

<400> SEQUENCE: 41

| | | | | | | | | | | | | | | | |
|---|---|---|---|---|---|---|---|---|---|---|---|---|---|---|---|
| atg | tcg | tac | tac | cat | cac | cat | cac | cat | cac | gat | tac | gat | atc | cca acg | 48 |
| Met | Ser | Tyr | Tyr | His | His | His | His | His | His | Asp | Tyr | Asp | Ile | Pro Thr | |
| 1 | | | | 5 | | | | | 10 | | | | | 15 | |
| acc | gaa | aac | ctg | tat | ttt | cag | ggc | gcc | atg | gat | ccg | gaa | ttc | atg ggg | 96 |
| Thr | Glu | Asn | Leu | Tyr | Phe | Gln | Gly | Ala | Met | Asp | Pro | Glu | Phe | Met Gly | |
| | | | 20 | | | | | 25 | | | | | 30 | | |
| caa | cat | cca | gca | aaa | tca | atg | gac | gtc | aga | cgg | ata | gaa | gga | gga gaa | 144 |
| Gln | His | Pro | Ala | Lys | Ser | Met | Asp | Val | Arg | Arg | Ile | Glu | Gly | Gly Glu | |
| | | 35 | | | | | 40 | | | | | 45 | | | |
| ata | ctg | tta | aac | caa | ctt | gcc | gga | agg | atg | atc | cca | aaa | ggg | act ttg | 192 |
| Ile | Leu | Leu | Asn | Gln | Leu | Ala | Gly | Arg | Met | Ile | Pro | Lys | Gly | Thr Leu | |
| | 50 | | | | | 55 | | | | | 60 | | | | |
| aca | tgg | tca | ggc | aag | ttt | cca | aca | cta | gat | cac | gtg | tta | gac | cat gtg | 240 |
| Thr | Trp | Ser | Gly | Lys | Phe | Pro | Thr | Leu | Asp | His | Val | Leu | Asp | His Val | |
| 65 | | | | | 70 | | | | | 75 | | | | | 80 |
| caa | aca | atg | gag | gag | ata | aac | acc | ctc | cag | aat | cag | gga | gct | tgg cct | 288 |
| Gln | Thr | Met | Glu | Glu | Ile | Asn | Thr | Leu | Gln | Asn | Gln | Gly | Ala | Trp Pro | |
| | | | | 85 | | | | | 90 | | | | | 95 | |
| gct | ggg | gcg | gga | agg | aga | gta | gga | tta | tca | aat | ccg | act | cct | caa gag | 336 |
| Ala | Gly | Ala | Gly | Arg | Arg | Val | Gly | Leu | Ser | Asn | Pro | Thr | Pro | Gln Glu | |
| | | | 100 | | | | | 105 | | | | | 110 | | |
| att | cct | cag | ccc | cag | tgg | act | ccc | gag | gaa | gac | caa | aaa | gca | cgc gaa | 384 |
| Ile | Pro | Gln | Pro | Gln | Trp | Thr | Pro | Glu | Glu | Asp | Gln | Lys | Ala | Arg Glu | |
| | | 115 | | | | | 120 | | | | | 125 | | | |
| gct | ttt | cgc | cgt | tat | caa | gaa | gaa | aga | cca | ccg | gaa | acc | acc | acc att | 432 |
| Ala | Phe | Arg | Arg | Tyr | Gln | Glu | Glu | Arg | Pro | Pro | Glu | Thr | Thr | Thr Ile | |
| | 130 | | | | | 135 | | | | | 140 | | | | |
| cct | ccg | tct | tcc | cct | cct | cag | tgg | aag | cta | caa | ccc | ggg | gac | gat cca | 480 |
| Pro | Pro | Ser | Ser | Pro | Pro | Gln | Trp | Lys | Leu | Gln | Pro | Gly | Asp | Asp Pro | |
| 145 | | | | | 150 | | | | | 155 | | | | | 160 |
| ctc | ctg | gga | aat | cag | tct | ctc | ctc | gag | act | cat | ccg | cta | tac | cag tca | 528 |
| Leu | Leu | Gly | Asn | Gln | Ser | Leu | Leu | Glu | Thr | His | Pro | Leu | Tyr | Gln Ser | |
| | | | | 165 | | | | | 170 | | | | | 175 | |
| gaa | cca | gcg | gtg | cca | gtg | ata | aaa | act | ccc | ccc | ttg | aag | aag | aaa acg | 576 |
| Glu | Pro | Ala | Val | Pro | Val | Ile | Lys | Thr | Pro | Pro | Leu | Lys | Lys | Lys Thr | |
| | | | 180 | | | | | 185 | | | | | 190 | | |
| cgg | ccg | caa | ggc | ggc | gga | tcc | gtg | gac | aag | aaa | att | gtg | ccc | agg gat | 624 |
| Arg | Pro | Gln | Gly | Gly | Gly | Ser | Val | Asp | Lys | Lys | Ile | Val | Pro | Arg Asp | |
| | | 195 | | | | | 200 | | | | | 205 | | | |
| tgt | ggt | tgt | aag | cct | tgc | ata | tgt | aca | gtc | cca | gaa | gta | tca | tct gtc | 672 |
| Cys | Gly | Cys | Lys | Pro | Cys | Ile | Cys | Thr | Val | Pro | Glu | Val | Ser | Ser Val | |
| | 210 | | | | | 215 | | | | | 220 | | | | |
| ttc | atc | ttc | ccc | cca | aag | ccc | aag | gat | gtg | ctc | acc | att | act | ctg act | 720 |
| Phe | Ile | Phe | Pro | Pro | Lys | Pro | Lys | Asp | Val | Leu | Thr | Ile | Thr | Leu Thr | |
| 225 | | | | | 230 | | | | | 235 | | | | | 240 |
| cct | aag | gtc | acg | tgt | gtt | gtg | gta | gac | atc | agc | aag | gat | gat | ccc gag | 768 |
| Pro | Lys | Val | Thr | Cys | Val | Val | Val | Asp | Ile | Ser | Lys | Asp | Asp | Pro Glu | |
| | | | | 245 | | | | | 250 | | | | | 255 | |
| gtc | cag | ttc | agc | tgg | ttt | gta | gat | gat | gtg | gag | gtg | cac | aca | gct cag | 816 |
| Val | Gln | Phe | Ser | Trp | Phe | Val | Asp | Asp | Val | Glu | Val | His | Thr | Ala Gln | |

-continued

```
                  260                 265                 270
acg caa ccc cgg gag gag cag ttc aac agc act ttc cgc tca gtc agt       864
Thr Gln Pro Arg Glu Glu Gln Phe Asn Ser Thr Phe Arg Ser Val Ser
            275                 280                 285 gaa ctt ccc atc atg cac cag gac tgg ctc aat ggc aag gag ttc aaa       912
Glu Leu Pro Ile Met His Gln Asp Trp Leu Asn Gly Lys Glu Phe Lys
        290                 295                 300 tgc agg gtc aac agt gca gct ttc cct gcc ccc atc gag aaa acc atc       960
Cys Arg Val Asn Ser Ala Ala Phe Pro Ala Pro Ile Glu Lys Thr Ile
305                 310                 315                 320 tcc aaa acc aaa ggc aga ccg aag gct cca cag gtg tac acc att cca      1008
Ser Lys Thr Lys Gly Arg Pro Lys Ala Pro Gln Val Tyr Thr Ile Pro
                325                 330                 335 cct ccc aag gag cag atg gcc aag gat aaa gtc agt ctg acc tgc atg      1056
Pro Pro Lys Glu Gln Met Ala Lys Asp Lys Val Ser Leu Thr Cys Met
            340                 345                 350 ata aca gac ttc ttc cct gaa gac att act gtg gag tgg cag tgg aat      1104
Ile Thr Asp Phe Phe Pro Glu Asp Ile Thr Val Glu Trp Gln Trp Asn
        355                 360                 365 ggg cag cca gcg gag aac tac aag aac act cag ccc atc atg gac aca      1152
Gly Gln Pro Ala Glu Asn Tyr Lys Asn Thr Gln Pro Ile Met Asp Thr
370                 375                 380 gat ggc tct tac ttc gtc tac agc aag ctc aat gtg cag aag agc aac      1200
Asp Gly Ser Tyr Phe Val Tyr Ser Lys Leu Asn Val Gln Lys Ser Asn
385                 390                 395                 400 tgg gag gca gga aat act ttc acc tgc tct gtg tta cat gag ggc ctg      1248
Trp Glu Ala Gly Asn Thr Phe Thr Cys Ser Val Leu His Glu Gly Leu
                405                 410                 415 cac aac cac cat act gag aag agc ctc tcc cac tct cct ggg ctg caa      1296
His Asn His His Thr Glu Lys Ser Leu Ser His Ser Pro Gly Leu Gln
            420                 425                 430 agc ttg tcg aga agt act aga gga tca taa                              1326
Ser Leu Ser Arg Ser Thr Arg Gly Ser
        435                 440
```

<210> SEQ ID NO 42
<211> LENGTH: 441
<212> TYPE: PRT
<213> ORGANISM: Artificial
<220> FEATURE:
<223> OTHER INFORMATION: Synthetic Construct

<400> SEQUENCE: 42

```
Met Ser Tyr Tyr His His His His His His Asp Tyr Asp Ile Pro Thr
1               5                   10                  15

Thr Glu Asn Leu Tyr Phe Gln Gly Ala Met Asp Pro Glu Phe Met Gly
            20                  25                  30

Gln His Pro Ala Lys Ser Met Asp Val Arg Arg Ile Glu Gly Gly Glu
        35                  40                  45

Ile Leu Leu Asn Gln Leu Ala Gly Arg Met Ile Pro Lys Gly Thr Leu
    50                  55                  60

Thr Trp Ser Gly Lys Phe Pro Thr Leu Asp His Val Leu Asp His Val
65                  70                  75                  80

Gln Thr Met Glu Glu Ile Asn Thr Leu Gln Asn Gln Gly Ala Trp Pro
                85                  90                  95

Ala Gly Ala Gly Arg Arg Val Gly Leu Ser Asn Pro Thr Pro Gln Glu
            100                 105                 110

Ile Pro Gln Pro Gln Trp Thr Pro Glu Glu Asp Gln Lys Ala Arg Glu
        115                 120                 125
```

```
Ala Phe Arg Arg Tyr Gln Glu Glu Arg Pro Pro Glu Thr Thr Thr Ile
        130                 135                 140

Pro Pro Ser Ser Pro Pro Gln Trp Lys Leu Gln Pro Gly Asp Asp Pro
145                 150                 155                 160

Leu Leu Gly Asn Gln Ser Leu Leu Glu Thr His Pro Leu Tyr Gln Ser
                165                 170                 175

Glu Pro Ala Val Pro Val Ile Lys Thr Pro Leu Lys Lys Lys Thr
            180                 185                 190

Arg Pro Gln Gly Gly Gly Ser Val Asp Lys Lys Ile Val Pro Arg Asp
                195                 200                 205

Cys Gly Cys Lys Pro Cys Ile Cys Thr Val Pro Glu Val Ser Ser Val
210                 215                 220

Phe Ile Phe Pro Pro Lys Pro Lys Asp Val Leu Thr Ile Thr Leu Thr
225                 230                 235                 240

Pro Lys Val Thr Cys Val Val Val Asp Ile Ser Lys Asp Asp Pro Glu
                245                 250                 255

Val Gln Phe Ser Trp Phe Val Asp Asp Val Glu Val His Thr Ala Gln
            260                 265                 270

Thr Gln Pro Arg Glu Glu Gln Phe Asn Ser Thr Phe Arg Ser Val Ser
        275                 280                 285

Glu Leu Pro Ile Met His Gln Asp Trp Leu Asn Gly Lys Glu Phe Lys
290                 295                 300

Cys Arg Val Asn Ser Ala Ala Phe Pro Ala Pro Ile Glu Lys Thr Ile
305                 310                 315                 320

Ser Lys Thr Lys Gly Arg Pro Lys Ala Pro Gln Val Tyr Thr Ile Pro
                325                 330                 335

Pro Pro Lys Glu Gln Met Ala Lys Asp Lys Val Ser Leu Thr Cys Met
            340                 345                 350

Ile Thr Asp Phe Phe Pro Glu Asp Ile Thr Val Glu Trp Gln Trp Asn
        355                 360                 365

Gly Gln Pro Ala Glu Asn Tyr Lys Asn Thr Gln Pro Ile Met Asp Thr
370                 375                 380

Asp Gly Ser Tyr Phe Val Tyr Ser Lys Leu Asn Val Gln Lys Ser Asn
385                 390                 395                 400

Trp Glu Ala Gly Asn Thr Phe Thr Cys Ser Val Leu His Glu Gly Leu
                405                 410                 415

His Asn His His Thr Glu Lys Ser Leu Ser His Ser Pro Gly Leu Gln
            420                 425                 430

Ser Leu Ser Arg Ser Thr Arg Gly Ser
        435                 440

<210> SEQ ID NO 43
<211> LENGTH: 654
<212> TYPE: DNA
<213> ORGANISM: Duck hepatitis B virus
<220> FEATURE:
<221> NAME/KEY: CDS
<222> LOCATION: (1)..(654)

<400> SEQUENCE: 43 atg tcg tac tac cat cac cat cac cat cac gat tac gat atc cca acg      48
Met Ser Tyr Tyr His His His His His His Asp Tyr Asp Ile Pro Thr
1               5                   10                  15 acc gaa aac ctg tat ttt cag ggc gcc atg gat ccg gaa ttc atg ggg      96
Thr Glu Asn Leu Tyr Phe Gln Gly Ala Met Asp Pro Glu Phe Met Gly
            20                  25                  30 caa cat cca gca aaa tca atg gac gtc aga cgg ata gaa gga gga gaa     144
```

```
Gln His Pro Ala Lys Ser Met Asp Val Arg Arg Ile Glu Gly Gly Glu
         35                  40                  45 ata ctg tta aac caa ctt gcc gga agg atg atc cca aaa ggg act ttg      192
Ile Leu Leu Asn Gln Leu Ala Gly Arg Met Ile Pro Lys Gly Thr Leu
 50                  55                  60 aca tgg tca ggc aag ttt cca aca cta gat cac gtg tta gac cat gtg      240
Thr Trp Ser Gly Lys Phe Pro Thr Leu Asp His Val Leu Asp His Val
 65                  70                  75                  80 caa aca atg gag gag ata aac acc ctc cag aat cag gga gct tgg cct      288
Gln Thr Met Glu Glu Ile Asn Thr Leu Gln Asn Gln Gly Ala Trp Pro
                 85                  90                  95 gct ggg gcg gga agg aga gta gga tta tca aat ccg act cct caa gag      336
Ala Gly Ala Gly Arg Arg Val Gly Leu Ser Asn Pro Thr Pro Gln Glu
                100                 105                 110 att cct cag ccc cag tgg act ccc gag gaa gac caa aaa gca cgc gaa      384
Ile Pro Gln Pro Gln Trp Thr Pro Glu Glu Asp Gln Lys Ala Arg Glu
            115                 120                 125 gct ttt cgc cgt tat caa gaa gaa aga cca ccg gaa acc acc acc att      432
Ala Phe Arg Arg Tyr Gln Glu Glu Arg Pro Pro Glu Thr Thr Thr Ile
        130                 135                 140 cct ccg tct tcc cct cct cag tgg aag cta caa ccc ggg gac gat cca      480
Pro Pro Ser Ser Pro Pro Gln Trp Lys Leu Gln Pro Gly Asp Asp Pro
145                 150                 155                 160 ctc ctg gga aat cag tct ctc ctc gag act cat ccg cta tac cag tca      528
Leu Leu Gly Asn Gln Ser Leu Leu Glu Thr His Pro Leu Tyr Gln Ser
                165                 170                 175 gaa cca gcg gtg cca gtg ata aaa act ccc ccc ttg aag aag aaa acg      576
Glu Pro Ala Val Pro Val Ile Lys Thr Pro Pro Leu Lys Lys Lys Thr
                180                 185                 190 cgg ccg ctt tcg aat cta gag cct gca gtc tcg agg cat gcg gta cca      624
Arg Pro Leu Ser Asn Leu Glu Pro Ala Val Ser Arg His Ala Val Pro
            195                 200                 205 agc ttg tcg aga agt act aga gga tca taa                              654
Ser Leu Ser Arg Ser Thr Arg Gly Ser
        210                 215

<210> SEQ ID NO 44
<211> LENGTH: 217
<212> TYPE: PRT
<213> ORGANISM: Duck hepatitis B virus

<400> SEQUENCE: 44

Met Ser Tyr Tyr His His His His His Asp Tyr Asp Ile Pro Thr
 1               5                  10                  15

Thr Glu Asn Leu Tyr Phe Gln Gly Ala Met Asp Pro Glu Phe Met Gly
             20                  25                  30

Gln His Pro Ala Lys Ser Met Asp Val Arg Arg Ile Glu Gly Gly Glu
         35                  40                  45

Ile Leu Leu Asn Gln Leu Ala Gly Arg Met Ile Pro Lys Gly Thr Leu
 50                  55                  60

Thr Trp Ser Gly Lys Phe Pro Thr Leu Asp His Val Leu Asp His Val
 65                  70                  75                  80

Gln Thr Met Glu Glu Ile Asn Thr Leu Gln Asn Gln Gly Ala Trp Pro
                 85                  90                  95

Ala Gly Ala Gly Arg Arg Val Gly Leu Ser Asn Pro Thr Pro Gln Glu
                100                 105                 110

Ile Pro Gln Pro Gln Trp Thr Pro Glu Glu Asp Gln Lys Ala Arg Glu
            115                 120                 125

Ala Phe Arg Arg Tyr Gln Glu Glu Arg Pro Pro Glu Thr Thr Thr Ile
```

```
                     130                 135                 140
Pro Pro Ser Ser Pro Pro Gln Trp Lys Leu Gln Pro Gly Asp Asp Pro
145                 150                 155                 160

Leu Leu Gly Asn Gln Ser Leu Leu Glu Thr His Pro Leu Tyr Gln Ser
                165                 170                 175

Glu Pro Ala Val Pro Val Ile Lys Thr Pro Pro Leu Lys Lys Lys Thr
            180                 185                 190

Arg Pro Leu Ser Asn Leu Glu Pro Ala Val Ser Arg His Ala Val Pro
        195                 200                 205

Ser Leu Ser Arg Ser Thr Arg Gly Ser
    210                 215

<210> SEQ ID NO 45
<211> LENGTH: 1824
<212> TYPE: DNA
<213> ORGANISM: Artificial
<220> FEATURE:
<223> OTHER INFORMATION: Duck hepatitis B virus plus murine
<220> FEATURE:
<221> NAME/KEY: CDS
<222> LOCATION: (1)..(1824)

<400> SEQUENCE: 45 atg tcg tac tac cat cac cat cac cat cac gat tac gat atc cca acg      48
Met Ser Tyr Tyr His His His His His His Asp Tyr Asp Ile Pro Thr
1               5                   10                  15 acc gaa aac ctg tat ttt cag ggc gcc atg gat ccg gaa ttc atg ggg      96
Thr Glu Asn Leu Tyr Phe Gln Gly Ala Met Asp Pro Glu Phe Met Gly
            20                  25                  30 caa cat cca gca aaa tca atg gac gtc aga cgg ata gaa gga gga gaa     144
Gln His Pro Ala Lys Ser Met Asp Val Arg Arg Ile Glu Gly Gly Glu
        35                  40                  45 ata ctg tta aac caa ctt gcc gga agg atg atc cca aaa ggg act ttg     192
Ile Leu Leu Asn Gln Leu Ala Gly Arg Met Ile Pro Lys Gly Thr Leu
    50                  55                  60 aca tgg tca ggc aag ttt cca aca cta gat cac gtg tta gac cat gtg     240
Thr Trp Ser Gly Lys Phe Pro Thr Leu Asp His Val Leu Asp His Val
65                  70                  75                  80 caa aca atg gag gag ata aac acc ctc cag aat cag gga gct tgg cct     288
Gln Thr Met Glu Glu Ile Asn Thr Leu Gln Asn Gln Gly Ala Trp Pro
                85                  90                  95 gct ggg gcg gga agg aga gta gga tta tca aat ccg act cct caa gag     336
Ala Gly Ala Gly Arg Arg Val Gly Leu Ser Asn Pro Thr Pro Gln Glu
            100                 105                 110 att cct cag ccc cag tgg act ccc gag gaa gaa caa aaa gca cgc gaa     384
Ile Pro Gln Pro Gln Trp Thr Pro Glu Glu Glu Gln Lys Ala Arg Glu
        115                 120                 125 gct ttt cgc cgt tat caa gaa gaa aga cca ccg gaa acc acc acc att     432
Ala Phe Arg Arg Tyr Gln Glu Glu Arg Pro Pro Glu Thr Thr Thr Ile
    130                 135                 140 cct ccg tct tcc cct cct cag tgg aag cta caa ccc ggg gac gat cca     480
Pro Pro Ser Ser Pro Pro Gln Trp Lys Leu Gln Pro Gly Asp Asp Pro
145                 150                 155                 160 ctc ctg gga aat cag tct ctc ctc gag act cat ccg cta tac cag tca     528
Leu Leu Gly Asn Gln Ser Leu Leu Glu Thr His Pro Leu Tyr Gln Ser
                165                 170                 175 gaa cca gcg gtg cca gtg ata aaa act ccc ccc ttg aag aag aaa atg     576
Glu Pro Ala Val Pro Val Ile Lys Thr Pro Pro Leu Lys Lys Lys Met
            180                 185                 190 tct ggt acc ttc ggg gga ata cta gct ggc cta atc gga tta ctg gta     624
Ser Gly Thr Phe Gly Gly Ile Leu Ala Gly Leu Ile Gly Leu Leu Val
```

```
                195                     200                     205
agc ttt ttc ttg ttg ata aaa att cta gaa ata ctg agg agg cta gat       672
Ser Phe Phe Leu Leu Ile Lys Ile Leu Glu Ile Leu Arg Arg Leu Asp
    210                     215                     220 tgg tgg tgg att tct ctc agt tct cca aag gga aaa atg caa tgc gct       720
Trp Trp Trp Ile Ser Leu Ser Ser Pro Lys Gly Lys Met Gln Cys Ala
225                     230                     235                 240 ttc caa gat act gga gcc caa atc tct cca cat tac gta gga tct tgc       768
Phe Gln Asp Thr Gly Ala Gln Ile Ser Pro His Tyr Val Gly Ser Cys
                245                     250                     255 ccg tgg gga tgc cca gga ttt ctt tgg acc tat ctc agg ctt ttt atc       816
Pro Trp Gly Cys Pro Gly Phe Leu Trp Thr Tyr Leu Arg Leu Phe Ile
            260                     265                     270 atc ttc ctc tta atc ctg cta gta gca gca ggc ttg ctg tat ctg acg       864
Ile Phe Leu Leu Ile Leu Leu Val Ala Ala Gly Leu Leu Tyr Leu Thr
        275                     280                     285 gac aac ggg tct act att tta gga aag ctc caa tgg gcg tcg gtc tca       912
Asp Asn Gly Ser Thr Ile Leu Gly Lys Leu Gln Trp Ala Ser Val Ser
    290                     295                     300 gcc ctt ttc tcc tcc atc tct tca cta ctg ccc tcg gat ccg aaa tct       960
Ala Leu Phe Ser Ser Ile Ser Ser Leu Leu Pro Ser Asp Pro Lys Ser
305                     310                     315                 320 ctc gtc gct tta acg ttt gga ctt tca ctt ata tgg atg act tcc tcc      1008
Leu Val Ala Leu Thr Phe Gly Leu Ser Leu Ile Trp Met Thr Ser Ser
                325                     330                     335 tct gcc acc caa acg ctc gtc acc tta acg caa tta gcc acg ctg tct      1056
Ser Ala Thr Gln Thr Leu Val Thr Leu Thr Gln Leu Ala Thr Leu Ser
            340                     345                     350 gct ctt ttt tac aag agt tcg cgg ccg caa ggc ggc gga tcc gtg gac      1104
Ala Leu Phe Tyr Lys Ser Ser Arg Pro Gln Gly Gly Gly Ser Val Asp
        355                     360                     365 aag aaa att gtg ccc agg gat tgt ggt tgt aag cct tgc ata tgt aca      1152
Lys Lys Ile Val Pro Arg Asp Cys Gly Cys Lys Pro Cys Ile Cys Thr
    370                     375                     380 gtc cca gaa gta tca tct gtc ttc atc ttc ccc cca aag ccc aag gat      1200
Val Pro Glu Val Ser Ser Val Phe Ile Phe Pro Pro Lys Pro Lys Asp
385                     390                     395                 400 gtg ctc acc att act ctg act cct aag gtc acg tgt gtt gtg gta gac      1248
Val Leu Thr Ile Thr Leu Thr Pro Lys Val Thr Cys Val Val Val Asp
                405                     410                     415 atc agc aag gat gat ccc gag gtc cag ttc agc tgg ttt gta gat gat      1296
Ile Ser Lys Asp Asp Pro Glu Val Gln Phe Ser Trp Phe Val Asp Asp
            420                     425                     430 gtg gag gtg cac aca gct cag acg caa ccc cgg gag gag cag ttc aac      1344
Val Glu Val His Thr Ala Gln Thr Gln Pro Arg Glu Glu Gln Phe Asn
        435                     440                     445 agc act ttc cgc tca gtc agt gaa ctt ccc atc atg cac cag gac tgg      1392
Ser Thr Phe Arg Ser Val Ser Glu Leu Pro Ile Met His Gln Asp Trp
    450                     455                     460 ctc aat ggc aag gag ttc aaa tgc agg gtc aac agt gca gct ttc cct      1440
Leu Asn Gly Lys Glu Phe Lys Cys Arg Val Asn Ser Ala Ala Phe Pro
465                     470                     475                 480 gcc ccc atc gag aaa acc atc tcc aaa acc aaa ggc aga ccg aag gct      1488
Ala Pro Ile Glu Lys Thr Ile Ser Lys Thr Lys Gly Arg Pro Lys Ala
                485                     490                     495 cca cag gtg tac acc att cca cct ccc aag gag cag atg gcc aag gat      1536
Pro Gln Val Tyr Thr Ile Pro Pro Pro Lys Glu Gln Met Ala Lys Asp
            500                     505                     510 aaa gtc agt ctg acc tgc atg ata aca gac ttc ttc cct gaa gac att      1584
Lys Val Ser Leu Thr Cys Met Ile Thr Asp Phe Phe Pro Glu Asp Ile
```

```
                515                 520                 525
act gtg gag tgg cag tgg aat ggg cag cca gcg gag aac tac aag aac    1632
Thr Val Glu Trp Gln Trp Asn Gly Gln Pro Ala Glu Asn Tyr Lys Asn
        530                 535                 540 act cag ccc atc atg gac aca gat ggc tct tac ttc gtc tac agc aag    1680
Thr Gln Pro Ile Met Asp Thr Asp Gly Ser Tyr Phe Val Tyr Ser Lys
545                 550                 555                 560 ctc aat gtg cag aag agc aac tgg gag gca gga aat act ttc acc tgc    1728
Leu Asn Val Gln Lys Ser Asn Trp Glu Ala Gly Asn Thr Phe Thr Cys
                565                 570                 575 tct gtg tta cat gag ggc ctg cac aac cac cat act gag aag agc ctc    1776
Ser Val Leu His Glu Gly Leu His Asn His His Thr Glu Lys Ser Leu
        580                 585                 590 tcc cac tct cct ggg ctg caa agc ttg tcg aga agt act aga gga tca    1824
Ser His Ser Pro Gly Leu Gln Ser Leu Ser Arg Ser Thr Arg Gly Ser
595                 600                 605

<210> SEQ ID NO 46
<211> LENGTH: 608
<212> TYPE: PRT
<213> ORGANISM: Artificial
<220> FEATURE:
<223> OTHER INFORMATION: Synthetic Construct

<400> SEQUENCE: 46

Met Ser Tyr Tyr His His His His His Asp Tyr Asp Ile Pro Thr
1               5                   10                  15

Thr Glu Asn Leu Tyr Phe Gln Gly Ala Met Asp Pro Glu Phe Met Gly
            20                  25                  30

Gln His Pro Ala Lys Ser Met Asp Val Arg Arg Ile Glu Gly Gly Glu
        35                  40                  45

Ile Leu Leu Asn Gln Leu Ala Gly Arg Met Ile Pro Lys Gly Thr Leu
    50                  55                  60

Thr Trp Ser Gly Lys Phe Pro Thr Leu Asp His Val Leu Asp His Val
65                  70                  75                  80

Gln Thr Met Glu Glu Ile Asn Thr Leu Gln Asn Gln Gly Ala Trp Pro
                85                  90                  95

Ala Gly Ala Gly Arg Arg Val Gly Leu Ser Asn Pro Thr Pro Gln Glu
            100                 105                 110

Ile Pro Gln Pro Gln Trp Thr Pro Glu Glu Gln Lys Ala Arg Glu
        115                 120                 125

Ala Phe Arg Arg Tyr Gln Glu Glu Arg Pro Glu Thr Thr Thr Ile
    130                 135                 140

Pro Pro Ser Ser Pro Pro Gln Trp Lys Leu Gln Pro Gly Asp Pro
145                 150                 155                 160

Leu Leu Gly Asn Gln Ser Leu Leu Glu Thr His Pro Leu Tyr Gln Ser
                165                 170                 175

Glu Pro Ala Val Pro Val Ile Lys Thr Pro Pro Leu Lys Lys Lys Met
            180                 185                 190

Ser Gly Thr Phe Gly Gly Ile Leu Ala Gly Leu Ile Gly Leu Leu Val
        195                 200                 205

Ser Phe Phe Leu Leu Ile Lys Ile Leu Glu Ile Leu Arg Arg Leu Asp
    210                 215                 220

Trp Trp Trp Ile Ser Leu Ser Ser Pro Lys Gly Lys Met Gln Cys Ala
225                 230                 235                 240

Phe Gln Asp Thr Gly Ala Gln Ile Ser Pro His Tyr Val Gly Ser Cys
                245                 250                 255
```

```
Pro Trp Gly Cys Pro Gly Phe Leu Trp Thr Tyr Leu Arg Leu Phe Ile
            260                 265                 270

Ile Phe Leu Leu Ile Leu Leu Val Ala Ala Gly Leu Leu Tyr Leu Thr
        275                 280                 285

Asp Asn Gly Ser Thr Ile Leu Gly Lys Leu Gln Trp Ala Ser Val Ser
    290                 295                 300

Ala Leu Phe Ser Ser Ile Ser Ser Leu Leu Pro Ser Asp Pro Lys Ser
305                 310                 315                 320

Leu Val Ala Leu Thr Phe Gly Leu Ser Leu Ile Trp Met Thr Ser Ser
                325                 330                 335

Ser Ala Thr Gln Thr Leu Val Thr Leu Thr Gln Leu Ala Thr Leu Ser
            340                 345                 350

Ala Leu Phe Tyr Lys Ser Ser Arg Pro Gln Gly Gly Gly Ser Val Asp
        355                 360                 365

Lys Lys Ile Val Pro Arg Asp Cys Gly Cys Lys Pro Cys Ile Cys Thr
    370                 375                 380

Val Pro Glu Val Ser Ser Val Phe Ile Phe Pro Lys Pro Lys Asp
385                 390                 395                 400

Val Leu Thr Ile Thr Leu Thr Pro Lys Val Thr Cys Val Val Val Asp
                405                 410                 415

Ile Ser Lys Asp Asp Pro Glu Val Gln Phe Ser Trp Phe Val Asp Asp
            420                 425                 430

Val Glu Val His Thr Ala Gln Thr Gln Pro Arg Glu Glu Gln Phe Asn
        435                 440                 445

Ser Thr Phe Arg Ser Val Ser Glu Leu Pro Ile Met His Gln Asp Trp
    450                 455                 460

Leu Asn Gly Lys Glu Phe Lys Cys Arg Val Asn Ser Ala Ala Phe Pro
465                 470                 475                 480

Ala Pro Ile Glu Lys Thr Ile Ser Lys Thr Lys Gly Arg Pro Lys Ala
                485                 490                 495

Pro Gln Val Tyr Thr Ile Pro Pro Lys Glu Gln Met Ala Lys Asp
            500                 505                 510

Lys Val Ser Leu Thr Cys Met Ile Thr Asp Phe Phe Pro Glu Asp Ile
        515                 520                 525

Thr Val Glu Trp Gln Trp Asn Gly Gln Pro Ala Glu Asn Tyr Lys Asn
    530                 535                 540

Thr Gln Pro Ile Met Asp Thr Asp Gly Ser Tyr Phe Val Tyr Ser Lys
545                 550                 555                 560

Leu Asn Val Gln Lys Ser Asn Trp Glu Ala Gly Asn Thr Phe Thr Cys
                565                 570                 575

Ser Val Leu His Glu Gly Leu His Asn His His Thr Glu Lys Ser Leu
            580                 585                 590

Ser His Ser Pro Gly Leu Gln Ser Leu Ser Arg Ser Thr Arg Gly Ser
        595                 600                 605

<210> SEQ ID NO 47
<211> LENGTH: 1152
<212> TYPE: DNA
<213> ORGANISM: Duck hepatitis B virus
<220> FEATURE:
<221> NAME/KEY: CDS
<222> LOCATION: (1)..(1152)

<400> SEQUENCE: 47 atg tcg tac tac cat cac cat cac cat cac gat tac gat atc cca acg    48
Met Ser Tyr Tyr His His His His His His Asp Tyr Asp Ile Pro Thr
1               5                   10                  15
```

```
acc gaa aac ctg tat ttt cag ggc gcc atg gat ccg gaa ttc atg ggg     96
Thr Glu Asn Leu Tyr Phe Gln Gly Ala Met Asp Pro Glu Phe Met Gly
         20                  25                  30 caa cat cca gca aaa tca atg gac gtc aga cgg ata gaa gga gga gaa    144
Gln His Pro Ala Lys Ser Met Asp Val Arg Arg Ile Glu Gly Gly Glu
     35                  40                  45 ata ctg tta aac caa ctt gcc gga agg atg atc cca aaa ggg act ttg    192
Ile Leu Leu Asn Gln Leu Ala Gly Arg Met Ile Pro Lys Gly Thr Leu
 50                  55                  60 aca tgg tca ggc aag ttt cca aca cta gat cac gtg tta gac cat gtg    240
Thr Trp Ser Gly Lys Phe Pro Thr Leu Asp His Val Leu Asp His Val
 65                  70                  75                  80 caa aca atg gag gag ata aac acc ctc cag aat cag gga gct tgg cct    288
Gln Thr Met Glu Glu Ile Asn Thr Leu Gln Asn Gln Gly Ala Trp Pro
                 85                  90                  95 gct ggg gcg gga agg aga gta gga tta tca aat ccg act cct caa gag    336
Ala Gly Ala Gly Arg Arg Val Gly Leu Ser Asn Pro Thr Pro Gln Glu
            100                 105                 110 att cct cag ccc cag tgg act ccc gag gaa gac caa aaa gca cgc gaa    384
Ile Pro Gln Pro Gln Trp Thr Pro Glu Glu Asp Gln Lys Ala Arg Glu
        115                 120                 125 gct ttt cgc cgt tat caa gaa gaa aga cca ccg gaa acc acc acc att    432
Ala Phe Arg Arg Tyr Gln Glu Glu Arg Pro Pro Glu Thr Thr Thr Ile
    130                 135                 140 cct ccg tct tcc cct cct cag tgg aag cta caa ccc ggg gac gat cca    480
Pro Pro Ser Ser Pro Pro Gln Trp Lys Leu Gln Pro Gly Asp Asp Pro
145                 150                 155                 160 ctc ctg gga aat cag tct ctc ctc gag act cat ccg cta tac cag tca    528
Leu Leu Gly Asn Gln Ser Leu Leu Glu Thr His Pro Leu Tyr Gln Ser
                165                 170                 175 gaa cca gcg gtg cca gtg ata aaa act ccc ccc ttg aag aag aaa atg    576
Glu Pro Ala Val Pro Val Ile Lys Thr Pro Pro Leu Lys Lys Lys Met
            180                 185                 190 tct ggt acc ttc ggg gga ata cta gct ggc cta atc gga tta ctg gta    624
Ser Gly Thr Phe Gly Gly Ile Leu Ala Gly Leu Ile Gly Leu Leu Val
        195                 200                 205 agc ttt ttc ttg ttg ata aaa att cta gaa ata ctg agg agg cta gat    672
Ser Phe Phe Leu Leu Ile Lys Ile Leu Glu Ile Leu Arg Arg Leu Asp
    210                 215                 220 tgg tgg tgg att tct ctc agt tct cca aag gga aaa atg caa tgc gct    720
Trp Trp Trp Ile Ser Leu Ser Ser Pro Lys Gly Lys Met Gln Cys Ala
225                 230                 235                 240 ttc caa gat act gga gcc caa atc tct cca cat tac gta gga tct tgc    768
Phe Gln Asp Thr Gly Ala Gln Ile Ser Pro His Tyr Val Gly Ser Cys
                245                 250                 255 ccg tgg gga tgc cca gga ttt ctt tgg acc tat ctc agg ctt ttt atc    816
Pro Trp Gly Cys Pro Gly Phe Leu Trp Thr Tyr Leu Arg Leu Phe Ile
            260                 265                 270 atc ttc ctc tta atc ctg cta gta gca gca ggc ttg ctg tat ctg acg    864
Ile Phe Leu Leu Ile Leu Leu Val Ala Ala Gly Leu Leu Tyr Leu Thr
        275                 280                 285 gac aac ggg tct act att tta gga aag ctc caa tgg gcg tcg gtc tca    912
Asp Asn Gly Ser Thr Ile Leu Gly Lys Leu Gln Trp Ala Ser Val Ser
    290                 295                 300 gcc ctt ttc tcc tcc atc tct tca cta ctg ccc tcg gat ccg aaa tct    960
Ala Leu Phe Ser Ser Ile Ser Ser Leu Leu Pro Ser Asp Pro Lys Ser
305                 310                 315                 320 ctc gtc gct tta acg ttt gga ctt tca ctt ata tgg atg act tcc tcc   1008
Leu Val Ala Leu Thr Phe Gly Leu Ser Leu Ile Trp Met Thr Ser Ser
                325                 330                 335
```

```
tct gcc acc caa acg ctc gtc acc tta acg caa tta gcc acg ctg tct    1056
Ser Ala Thr Gln Thr Leu Val Thr Leu Thr Gln Leu Ala Thr Leu Ser
                340                 345                 350 gct ctt ttt tac aag agt tcg cgg ccg ctt tcg aat cta gag cct gca    1104
Ala Leu Phe Tyr Lys Ser Ser Arg Pro Leu Ser Asn Leu Glu Pro Ala
            355                 360                 365 gtc tcg agg cat gcg gta cca agc ttg tcg aga agt act aga gga tca    1152
Val Ser Arg His Ala Val Pro Ser Leu Ser Arg Ser Thr Arg Gly Ser
        370                 375                 380
```

<210> SEQ ID NO 48
<211> LENGTH: 384
<212> TYPE: PRT
<213> ORGANISM: Duck hepatitis B virus

<400> SEQUENCE: 48

```
Met Ser Tyr Tyr His His His His His Asp Tyr Asp Ile Pro Thr
1               5                   10                  15

Thr Glu Asn Leu Tyr Phe Gln Gly Ala Met Asp Pro Glu Phe Met Gly
                20                  25                  30

Gln His Pro Ala Lys Ser Met Asp Val Arg Arg Ile Glu Gly Gly Glu
            35                  40                  45

Ile Leu Leu Asn Gln Leu Ala Gly Arg Met Ile Pro Lys Gly Thr Leu
        50                  55                  60

Thr Trp Ser Gly Lys Phe Pro Thr Leu Asp His Val Leu Asp His Val
65                  70                  75                  80

Gln Thr Met Glu Glu Ile Asn Thr Leu Gln Asn Gln Gly Ala Trp Pro
                85                  90                  95

Ala Gly Ala Gly Arg Arg Val Gly Leu Ser Asn Pro Thr Pro Gln Glu
            100                 105                 110

Ile Pro Gln Pro Gln Trp Thr Pro Glu Glu Asp Gln Lys Ala Arg Glu
        115                 120                 125

Ala Phe Arg Arg Tyr Gln Glu Glu Arg Pro Pro Glu Thr Thr Thr Ile
    130                 135                 140

Pro Pro Ser Ser Pro Pro Gln Trp Lys Leu Gln Pro Gly Asp Asp Pro
145                 150                 155                 160

Leu Leu Gly Asn Gln Ser Leu Leu Glu Thr His Pro Leu Tyr Gln Ser
                165                 170                 175

Glu Pro Ala Val Pro Val Ile Lys Thr Pro Pro Leu Lys Lys Lys Met
            180                 185                 190

Ser Gly Thr Phe Gly Gly Ile Leu Ala Gly Leu Ile Gly Leu Leu Val
        195                 200                 205

Ser Phe Phe Leu Leu Ile Lys Ile Leu Glu Ile Leu Arg Arg Leu Asp
    210                 215                 220

Trp Trp Trp Ile Ser Leu Ser Ser Pro Lys Gly Lys Met Gln Cys Ala
225                 230                 235                 240

Phe Gln Asp Thr Gly Ala Gln Ile Ser Pro His Tyr Val Gly Ser Cys
                245                 250                 255

Pro Trp Gly Cys Pro Gly Phe Leu Trp Thr Tyr Leu Arg Leu Phe Ile
            260                 265                 270

Ile Phe Leu Leu Ile Leu Leu Val Ala Ala Gly Leu Leu Tyr Leu Thr
        275                 280                 285

Asp Asn Gly Ser Thr Ile Leu Gly Lys Leu Gln Trp Ala Ser Val Ser
    290                 295                 300

Ala Leu Phe Ser Ser Ile Ser Ser Leu Leu Pro Ser Asp Pro Lys Ser
305                 310                 315                 320
```

```
Leu Val Ala Leu Thr Phe Gly Leu Ser Leu Ile Trp Met Thr Ser Ser
                325                 330                 335

Ser Ala Thr Gln Thr Leu Val Thr Leu Thr Gln Leu Ala Thr Leu Ser
                340                 345                 350

Ala Leu Phe Tyr Lys Ser Ser Arg Pro Leu Ser Asn Leu Glu Pro Ala
            355                 360                 365

Val Ser Arg His Ala Val Pro Ser Leu Ser Arg Ser Thr Arg Gly Ser
        370                 375                 380

<210> SEQ ID NO 49
<211> LENGTH: 1611
<212> TYPE: DNA
<213> ORGANISM: Artificial
<220> FEATURE:
<223> OTHER INFORMATION: Duck hepatitis B virus plus murine
<220> FEATURE:
<221> NAME/KEY: CDS
<222> LOCATION: (1)..(1611)

<400> SEQUENCE: 49
```

| | | | | | | | | | | | | | | | | |
|---|---|---|---|---|---|---|---|---|---|---|---|---|---|---|---|---|
| atg | tcg | tac | tac | cat | cac | cat | cac | cat | cac | gat | tac | gat | atc | cca | acg | 48 |
| Met | Ser | Tyr | Tyr | His | His | His | His | His | His | Asp | Tyr | Asp | Ile | Pro | Thr | |
| 1 | | | | 5 | | | | | 10 | | | | | 15 | | |
| acc | gaa | aac | ctg | tat | ttt | cag | ggc | gcc | atg | gat | atc | aat | gct | tct | aga | 96 |
| Thr | Glu | Asn | Leu | Tyr | Phe | Gln | Gly | Ala | Met | Asp | Ile | Asn | Ala | Ser | Arg | |
| | | | 20 | | | | | 25 | | | | | 30 | | | |
| gcc | tta | gcc | aat | gtg | tat | gat | cta | cca | gat | gat | ttc | ttt | cca | aaa | ata | 144 |
| Ala | Leu | Ala | Asn | Val | Tyr | Asp | Leu | Pro | Asp | Asp | Phe | Phe | Pro | Lys | Ile | |
| | | 35 | | | | | 40 | | | | | 45 | | | | |
| gat | gat | ctt | gtt | aga | gat | gct | aaa | gac | gct | tta | gag | cct | tat | tgg | aaa | 192 |
| Asp | Asp | Leu | Val | Arg | Asp | Ala | Lys | Asp | Ala | Leu | Glu | Pro | Tyr | Trp | Lys | |
| 50 | | | | | 55 | | | | | 60 | | | | | | |
| tca | gat | tca | ata | aag | aaa | cat | gtt | ttg | att | gca | act | cac | ttt | gtg | gat | 240 |
| Ser | Asp | Ser | Ile | Lys | Lys | His | Val | Leu | Ile | Ala | Thr | His | Phe | Val | Asp | |
| 65 | | | | 70 | | | | | 75 | | | | | 80 | | |
| ctc | att | gaa | gac | ttc | tgg | cag | act | aca | cag | ggc | atg | cat | gaa | ata | gcc | 288 |
| Leu | Ile | Glu | Asp | Phe | Trp | Gln | Thr | Thr | Gln | Gly | Met | His | Glu | Ile | Ala | |
| | | | | 85 | | | | | 90 | | | | | 95 | | |
| gaa | tca | tta | aga | gct | gtt | ata | cct | ccc | act | act | act | cct | gtt | cca | ccg | 336 |
| Glu | Ser | Leu | Arg | Ala | Val | Ile | Pro | Pro | Thr | Thr | Thr | Pro | Val | Pro | Pro | |
| | | | 100 | | | | | 105 | | | | | 110 | | | |
| ggt | tat | ctt | att | cag | cac | gag | gaa | gct | gaa | gag | ata | cct | ttg | gga | gat | 384 |
| Gly | Tyr | Leu | Ile | Gln | His | Glu | Glu | Ala | Glu | Glu | Ile | Pro | Leu | Gly | Asp | |
| | | | | 115 | | | | | 120 | | | | | 125 | | |
| tta | ttt | aaa | cac | caa | gaa | gaa | agg | ata | gta | agt | ttc | caa | ccc | gac | tat | 432 |
| Leu | Phe | Lys | His | Gln | Glu | Glu | Arg | Ile | Val | Ser | Phe | Gln | Pro | Asp | Tyr | |
| | | 130 | | | | | 135 | | | | | 140 | | | | |
| ccg | att | acg | gct | aga | att | cat | gct | cat | ttg | aaa | gct | tat | gca | aaa | att | 480 |
| Pro | Ile | Thr | Ala | Arg | Ile | His | Ala | His | Leu | Lys | Ala | Tyr | Ala | Lys | Ile | |
| 145 | | | | | 150 | | | | | 155 | | | | | 160 | |
| aac | gag | gaa | tca | ctg | gat | agg | gct | agg | aga | ttg | ctt | tgg | tgg | cat | tac | 528 |
| Asn | Glu | Glu | Ser | Leu | Asp | Arg | Ala | Arg | Arg | Leu | Leu | Trp | Trp | His | Tyr | |
| | | | | 165 | | | | | 170 | | | | | 175 | | |
| aac | tgt | tta | ctg | tgg | gga | gaa | gct | caa | gtt | act | aac | tat | att | tct | cgt | 576 |
| Asn | Cys | Leu | Leu | Trp | Gly | Glu | Ala | Gln | Val | Thr | Asn | Tyr | Ile | Ser | Arg | |
| | | | 180 | | | | | 185 | | | | | 190 | | | |
| ttg | cgt | act | tgg | ttg | tca | act | cct | gag | aaa | tat | aga | ggt | aga | gat | gcc | 624 |
| Leu | Arg | Thr | Trp | Leu | Ser | Thr | Pro | Glu | Lys | Tyr | Arg | Gly | Arg | Asp | Ala | |
| | | | | 195 | | | | | 200 | | | | | 205 | | |
| ccg | acc | att | gaa | gca | atc | act | aga | cca | atc | cag | gtg | gct | cag | gga | ggc | 672 |
| Pro | Thr | Ile | Glu | Ala | Ile | Thr | Arg | Pro | Ile | Gln | Val | Ala | Gln | Gly | Gly | |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     | 210 |     |     |     | 215 |     |     |     |     | 220 |     |     |     |     |     |      |
| aga | aaa | aca | act | acg | ggt | act | aga | aaa | cct | cgt | gga | ctc | gaa | cct | aga | 720  |
| Arg | Lys | Thr | Thr | Thr | Gly | Thr | Arg | Lys | Pro | Arg | Gly | Leu | Glu | Pro | Arg |      |
| 225 |     |     |     | 230 |     |     |     |     | 235 |     |     |     |     | 240 |     |      |
| aga | aga | aaa | gtt | aaa | acc | aca | gtt | gtc | tat | ggg | aga | aga | cgt | tca | aag | 768  |
| Arg | Arg | Lys | Val | Lys | Thr | Thr | Val | Val | Tyr | Gly | Arg | Arg | Arg | Ser | Lys |      |
|     |     |     |     | 245 |     |     |     |     | 250 |     |     |     |     | 255 |     |      |
| tcc | cgg | gaa | agg | aga | gcc | cct | aca | ccc | caa | cgt | gcg | ggc | tcc | cct | ctc | 816  |
| Ser | Arg | Glu | Arg | Arg | Ala | Pro | Thr | Pro | Gln | Arg | Ala | Gly | Ser | Pro | Leu |      |
|     |     |     | 260 |     |     |     |     | 265 |     |     |     |     | 270 |     |     |      |
| cca | cgt | agt | tcg | agc | agc | cac | cat | aga | tct | ccc | tcg | cct | agg | aaa | tcg | 864  |
| Pro | Arg | Ser | Ser | Ser | Ser | His | His | Arg | Ser | Pro | Ser | Pro | Arg | Lys | Ser |      |
|     |     | 275 |     |     |     |     | 280 |     |     |     |     | 285 |     |     |     |      |
| cgg | ccg | caa | ggc | ggc | gga | tcc | gtg | gac | aag | aaa | att | gtg | ccc | agg | gat | 912  |
| Arg | Pro | Gln | Gly | Gly | Gly | Ser | Val | Asp | Lys | Lys | Ile | Val | Pro | Arg | Asp |      |
| 290 |     |     |     |     | 295 |     |     |     |     | 300 |     |     |     |     |     |      |
| tgt | ggt | tgt | aag | cct | tgc | ata | tgt | aca | gtc | cca | gaa | gta | tca | tct | gtc | 960  |
| Cys | Gly | Cys | Lys | Pro | Cys | Ile | Cys | Thr | Val | Pro | Glu | Val | Ser | Ser | Val |      |
| 305 |     |     |     | 310 |     |     |     |     | 315 |     |     |     |     | 320 |     |      |
| ttc | atc | ttc | ccc | cca | aag | ccc | aag | gat | gtg | ctc | acc | att | act | ctg | act | 1008 |
| Phe | Ile | Phe | Pro | Pro | Lys | Pro | Lys | Asp | Val | Leu | Thr | Ile | Thr | Leu | Thr |      |
|     |     |     |     | 325 |     |     |     |     | 330 |     |     |     |     | 335 |     |      |
| cct | aag | gtc | acg | tgt | gtt | gtg | gta | gac | atc | agc | aag | gat | gat | ccc | gag | 1056 |
| Pro | Lys | Val | Thr | Cys | Val | Val | Val | Asp | Ile | Ser | Lys | Asp | Asp | Pro | Glu |      |
|     |     |     | 340 |     |     |     |     | 345 |     |     |     |     | 350 |     |     |      |
| gtc | cag | ttc | agc | tgg | ttt | gta | gat | gat | gtg | gag | gtg | cac | aca | gct | cag | 1104 |
| Val | Gln | Phe | Ser | Trp | Phe | Val | Asp | Asp | Val | Glu | Val | His | Thr | Ala | Gln |      |
|     |     | 355 |     |     |     |     | 360 |     |     |     |     | 365 |     |     |     |      |
| acg | caa | ccc | cgg | gag | gag | cag | ttc | aac | agc | act | ttc | cgc | tca | gtc | agt | 1152 |
| Thr | Gln | Pro | Arg | Glu | Glu | Gln | Phe | Asn | Ser | Thr | Phe | Arg | Ser | Val | Ser |      |
| 370 |     |     |     |     | 375 |     |     |     |     | 380 |     |     |     |     |     |      |
| gaa | ctt | ccc | atc | atg | cac | cag | gac | tgg | ctc | aat | ggc | aag | gag | ttc | aaa | 1200 |
| Glu | Leu | Pro | Ile | Met | His | Gln | Asp | Trp | Leu | Asn | Gly | Lys | Glu | Phe | Lys |      |
| 385 |     |     |     | 390 |     |     |     |     | 395 |     |     |     |     | 400 |     |      |
| tgc | agg | gtc | aac | agt | gca | gct | ttc | cct | gcc | ccc | atc | gag | aaa | acc | atc | 1248 |
| Cys | Arg | Val | Asn | Ser | Ala | Ala | Phe | Pro | Ala | Pro | Ile | Glu | Lys | Thr | Ile |      |
|     |     |     |     | 405 |     |     |     |     | 410 |     |     |     |     | 415 |     |      |
| tcc | aaa | acc | aaa | ggc | aga | ccg | aag | gct | cca | cag | gtg | tac | acc | att | cca | 1296 |
| Ser | Lys | Thr | Lys | Gly | Arg | Pro | Lys | Ala | Pro | Gln | Val | Tyr | Thr | Ile | Pro |      |
|     |     |     | 420 |     |     |     |     | 425 |     |     |     |     | 430 |     |     |      |
| cct | ccc | aag | gag | cag | atg | gcc | aag | gat | aaa | gtc | agt | ctg | acc | tgc | atg | 1344 |
| Pro | Pro | Lys | Glu | Gln | Met | Ala | Lys | Asp | Lys | Val | Ser | Leu | Thr | Cys | Met |      |
|     |     | 435 |     |     |     |     | 440 |     |     |     |     | 445 |     |     |     |      |
| ata | aca | gac | ttc | ttc | cct | gaa | gac | att | act | gtg | gag | tgg | cag | tgg | aat | 1392 |
| Ile | Thr | Asp | Phe | Phe | Pro | Glu | Asp | Ile | Thr | Val | Glu | Trp | Gln | Trp | Asn |      |
| 450 |     |     |     |     | 455 |     |     |     |     | 460 |     |     |     |     |     |      |
| ggg | cag | cca | gcg | gag | aac | tac | aag | aac | act | cag | ccc | atc | atg | gac | aca | 1440 |
| Gly | Gln | Pro | Ala | Glu | Asn | Tyr | Lys | Asn | Thr | Gln | Pro | Ile | Met | Asp | Thr |      |
| 465 |     |     |     | 470 |     |     |     |     | 475 |     |     |     |     | 480 |     |      |
| gat | ggc | tct | tac | ttc | gtc | tac | agc | aag | ctc | aat | gtg | cag | aag | agc | aac | 1488 |
| Asp | Gly | Ser | Tyr | Phe | Val | Tyr | Ser | Lys | Leu | Asn | Val | Gln | Lys | Ser | Asn |      |
|     |     |     | 485 |     |     |     |     | 490 |     |     |     |     | 495 |     |     |      |
| tgg | gag | gca | gga | aat | act | ttc | acc | tgc | tct | gtg | tta | cat | gag | ggc | ctg | 1536 |
| Trp | Glu | Ala | Gly | Asn | Thr | Phe | Thr | Cys | Ser | Val | Leu | His | Glu | Gly | Leu |      |
|     |     | 500 |     |     |     |     | 505 |     |     |     |     | 510 |     |     |     |      |
| cac | aac | cac | cat | act | gag | aag | agc | ctc | tcc | cac | tct | cct | ggg | ctg | caa | 1584 |
| His | Asn | His | His | Thr | Glu | Lys | Ser | Leu | Ser | His | Ser | Pro | Gly | Leu | Gln |      |
| 515 |     |     |     |     | 520 |     |     |     |     | 525 |     |     |     |     |     |      |
| agc | ttg | tcg | aga | agt | act | aga | gga | tca |     |     |     |     |     |     |     | 1611 |
| Ser | Leu | Ser | Arg | Ser | Thr | Arg | Gly | Ser |     |     |     |     |     |     |     |      |

530             535

<210> SEQ ID NO 50
<211> LENGTH: 537
<212> TYPE: PRT
<213> ORGANISM: Artificial
<220> FEATURE:
<223> OTHER INFORMATION: Synthetic Construct

<400> SEQUENCE: 50

Met Ser Tyr Tyr His His His His His Asp Tyr Asp Ile Pro Thr
1               5                   10                  15

Thr Glu Asn Leu Tyr Phe Gln Gly Ala Met Asp Ile Asn Ala Ser Arg
            20                  25                  30

Ala Leu Ala Asn Val Tyr Asp Leu Pro Asp Asp Phe Phe Pro Lys Ile
        35                  40                  45

Asp Asp Leu Val Arg Asp Ala Lys Asp Ala Leu Glu Pro Tyr Trp Lys
50                  55                  60

Ser Asp Ser Ile Lys Lys His Val Leu Ile Ala Thr His Phe Val Asp
65                  70                  75                  80

Leu Ile Glu Asp Phe Trp Gln Thr Thr Gln Gly Met His Glu Ile Ala
                85                  90                  95

Glu Ser Leu Arg Ala Val Ile Pro Pro Thr Thr Thr Pro Val Pro Pro
            100                 105                 110

Gly Tyr Leu Ile Gln His Glu Glu Ala Glu Ile Pro Leu Gly Asp
        115                 120                 125

Leu Phe Lys His Gln Glu Glu Arg Ile Val Ser Phe Gln Pro Asp Tyr
130                 135                 140

Pro Ile Thr Ala Arg Ile His Ala His Leu Lys Ala Tyr Ala Lys Ile
145                 150                 155                 160

Asn Glu Glu Ser Leu Asp Arg Ala Arg Arg Leu Leu Trp Trp His Tyr
                165                 170                 175

Asn Cys Leu Leu Trp Gly Glu Ala Gln Val Thr Asn Tyr Ile Ser Arg
            180                 185                 190

Leu Arg Thr Trp Leu Ser Thr Pro Glu Lys Tyr Arg Gly Arg Asp Ala
        195                 200                 205

Pro Thr Ile Glu Ala Ile Thr Arg Pro Ile Gln Val Ala Gln Gly Gly
210                 215                 220

Arg Lys Thr Thr Thr Gly Thr Arg Lys Pro Arg Gly Leu Glu Pro Arg
225                 230                 235                 240

Arg Arg Lys Val Lys Thr Thr Val Val Tyr Gly Arg Arg Ser Lys
                245                 250                 255

Ser Arg Glu Arg Arg Ala Pro Thr Pro Gln Arg Ala Gly Ser Pro Leu
            260                 265                 270

Pro Arg Ser Ser Ser His His Arg Ser Pro Ser Arg Lys Ser
        275                 280                 285

Arg Pro Gln Gly Gly Gly Ser Val Asp Lys Lys Ile Val Pro Arg Asp
        290                 295                 300

Cys Gly Cys Lys Pro Cys Ile Cys Thr Val Pro Glu Val Ser Ser Val
305                 310                 315                 320

Phe Ile Phe Pro Pro Lys Pro Lys Asp Val Leu Thr Ile Thr Leu Thr
                325                 330                 335

Pro Lys Val Thr Cys Val Val Val Asp Ile Ser Lys Asp Asp Pro Glu
            340                 345                 350

Val Gln Phe Ser Trp Phe Val Asp Asp Val Glu Val His Thr Ala Gln
        355                 360                 365

```
Thr Gln Pro Arg Glu Glu Gln Phe Asn Ser Thr Phe Arg Ser Val Ser
    370                 375                 380

Glu Leu Pro Ile Met His Gln Asp Trp Leu Asn Gly Lys Glu Phe Lys
385                 390                 395                 400

Cys Arg Val Asn Ser Ala Ala Phe Pro Ala Pro Ile Glu Lys Thr Ile
                405                 410                 415

Ser Lys Thr Lys Gly Arg Pro Lys Ala Pro Gln Val Tyr Thr Ile Pro
                420                 425                 430

Pro Pro Lys Glu Gln Met Ala Lys Asp Lys Val Ser Leu Thr Cys Met
                435                 440                 445

Ile Thr Asp Phe Phe Pro Glu Asp Ile Thr Val Glu Trp Gln Trp Asn
    450                 455                 460

Gly Gln Pro Ala Glu Asn Tyr Lys Asn Thr Gln Pro Ile Met Asp Thr
465                 470                 475                 480

Asp Gly Ser Tyr Phe Val Tyr Ser Lys Leu Asn Val Gln Lys Ser Asn
                485                 490                 495

Trp Glu Ala Gly Asn Thr Phe Thr Cys Ser Val Leu His Glu Gly Leu
                500                 505                 510

His Asn His His Thr Glu Lys Ser Leu Ser His Ser Pro Gly Leu Gln
                515                 520                 525

Ser Leu Ser Arg Ser Thr Arg Gly Ser
    530                 535
```

<210> SEQ ID NO 51
<211> LENGTH: 939
<212> TYPE: DNA
<213> ORGANISM: Duck hepatitis B virus
<220> FEATURE:
<221> NAME/KEY: CDS
<222> LOCATION: (1)..(939)

<400> SEQUENCE: 51

```
atg tcg tac tac cat cac cat cac cat cac gat tac gat atc cca acg        48
Met Ser Tyr Tyr His His His His His His Asp Tyr Asp Ile Pro Thr
1               5                   10                  15 acc gaa aac ctg tat ttt cag ggc gcc atg gat atc aat gct tct aga        96
Thr Glu Asn Leu Tyr Phe Gln Gly Ala Met Asp Ile Asn Ala Ser Arg
            20                  25                  30 gcc tta gcc aat gtg tat gat cta cca gat gat ttc ttt cca aaa ata       144
Ala Leu Ala Asn Val Tyr Asp Leu Pro Asp Asp Phe Phe Pro Lys Ile
        35                  40                  45 gat gat ctt gtt aga gat gct aaa gac gct tta gag cct tat tgg aaa       192
Asp Asp Leu Val Arg Asp Ala Lys Asp Ala Leu Glu Pro Tyr Trp Lys
    50                  55                  60 tca gat tca ata aag aaa cat gtt ttg att gca act cac ttt gtg gat       240
Ser Asp Ser Ile Lys Lys His Val Leu Ile Ala Thr His Phe Val Asp
65                  70                  75                  80 ctc att gaa gac ttc tgg cag act aca cag ggc atg cat gaa ata gcc       288
Leu Ile Glu Asp Phe Trp Gln Thr Thr Gln Gly Met His Glu Ile Ala
                85                  90                  95 gaa tca tta aga gct gtt ata cct ccc act act act cct gtt cca ccg       336
Glu Ser Leu Arg Ala Val Ile Pro Pro Thr Thr Thr Pro Val Pro Pro
            100                 105                 110 ggt tat ctt att cag cac gag gaa gct gaa gag ata cct ttg gga gat       384
Gly Tyr Leu Ile Gln His Glu Glu Ala Glu Glu Ile Pro Leu Gly Asp
        115                 120                 125 tta ttt aaa cac caa gaa gaa agg ata gta agt ttc caa ccc gac tat       432
Leu Phe Lys His Gln Glu Glu Arg Ile Val Ser Phe Gln Pro Asp Tyr
    130                 135                 140
```

```
ccg att acg gct aga att cat gct cat ttg aaa gct tat gca aaa att      480
Pro Ile Thr Ala Arg Ile His Ala His Leu Lys Ala Tyr Ala Lys Ile
145                 150                 155                 160 aac gag gaa tca ctg gat agg gct agg aga ttg ctt tgg tgg cat tac      528
Asn Glu Glu Ser Leu Asp Arg Ala Arg Arg Leu Leu Trp Trp His Tyr
                165                 170                 175 aac tgt tta ctg tgg gga gaa gct caa gtt act aac tat att tct cgt      576
Asn Cys Leu Leu Trp Gly Glu Ala Gln Val Thr Asn Tyr Ile Ser Arg
            180                 185                 190 ttg cgt act tgg ttg tca act cct gag aaa tat aga ggt aga gat gcc      624
Leu Arg Thr Trp Leu Ser Thr Pro Glu Lys Tyr Arg Gly Arg Asp Ala
        195                 200                 205 ccg acc att gaa gca atc act aga cca atc cag gtg gct cag gga ggc      672
Pro Thr Ile Glu Ala Ile Thr Arg Pro Ile Gln Val Ala Gln Gly Gly
    210                 215                 220 aga aaa aca act acg ggt act aga aaa cct cgt gga ctc gaa cct aga      720
Arg Lys Thr Thr Thr Gly Thr Arg Lys Pro Arg Gly Leu Glu Pro Arg
225                 230                 235                 240 aga aga aaa gtt aaa acc aca gtt gtc tat ggg aga aga cgt tca aag      768
Arg Arg Lys Val Lys Thr Thr Val Val Tyr Gly Arg Arg Arg Ser Lys
                245                 250                 255 tcc cgg gaa agg aga gcc cct aca ccc caa cgt gcg ggc tcc cct ctc      816
Ser Arg Glu Arg Arg Ala Pro Thr Pro Gln Arg Ala Gly Ser Pro Leu
            260                 265                 270 cca cgt agt tcg agc agc cac cat aga tct ccc tcc cct agg aaa tcg      864
Pro Arg Ser Ser Ser Ser His His Arg Ser Pro Ser Pro Arg Lys Ser
        275                 280                 285 cgg ccg ctt tcg aat cta gag cct gca gtc tcg agg cat gcg gta cca      912
Arg Pro Leu Ser Asn Leu Glu Pro Ala Val Ser Arg His Ala Val Pro
    290                 295                 300 agc ttg tcg aga agt act aga gga tca                                  939
Ser Leu Ser Arg Ser Thr Arg Gly Ser
305                 310
```

<210> SEQ ID NO 52
<211> LENGTH: 313
<212> TYPE: PRT
<213> ORGANISM: Duck hepatitis B virus

<400> SEQUENCE: 52

```
Met Ser Tyr Tyr His His His His Asp Tyr Asp Ile Pro Thr
1               5                   10                  15

Thr Glu Asn Leu Tyr Phe Gln Gly Ala Met Asp Ile Asn Ala Ser Arg
                20                  25                  30

Ala Leu Ala Asn Val Tyr Asp Leu Pro Asp Asp Phe Phe Pro Lys Ile
            35                  40                  45

Asp Asp Leu Val Arg Asp Ala Lys Asp Ala Leu Glu Pro Tyr Trp Lys
        50                  55                  60

Ser Asp Ser Ile Lys Lys His Val Leu Ile Ala Thr His Phe Val Asp
65                  70                  75                  80

Leu Ile Glu Asp Phe Trp Gln Thr Thr Gln Gly Met His Glu Ile Ala
                85                  90                  95

Glu Ser Leu Arg Ala Val Ile Pro Pro Thr Thr Thr Val Pro Pro
            100                 105                 110

Gly Tyr Leu Ile Gln His Glu Glu Ala Glu Glu Ile Pro Leu Gly Asp
        115                 120                 125

Leu Phe Lys His Gln Glu Glu Arg Ile Val Ser Phe Gln Pro Asp Tyr
    130                 135                 140
```

```
Pro Ile Thr Ala Arg Ile His Ala His Leu Lys Ala Tyr Ala Lys Ile
145                 150                 155                 160

Asn Glu Glu Ser Leu Asp Arg Ala Arg Arg Leu Leu Trp Trp His Tyr
                165                 170                 175

Asn Cys Leu Leu Trp Gly Glu Ala Gln Val Thr Asn Tyr Ile Ser Arg
            180                 185                 190

Leu Arg Thr Trp Leu Ser Thr Pro Glu Lys Tyr Arg Gly Arg Asp Ala
        195                 200                 205

Pro Thr Ile Glu Ala Ile Thr Arg Pro Ile Gln Val Ala Gln Gly Gly
    210                 215                 220

Arg Lys Thr Thr Thr Gly Thr Arg Lys Pro Arg Gly Leu Glu Pro Arg
225                 230                 235                 240

Arg Arg Lys Val Lys Thr Thr Val Val Tyr Gly Arg Arg Ser Lys
                245                 250                 255

Ser Arg Glu Arg Arg Ala Pro Thr Pro Gln Arg Ala Gly Ser Pro Leu
            260                 265                 270

Pro Arg Ser Ser Ser His His Arg Ser Pro Ser Pro Arg Lys Ser
        275                 280                 285

Arg Pro Leu Ser Asn Leu Glu Pro Ala Val Ser Arg His Ala Val Pro
    290                 295                 300

Ser Leu Ser Arg Ser Thr Arg Gly Ser
305                 310

<210> SEQ ID NO 53
<211> LENGTH: 750
<212> TYPE: DNA
<213> ORGANISM: Hepatitis C virus
<220> FEATURE:
<221> NAME/KEY: CDS
<222> LOCATION: (1)..(750)

<400> SEQUENCE: 53 atg tcg tac tac cat cac cat cac cat cac gat tac gat atc cca acg     48
Met Ser Tyr Tyr His His His His His His Asp Tyr Asp Ile Pro Thr
1               5                   10                  15 acc gaa aac ctg tat ttt cag ggc gcc atg gat ccg gaa ttc atg agc     96
Thr Glu Asn Leu Tyr Phe Gln Gly Ala Met Asp Pro Glu Phe Met Ser
            20                  25                  30 acg aat cct aaa cct caa aga aaa acc aaa cgt aac acc aac cgt cgc    144
Thr Asn Pro Lys Pro Gln Arg Lys Thr Lys Arg Asn Thr Asn Arg Arg
        35                  40                  45 cca cag gac gtc aag ttc ccg ggt ggc ggt cag atc gtt ggt gga gtt    192
Pro Gln Asp Val Lys Phe Pro Gly Gly Gly Gln Ile Val Gly Gly Val
    50                  55                  60 tac ttg ttg ccg cgc agg ggc cct aga ttg ggt gtg cgc gcg acg agg    240
Tyr Leu Leu Pro Arg Arg Gly Pro Arg Leu Gly Val Arg Ala Thr Arg
65                  70                  75                  80 aag act tcc gag cgg tcg caa cct cga ggt aga cgt cag cct atc ccc    288
Lys Thr Ser Glu Arg Ser Gln Pro Arg Gly Arg Arg Gln Pro Ile Pro
            85                  90                  95 aag gca cgt cgg ccc gag ggc agg acc tgg gct cag ccc ggg tac cct    336
Lys Ala Arg Arg Pro Glu Gly Arg Thr Trp Ala Gln Pro Gly Tyr Pro
        100                 105                 110 tgg ccc ctc tat ggc aat gag ggt tgc ggg tgg gcg gga tgg ctc ctg    384
Trp Pro Leu Tyr Gly Asn Glu Gly Cys Gly Trp Ala Gly Trp Leu Leu
    115                 120                 125 tct ccc cgt ggc tct cgg cct agc tgg ggc ccc aca gac ccc cgg cgt    432
Ser Pro Arg Gly Ser Arg Pro Ser Trp Gly Pro Thr Asp Pro Arg Arg
130                 135                 140
```

```
agg tcg cgc aat ttg ggt aag gtc atc gat acc ctt acg tgc ggc ttc    480
Arg Ser Arg Asn Leu Gly Lys Val Ile Asp Thr Leu Thr Cys Gly Phe
145                 150                 155                 160 gcc gac ctc atg ggg tac ata ccg ctc gtc ggc gcc cct ctt gga ggc    528
Ala Asp Leu Met Gly Tyr Ile Pro Leu Val Gly Ala Pro Leu Gly Gly
                165                 170                 175 gct gcc agg gcc ctg gcg cat ggc gtc cgg gtt ctg gaa gac ggc gtg    576
Ala Ala Arg Ala Leu Ala His Gly Val Arg Val Leu Glu Asp Gly Val
            180                 185                 190 aac tat gca aca ggg aac ctt cct ggt tgc tct ttc tct atc ttc ctt    624
Asn Tyr Ala Thr Gly Asn Leu Pro Gly Cys Ser Phe Ser Ile Phe Leu
        195                 200                 205 ctg gcc ctg ctc tct tgc ctg act gtg ccc gct tca gcc gga cta gtg    672
Leu Ala Leu Leu Ser Cys Leu Thr Val Pro Ala Ser Ala Gly Leu Val
    210                 215                 220 cgg ccg ctt tcg aat cta gag cct gca gtc tcg agg cat gcg gta cca    720
Arg Pro Leu Ser Asn Leu Glu Pro Ala Val Ser Arg His Ala Val Pro
225                 230                 235                 240 agc ttg tcg aga agt act aga gga tca taa                            750
Ser Leu Ser Arg Ser Thr Arg Gly Ser
                245

<210> SEQ ID NO 54
<211> LENGTH: 249
<212> TYPE: PRT
<213> ORGANISM: Hepatitis C virus

<400> SEQUENCE: 54

Met Ser Tyr Tyr His His His His His Asp Tyr Asp Ile Pro Thr
1               5                   10                  15

Thr Glu Asn Leu Tyr Phe Gln Gly Ala Met Asp Pro Glu Phe Met Ser
            20                  25                  30

Thr Asn Pro Lys Pro Gln Arg Lys Thr Lys Arg Asn Thr Asn Arg Arg
        35                  40                  45

Pro Gln Asp Val Lys Phe Pro Gly Gly Gly Gln Ile Val Gly Gly Val
    50                  55                  60

Tyr Leu Leu Pro Arg Arg Gly Pro Arg Leu Gly Val Arg Ala Thr Arg
65                  70                  75                  80

Lys Thr Ser Glu Arg Ser Gln Pro Arg Gly Arg Arg Gln Pro Ile Pro
                85                  90                  95

Lys Ala Arg Arg Pro Glu Gly Arg Thr Trp Ala Gln Pro Gly Tyr Pro
            100                 105                 110

Trp Pro Leu Tyr Gly Asn Glu Gly Cys Gly Trp Ala Gly Trp Leu Leu
        115                 120                 125

Ser Pro Arg Gly Ser Arg Pro Ser Trp Gly Pro Thr Asp Pro Arg Arg
    130                 135                 140

Arg Ser Arg Asn Leu Gly Lys Val Ile Asp Thr Leu Thr Cys Gly Phe
145                 150                 155                 160

Ala Asp Leu Met Gly Tyr Ile Pro Leu Val Gly Ala Pro Leu Gly Gly
                165                 170                 175

Ala Ala Arg Ala Leu Ala His Gly Val Arg Val Leu Glu Asp Gly Val
            180                 185                 190

Asn Tyr Ala Thr Gly Asn Leu Pro Gly Cys Ser Phe Ser Ile Phe Leu
        195                 200                 205

Leu Ala Leu Leu Ser Cys Leu Thr Val Pro Ala Ser Ala Gly Leu Val
    210                 215                 220

Arg Pro Leu Ser Asn Leu Glu Pro Ala Val Ser Arg His Ala Val Pro
225                 230                 235                 240
```

```
Ser Leu Ser Arg Ser Thr Arg Gly Ser
            245

<210> SEQ ID NO 55
<211> LENGTH: 1422
<212> TYPE: DNA
<213> ORGANISM: Artificial
<220> FEATURE:
<223> OTHER INFORMATION: Hepatitis C virus plus murine
<220> FEATURE:
<221> NAME/KEY: CDS
<222> LOCATION: (1)..(1422)

<400> SEQUENCE: 55 atg tcg tac tac cat cac cat cac cat cac gat tac gat atc cca acg      48
Met Ser Tyr Tyr His His His His His His Asp Tyr Asp Ile Pro Thr
1               5                   10                  15 acc gaa aac ctg tat ttt cag ggc gcc atg gat ccg gaa ttc atg agc      96
Thr Glu Asn Leu Tyr Phe Gln Gly Ala Met Asp Pro Glu Phe Met Ser
            20                  25                  30 acg aat cct aaa cct caa aga aaa acc aaa cgt aac acc aac cgt cgc     144
Thr Asn Pro Lys Pro Gln Arg Lys Thr Lys Arg Asn Thr Asn Arg Arg
        35                  40                  45 cca cag gac gtc aag ttc ccg ggt ggc ggt cag atc gtt ggt gga gtt     192
Pro Gln Asp Val Lys Phe Pro Gly Gly Gly Gln Ile Val Gly Gly Val
    50                  55                  60 tac ttg ttg ccg cgc agg ggc cct aga ttg ggt gtg cgc gcg acg agg     240
Tyr Leu Leu Pro Arg Arg Gly Pro Arg Leu Gly Val Arg Ala Thr Arg
65                  70                  75                  80 aag act tcc gag cgg tcg caa cct cga ggt aga cgt cag cct atc ccc     288
Lys Thr Ser Glu Arg Ser Gln Pro Arg Gly Arg Arg Gln Pro Ile Pro
                85                  90                  95 aag gca cgt cgg ccc gag ggc agg acc tgg gct cag ccc ggg tac cct     336
Lys Ala Arg Arg Pro Glu Gly Arg Thr Trp Ala Gln Pro Gly Tyr Pro
            100                 105                 110 tgg ccc ctc tat ggc aat gag ggt tgc ggg tgg gcg gga tgg ctc ctg     384
Trp Pro Leu Tyr Gly Asn Glu Gly Cys Gly Trp Ala Gly Trp Leu Leu
        115                 120                 125 tct ccc cgt ggc tct cgg cct agc tgg ggc ccc aca gac ccc cgg cgt     432
Ser Pro Arg Gly Ser Arg Pro Ser Trp Gly Pro Thr Asp Pro Arg Arg
    130                 135                 140 agg tcg cgc aat ttg ggt aag gtc atc gat acc ctt acg tgc ggc ttc     480
Arg Ser Arg Asn Leu Gly Lys Val Ile Asp Thr Leu Thr Cys Gly Phe
145                 150                 155                 160 gcc gac ctc atg ggg tac ata ccg ctc gtc ggc gcc cct ctt gga ggc     528
Ala Asp Leu Met Gly Tyr Ile Pro Leu Val Gly Ala Pro Leu Gly Gly
                165                 170                 175 gct gcc agg gcc ctg gcg cat ggc gtc cgg gtt ctg gaa gac ggc gtg     576
Ala Ala Arg Ala Leu Ala His Gly Val Arg Val Leu Glu Asp Gly Val
            180                 185                 190 aac tat gca aca ggg aac ctt cct ggt tgc tct ttc tct atc ttc ctt     624
Asn Tyr Ala Thr Gly Asn Leu Pro Gly Cys Ser Phe Ser Ile Phe Leu
        195                 200                 205 ctg gcc ctg ctc tct tgc ctg act gtg ccc gct tca gcc gga cta gtg     672
Leu Ala Leu Leu Ser Cys Leu Thr Val Pro Ala Ser Ala Gly Leu Val
    210                 215                 220 cgg ccg caa ggc ggc gga tcc gtg gac aag aaa att gtg ccc agg gat     720
Arg Pro Gln Gly Gly Gly Ser Val Asp Lys Lys Ile Val Pro Arg Asp
225                 230                 235                 240 tgt ggt tgt aag cct tgc ata tgt aca gtc cca gaa gta tca tct gtc     768
Cys Gly Cys Lys Pro Cys Ile Cys Thr Val Pro Glu Val Ser Ser Val
                245                 250                 255
```

```
ttc atc ttc ccc cca aag ccc aag gat gtg ctc acc att act ctg act    816
Phe Ile Phe Pro Pro Lys Pro Lys Asp Val Leu Thr Ile Thr Leu Thr
            260             265             270 cct aag gtc acg tgt gtt gtg gta gac atc agc aag gat gat ccc gag    864
Pro Lys Val Thr Cys Val Val Val Asp Ile Ser Lys Asp Asp Pro Glu
            275             280             285 gtc cag ttc agc tgg ttt gta gat gat gtg gag gtg cac aca gct cag    912
Val Gln Phe Ser Trp Phe Val Asp Asp Val Glu Val His Thr Ala Gln
        290             295             300 acg caa ccc cgg gag gag cag ttc aac agc act ttc cgc tca gtc agt    960
Thr Gln Pro Arg Glu Glu Gln Phe Asn Ser Thr Phe Arg Ser Val Ser
305             310             315             320 gaa ctt ccc atc atg cac cag gac tgg ctc aat ggc aag gag ttc aaa   1008
Glu Leu Pro Ile Met His Gln Asp Trp Leu Asn Gly Lys Glu Phe Lys
            325             330             335 tgc agg gtc aac agt gca gct ttc cct gcc ccc atc gag aaa acc atc   1056
Cys Arg Val Asn Ser Ala Ala Phe Pro Ala Pro Ile Glu Lys Thr Ile
            340             345             350 tcc aaa acc aaa ggc aga ccg aag gct cca cag gtg tac acc att cca   1104
Ser Lys Thr Lys Gly Arg Pro Lys Ala Pro Gln Val Tyr Thr Ile Pro
            355             360             365 cct ccc aag gag cag atg gcc aag gat aaa gtc agt ctg acc tgc atg   1152
Pro Pro Lys Glu Gln Met Ala Lys Asp Lys Val Ser Leu Thr Cys Met
370             375             380 ata aca gac ttc ttc cct gaa gac att act gtg gag tgg cag tgg aat   1200
Ile Thr Asp Phe Phe Pro Glu Asp Ile Thr Val Glu Trp Gln Trp Asn
385             390             395             400 ggg cag cca gcg gag aac tac aag aac act cag ccc atc atg gac aca   1248
Gly Gln Pro Ala Glu Asn Tyr Lys Asn Thr Gln Pro Ile Met Asp Thr
            405             410             415 gat ggc tct tac ttc gtc tac agc aag ctc aat gtg cag aag agc aac   1296
Asp Gly Ser Tyr Phe Val Tyr Ser Lys Leu Asn Val Gln Lys Ser Asn
            420             425             430 tgg gag gca gga aat act ttc acc tgc tct gtg tta cat gag ggc ctg   1344
Trp Glu Ala Gly Asn Thr Phe Thr Cys Ser Val Leu His Glu Gly Leu
            435             440             445 cac aac cac cat act gag aag agc ctc tcc cac tct cct ggg ctg caa   1392
His Asn His His Thr Glu Lys Ser Leu Ser His Ser Pro Gly Leu Gln
450             455             460 agc ttg tcg aga agt act aga gga tca taa                           1422
Ser Leu Ser Arg Ser Thr Arg Gly Ser
465             470

<210> SEQ ID NO 56
<211> LENGTH: 473
<212> TYPE: PRT
<213> ORGANISM: Artificial
<220> FEATURE:
<223> OTHER INFORMATION: Synthetic Construct

<400> SEQUENCE: 56

Met Ser Tyr Tyr His His His His His His Asp Tyr Asp Ile Pro Thr
1               5                   10                  15

Thr Glu Asn Leu Tyr Phe Gln Gly Ala Met Asp Pro Glu Phe Met Ser
            20                  25                  30

Thr Asn Pro Lys Pro Gln Arg Lys Thr Lys Arg Asn Thr Asn Arg Arg
        35                  40                  45

Pro Gln Asp Val Lys Phe Pro Gly Gly Gly Gln Ile Val Gly Gly Val
    50                  55                  60

Tyr Leu Leu Pro Arg Arg Gly Pro Arg Leu Gly Val Arg Ala Thr Arg
```

```
              65                  70                  75                  80
Lys Thr Ser Glu Arg Ser Gln Pro Arg Gly Arg Gln Pro Ile Pro
                        85                  90                  95
Lys Ala Arg Arg Pro Glu Gly Arg Thr Trp Ala Gln Pro Gly Tyr Pro
                100                 105                 110
Trp Pro Leu Tyr Gly Asn Glu Gly Cys Gly Trp Ala Gly Trp Leu Leu
            115                 120                 125
Ser Pro Arg Gly Ser Arg Pro Ser Trp Gly Pro Thr Asp Pro Arg Arg
    130                 135                 140
Arg Ser Arg Asn Leu Gly Lys Val Ile Asp Thr Leu Thr Cys Gly Phe
145                 150                 155                 160
Ala Asp Leu Met Gly Tyr Ile Pro Leu Val Gly Ala Pro Leu Gly Gly
                165                 170                 175
Ala Ala Arg Ala Leu Ala His Gly Val Arg Val Leu Glu Asp Gly Val
            180                 185                 190
Asn Tyr Ala Thr Gly Asn Leu Pro Gly Cys Ser Phe Ser Ile Phe Leu
        195                 200                 205
Leu Ala Leu Leu Ser Cys Leu Thr Val Pro Ala Ser Ala Gly Leu Val
    210                 215                 220
Arg Pro Gln Gly Gly Gly Ser Val Asp Lys Ile Val Pro Arg Asp
225                 230                 235                 240
Cys Gly Cys Lys Pro Cys Ile Cys Thr Val Pro Glu Val Ser Ser Val
                245                 250                 255
Phe Ile Phe Pro Pro Lys Pro Lys Asp Val Leu Thr Ile Thr Leu Thr
            260                 265                 270
Pro Lys Val Thr Cys Val Val Asp Ile Ser Lys Asp Asp Pro Glu
        275                 280                 285
Val Gln Phe Ser Trp Phe Val Asp Asp Val Glu Val His Thr Ala Gln
    290                 295                 300
Thr Gln Pro Arg Glu Glu Gln Phe Asn Ser Thr Phe Arg Ser Val Ser
305                 310                 315                 320
Glu Leu Pro Ile Met His Gln Asp Trp Leu Asn Gly Lys Glu Phe Lys
                325                 330                 335
Cys Arg Val Asn Ser Ala Ala Phe Pro Ala Pro Ile Glu Lys Thr Ile
            340                 345                 350
Ser Lys Thr Lys Gly Arg Pro Lys Ala Pro Gln Val Tyr Thr Ile Pro
        355                 360                 365
Pro Pro Lys Glu Gln Met Ala Lys Asp Lys Val Ser Leu Thr Cys Met
    370                 375                 380
Ile Thr Asp Phe Phe Pro Glu Asp Ile Thr Val Glu Trp Gln Trp Asn
385                 390                 395                 400
Gly Gln Pro Ala Glu Asn Tyr Lys Asn Thr Gln Pro Ile Met Asp Thr
                405                 410                 415
Asp Gly Ser Tyr Phe Val Tyr Ser Lys Leu Asn Val Gln Lys Ser Asn
            420                 425                 430
Trp Glu Ala Gly Asn Thr Phe Thr Cys Ser Val Leu His Glu Gly Leu
        435                 440                 445
His Asn His His Thr Glu Lys Ser Leu Ser His Ser Pro Gly Leu Gln
    450                 455                 460
Ser Leu Ser Arg Ser Thr Arg Gly Ser
465                 470

<210> SEQ ID NO 57
<211> LENGTH: 708
```

```
<212> TYPE: DNA
<213> ORGANISM: Hepatitis C virus
<220> FEATURE:
<221> NAME/KEY: CDS
<222> LOCATION: (1)..(708)

<400> SEQUENCE: 57 atg tcg tac tac cat cac cat cac cat cac gat tac gat atc cca acg      48
Met Ser Tyr Tyr His His His His His His Asp Tyr Asp Ile Pro Thr
1               5                   10                  15 acc gaa aac ctg tat ttt cag ggc gcc atg gat ccg gaa ttc atg agc      96
Thr Glu Asn Leu Tyr Phe Gln Gly Ala Met Asp Pro Glu Phe Met Ser
                20                  25                  30 acg aat cct aaa cct caa aga aaa acc aaa cgt aac acc aac cgt cgc     144
Thr Asn Pro Lys Pro Gln Arg Lys Thr Lys Arg Asn Thr Asn Arg Arg
            35                  40                  45 cca cag gac gtc aag ttc ccg ggt ggc ggt cag atc gtt ggt gga gtt     192
Pro Gln Asp Val Lys Phe Pro Gly Gly Gly Gln Ile Val Gly Gly Val
        50                  55                  60 tac ttg ttg ccg cgc agg ggc cct aga ttg ggt gtg cgc gcg acg agg     240
Tyr Leu Leu Pro Arg Arg Gly Pro Arg Leu Gly Val Arg Ala Thr Arg
65                  70                  75                  80 aag act tcc gag cgg tcg caa cct cga ggt aga cgt cag cct atc ccc     288
Lys Thr Ser Glu Arg Ser Gln Pro Arg Gly Arg Arg Gln Pro Ile Pro
                85                  90                  95 aag gca cgt cgg ccc gag ggc agg acc tgg gct cag ccc ggg tac cct     336
Lys Ala Arg Arg Pro Glu Gly Arg Thr Trp Ala Gln Pro Gly Tyr Pro
            100                 105                 110 tgg ccc ctc tat ggc aat gag ggt tgc ggg tgg gcg gga tgg ctc ctg     384
Trp Pro Leu Tyr Gly Asn Glu Gly Cys Gly Trp Ala Gly Trp Leu Leu
        115                 120                 125 tct ccc cgt ggc tct cgg cct agc tgg ggc ccc aca gac ccc cgg cgt     432
Ser Pro Arg Gly Ser Arg Pro Ser Trp Gly Pro Thr Asp Pro Arg Arg
130                 135                 140 agg tcg cgc aat ttg ggt aag gtc atc gat acc ctt acg tgc ggc ttc     480
Arg Ser Arg Asn Leu Gly Lys Val Ile Asp Thr Leu Thr Cys Gly Phe
145                 150                 155                 160 gcc gac ctc atg ggg tac ata ccg ctc gtc ggc gcc cct ctt gga ggc     528
Ala Asp Leu Met Gly Tyr Ile Pro Leu Val Gly Ala Pro Leu Gly Gly
                165                 170                 175 gct gcc agg gcc ctg gcg cat ggc gtc cgg gtt ctg gaa gac ggc gtg     576
Ala Ala Arg Ala Leu Ala His Gly Val Arg Val Leu Glu Asp Gly Val
            180                 185                 190 aac tat gca aca ggg aac ctt cct ggt tgc tct ttc tct atc ttc gga     624
Asn Tyr Ala Thr Gly Asn Leu Pro Gly Cys Ser Phe Ser Ile Phe Gly
        195                 200                 205 cta gtg cgg ccg ctt tcg aat cta gag cct gca gtc tcg agg cat gcg     672
Leu Val Arg Pro Leu Ser Asn Leu Glu Pro Ala Val Ser Arg His Ala
    210                 215                 220 gta cca agc ttg tcg aga agt act aga gga tca taa                     708
Val Pro Ser Leu Ser Arg Ser Thr Arg Gly Ser
225                 230                 235

<210> SEQ ID NO 58
<211> LENGTH: 235
<212> TYPE: PRT
<213> ORGANISM: Hepatitis C virus

<400> SEQUENCE: 58

Met Ser Tyr Tyr His His His His His His Asp Tyr Asp Ile Pro Thr
1               5                   10                  15

Thr Glu Asn Leu Tyr Phe Gln Gly Ala Met Asp Pro Glu Phe Met Ser
```

```
                    20                  25                  30
Thr Asn Pro Lys Pro Gln Arg Lys Thr Lys Arg Asn Thr Asn Arg Arg
        35                  40                  45

Pro Gln Asp Val Lys Phe Pro Gly Gly Gly Gln Ile Val Gly Gly Val
    50                  55                  60

Tyr Leu Leu Pro Arg Arg Gly Pro Arg Leu Gly Val Arg Ala Thr Arg
65                  70                  75                  80

Lys Thr Ser Glu Arg Ser Gln Pro Arg Gly Arg Arg Gln Pro Ile Pro
                85                  90                  95

Lys Ala Arg Arg Pro Glu Gly Arg Thr Trp Ala Gln Pro Gly Tyr Pro
            100                 105                 110

Trp Pro Leu Tyr Gly Asn Glu Gly Cys Gly Trp Ala Gly Trp Leu Leu
        115                 120                 125

Ser Pro Arg Gly Ser Arg Pro Ser Trp Gly Pro Thr Asp Pro Arg Arg
    130                 135                 140

Arg Ser Arg Asn Leu Gly Lys Val Ile Asp Thr Leu Thr Cys Gly Phe
145                 150                 155                 160

Ala Asp Leu Met Gly Tyr Ile Pro Leu Val Gly Ala Pro Leu Gly Gly
                165                 170                 175

Ala Ala Arg Ala Leu Ala His Gly Val Arg Val Leu Glu Asp Gly Val
            180                 185                 190

Asn Tyr Ala Thr Gly Asn Leu Pro Gly Cys Ser Phe Ser Ile Phe Gly
        195                 200                 205

Leu Val Arg Pro Leu Ser Asn Leu Glu Pro Ala Val Ser Arg His Ala
    210                 215                 220

Val Pro Ser Leu Ser Arg Ser Thr Arg Gly Ser
225                 230                 235

<210> SEQ ID NO 59
<211> LENGTH: 1380
<212> TYPE: DNA
<213> ORGANISM: Artificial
<220> FEATURE:
<223> OTHER INFORMATION: Hepatitis C virus plus murine
<220> FEATURE:
<221> NAME/KEY: CDS
<222> LOCATION: (1)..(1380)

<400> SEQUENCE: 59 atg tcg tac tac cat cac cat cac cat cac gat tac gat atc cca acg    48
Met Ser Tyr Tyr His His His His His His Asp Tyr Asp Ile Pro Thr
1               5                   10                  15 acc gaa aac ctg tat ttt cag ggc gcc atg gat ccg gaa ttc atg agc    96
Thr Glu Asn Leu Tyr Phe Gln Gly Ala Met Asp Pro Glu Phe Met Ser
            20                  25                  30 acg aat cct aaa cct caa aga aaa acc aaa cgt aac acc aac cgt cgc   144
Thr Asn Pro Lys Pro Gln Arg Lys Thr Lys Arg Asn Thr Asn Arg Arg
        35                  40                  45 cca cag gac gtc aag ttc ccg ggt ggc ggt cag atc gtt ggt gga gtt   192
Pro Gln Asp Val Lys Phe Pro Gly Gly Gly Gln Ile Val Gly Gly Val
    50                  55                  60 tac ttg ttg ccg cgc agg ggc cct aga ttg ggt gtg cgc gcg acg agg   240
Tyr Leu Leu Pro Arg Arg Gly Pro Arg Leu Gly Val Arg Ala Thr Arg
65                  70                  75                  80 aag act tcc gag cgg tcg caa cct cga ggt aga cgt cag cct atc ccc   288
Lys Thr Ser Glu Arg Ser Gln Pro Arg Gly Arg Arg Gln Pro Ile Pro
                85                  90                  95 aag gca cgt cgg ccc gag ggc agg acc tgg gct cag ccc ggg tac cct   336
Lys Ala Arg Arg Pro Glu Gly Arg Thr Trp Ala Gln Pro Gly Tyr Pro
```

```
                    100                 105                 110
tgg ccc ctc tat ggc aat gag ggt tgc ggg tgg gcg gga tgg ctc ctg     384
Trp Pro Leu Tyr Gly Asn Glu Gly Cys Gly Trp Ala Gly Trp Leu Leu
            115                 120                 125 tct ccc cgt ggc tct cgg cct agc tgg ggc ccc aca gac ccc cgg cgt     432
Ser Pro Arg Gly Ser Arg Pro Ser Trp Gly Pro Thr Asp Pro Arg Arg
    130                 135                 140 agg tcg cgc aat ttg ggt aag gtc atc gat acc ctt acg tgc ggc ttc     480
Arg Ser Arg Asn Leu Gly Lys Val Ile Asp Thr Leu Thr Cys Gly Phe
145                 150                 155                 160 gcc gac ctc atg ggg tac ata ccg ctc gtc ggc gcc cct ctt gga ggc     528
Ala Asp Leu Met Gly Tyr Ile Pro Leu Val Gly Ala Pro Leu Gly Gly
                165                 170                 175 gct gcc agg gcc ctg gcg cat ggc gtc cgg gtt ctg gaa gac ggc gtg     576
Ala Ala Arg Ala Leu Ala His Gly Val Arg Val Leu Glu Asp Gly Val
            180                 185                 190 aac tat gca aca ggg aac ctt cct ggt tgc tct ttc tct atc ttc gga     624
Asn Tyr Ala Thr Gly Asn Leu Pro Gly Cys Ser Phe Ser Ile Phe Gly
    195                 200                 205 cta gtg cgg ccg caa ggc ggc gga tcc gtg gac aag aaa att gtg ccc     672
Leu Val Arg Pro Gln Gly Gly Gly Ser Val Asp Lys Lys Ile Val Pro
210                 215                 220 agg gat tgt ggt tgt aag cct tgc ata tgt aca gtc cca gaa gta tca     720
Arg Asp Cys Gly Cys Lys Pro Cys Ile Cys Thr Val Pro Glu Val Ser
225                 230                 235                 240 tct gtc ttc atc ttc ccc cca aag ccc aag gat gtg ctc acc att act     768
Ser Val Phe Ile Phe Pro Pro Lys Pro Lys Asp Val Leu Thr Ile Thr
                245                 250                 255 ctg act cct aag gtc acg tgt gtt gtg gta gac atc agc aag gat gat     816
Leu Thr Pro Lys Val Thr Cys Val Val Val Asp Ile Ser Lys Asp Asp
            260                 265                 270 ccc gag gtc cag ttc agc tgg ttt gta gat gat gtg gag gtg cac aca     864
Pro Glu Val Gln Phe Ser Trp Phe Val Asp Asp Val Glu Val His Thr
    275                 280                 285 gct cag acg caa ccc cgg gag gag cag ttc aac agc act ttc cgc tca     912
Ala Gln Thr Gln Pro Arg Glu Glu Gln Phe Asn Ser Thr Phe Arg Ser
290                 295                 300 gtc agt gaa ctt ccc atc atg cac cag gac tgg ctc aat ggc aag gag     960
Val Ser Glu Leu Pro Ile Met His Gln Asp Trp Leu Asn Gly Lys Glu
305                 310                 315                 320 ttc aaa tgc agg gtc aac agt gca gct ttc cct gcc ccc atc gag aaa    1008
Phe Lys Cys Arg Val Asn Ser Ala Ala Phe Pro Ala Pro Ile Glu Lys
                325                 330                 335 acc atc tcc aaa acc aaa ggc aga ccg aag gct cca cag gtg tac acc    1056
Thr Ile Ser Lys Thr Lys Gly Arg Pro Lys Ala Pro Gln Val Tyr Thr
            340                 345                 350 att cca cct ccc aag gag cag atg gcc aag gat aaa gtc agt ctg acc    1104
Ile Pro Pro Pro Lys Glu Gln Met Ala Lys Asp Lys Val Ser Leu Thr
    355                 360                 365 tgc atg ata aca gac ttc ttc cct gaa gac att act gtg gag tgg cag    1152
Cys Met Ile Thr Asp Phe Phe Pro Glu Asp Ile Thr Val Glu Trp Gln
370                 375                 380 tgg aat ggg cag cca gcg gag aac tac aag aac act cag ccc atc atg    1200
Trp Asn Gly Gln Pro Ala Glu Asn Tyr Lys Asn Thr Gln Pro Ile Met
385                 390                 395                 400 gac aca gat ggc tct tac ttc gtc tac agc aag ctc aat gtg cag aag    1248
Asp Thr Asp Gly Ser Tyr Phe Val Tyr Ser Lys Leu Asn Val Gln Lys
                405                 410                 415 agc aac tgg gag gca gga aat act ttc acc tgc tct gtg tta cat gag    1296
Ser Asn Trp Glu Ala Gly Asn Thr Phe Thr Cys Ser Val Leu His Glu
```

-continued

```
                           420                 425                 430
ggc ctg cac aac cac cat act gag aag agc ctc tcc cac tct cct ggg      1344
Gly Leu His Asn His His Thr Glu Lys Ser Leu Ser His Ser Pro Gly
            435                 440                 445 ctg caa agc ttg tcg aga agt act aga gga tca taa                      1380
Leu Gln Ser Leu Ser Arg Ser Thr Arg Gly Ser
    450                 455
```

<210> SEQ ID NO 60
<211> LENGTH: 459
<212> TYPE: PRT
<213> ORGANISM: Artificial
<220> FEATURE:
<223> OTHER INFORMATION: Synthetic Construct

<400> SEQUENCE: 60

```
Met Ser Tyr Tyr His His His His His Asp Tyr Asp Ile Pro Thr
1               5                   10                  15

Thr Glu Asn Leu Tyr Phe Gln Gly Ala Met Asp Pro Glu Phe Met Ser
            20                  25                  30

Thr Asn Pro Lys Pro Gln Arg Lys Thr Lys Arg Asn Thr Asn Arg Arg
        35                  40                  45

Pro Gln Asp Val Lys Phe Pro Gly Gly Gly Gln Ile Val Gly Gly Val
    50                  55                  60

Tyr Leu Leu Pro Arg Arg Gly Pro Arg Leu Gly Val Arg Ala Thr Arg
65                  70                  75                  80

Lys Thr Ser Glu Arg Ser Gln Pro Arg Gly Arg Arg Gln Pro Ile Pro
                85                  90                  95

Lys Ala Arg Arg Pro Glu Gly Arg Thr Trp Ala Gln Pro Gly Tyr Pro
            100                 105                 110

Trp Pro Leu Tyr Gly Asn Glu Gly Cys Gly Trp Ala Gly Trp Leu Leu
        115                 120                 125

Ser Pro Arg Gly Ser Arg Pro Ser Trp Gly Pro Thr Asp Pro Arg Arg
    130                 135                 140

Arg Ser Arg Asn Leu Gly Lys Val Ile Asp Thr Leu Thr Cys Gly Phe
145                 150                 155                 160

Ala Asp Leu Met Gly Tyr Ile Pro Leu Val Gly Ala Pro Leu Gly Gly
                165                 170                 175

Ala Ala Arg Ala Leu Ala His Gly Val Arg Val Leu Glu Asp Gly Val
            180                 185                 190

Asn Tyr Ala Thr Gly Asn Leu Pro Gly Cys Ser Phe Ser Ile Phe Gly
        195                 200                 205

Leu Val Arg Pro Gln Gly Gly Gly Ser Val Asp Lys Lys Ile Val Pro
    210                 215                 220

Arg Asp Cys Gly Cys Lys Pro Cys Ile Cys Thr Val Pro Glu Val Ser
225                 230                 235                 240

Ser Val Phe Ile Phe Pro Pro Lys Pro Lys Asp Val Leu Thr Ile Thr
                245                 250                 255

Leu Thr Pro Lys Val Thr Cys Val Val Val Asp Ile Ser Lys Asp Asp
            260                 265                 270

Pro Glu Val Gln Phe Ser Trp Phe Val Asp Asp Val Glu Val His Thr
        275                 280                 285

Ala Gln Thr Gln Pro Arg Glu Glu Gln Phe Asn Ser Thr Phe Arg Ser
    290                 295                 300

Val Ser Glu Leu Pro Ile Met His Gln Asp Trp Leu Asn Gly Lys Glu
305                 310                 315                 320
```

-continued

```
        Phe Lys Cys Arg Val Asn Ser Ala Ala Phe Pro Ala Pro Ile Glu Lys
                        325                 330                 335

Thr Ile Ser Lys Thr Lys Gly Arg Pro Lys Ala Pro Gln Val Tyr Thr
                    340                 345                 350

Ile Pro Pro Lys Glu Gln Met Ala Lys Asp Lys Val Ser Leu Thr
                355                 360                 365

Cys Met Ile Thr Asp Phe Phe Pro Glu Asp Ile Thr Val Glu Trp Gln
        370                 375                 380

Trp Asn Gly Gln Pro Ala Glu Asn Tyr Lys Asn Thr Gln Pro Ile Met
        385                 390                 395                 400

Asp Thr Asp Gly Ser Tyr Phe Val Tyr Ser Lys Leu Asn Val Gln Lys
                        405                 410                 415

Ser Asn Trp Glu Ala Gly Asn Thr Phe Thr Cys Ser Val Leu His Glu
                    420                 425                 430

Gly Leu His Asn His His Thr Glu Lys Ser Leu Ser His Ser Pro Gly
                435                 440                 445

Leu Gln Ser Leu Ser Arg Ser Thr Arg Gly Ser
            450                 455

<210> SEQ ID NO 61
<211> LENGTH: 1518
<212> TYPE: DNA
<213> ORGANISM: Hepatitis C virus
<220> FEATURE:
<221> NAME/KEY: CDS
<222> LOCATION: (1)..(1518)

<400> SEQUENCE: 61 atg tcg tac tac cat cac cat cac cat cac gat tac gat atc cca acg        48
Met Ser Tyr Tyr His His His His His His Asp Tyr Asp Ile Pro Thr
1               5                   10                  15 acc gaa aac ctg tat ttt cag ggc gcc atg gat ccg gaa ttc tcc ggt        96
Thr Glu Asn Leu Tyr Phe Gln Gly Ala Met Asp Pro Glu Phe Ser Gly
                20                  25                  30 tcc tgg cta agg gac atc tgg gac tgg ata tgc gag gtg ctg agc gac       144
Ser Trp Leu Arg Asp Ile Trp Asp Trp Ile Cys Glu Val Leu Ser Asp
            35                  40                  45 ttt aag acc tgg ctg aaa gcc aag ctc atg cca caa ctg cct ggg att       192
Phe Lys Thr Trp Leu Lys Ala Lys Leu Met Pro Gln Leu Pro Gly Ile
        50                  55                  60 ccc ttt gtg tcc tgc cag cgc ggg tat agg ggg gtc tgg cga gga gac       240
Pro Phe Val Ser Cys Gln Arg Gly Tyr Arg Gly Val Trp Arg Gly Asp
65                  70                  75                  80 ggc att atg cac act cgc tgc cac tgt gga gct gag atc act gga cat       288
Gly Ile Met His Thr Arg Cys His Cys Gly Ala Glu Ile Thr Gly His
                85                  90                  95 gtc aaa aac ggg acg atg agg atc gtc ggt cct agg acc tgc agg aac       336
Val Lys Asn Gly Thr Met Arg Ile Val Gly Pro Arg Thr Cys Arg Asn
                100                 105                 110 atg tgg agt ggg acg ttc ccc att aac gcc tac acc acg ggc ccc tgt       384
Met Trp Ser Gly Thr Phe Pro Ile Asn Ala Tyr Thr Thr Gly Pro Cys
            115                 120                 125 act ccc ctt cct gcg ccg aac tat aag ttc gcg ctg tgg agg gtg tct       432
Thr Pro Leu Pro Ala Pro Asn Tyr Lys Phe Ala Leu Trp Arg Val Ser
        130                 135                 140 gca gag gaa tac gtg gag ata agg cgg gtg ggg gac ttc cac tac gta       480
Ala Glu Glu Tyr Val Glu Ile Arg Arg Val Gly Asp Phe His Tyr Val
145                 150                 155                 160 tcg ggt atg act act gac aat ctt aaa tgc ccg tgc cag atc cca tcg       528
Ser Gly Met Thr Thr Asp Asn Leu Lys Cys Pro Cys Gln Ile Pro Ser
```

```
                            165                 170                 175
cccgaattttcacagaattgacgggtgcgctacacaggtttgcg              576
Pro Glu Phe Phe Thr Glu Leu Asp Gly Val Arg Leu His Arg Phe Ala
                180                 185                 190 ccc cct tgc aag ccc ttg ctg cgg gag gag gta tca ttc aga gta gga   624
Pro Pro Cys Lys Pro Leu Leu Arg Glu Glu Val Ser Phe Arg Val Gly
            195                 200                 205 ctc cac gag tac ccg gtg ggg tcg caa tta cct tgc gag ccc gaa ccg   672
Leu His Glu Tyr Pro Val Gly Ser Gln Leu Pro Cys Glu Pro Glu Pro
        210                 215                 220 gac gta gcc gtg ttg acg tcc atg ctc act gat ccc tcc cat ata aca   720
Asp Val Ala Val Leu Thr Ser Met Leu Thr Asp Pro Ser His Ile Thr
225                 230                 235                 240 gca gag gcg gcc ggg aga agg ttg gcg aga ggg tca ccc cct tct atg   768
Ala Glu Ala Ala Gly Arg Arg Leu Ala Arg Gly Ser Pro Pro Ser Met
                245                 250                 255 gcc agc tcc tcg gct agc cag ctg tcc gct cca tct ctc aag gca act   816
Ala Ser Ser Ser Ala Ser Gln Leu Ser Ala Pro Ser Leu Lys Ala Thr
            260                 265                 270 tgc acc gcc aac cat gac tcc cct gac gcc gag ctc ata gag gct aac   864
Cys Thr Ala Asn His Asp Ser Pro Asp Ala Glu Leu Ile Glu Ala Asn
        275                 280                 285 ctc ctg tgg agg cag gag atg ggc ggc aac atc acc agg gtt gag tca   912
Leu Leu Trp Arg Gln Glu Met Gly Gly Asn Ile Thr Arg Val Glu Ser
        290                 295                 300 gag aac aaa gtg gtg att ctg gac tcc ttc gat ccg ctt gtg gca gag   960
Glu Asn Lys Val Val Ile Leu Asp Ser Phe Asp Pro Leu Val Ala Glu
305                 310                 315                 320 gag gat gag cgg gag gtc tcc gta cct gca gaa att ctg cgg aag tct   1008
Glu Asp Glu Arg Glu Val Ser Val Pro Ala Glu Ile Leu Arg Lys Ser
                325                 330                 335 cgg aga ttc gcc cgg gcc ctg ccc gtc tgg gcg cgg ccg gac tac aac   1056
Arg Arg Phe Ala Arg Ala Leu Pro Val Trp Ala Arg Pro Asp Tyr Asn
            340                 345                 350 ccc ccg cta gta gag acg tgg aaa aag cct gac tac gaa cca cct gtg   1104
Pro Pro Leu Val Glu Thr Trp Lys Lys Pro Asp Tyr Glu Pro Pro Val
        355                 360                 365 gtc cat ggc tgc ccg cta cca cct cca cgg tcc cct cct gtg cct ccg   1152
Val His Gly Cys Pro Leu Pro Pro Pro Arg Ser Pro Pro Val Pro Pro
370                 375                 380 cct cgg aaa aag cgt acg gtg gtc ctc acc gaa tca acc cta tct act   1200
Pro Arg Lys Lys Arg Thr Val Val Leu Thr Glu Ser Thr Leu Ser Thr
385                 390                 395                 400 gcc ttg gcc gag ctt gcc acc aaa agt ttt ggc agc tcc tca act tcc   1248
Ala Leu Ala Glu Leu Ala Thr Lys Ser Phe Gly Ser Ser Ser Thr Ser
                405                 410                 415 ggc att acg ggc gac aat acg aca aca tcc tct gag ccc gcc cct tct   1296
Gly Ile Thr Gly Asp Asn Thr Thr Thr Ser Ser Glu Pro Ala Pro Ser
            420                 425                 430 ggc tgc ccc ccc gac tcc gac gtt gag tcc tat tct tcc atg ccc ccc   1344
Gly Cys Pro Pro Asp Ser Asp Val Glu Ser Tyr Ser Ser Met Pro Pro
        435                 440                 445 ctg gag ggg gag cct ggg gat ccg gat ctc agc gac ggg tca tgg tcg   1392
Leu Glu Gly Glu Pro Gly Asp Pro Asp Leu Ser Asp Gly Ser Trp Ser
450                 455                 460 acg gtc agt agt ggg gcc gac acg gaa gat gtc gtg tgc gga cta gtg   1440
Thr Val Ser Ser Gly Ala Asp Thr Glu Asp Val Val Cys Gly Leu Val
465                 470                 475                 480 cgg ccg ctt tcg aat cta gag cct gca gtc tcg agg cat gcg gta cca   1488
Arg Pro Leu Ser Asn Leu Glu Pro Ala Val Ser Arg His Ala Val Pro
```

```
                     485          490          495
agc ttg tcg aga agt act aga gga tca taa                              1518
Ser Leu Ser Arg Ser Thr Arg Gly Ser
        500                  505

<210> SEQ ID NO 62
<211> LENGTH: 505
<212> TYPE: PRT
<213> ORGANISM: Hepatitis C virus

<400> SEQUENCE: 62

Met Ser Tyr Tyr His His His His His His Asp Tyr Asp Ile Pro Thr
 1               5                  10                  15

Thr Glu Asn Leu Tyr Phe Gln Gly Ala Met Asp Pro Glu Phe Ser Gly
                20                  25                  30

Ser Trp Leu Arg Asp Ile Trp Asp Trp Ile Cys Glu Val Leu Ser Asp
            35                  40                  45

Phe Lys Thr Trp Leu Lys Ala Lys Leu Met Pro Gln Leu Pro Gly Ile
50                  55                  60

Pro Phe Val Ser Cys Gln Arg Gly Tyr Arg Gly Val Trp Arg Gly Asp
65                  70                  75                  80

Gly Ile Met His Thr Arg Cys His Cys Gly Ala Glu Ile Thr Gly His
                85                  90                  95

Val Lys Asn Gly Thr Met Arg Ile Val Gly Pro Arg Thr Cys Arg Asn
            100                 105                 110

Met Trp Ser Gly Thr Phe Pro Ile Asn Ala Tyr Thr Thr Gly Pro Cys
        115                 120                 125

Thr Pro Leu Pro Ala Pro Asn Tyr Lys Phe Ala Leu Trp Arg Val Ser
130                 135                 140

Ala Glu Glu Tyr Val Glu Ile Arg Arg Val Gly Asp Phe His Tyr Val
145                 150                 155                 160

Ser Gly Met Thr Thr Asp Asn Leu Lys Cys Pro Cys Gln Ile Pro Ser
                165                 170                 175

Pro Glu Phe Phe Thr Glu Leu Asp Gly Val Arg Leu His Arg Phe Ala
            180                 185                 190

Pro Pro Cys Lys Pro Leu Leu Arg Glu Glu Val Ser Phe Arg Val Gly
        195                 200                 205

Leu His Glu Tyr Pro Val Gly Ser Gln Leu Pro Cys Glu Pro Glu Pro
210                 215                 220

Asp Val Ala Val Leu Thr Ser Met Leu Thr Asp Pro Ser His Ile Thr
225                 230                 235                 240

Ala Glu Ala Ala Gly Arg Arg Leu Ala Arg Gly Ser Pro Pro Ser Met
                245                 250                 255

Ala Ser Ser Ser Ala Ser Gln Leu Ser Ala Pro Ser Leu Lys Ala Thr
            260                 265                 270

Cys Thr Ala Asn His Asp Ser Pro Asp Ala Glu Leu Ile Glu Ala Asn
        275                 280                 285

Leu Leu Trp Arg Gln Glu Met Gly Gly Asn Ile Thr Arg Val Glu Ser
290                 295                 300

Glu Asn Lys Val Val Ile Leu Asp Ser Phe Asp Pro Leu Val Ala Glu
305                 310                 315                 320

Glu Asp Glu Arg Glu Val Ser Val Pro Ala Glu Ile Leu Arg Lys Ser
                325                 330                 335

Arg Arg Phe Ala Arg Ala Leu Pro Val Trp Ala Arg Pro Asp Tyr Asn
            340                 345                 350
```

-continued

```
Pro Pro Leu Val Glu Thr Trp Lys Lys Pro Asp Tyr Glu Pro Pro Val
        355                 360                 365

Val His Gly Cys Pro Leu Pro Pro Arg Ser Pro Val Pro Pro
    370                 375                 380

Pro Arg Lys Lys Arg Thr Val Val Leu Thr Glu Ser Thr Leu Ser Thr
385                 390                 395                 400

Ala Leu Ala Glu Leu Ala Thr Lys Ser Phe Gly Ser Ser Thr Ser
                405                 410                 415

Gly Ile Thr Gly Asp Asn Thr Thr Ser Ser Glu Pro Ala Pro Ser
                420                 425                 430

Gly Cys Pro Pro Asp Ser Asp Val Glu Ser Tyr Ser Ser Met Pro Pro
                435                 440                 445

Leu Glu Gly Glu Pro Gly Asp Pro Asp Leu Ser Asp Gly Ser Trp Ser
450                 455                 460

Thr Val Ser Ser Gly Ala Asp Thr Glu Asp Val Val Cys Gly Leu Val
465                 470                 475                 480

Arg Pro Leu Ser Asn Leu Glu Pro Ala Val Ser Arg His Ala Val Pro
                485                 490                 495

Ser Leu Ser Arg Ser Thr Arg Gly Ser
                500                 505

<210> SEQ ID NO 63
<211> LENGTH: 2190
<212> TYPE: DNA
<213> ORGANISM: Artificial
<220> FEATURE:
<223> OTHER INFORMATION: Hepatitis C virus plus murine
<220> FEATURE:
<221> NAME/KEY: CDS
<222> LOCATION: (1)..(2190)

<400> SEQUENCE: 63 atg tcg tac tac cat cac cat cac cat cac gat tac gat atc cca acg    48
Met Ser Tyr Tyr His His His His His His Asp Tyr Asp Ile Pro Thr
1               5                   10                  15 acc gaa aac ctg tat ttt cag ggc gcc atg gat ccg gaa ttc tcc ggt    96
Thr Glu Asn Leu Tyr Phe Gln Gly Ala Met Asp Pro Glu Phe Ser Gly
            20                  25                  30 tcc tgg cta agg gac atc tgg gac tgg ata tgc gag gtg ctg agc gac   144
Ser Trp Leu Arg Asp Ile Trp Asp Trp Ile Cys Glu Val Leu Ser Asp
        35                  40                  45 ttt aag acc tgg ctg aaa gcc aag ctc atg cca caa ctg cct ggg att   192
Phe Lys Thr Trp Leu Lys Ala Lys Leu Met Pro Gln Leu Pro Gly Ile
    50                  55                  60 ccc ttt gtg tcc tgc cag cgc ggg tat agg ggg gtc tgg cga gga gac   240
Pro Phe Val Ser Cys Gln Arg Gly Tyr Arg Gly Val Trp Arg Gly Asp
65                  70                  75                  80 ggc att atg cac act cgc tgc cac tgt gga gct gag atc act gga cat   288
Gly Ile Met His Thr Arg Cys His Cys Gly Ala Glu Ile Thr Gly His
                85                  90                  95 gtc aaa aac ggg acg atg agg atc gtc ggt cct agg acc tgc agg aac   336
Val Lys Asn Gly Thr Met Arg Ile Val Gly Pro Arg Thr Cys Arg Asn
            100                 105                 110 atg tgg agt ggg acg ttc ccc att aac gcc tac acc acg ggc ccc tgt   384
Met Trp Ser Gly Thr Phe Pro Ile Asn Ala Tyr Thr Thr Gly Pro Cys
        115                 120                 125 act ccc ctt cct gcg ccg aac tat aag ttc gcg ctg tgg agg gtg tct   432
Thr Pro Leu Pro Ala Pro Asn Tyr Lys Phe Ala Leu Trp Arg Val Ser
    130                 135                 140 gca gag gaa tac gtg gag ata agg cgg gtg ggg gac ttc cac tac gta   480
```

```
             -continued

Ala Glu Glu Tyr Val Glu Ile Arg Arg Val Gly Asp Phe His Tyr Val
145             150                 155                 160 tcg ggt atg act act gac aat ctt aaa tgc ccg tgc cag atc cca tcg     528
Ser Gly Met Thr Thr Asp Asn Leu Lys Cys Pro Cys Gln Ile Pro Ser
            165                 170                 175 ccc gaa ttt ttc aca gaa ttg gac ggg gtg cgc cta cac agg ttt gcg     576
Pro Glu Phe Phe Thr Glu Leu Asp Gly Val Arg Leu His Arg Phe Ala
        180                 185                 190 ccc cct tgc aag ccc ttg ctg cgg gag gag gta tca ttc aga gta gga     624
Pro Pro Cys Lys Pro Leu Leu Arg Glu Glu Val Ser Phe Arg Val Gly
            195                 200                 205 ctc cac gag tac ccg gtg ggg tcg caa tta cct tgc gag ccc gaa ccg     672
Leu His Glu Tyr Pro Val Gly Ser Gln Leu Pro Cys Glu Pro Glu Pro
    210                 215                 220 gac gta gcc gtg ttg acg tcc atg ctc act gat ccc tcc cat ata aca     720
Asp Val Ala Val Leu Thr Ser Met Leu Thr Asp Pro Ser His Ile Thr
225                 230                 235                 240 gca gag gcg gcc ggg aga agg ttg gcg aga ggg tca ccc cct tct atg     768
Ala Glu Ala Ala Gly Arg Arg Leu Ala Arg Gly Ser Pro Pro Ser Met
                245                 250                 255 gcc agc tcc tcg gct agc cag ctg tcc gct cca tct ctc aag gca act     816
Ala Ser Ser Ser Ala Ser Gln Leu Ser Ala Pro Ser Leu Lys Ala Thr
            260                 265                 270 tgc acc gcc aac cat gac tcc cct gac gcc gag ctc ata gag gct aac     864
Cys Thr Ala Asn His Asp Ser Pro Asp Ala Glu Leu Ile Glu Ala Asn
        275                 280                 285 ctc ctg tgg agg cag gag atg ggc ggc aac atc acc agg gtt gag tca     912
Leu Leu Trp Arg Gln Glu Met Gly Gly Asn Ile Thr Arg Val Glu Ser
    290                 295                 300 gag aac aaa gtg gtg att ctg gac tcc ttc gat ccg ctt gtg gca gag     960
Glu Asn Lys Val Val Ile Leu Asp Ser Phe Asp Pro Leu Val Ala Glu
305                 310                 315                 320 gag gat gag cgg gag gtc tcc gta cct gca gaa att ctg cgg aag tct    1008
Glu Asp Glu Arg Glu Val Ser Val Pro Ala Glu Ile Leu Arg Lys Ser
                325                 330                 335 cgg aga ttc gcc cgg gcc ctg ccc gtc tgg gcg cgg ccg gac tac aac    1056
Arg Arg Phe Ala Arg Ala Leu Pro Val Trp Ala Arg Pro Asp Tyr Asn
            340                 345                 350 ccc ccg cta gta gag acg tgg aaa aag cct gac tac gaa cca cct gtg    1104
Pro Pro Leu Val Glu Thr Trp Lys Lys Pro Asp Tyr Glu Pro Pro Val
        355                 360                 365 gtc cat ggc tgc ccg cta cca cct cca cgg tcc cct cct gtg cct ccg    1152
Val His Gly Cys Pro Leu Pro Pro Pro Arg Ser Pro Pro Val Pro Pro
    370                 375                 380 cct cgg aaa aag cgt acg gtg gtc ctc acc gaa tca acc cta tct act    1200
Pro Arg Lys Lys Arg Thr Val Val Leu Thr Glu Ser Thr Leu Ser Thr
385                 390                 395                 400 gcc ttg gcc gag ctt gcc acc aaa agt ttt ggc agc tcc tca act tcc    1248
Ala Leu Ala Glu Leu Ala Thr Lys Ser Phe Gly Ser Ser Ser Thr Ser
                405                 410                 415 ggc att acg ggc gac aat acg aca acc tcc tct gag ccc gcc cct tct    1296
Gly Ile Thr Gly Asp Asn Thr Thr Thr Ser Ser Glu Pro Ala Pro Ser
            420                 425                 430 ggc tgc ccc ccc gac tcc gac gtt gag tcc tat tct tcc atg ccc ccc    1344
Gly Cys Pro Pro Asp Ser Asp Val Glu Ser Tyr Ser Ser Met Pro Pro
        435                 440                 445 ctg gag ggg gag cct ggg gat ccg gat ctc agc gac ggg tca tgg tcg    1392
Leu Glu Gly Glu Pro Gly Asp Pro Asp Leu Ser Asp Gly Ser Trp Ser
    450                 455                 460 acg gtc agt agt ggg gcc gac acg gaa gat gtc gtg tgc gga cta gtg    1440
```

```
                                                                           -continued Thr Val Ser Ser Gly Ala Asp Thr Glu Asp Val Val Cys Gly Leu Val
465                 470                 475                 480 cgg ccg caa ggc ggc gga tcc gtg gac aag aaa att gtg ccc agg gat         1488
Arg Pro Gln Gly Gly Gly Ser Val Asp Lys Lys Ile Val Pro Arg Asp
                485                 490                 495 tgt ggt tgt aag cct tgc ata tgt aca gtc cca gaa gta tca tct gtc         1536
Cys Gly Cys Lys Pro Cys Ile Cys Thr Val Pro Glu Val Ser Ser Val
            500                 505                 510 ttc atc ttc ccc cca aag ccc aag gat gtg ctc acc att act ctg act         1584
Phe Ile Phe Pro Pro Lys Pro Lys Asp Val Leu Thr Ile Thr Leu Thr
        515                 520                 525 cct aag gtc acg tgt gtt gtg gta gac atc agc aag gat gat ccc gag         1632
Pro Lys Val Thr Cys Val Val Val Asp Ile Ser Lys Asp Asp Pro Glu
    530                 535                 540 gtc cag ttc agc tgg ttt gta gat gat gtg gag gtg cac aca gct cag         1680
Val Gln Phe Ser Trp Phe Val Asp Asp Val Glu Val His Thr Ala Gln
545                 550                 555                 560 acg caa ccc cgg gag gag cag ttc aac agc act ttc cgc tca gtc agt         1728
Thr Gln Pro Arg Glu Glu Gln Phe Asn Ser Thr Phe Arg Ser Val Ser
                565                 570                 575 gaa ctt ccc atc atg cac cag gac tgg ctc aat ggc aag gag ttc aaa         1776
Glu Leu Pro Ile Met His Gln Asp Trp Leu Asn Gly Lys Glu Phe Lys
            580                 585                 590 tgc agg gtc aac agt gca gct ttc cct gcc ccc atc gag aaa acc atc         1824
Cys Arg Val Asn Ser Ala Ala Phe Pro Ala Pro Ile Glu Lys Thr Ile
        595                 600                 605 tcc aaa acc aaa ggc aga ccg aag gct cca cag gtg tac acc att cca         1872
Ser Lys Thr Lys Gly Arg Pro Lys Ala Pro Gln Val Tyr Thr Ile Pro
    610                 615                 620 cct ccc aag gag cag atg gcc aag gat aaa gtc agt ctg acc tgc atg         1920
Pro Pro Lys Glu Gln Met Ala Lys Asp Lys Val Ser Leu Thr Cys Met
625                 630                 635                 640 ata aca gac ttc ttc cct gaa gac att act gtg gag tgg cag tgg aat         1968
Ile Thr Asp Phe Phe Pro Glu Asp Ile Thr Val Glu Trp Gln Trp Asn
                645                 650                 655 ggg cag cca gcg gag aac tac aag aac act cag ccc atc atg gac aca         2016
Gly Gln Pro Ala Glu Asn Tyr Lys Asn Thr Gln Pro Ile Met Asp Thr
            660                 665                 670 gat ggc tct tac ttc gtc tac agc aag ctc aat gtg cag aag agc aac         2064
Asp Gly Ser Tyr Phe Val Tyr Ser Lys Leu Asn Val Gln Lys Ser Asn
        675                 680                 685 tgg gag gca gga aat act ttc acc tgc tct gtg tta cat gag ggc ctg         2112
Trp Glu Ala Gly Asn Thr Phe Thr Cys Ser Val Leu His Glu Gly Leu
    690                 695                 700 cac aac cac cat act gag aag agc ctc tcc cac tct cct ggg ctg caa         2160
His Asn His His Thr Glu Lys Ser Leu Ser His Ser Pro Gly Leu Gln
705                 710                 715                 720 agc ttg tcg aga agt act aga gga tca taa                                 2190
Ser Leu Ser Arg Ser Thr Arg Gly Ser
                725

<210> SEQ ID NO 64
<211> LENGTH: 729
<212> TYPE: PRT
<213> ORGANISM: Artificial
<220> FEATURE:
<223> OTHER INFORMATION: Synthetic Construct

<400> SEQUENCE: 64

Met Ser Tyr Tyr His His His His His His Asp Tyr Asp Ile Pro Thr
1               5                   10                  15
```

-continued

```
Thr Glu Asn Leu Tyr Phe Gln Gly Ala Met Asp Pro Glu Phe Ser Gly
             20                  25                  30

Ser Trp Leu Arg Asp Ile Trp Asp Trp Ile Cys Glu Val Leu Ser Asp
         35                  40                  45

Phe Lys Thr Trp Leu Lys Ala Lys Leu Met Pro Gln Leu Pro Gly Ile
 50                  55                  60

Pro Phe Val Ser Cys Gln Arg Gly Tyr Arg Gly Val Trp Arg Gly Asp
 65                  70                  75                  80

Gly Ile Met His Thr Arg Cys His Cys Gly Ala Glu Ile Thr Gly His
                 85                  90                  95

Val Lys Asn Gly Thr Met Arg Ile Val Gly Pro Arg Thr Cys Arg Asn
            100                 105                 110

Met Trp Ser Gly Thr Phe Pro Ile Asn Ala Tyr Thr Thr Gly Pro Cys
        115                 120                 125

Thr Pro Leu Pro Ala Pro Asn Tyr Lys Phe Ala Leu Trp Arg Val Ser
    130                 135                 140

Ala Glu Glu Tyr Val Glu Ile Arg Arg Val Gly Asp Phe His Tyr Val
145                 150                 155                 160

Ser Gly Met Thr Thr Asp Asn Leu Lys Cys Pro Cys Gln Ile Pro Ser
            165                 170                 175

Pro Glu Phe Phe Thr Glu Leu Asp Gly Val Arg Leu His Arg Phe Ala
        180                 185                 190

Pro Pro Cys Lys Pro Leu Leu Arg Glu Glu Val Ser Phe Arg Val Gly
    195                 200                 205

Leu His Glu Tyr Pro Val Gly Ser Gln Leu Pro Cys Glu Pro Glu Pro
210                 215                 220

Asp Val Ala Val Leu Thr Ser Met Leu Thr Asp Pro Ser His Ile Thr
225                 230                 235                 240

Ala Glu Ala Ala Gly Arg Arg Leu Ala Arg Gly Ser Pro Pro Ser Met
            245                 250                 255

Ala Ser Ser Ser Ala Ser Gln Leu Ser Ala Pro Ser Leu Lys Ala Thr
        260                 265                 270

Cys Thr Ala Asn His Asp Ser Pro Asp Ala Glu Leu Ile Glu Ala Asn
    275                 280                 285

Leu Leu Trp Arg Gln Glu Met Gly Gly Asn Ile Thr Arg Val Glu Ser
290                 295                 300

Glu Asn Lys Val Val Ile Leu Asp Ser Phe Asp Pro Leu Val Ala Glu
305                 310                 315                 320

Glu Asp Glu Arg Glu Val Ser Val Pro Ala Glu Ile Leu Arg Lys Ser
            325                 330                 335

Arg Arg Phe Ala Arg Ala Leu Pro Val Trp Ala Arg Pro Asp Tyr Asn
        340                 345                 350

Pro Pro Leu Val Glu Thr Trp Lys Lys Pro Asp Tyr Glu Pro Pro Val
    355                 360                 365

Val His Gly Cys Pro Leu Pro Pro Arg Ser Pro Pro Val Pro Pro Pro
370                 375                 380

Pro Arg Lys Lys Arg Thr Val Val Leu Thr Glu Ser Thr Leu Ser Thr
385                 390                 395                 400

Ala Leu Ala Glu Leu Ala Thr Lys Ser Phe Gly Ser Ser Ser Thr Ser
            405                 410                 415

Gly Ile Thr Gly Asp Asn Thr Thr Thr Ser Ser Glu Pro Ala Pro Ser
        420                 425                 430

Gly Cys Pro Pro Asp Ser Asp Val Glu Ser Tyr Ser Ser Met Pro Pro
    435                 440                 445
```

```
Leu Glu Gly Glu Pro Gly Asp Pro Asp Leu Ser Asp Gly Ser Trp Ser
    450                 455                 460

Thr Val Ser Ser Gly Ala Asp Thr Glu Asp Val Val Cys Gly Leu Val
465                 470                 475                 480

Arg Pro Gln Gly Gly Ser Val Asp Lys Lys Ile Val Pro Arg Asp
                    485                 490                 495

Cys Gly Cys Lys Pro Cys Ile Cys Thr Val Pro Glu Val Ser Ser Val
                500                 505                 510

Phe Ile Phe Pro Pro Lys Pro Lys Asp Val Leu Thr Ile Thr Leu Thr
            515                 520                 525

Pro Lys Val Thr Cys Val Val Val Asp Ile Ser Lys Asp Asp Pro Glu
        530                 535                 540

Val Gln Phe Ser Trp Phe Val Asp Asp Val Glu Val His Thr Ala Gln
545                 550                 555                 560

Thr Gln Pro Arg Glu Glu Gln Phe Asn Ser Thr Phe Arg Ser Val Ser
                565                 570                 575

Glu Leu Pro Ile Met His Gln Asp Trp Leu Asn Gly Lys Glu Phe Lys
                    580                 585                 590

Cys Arg Val Asn Ser Ala Ala Phe Pro Ala Pro Ile Glu Lys Thr Ile
                595                 600                 605

Ser Lys Thr Lys Gly Arg Pro Lys Ala Pro Gln Val Tyr Thr Ile Pro
            610                 615                 620

Pro Pro Lys Glu Gln Met Ala Lys Asp Lys Val Ser Leu Thr Cys Met
625                 630                 635                 640

Ile Thr Asp Phe Phe Pro Glu Asp Ile Thr Val Glu Trp Gln Trp Asn
                645                 650                 655

Gly Gln Pro Ala Glu Asn Tyr Lys Asn Thr Gln Pro Ile Met Asp Thr
                660                 665                 670

Asp Gly Ser Tyr Phe Val Tyr Ser Lys Leu Asn Val Gln Lys Ser Asn
            675                 680                 685

Trp Glu Ala Gly Asn Thr Phe Thr Cys Ser Val Leu His Glu Gly Leu
690                 695                 700

His Asn His His Thr Glu Lys Ser Leu Ser His Ser Pro Gly Leu Gln
705                 710                 715                 720

Ser Leu Ser Arg Ser Thr Arg Gly Ser
                725

<210> SEQ ID NO 65
<211> LENGTH: 756
<212> TYPE: DNA
<213> ORGANISM: Hepatitis C virus
<220> FEATURE:
<221> NAME/KEY: CDS
<222> LOCATION: (1)..(756)

<400> SEQUENCE: 65 atg tcg tac tac cat cac cat cac cat cac gat tac gat atc cca acg      48
Met Ser Tyr Tyr His His His His His His Asp Tyr Asp Ile Pro Thr
1               5                   10                  15 acc gaa aac ctg tat ttt cag ggc gcc atg gat ccg gaa ttc tac caa      96
Thr Glu Asn Leu Tyr Phe Gln Gly Ala Met Asp Pro Glu Phe Tyr Gln
            20                  25                  30 gtg cgc aat tcc tcg ggg ctt tac cat gtc acc aat gat tgc cct aac     144
Val Arg Asn Ser Ser Gly Leu Tyr His Val Thr Asn Asp Cys Pro Asn
        35                  40                  45 tcg agt att gtg tac gag gcg gcc gat gcc atc ctg cac act ccg ggg     192
Ser Ser Ile Val Tyr Glu Ala Ala Asp Ala Ile Leu His Thr Pro Gly
```

```
            50                  55                  60
tgt gtc cct tgc gtt cgc gag ggt aac gcc tcg agg tgt tgg gtg gcg    240
Cys Val Pro Cys Val Arg Glu Gly Asn Ala Ser Arg Cys Trp Val Ala
 65                  70                  75                  80 gtg acc ccc acg gtg gcc acc agg gac ggc aaa ctc ccc aca acg cag    288
Val Thr Pro Thr Val Ala Thr Arg Asp Gly Lys Leu Pro Thr Thr Gln
                     85                  90                  95 ctt cga cgt cat atc gat ctg ctt gtc ggg agc gcc acc ctc tgc tcg    336
Leu Arg Arg His Ile Asp Leu Leu Val Gly Ser Ala Thr Leu Cys Ser
                100                 105                 110 gcc ctc tac gtg ggg gac ctg tgc ggg tct gtc ttt ctt gtt ggt caa    384
Ala Leu Tyr Val Gly Asp Leu Cys Gly Ser Val Phe Leu Val Gly Gln
            115                 120                 125 ctg ttt acc ttc tct ccc agg cgc cac tgg acg acg caa gac tgc aat    432
Leu Phe Thr Phe Ser Pro Arg Arg His Trp Thr Thr Gln Asp Cys Asn
        130                 135                 140 tgt tct atc tat ccc ggc cat ata acg ggt cat cgc atg gca tgg gat    480
Cys Ser Ile Tyr Pro Gly His Ile Thr Gly His Arg Met Ala Trp Asp
145                 150                 155                 160 atg atg atg aac tgg tcc cct acg gca gcg ttg gtg gta gct cag ctg    528
Met Met Met Asn Trp Ser Pro Thr Ala Ala Leu Val Val Ala Gln Leu
                165                 170                 175 ctc cgg atc cca caa gcc atc atg gac atg atc gct ggt gct cac tgg    576
Leu Arg Ile Pro Gln Ala Ile Met Asp Met Ile Ala Gly Ala His Trp
                180                 185                 190 gga gtc ctg gcg ggc ata gcg tat ttc tcc atg gtg ggg aac tgg gcg    624
Gly Val Leu Ala Gly Ile Ala Tyr Phe Ser Met Val Gly Asn Trp Ala
            195                 200                 205 aag gtc ctg gta gtg ctg ctg cta ttt gcc ggc gtc gac gcg gaa gga    672
Lys Val Leu Val Val Leu Leu Leu Phe Ala Gly Val Asp Ala Glu Gly
        210                 215                 220 cta gtg cgg ccg ctt tcg aat cta gag cct gca gtc tcg agg cat gcg    720
Leu Val Arg Pro Leu Ser Asn Leu Glu Pro Ala Val Ser Arg His Ala
225                 230                 235                 240 gta cca agc ttg tcg aga agt act aga gga tca taa                    756
Val Pro Ser Leu Ser Arg Ser Thr Arg Gly Ser
                245                 250

<210> SEQ ID NO 66
<211> LENGTH: 251
<212> TYPE: PRT
<213> ORGANISM: Hepatitis C virus

<400> SEQUENCE: 66

Met Ser Tyr Tyr His His His His His His Asp Tyr Asp Ile Pro Thr
 1               5                   10                  15

Thr Glu Asn Leu Tyr Phe Gln Gly Ala Met Asp Pro Glu Phe Tyr Gln
                20                  25                  30

Val Arg Asn Ser Ser Gly Leu Tyr His Val Thr Asn Asp Cys Pro Asn
            35                  40                  45

Ser Ser Ile Val Tyr Glu Ala Ala Asp Ala Ile Leu His Thr Pro Gly
        50                  55                  60

Cys Val Pro Cys Val Arg Glu Gly Asn Ala Ser Arg Cys Trp Val Ala
 65                  70                  75                  80

Val Thr Pro Thr Val Ala Thr Arg Asp Gly Lys Leu Pro Thr Thr Gln
                85                  90                  95

Leu Arg Arg His Ile Asp Leu Leu Val Gly Ser Ala Thr Leu Cys Ser
            100                 105                 110

Ala Leu Tyr Val Gly Asp Leu Cys Gly Ser Val Phe Leu Val Gly Gln
```

```
                    115                 120                 125
Leu Phe Thr Phe Ser Pro Arg Arg His Trp Thr Thr Gln Asp Cys Asn
    130                 135                 140

Cys Ser Ile Tyr Pro Gly His Ile Thr Gly His Arg Met Ala Trp Asp
145                 150                 155                 160

Met Met Met Asn Trp Ser Pro Thr Ala Ala Leu Val Val Ala Gln Leu
                165                 170                 175

Leu Arg Ile Pro Gln Ala Ile Met Asp Met Ile Ala Gly Ala His Trp
            180                 185                 190

Gly Val Leu Ala Gly Ile Ala Tyr Phe Ser Met Val Gly Asn Trp Ala
        195                 200                 205

Lys Val Leu Val Val Leu Leu Leu Phe Ala Gly Val Asp Ala Glu Gly
    210                 215                 220

Leu Val Arg Pro Leu Ser Asn Leu Glu Pro Ala Val Ser Arg His Ala
225                 230                 235                 240

Val Pro Ser Leu Ser Arg Ser Thr Arg Gly Ser
                245                 250

<210> SEQ ID NO 67
<211> LENGTH: 1428
<212> TYPE: DNA
<213> ORGANISM: Artificial
<220> FEATURE:
<223> OTHER INFORMATION: Hepatitis C virus plus murine
<220> FEATURE:
<221> NAME/KEY: CDS
<222> LOCATION: (1)..(1428)

<400> SEQUENCE: 67 atg tcg tac tac cat cac cat cac cat cac gat tac gat atc cca acg      48
Met Ser Tyr Tyr His His His His His His Asp Tyr Asp Ile Pro Thr
1               5                   10                  15 acc gaa aac ctg tat ttt cag ggc gcc atg gat ccg gaa ttc tac caa      96
Thr Glu Asn Leu Tyr Phe Gln Gly Ala Met Asp Pro Glu Phe Tyr Gln
            20                  25                  30 gtg cgc aat tcc tcg ggg ctt tac cat gtc acc aat gat tgc cct aac     144
Val Arg Asn Ser Ser Gly Leu Tyr His Val Thr Asn Asp Cys Pro Asn
        35                  40                  45 tcg agt att gtg tac gag gcg gcc gat gcc atc ctg cac act ccg ggg     192
Ser Ser Ile Val Tyr Glu Ala Ala Asp Ala Ile Leu His Thr Pro Gly
    50                  55                  60 tgt gtc cct tgc gtt cgc gag ggt aac gcc tcg agg tgt tgg gtg gcg     240
Cys Val Pro Cys Val Arg Glu Gly Asn Ala Ser Arg Cys Trp Val Ala
65                  70                  75                  80 gtg acc ccc acg gtg gcc acc agg gac ggc aaa ctc ccc aca acg cag     288
Val Thr Pro Thr Val Ala Thr Arg Asp Gly Lys Leu Pro Thr Thr Gln
                85                  90                  95 ctt cga cgt cat atc gat ctg ctt gtc ggg agc gcc acc ctc tgc tcg     336
Leu Arg Arg His Ile Asp Leu Leu Val Gly Ser Ala Thr Leu Cys Ser
            100                 105                 110 gcc ctc tac gtg ggg gac ctg tgc ggg tct gtc ttt ctt gtt ggt caa     384
Ala Leu Tyr Val Gly Asp Leu Cys Gly Ser Val Phe Leu Val Gly Gln
        115                 120                 125 ctg ttt acc ttc tct ccc agg cgc cac tgg acg acg caa gac tgc aat     432
Leu Phe Thr Phe Ser Pro Arg Arg His Trp Thr Thr Gln Asp Cys Asn
    130                 135                 140 tgt tct atc tat ccc ggc cat ata acg ggt cat cgc atg gca tgg gat     480
Cys Ser Ile Tyr Pro Gly His Ile Thr Gly His Arg Met Ala Trp Asp
145                 150                 155                 160 atg atg atg aac tgg tcc cct acg gca gcg ttg gtg gta gct cag ctg     528
```

```
                 Met Met Met Asn Trp Ser Pro Thr Ala Ala Leu Val Val Ala Gln Leu
                                 165                 170                 175 ctc cgg atc cca caa gcc atc atg gac atg atc gct ggt gct cac tgg            576
Leu Arg Ile Pro Gln Ala Ile Met Asp Met Ile Ala Gly Ala His Trp
            180                 185                 190 gga gtc ctg gcg ggc ata gcg tat ttc tcc atg gtg ggg aac tgg gcg            624
Gly Val Leu Ala Gly Ile Ala Tyr Phe Ser Met Val Gly Asn Trp Ala
                195                 200                 205 aag gtc ctg gta gtg ctg ctg cta ttt gcc ggc gtc gac gcg gaa gga            672
Lys Val Leu Val Val Leu Leu Leu Phe Ala Gly Val Asp Ala Glu Gly
        210                 215                 220 cta gtg cgg ccg caa ggc ggc gga tcc gtg gac aag aaa att gtg ccc            720
Leu Val Arg Pro Gln Gly Gly Gly Ser Val Asp Lys Lys Ile Val Pro
225                 230                 235                 240 agg gat tgt ggt tgt aag cct tgc ata tgt aca gtc cca gaa gta tca            768
Arg Asp Cys Gly Cys Lys Pro Cys Ile Cys Thr Val Pro Glu Val Ser
                    245                 250                 255 tct gtc ttc atc ttc ccc cca aag ccc aag gat gtg ctc acc att act            816
Ser Val Phe Ile Phe Pro Pro Lys Pro Lys Asp Val Leu Thr Ile Thr
                260                 265                 270 ctg act cct aag gtc acg tgt gtt gtg gta gac atc agc aag gat gat            864
Leu Thr Pro Lys Val Thr Cys Val Val Val Asp Ile Ser Lys Asp Asp
            275                 280                 285 ccc gag gtc cag ttc agc tgg ttt gta gat gat gtg gag gtg cac aca            912
Pro Glu Val Gln Phe Ser Trp Phe Val Asp Asp Val Glu Val His Thr
        290                 295                 300 gct cag acg caa ccc cgg gag gag cag ttc aac agc act ttc cgc tca            960
Ala Gln Thr Gln Pro Arg Glu Glu Gln Phe Asn Ser Thr Phe Arg Ser
305                 310                 315                 320 gtc agt gaa ctt ccc atc atg cac cag gac tgg ctc aat ggc aag gag           1008
Val Ser Glu Leu Pro Ile Met His Gln Asp Trp Leu Asn Gly Lys Glu
                    325                 330                 335 ttc aaa tgc agg gtc aac agt gca gct ttc cct gcc ccc atc gag aaa           1056
Phe Lys Cys Arg Val Asn Ser Ala Ala Phe Pro Ala Pro Ile Glu Lys
                340                 345                 350 acc atc tcc aaa acc aaa ggc aga ccg aag gct cca cag gtg tac acc           1104
Thr Ile Ser Lys Thr Lys Gly Arg Pro Lys Ala Pro Gln Val Tyr Thr
            355                 360                 365 att cca cct ccc aag gag cag atg gcc aag gat aaa gtc agt ctg acc           1152
Ile Pro Pro Pro Lys Glu Gln Met Ala Lys Asp Lys Val Ser Leu Thr
        370                 375                 380 tgc atg ata aca gac ttc ttc cct gaa gac att act gtg gag tgg cag           1200
Cys Met Ile Thr Asp Phe Phe Pro Glu Asp Ile Thr Val Glu Trp Gln
385                 390                 395                 400 tgg aat ggg cag cca gcg gag aac tac aag aac act cag ccc atc atg           1248
Trp Asn Gly Gln Pro Ala Glu Asn Tyr Lys Asn Thr Gln Pro Ile Met
                    405                 410                 415 gac aca gat ggc tct tac ttc gtc tac agc aag ctc aat gtg cag aag           1296
Asp Thr Asp Gly Ser Tyr Phe Val Tyr Ser Lys Leu Asn Val Gln Lys
                420                 425                 430 agc aac tgg gag gca gga aat act ttc acc tgc tct gtg tta cat gag           1344
Ser Asn Trp Glu Ala Gly Asn Thr Phe Thr Cys Ser Val Leu His Glu
            435                 440                 445 ggc ctg cac aac cac cat act gag aag agc ctc tcc cac tct cct ggg           1392
Gly Leu His Asn His His Thr Glu Lys Ser Leu Ser His Ser Pro Gly
450                 455                 460 ctg caa agc ttg tcg aga agt act aga gga tca taa                           1428
Leu Gln Ser Leu Ser Arg Ser Thr Arg Gly Ser
465                 470                 475
```

<210> SEQ ID NO 68
<211> LENGTH: 475
<212> TYPE: PRT
<213> ORGANISM: Artificial
<220> FEATURE:
<223> OTHER INFORMATION: Synthetic Construct

<400> SEQUENCE: 68

```
Met Ser Tyr Tyr His His His His His His Asp Tyr Asp Ile Pro Thr
1               5                   10                  15

Thr Glu Asn Leu Tyr Phe Gln Gly Ala Met Asp Pro Glu Phe Tyr Gln
            20                  25                  30

Val Arg Asn Ser Ser Gly Leu Tyr His Val Thr Asn Asp Cys Pro Asn
        35                  40                  45

Ser Ser Ile Val Tyr Glu Ala Ala Asp Ala Ile Leu His Thr Pro Gly
    50                  55                  60

Cys Val Pro Cys Val Arg Glu Gly Asn Ala Ser Arg Cys Trp Val Ala
65                  70                  75                  80

Val Thr Pro Thr Val Ala Thr Arg Asp Gly Lys Leu Pro Thr Thr Gln
                85                  90                  95

Leu Arg Arg His Ile Asp Leu Leu Val Gly Ser Ala Thr Leu Cys Ser
            100                 105                 110

Ala Leu Tyr Val Gly Asp Leu Cys Gly Ser Val Phe Leu Val Gly Gln
        115                 120                 125

Leu Phe Thr Phe Ser Pro Arg Arg His Trp Thr Thr Gln Asp Cys Asn
    130                 135                 140

Cys Ser Ile Tyr Pro Gly His Ile Thr Gly His Arg Met Ala Trp Asp
145                 150                 155                 160

Met Met Met Asn Trp Ser Pro Thr Ala Ala Leu Val Val Ala Gln Leu
                165                 170                 175

Leu Arg Ile Pro Gln Ala Ile Met Asp Met Ile Ala Gly Ala His Trp
            180                 185                 190

Gly Val Leu Ala Gly Ile Ala Tyr Phe Ser Met Val Gly Asn Trp Ala
        195                 200                 205

Lys Val Leu Val Val Leu Leu Leu Phe Ala Gly Val Asp Ala Glu Gly
    210                 215                 220

Leu Val Arg Pro Gln Gly Gly Gly Ser Val Asp Lys Lys Ile Val Pro
225                 230                 235                 240

Arg Asp Cys Gly Cys Lys Pro Cys Ile Cys Thr Val Pro Glu Val Ser
                245                 250                 255

Ser Val Phe Ile Phe Pro Pro Lys Pro Lys Asp Val Leu Thr Ile Thr
            260                 265                 270

Leu Thr Pro Lys Val Thr Cys Val Val Val Asp Ile Ser Lys Asp Asp
        275                 280                 285

Pro Glu Val Gln Phe Ser Trp Phe Val Asp Asp Val Glu Val His Thr
    290                 295                 300

Ala Gln Thr Gln Pro Arg Glu Glu Gln Phe Asn Ser Thr Phe Arg Ser
305                 310                 315                 320

Val Ser Glu Leu Pro Ile Met His Gln Asp Trp Leu Asn Gly Lys Glu
                325                 330                 335

Phe Lys Cys Arg Val Asn Ser Ala Ala Phe Pro Ala Pro Ile Glu Lys
            340                 345                 350

Thr Ile Ser Lys Thr Lys Gly Arg Pro Lys Ala Pro Gln Val Tyr Thr
        355                 360                 365

Ile Pro Pro Pro Lys Glu Gln Met Ala Lys Asp Lys Val Ser Leu Thr
    370                 375                 380
```

-continued

| | | | | | | | | | | | | | | |
|---|---|---|---|---|---|---|---|---|---|---|---|---|---|---|
|Cys|Met|Ile|Thr|Asp|Phe|Phe|Pro|Glu|Asp|Ile|Thr|Val|Glu|Trp|Gln|
|385| | | | |390| | | | |395| | | | |400|

| | | | | | | | | | | | | |
|---|---|---|---|---|---|---|---|---|---|---|---|---|
|Trp|Asn|Gly|Gln|Pro|Ala|Glu|Asn|Tyr|Lys|Asn|Thr|Gln|Pro|Ile|Met|
| | | | |405| | | | |410| | | | |415| |

| | | | | | | | | | | | | |
|---|---|---|---|---|---|---|---|---|---|---|---|---|
|Asp|Thr|Asp|Gly|Ser|Tyr|Phe|Val|Tyr|Ser|Lys|Leu|Asn|Val|Gln|Lys|
| | | |420| | | | |425| | | | |430| | |

|Ser|Asn|Trp|Glu|Ala|Gly|Asn|Thr|Phe|Thr|Cys|Ser|Val|Leu|His|Glu|
|---|---|---|---|---|---|---|---|---|---|---|---|---|---|---|---|
| | |435| | | | |440| | | | |445| | | |

|Gly|Leu|His|Asn|His|His|Thr|Glu|Lys|Ser|Leu|Ser|His|Ser|Pro|Gly|
|---|---|---|---|---|---|---|---|---|---|---|---|---|---|---|---|
| |450| | | | |455| | | | |460| | | | |

|Leu|Gln|Ser|Leu|Ser|Arg|Ser|Thr|Arg|Gly|Ser|
|---|---|---|---|---|---|---|---|---|---|---|
|465| | | |470| | | |475| | |

```
<210> SEQ ID NO 69
<211> LENGTH: 1266
<212> TYPE: DNA
<213> ORGANISM: Hepatitis C virus
<220> FEATURE:
<221> NAME/KEY: CDS
<222> LOCATION: (1)..(1266)

<400> SEQUENCE: 69
```

| | | | | | | | | | | | | | | | |
|---|---|---|---|---|---|---|---|---|---|---|---|---|---|---|---|
|atg|tcg|tac|tac|cat|cac|cat|cac|cat|cac|gat|tac|gat|atc|cca|acg|48|
|Met|Ser|Tyr|Tyr|His|His|His|His|His|His|Asp|Tyr|Asp|Ile|Pro|Thr| |
|1| | | |5| | | | |10| | | | |15| | |

|acc|gaa|aac|ctg|ggg|gtc|gag|cac|agg|ctg|gaa|gcg|gcc|tgc|aac|tgg|96|
|---|---|---|---|---|---|---|---|---|---|---|---|---|---|---|---|---|
|Thr|Glu|Asn|Leu|Gly|Val|Glu|His|Arg|Leu|Glu|Ala|Ala|Cys|Asn|Trp| |
| | | |20| | | | |25| | | | |30| | | |

|acg|cgg|ggc|gaa|cgc|tgt|gat|tat|ttt|cag|ggc|gcc|atg|gat|ccg|gaa|144|
|---|---|---|---|---|---|---|---|---|---|---|---|---|---|---|---|---|
|Thr|Arg|Gly|Glu|Arg|Cys|Asp|Tyr|Phe|Gln|Gly|Ala|Met|Asp|Pro|Glu| |
| |35| | | | |40| | | | |45| | | | | |

|ttc|acc|cac|gtc|acc|ggg|gga|aat|gcc|ggc|cgc|acc|acg|gct|ggg|ctt|192|
|---|---|---|---|---|---|---|---|---|---|---|---|---|---|---|---|---|
|Phe|Thr|His|Val|Thr|Gly|Gly|Asn|Ala|Gly|Arg|Thr|Thr|Ala|Gly|Leu| |
| |50| | | | |55| | | | |60| | | | | |

|gtt|ggt|ctc|ctt|aca|cca|ggc|gcc|aag|cag|aac|atc|caa|ctg|atc|aac|240|
|---|---|---|---|---|---|---|---|---|---|---|---|---|---|---|---|---|
|Val|Gly|Leu|Leu|Thr|Pro|Gly|Ala|Lys|Gln|Asn|Ile|Gln|Leu|Ile|Asn| |
|65| | | | |70| | | | |75| | | | |80| |

|acc|aac|ggc|agt|tgg|cac|atc|aat|agc|acg|gcc|ttg|aat|tgc|aat|gaa|288|
|---|---|---|---|---|---|---|---|---|---|---|---|---|---|---|---|---|
|Thr|Asn|Gly|Ser|Trp|His|Ile|Asn|Ser|Thr|Ala|Leu|Asn|Cys|Asn|Glu| |
| | | | |85| | | | |90| | | | |95| | |

|agc|ctt|aac|acc|ggc|tgg|tta|gca|ggg|ctc|ttc|tat|caa|cac|aaa|ttc|336|
|---|---|---|---|---|---|---|---|---|---|---|---|---|---|---|---|---|
|Ser|Leu|Asn|Thr|Gly|Trp|Leu|Ala|Gly|Leu|Phe|Tyr|Gln|His|Lys|Phe| |
| | | |100| | | | |105| | | | |110| | | |

|aac|tct|tca|ggc|tgt|cct|gag|agg|ttg|gcc|agc|tgc|cga|cgc|ctt|acc|384|
|---|---|---|---|---|---|---|---|---|---|---|---|---|---|---|---|---|
|Asn|Ser|Ser|Gly|Cys|Pro|Glu|Arg|Leu|Ala|Ser|Cys|Arg|Arg|Leu|Thr| |
| | |115| | | | |120| | | | |125| | | | |

|gat|ttt|gcc|cag|ggc|tgg|ggt|cct|atc|agt|tat|gcc|aac|gga|agc|ggc|432|
|---|---|---|---|---|---|---|---|---|---|---|---|---|---|---|---|---|
|Asp|Phe|Ala|Gln|Gly|Trp|Gly|Pro|Ile|Ser|Tyr|Ala|Asn|Gly|Ser|Gly| |
| |130| | | | |135| | | | |140| | | | | |

|ctc|gac|gaa|cgc|ccc|tac|tgc|tgg|cac|tac|cct|cca|aga|cct|tgt|ggc|480|
|---|---|---|---|---|---|---|---|---|---|---|---|---|---|---|---|---|
|Leu|Asp|Glu|Arg|Pro|Tyr|Cys|Trp|His|Tyr|Pro|Pro|Arg|Pro|Cys|Gly| |
|145| | | | |150| | | | |155| | | | |160| |

|att|gtg|ccc|gca|aag|agc|gtg|tgt|ggc|ccg|gta|tat|tgc|ttc|act|ccc|528|
|---|---|---|---|---|---|---|---|---|---|---|---|---|---|---|---|---|
|Ile|Val|Pro|Ala|Lys|Ser|Val|Cys|Gly|Pro|Val|Tyr|Cys|Phe|Thr|Pro| |
| | | | |165| | | | |170| | | | |175| | |

|agc|ccc|gtg|gtg|gtg|gga|acg|acc|gac|agg|tcg|ggc|gcg|cct|acc|tac|576|
|---|---|---|---|---|---|---|---|---|---|---|---|---|---|---|---|---|
|Ser|Pro|Val|Val|Val|Gly|Thr|Thr|Asp|Arg|Ser|Gly|Ala|Pro|Thr|Tyr| |
| | | |180| | | | |185| | | | |190| | | |

|agc|tgg|ggt|gca|aat|gat|acg|gat|gtc|ttc|gtc|ctt|aac|aac|acc|agg|624|
|---|---|---|---|---|---|---|---|---|---|---|---|---|---|---|---|---|
|Ser|Trp|Gly|Ala|Asn|Asp|Thr|Asp|Val|Phe|Val|Leu|Asn|Asn|Thr|Arg| |

```
                       195                   200                   205
cca ccg ctg ggc aat tgg ttc ggt tgt acc tgg atg aac tca act gga      672
Pro Pro Leu Gly Asn Trp Phe Gly Cys Thr Trp Met Asn Ser Thr Gly
        210                 215                 220 ttc acc aaa gtg tgc gga gcg ccc cct tgt gtc atc gga ggg gtg ggc      720
Phe Thr Lys Val Cys Gly Ala Pro Pro Cys Val Ile Gly Gly Val Gly
225                 230                 235                 240 aac aac acc ttg ctc tgc ccc act gat gcg ttc cgc aaa cat ccg gaa      768
Asn Asn Thr Leu Leu Cys Pro Thr Asp Cys Phe Arg Lys His Pro Glu
                245                 250                 255 gcc aca tac tct cgg tgc ggc tcc ggt ccc tgg att aca ccc agg tgc      816
Ala Thr Tyr Ser Arg Cys Gly Ser Gly Pro Trp Ile Thr Pro Arg Cys
        260                 265                 270 atg gtc gac tac ccg tat agg ctt tgg cac tat cct tgt acc atc aat      864
Met Val Asp Tyr Pro Tyr Arg Leu Trp His Tyr Pro Cys Thr Ile Asn
            275                 280                 285 tac acc ata ttc aaa gtc agg atg tac gtg gga ctg gaa gac agg gac      912
Tyr Thr Ile Phe Lys Val Arg Met Tyr Val Gly Leu Glu Asp Arg Asp
        290                 295                 300 agg tcc gag ctc agc ccg ttg ctg ctg tcc acc aca cag tgg cag gtc      960
Arg Ser Glu Leu Ser Pro Leu Leu Leu Ser Thr Thr Gln Trp Gln Val
305                 310                 315                 320 ctt ccg tgt tct ttc acg acc ctg cca gcc ttg tcc acc ggc ctc atc     1008
Leu Pro Cys Ser Phe Thr Thr Leu Pro Ala Leu Ser Thr Gly Leu Ile
                325                 330                 335 cac ctc cac cag aac att gtg gac gtg cag tac ttg tac ggg gta ggg     1056
His Leu His Gln Asn Ile Val Asp Val Gln Tyr Leu Tyr Gly Val Gly
            340                 345                 350 tca agc atc gcg tcc tgg gcc att aag tgg gag tac gtc gtt ctc ctg     1104
Ser Ser Ile Ala Ser Trp Ala Ile Lys Trp Glu Tyr Val Val Leu Leu
        355                 360                 365 ttc ctt ctg ctt gca gac gcg cgc gtc tgc tcc tgc ttg tgg atg atg     1152
Phe Leu Leu Leu Ala Asp Ala Arg Val Cys Ser Cys Leu Trp Met Met
370                 375                 380 tta ctc ata tcc caa gcg gag gcg gct gga cta gtg cgg ccg ctt tcg     1200
Leu Leu Ile Ser Gln Ala Glu Ala Ala Gly Leu Val Arg Pro Leu Ser
                385                 390                 395                 400 aat cta gag cct gca gtc tcg agg cat gcg gta cca agc ttg tcg aga     1248
Asn Leu Glu Pro Ala Val Ser Arg His Ala Val Pro Ser Leu Ser Arg
                    405                 410                 415 agt act aga gga tca taa                                             1266
Ser Thr Arg Gly Ser
                420

<210> SEQ ID NO 70
<211> LENGTH: 421
<212> TYPE: PRT
<213> ORGANISM: Hepatitis C virus

<400> SEQUENCE: 70

Met Ser Tyr Tyr His His His His His His Asp Tyr Asp Ile Pro Thr
1               5                   10                  15

Thr Glu Asn Leu Gly Val Glu His Arg Leu Glu Ala Ala Cys Asn Trp
            20                  25                  30

Thr Arg Gly Glu Arg Cys Asp Tyr Phe Gln Gly Ala Met Asp Pro Glu
        35                  40                  45

Phe Thr His Val Thr Gly Gly Asn Ala Gly Arg Thr Thr Ala Gly Leu
    50                  55                  60

Val Gly Leu Leu Thr Pro Gly Ala Lys Gln Asn Ile Gln Leu Ile Asn
65                  70                  75                  80
```

```
Thr Asn Gly Ser Trp His Ile Asn Ser Thr Ala Leu Asn Cys Asn Glu
                85                  90                  95

Ser Leu Asn Thr Gly Trp Leu Ala Gly Leu Phe Tyr Gln His Lys Phe
            100                 105                 110

Asn Ser Ser Gly Cys Pro Glu Arg Leu Ala Ser Cys Arg Arg Leu Thr
        115                 120                 125

Asp Phe Ala Gln Gly Trp Gly Pro Ile Ser Tyr Ala Asn Gly Ser Gly
130                 135                 140

Leu Asp Glu Arg Pro Tyr Cys Trp His Tyr Pro Pro Arg Pro Cys Gly
145                 150                 155                 160

Ile Val Pro Ala Lys Ser Val Cys Gly Pro Val Tyr Cys Phe Thr Pro
                165                 170                 175

Ser Pro Val Val Val Gly Thr Thr Asp Arg Ser Gly Ala Pro Thr Tyr
            180                 185                 190

Ser Trp Gly Ala Asn Asp Thr Asp Val Phe Val Leu Asn Asn Thr Arg
        195                 200                 205

Pro Pro Leu Gly Asn Trp Phe Gly Cys Thr Trp Met Asn Ser Thr Gly
210                 215                 220

Phe Thr Lys Val Cys Gly Ala Pro Pro Cys Val Ile Gly Gly Val Gly
225                 230                 235                 240

Asn Asn Thr Leu Leu Cys Pro Thr Asp Cys Phe Arg Lys His Pro Glu
                245                 250                 255

Ala Thr Tyr Ser Arg Cys Gly Ser Gly Pro Trp Ile Thr Pro Arg Cys
            260                 265                 270

Met Val Asp Tyr Pro Tyr Arg Leu Trp His Tyr Pro Cys Thr Ile Asn
        275                 280                 285

Tyr Thr Ile Phe Lys Val Arg Met Tyr Val Gly Leu Glu Asp Arg Asp
290                 295                 300

Arg Ser Glu Leu Ser Pro Leu Leu Leu Ser Thr Thr Gln Trp Gln Val
305                 310                 315                 320

Leu Pro Cys Ser Phe Thr Thr Leu Pro Ala Leu Ser Thr Gly Leu Ile
                325                 330                 335

His Leu His Gln Asn Ile Val Asp Val Gln Tyr Leu Tyr Gly Val Gly
            340                 345                 350

Ser Ser Ile Ala Ser Trp Ala Ile Lys Trp Glu Tyr Val Val Leu Leu
        355                 360                 365

Phe Leu Leu Leu Ala Asp Ala Arg Val Cys Ser Cys Leu Trp Met Met
370                 375                 380

Leu Leu Ile Ser Gln Ala Glu Ala Ala Gly Leu Val Arg Pro Leu Ser
385                 390                 395                 400

Asn Leu Glu Pro Ala Val Ser Arg His Ala Val Pro Ser Leu Ser Arg
                405                 410                 415

Ser Thr Arg Gly Ser
            420

<210> SEQ ID NO 71
<211> LENGTH: 1938
<212> TYPE: DNA
<213> ORGANISM: Artificial
<220> FEATURE:
<223> OTHER INFORMATION: Hepatitis C virus plus murine
<220> FEATURE:
<221> NAME/KEY: CDS
<222> LOCATION: (1)..(1938)

<400> SEQUENCE: 71
```

```
atg tcg tac tac cat cac cat cac cat cac gat tac gat atc cca acg    48
Met Ser Tyr Tyr His His His His His His Asp Tyr Asp Ile Pro Thr
1               5                   10                  15 acc gaa aac ctg tat ttt cag ggc gcc atg gat ccg gaa ttc acc cac    96
Thr Glu Asn Leu Tyr Phe Gln Gly Ala Met Asp Pro Glu Phe Thr His
            20                  25                  30 gtc acc ggg gga aat gcc ggc cgc acc acg gct ggg ctt gtt ggt ctc   144
Val Thr Gly Gly Asn Ala Gly Arg Thr Thr Ala Gly Leu Val Gly Leu
        35                  40                  45 ctt aca cca ggc gcc aag cag aac atc caa ctg atc aac acc aac ggc   192
Leu Thr Pro Gly Ala Lys Gln Asn Ile Gln Leu Ile Asn Thr Asn Gly
    50                  55                  60 agt tgg cac atc aat agc acg gcc ttg aat tgc aat gaa agc ctt aac   240
Ser Trp His Ile Asn Ser Thr Ala Leu Asn Cys Asn Glu Ser Leu Asn
65                  70                  75                  80 acc ggc tgg tta gca ggg ctc ttc tat caa cac aaa ttc aac tct tca   288
Thr Gly Trp Leu Ala Gly Leu Phe Tyr Gln His Lys Phe Asn Ser Ser
                85                  90                  95 ggc tgt cct gag agg ttg gcc agc tgc cga cgc ctt acc gat ttt gcc   336
Gly Cys Pro Glu Arg Leu Ala Ser Cys Arg Arg Leu Thr Asp Phe Ala
            100                 105                 110 cag ggc tgg ggt cct atc agt tat gcc aac gga agc ggc ctc gac gaa   384
Gln Gly Trp Gly Pro Ile Ser Tyr Ala Asn Gly Ser Gly Leu Asp Glu
        115                 120                 125 cgc ccc tac tgc tgg cac tac cct cca aga cct tgt ggc att gtg ccc   432
Arg Pro Tyr Cys Trp His Tyr Pro Pro Arg Pro Cys Gly Ile Val Pro
    130                 135                 140 gca aag agc gtg tgt ggc ccg gta tat tgc ttc act ccc agc ccc gtg   480
Ala Lys Ser Val Cys Gly Pro Val Tyr Cys Phe Thr Pro Ser Pro Val
145                 150                 155                 160 gtg gtg gga acg acc gac agg tcg ggc gcg cct acc tac agc tgg ggt   528
Val Val Gly Thr Thr Asp Arg Ser Gly Ala Pro Thr Tyr Ser Trp Gly
                165                 170                 175 gca aat gat acg gat gtc ttc gtc ctt aac aac acc agg cca ccg ctg   576
Ala Asn Asp Thr Asp Val Phe Val Leu Asn Asn Thr Arg Pro Pro Leu
            180                 185                 190 ggc aat tgg ttc ggt tgt acc tgg atg aac tca act gga ttc acc aaa   624
Gly Asn Trp Phe Gly Cys Thr Trp Met Asn Ser Thr Gly Phe Thr Lys
        195                 200                 205 gtg tgc gga gcg ccc cct tgt gtc atc gga ggg gtg ggc aac aac acc   672
Val Cys Gly Ala Pro Pro Cys Val Ile Gly Gly Val Gly Asn Asn Thr
    210                 215                 220 ttg ctc tgc ccc act gat tgc ttc cgc aaa cat ccg gaa gcc aca tac   720
Leu Leu Cys Pro Thr Asp Cys Phe Arg Lys His Pro Glu Ala Thr Tyr
225                 230                 235                 240 tct cgg tgc ggc tcc ggt ccc tgg att aca ccc agg tgc atg gtc gac   768
Ser Arg Cys Gly Ser Gly Pro Trp Ile Thr Pro Arg Cys Met Val Asp
                245                 250                 255 tac ccg tat agg ctt tgg cac tat cct tgt acc atc aat tac acc ata   816
Tyr Pro Tyr Arg Leu Trp His Tyr Pro Cys Thr Ile Asn Tyr Thr Ile
            260                 265                 270 ttc aaa gtc agg atg tac gtg gga ggg gtc gag cac agg ctg gaa gcg   864
Phe Lys Val Arg Met Tyr Val Gly Gly Val Glu His Arg Leu Glu Ala
        275                 280                 285 gcc tgc aac tgg acg cgg ggc gaa cgc tgt gat ctg gaa gac agg gac   912
Ala Cys Asn Trp Thr Arg Gly Glu Arg Cys Asp Leu Glu Asp Arg Asp
    290                 295                 300 agg tcc gag ctc agc ccg ttg ctg ctg tcc acc aca cag tgg cag gtc   960
Arg Ser Glu Leu Ser Pro Leu Leu Leu Ser Thr Thr Gln Trp Gln Val
305                 310                 315                 320
```

```
ctt ccg tgt tct ttc acg acc ctg cca gcc ttg tcc acc ggc ctc atc      1008
Leu Pro Cys Ser Phe Thr Thr Leu Pro Ala Leu Ser Thr Gly Leu Ile
            325                 330                 335 cac ctc cac cag aac att gtg gac gtg cag tac ttg tac ggg gta ggg      1056
His Leu His Gln Asn Ile Val Asp Val Gln Tyr Leu Tyr Gly Val Gly
        340                 345                 350 tca agc atc gcg tcc tgg gcc att aag tgg gag tac gtc gtt ctc ctg      1104
Ser Ser Ile Ala Ser Trp Ala Ile Lys Trp Glu Tyr Val Val Leu Leu
    355                 360                 365 ttc ctt ctg ctt gca gac gcg cgc gtc tgc tcc tgc ttg tgg atg atg      1152
Phe Leu Leu Leu Ala Asp Ala Arg Val Cys Ser Cys Leu Trp Met Met
370                 375                 380 tta ctc ata tcc caa gcg gag gcg gct gga cta gtg cgg ccg caa ggc      1200
Leu Leu Ile Ser Gln Ala Glu Ala Ala Gly Leu Val Arg Pro Gln Gly
385                 390                 395                 400 ggc gga tcc gtg gac aag aaa att gtg ccc agg gat tgt ggt tgt aag      1248
Gly Gly Ser Val Asp Lys Lys Ile Val Pro Arg Asp Cys Gly Cys Lys
                405                 410                 415 cct tgc ata tgt aca gtc cca gaa gta tca tct gtc ttc atc ttc ccc      1296
Pro Cys Ile Cys Thr Val Pro Glu Val Ser Ser Val Phe Ile Phe Pro
            420                 425                 430 cca aag ccc aag gat gtg ctc acc att act ctg act cct aag gtc acg      1344
Pro Lys Pro Lys Asp Val Leu Thr Ile Thr Leu Thr Pro Lys Val Thr
        435                 440                 445 tgt gtt gtg gta gac atc agc aag gat gat ccc gag gtc cag ttc agc      1392
Cys Val Val Val Asp Ile Ser Lys Asp Asp Pro Glu Val Gln Phe Ser
    450                 455                 460 tgg ttt gta gat gat gtg gag gtg cac aca gct cag acg caa ccc cgg      1440
Trp Phe Val Asp Asp Val Glu Val His Thr Ala Gln Thr Gln Pro Arg
465                 470                 475                 480 gag gag cag ttc aac agc act ttc cgc tca gtc agt gaa ctt ccc atc      1488
Glu Glu Gln Phe Asn Ser Thr Phe Arg Ser Val Ser Glu Leu Pro Ile
                485                 490                 495 atg cac cag gac tgg ctc aat ggc aag gag ttc aaa tgc agg gtc aac      1536
Met His Gln Asp Trp Leu Asn Gly Lys Glu Phe Lys Cys Arg Val Asn
            500                 505                 510 agt gca gct ttc cct gcc ccc atc gag aaa acc atc tcc aaa acc aaa      1584
Ser Ala Ala Phe Pro Ala Pro Ile Glu Lys Thr Ile Ser Lys Thr Lys
        515                 520                 525 ggc aga ccg aag gct cca cag gtg tac acc att cca cct ccc aag gag      1632
Gly Arg Pro Lys Ala Pro Gln Val Tyr Thr Ile Pro Pro Pro Lys Glu
    530                 535                 540 cag atg gcc aag gat aaa gtc agt ctg acc tgc atg ata aca gac ttc      1680
Gln Met Ala Lys Asp Lys Val Ser Leu Thr Cys Met Ile Thr Asp Phe
545                 550                 555                 560 ttc cct gaa gac att act gtg gag tgg cag tgg aat ggg cag cca gcg      1728
Phe Pro Glu Asp Ile Thr Val Glu Trp Gln Trp Asn Gly Gln Pro Ala
                565                 570                 575 gag aac tac aag aac act cag ccc atc atg gac aca gat ggc tct tac      1776
Glu Asn Tyr Lys Asn Thr Gln Pro Ile Met Asp Thr Asp Gly Ser Tyr
            580                 585                 590 ttc gtc tac agc aag ctc aat gtg cag aag agc aac tgg gag gca gga      1824
Phe Val Tyr Ser Lys Leu Asn Val Gln Lys Ser Asn Trp Glu Ala Gly
        595                 600                 605 aat act ttc acc tgc tct gtg tta cat gag ggc ctg cac aac cac cat      1872
Asn Thr Phe Thr Cys Ser Val Leu His Glu Gly Leu His Asn His His
    610                 615                 620 act gag aag agc ctc tcc cac tct cct ggg ctg caa agc ttg tcg aga      1920
Thr Glu Lys Ser Leu Ser His Ser Pro Gly Leu Gln Ser Leu Ser Arg
625                 630                 635                 640
```

```
agt act aga gga tca taa                                              1938
Ser Thr Arg Gly Ser
            645

<210> SEQ ID NO 72
<211> LENGTH: 645
<212> TYPE: PRT
<213> ORGANISM: Artificial
<220> FEATURE:
<223> OTHER INFORMATION: Synthetic Construct

<400> SEQUENCE: 72

Met Ser Tyr Tyr His His His His His His Asp Tyr Asp Ile Pro Thr
1               5                   10                  15

Thr Glu Asn Leu Tyr Phe Gln Gly Ala Met Asp Pro Glu Phe Thr His
            20                  25                  30

Val Thr Gly Gly Asn Ala Gly Arg Thr Thr Ala Gly Leu Val Gly Leu
        35                  40                  45

Leu Thr Pro Gly Ala Lys Gln Asn Ile Gln Leu Ile Asn Thr Asn Gly
    50                  55                  60

Ser Trp His Ile Asn Ser Thr Ala Leu Asn Cys Asn Glu Ser Leu Asn
65                  70                  75                  80

Thr Gly Trp Leu Ala Gly Leu Phe Tyr Gln His Lys Phe Asn Ser Ser
                85                  90                  95

Gly Cys Pro Glu Arg Leu Ala Ser Cys Arg Arg Leu Thr Asp Phe Ala
            100                 105                 110

Gln Gly Trp Gly Pro Ile Ser Tyr Ala Asn Gly Ser Gly Leu Asp Glu
        115                 120                 125

Arg Pro Tyr Cys Trp His Tyr Pro Pro Arg Pro Cys Gly Ile Val Pro
    130                 135                 140

Ala Lys Ser Val Cys Gly Pro Val Tyr Cys Phe Thr Pro Ser Pro Val
145                 150                 155                 160

Val Val Gly Thr Thr Asp Arg Ser Gly Ala Pro Thr Tyr Ser Trp Gly
                165                 170                 175

Ala Asn Asp Thr Asp Val Phe Val Leu Asn Asn Thr Arg Pro Pro Leu
            180                 185                 190

Gly Asn Trp Phe Gly Cys Thr Trp Met Asn Ser Thr Gly Phe Thr Lys
        195                 200                 205

Val Cys Gly Ala Pro Pro Cys Val Ile Gly Gly Val Gly Asn Asn Thr
    210                 215                 220

Leu Leu Cys Pro Thr Asp Cys Phe Arg Lys His Pro Glu Ala Thr Tyr
225                 230                 235                 240

Ser Arg Cys Gly Ser Gly Pro Trp Ile Thr Pro Arg Cys Met Val Asp
                245                 250                 255

Tyr Pro Tyr Arg Leu Trp His Tyr Pro Cys Thr Ile Asn Tyr Thr Ile
            260                 265                 270

Phe Lys Val Arg Met Tyr Val Gly Gly Val Glu His Arg Leu Glu Ala
        275                 280                 285

Ala Cys Asn Trp Thr Arg Gly Glu Arg Cys Asp Leu Glu Asp Arg Asp
    290                 295                 300

Arg Ser Glu Leu Ser Pro Leu Leu Leu Ser Thr Thr Gln Trp Gln Val
305                 310                 315                 320

Leu Pro Cys Ser Phe Thr Thr Leu Pro Ala Leu Ser Thr Gly Leu Ile
                325                 330                 335

His Leu His Gln Asn Ile Val Asp Val Gln Tyr Leu Tyr Gly Val Gly
            340                 345                 350
```

```
Ser Ser Ile Ala Ser Trp Ala Ile Lys Trp Glu Tyr Val Val Leu Leu
        355                 360                 365

Phe Leu Leu Leu Ala Asp Ala Arg Val Cys Ser Cys Leu Trp Met Met
370                 375                 380

Leu Leu Ile Ser Gln Ala Glu Ala Ala Gly Leu Val Arg Pro Gln Gly
385                 390                 395                 400

Gly Gly Ser Val Asp Lys Lys Ile Val Pro Arg Asp Cys Gly Cys Lys
            405                 410                 415

Pro Cys Ile Cys Thr Val Pro Glu Val Ser Ser Val Phe Ile Phe Pro
                420                 425                 430

Pro Lys Pro Lys Asp Val Leu Thr Ile Thr Leu Thr Pro Lys Val Thr
                    435                 440                 445

Cys Val Val Val Asp Ile Ser Lys Asp Asp Pro Glu Val Gln Phe Ser
450                 455                 460

Trp Phe Val Asp Asp Val Glu Val His Thr Ala Gln Thr Gln Pro Arg
465                 470                 475                 480

Glu Glu Gln Phe Asn Ser Thr Phe Arg Ser Val Ser Glu Leu Pro Ile
                485                 490                 495

Met His Gln Asp Trp Leu Asn Gly Lys Glu Phe Lys Cys Arg Val Asn
            500                 505                 510

Ser Ala Ala Phe Pro Ala Pro Ile Glu Lys Thr Ile Ser Lys Thr Lys
                515                 520                 525

Gly Arg Pro Lys Ala Pro Gln Val Tyr Thr Ile Pro Pro Pro Lys Glu
            530                 535                 540

Gln Met Ala Lys Asp Lys Val Ser Leu Thr Cys Met Ile Thr Asp Phe
545                 550                 555                 560

Phe Pro Glu Asp Ile Thr Val Glu Trp Gln Trp Asn Gly Gln Pro Ala
                565                 570                 575

Glu Asn Tyr Lys Asn Thr Gln Pro Ile Met Asp Thr Asp Gly Ser Tyr
            580                 585                 590

Phe Val Tyr Ser Lys Leu Asn Val Gln Lys Ser Asn Trp Glu Ala Gly
            595                 600                 605

Asn Thr Phe Thr Cys Ser Val Leu His Glu Gly Leu His Asn His His
            610                 615                 620

Thr Glu Lys Ser Leu Ser His Ser Pro Gly Leu Gln Ser Leu Ser Arg
625                 630                 635                 640

Ser Thr Arg Gly Ser
                645

<210> SEQ ID NO 73
<211> LENGTH: 1845
<212> TYPE: DNA
<213> ORGANISM: Hepatitis C virus
<220> FEATURE:
<221> NAME/KEY: CDS
<222> LOCATION: (1)..(1845)

<400> SEQUENCE: 73 atg tcg tac tac cat cac cat cac cat cac gat tac gat atc cca acg      48
Met Ser Tyr Tyr His His His His His His Asp Tyr Asp Ile Pro Thr
1               5                   10                  15 acc gaa aac ctg tat ttt cag ggc gcc atg gat ccg gaa ttc tac caa      96
Thr Glu Asn Leu Tyr Phe Gln Gly Ala Met Asp Pro Glu Phe Tyr Gln
                20                  25                  30 gtg cgc aat tcc tcg ggg ctt tac cat gtc acc aat gat tgc cct aac     144
Val Arg Asn Ser Ser Gly Leu Tyr His Val Thr Asn Asp Cys Pro Asn
            35                  40                  45
```

```
tcg agt att gtg tac gag gcg gcc gat gcc atc ctg cac act ccg ggg      192
Ser Ser Ile Val Tyr Glu Ala Ala Asp Ala Ile Leu His Thr Pro Gly
    50              55                  60 tgt gtc cct tgc gtt cgc gag ggt aac gcc tcg agg tgt tgg gtg gcg      240
Cys Val Pro Cys Val Arg Glu Gly Asn Ala Ser Arg Cys Trp Val Ala
65              70                  75                  80 gtg acc ccc acg gtg gcc acc agg gac ggc aaa ctc ccc aca acg cag      288
Val Thr Pro Thr Val Ala Thr Arg Asp Gly Lys Leu Pro Thr Thr Gln
                85                  90                  95 ctt cga cgt cat atc gat ctg ctt gtc ggg agc gcc acc ctc tgc tcg      336
Leu Arg Arg His Ile Asp Leu Leu Val Gly Ser Ala Thr Leu Cys Ser
            100                 105                 110 gcc ctc tac gtg ggg gac ctg tgc ggg tct gtc ttt ctt gtt ggt caa      384
Ala Leu Tyr Val Gly Asp Leu Cys Gly Ser Val Phe Leu Val Gly Gln
        115                 120                 125 ctg ttt acc ttc tct ccc agg cgc cac tgg acg acg caa gac tgc aat      432
Leu Phe Thr Phe Ser Pro Arg Arg His Trp Thr Thr Gln Asp Cys Asn
    130                 135                 140 tgt tct atc tat ccc ggc cat ata acg ggt cat cgc atg gca tgg gat      480
Cys Ser Ile Tyr Pro Gly His Ile Thr Gly His Arg Met Ala Trp Asp
145                 150                 155                 160 atg atg atg aac tgg tcc cct acg gca gcg ttg gtg gta gct cag ctg      528
Met Met Met Asn Trp Ser Pro Thr Ala Ala Leu Val Val Ala Gln Leu
                165                 170                 175 ctc cgg atc cca caa gcc atc atg gac atg atc gct ggt gct cac tgg      576
Leu Arg Ile Pro Gln Ala Ile Met Asp Met Ile Ala Gly Ala His Trp
            180                 185                 190 gga gtc ctg gcg ggc ata gcg tat ttc tcc atg gtg ggg aac tgg gcg      624
Gly Val Leu Ala Gly Ile Ala Tyr Phe Ser Met Val Gly Asn Trp Ala
        195                 200                 205 aag gtc ctg gta gtg ctg ctg cta ttt gcc ggc gtc gac gcg gaa acc      672
Lys Val Leu Val Val Leu Leu Leu Phe Ala Gly Val Asp Ala Glu Thr
    210                 215                 220 cac gtc acc ggg gga aat gcc ggc cgc acc acg gct ggg ctt gtt ggt      720
His Val Thr Gly Gly Asn Ala Gly Arg Thr Thr Ala Gly Leu Val Gly
225                 230                 235                 240 ctc ctt aca cca ggc gcc aag cag aac atc caa ctg atc aac acc aac      768
Leu Leu Thr Pro Gly Ala Lys Gln Asn Ile Gln Leu Ile Asn Thr Asn
                245                 250                 255 ggc agt tgg cac atc aat agc acg gcc ttg aat tgc aat gaa agc ctt      816
Gly Ser Trp His Ile Asn Ser Thr Ala Leu Asn Cys Asn Glu Ser Leu
            260                 265                 270 aac acc ggc tgg tta gca ggg ctc ttc tat caa cac aaa ttc aac tct      864
Asn Thr Gly Trp Leu Ala Gly Leu Phe Tyr Gln His Lys Phe Asn Ser
        275                 280                 285 tca ggc tgt cct gag agg ttg gcc agc tgc cga cgc ctt acc gat ttt      912
Ser Gly Cys Pro Glu Arg Leu Ala Ser Cys Arg Arg Leu Thr Asp Phe
    290                 295                 300 gcc cag ggc tgg ggt cct atc agt tat gcc aac gga agc ggc ctc gac      960
Ala Gln Gly Trp Gly Pro Ile Ser Tyr Ala Asn Gly Ser Gly Leu Asp
305                 310                 315                 320 gaa cgc ccc tac tgc tgg cac tac cct cca aga cct tgt ggc att gtg     1008
Glu Arg Pro Tyr Cys Trp His Tyr Pro Pro Arg Pro Cys Gly Ile Val
                325                 330                 335 ccc gca aag agc gtg tgt ggc ccg gta tat tgc ttc act ccc agc ccc     1056
Pro Ala Lys Ser Val Cys Gly Pro Val Tyr Cys Phe Thr Pro Ser Pro
            340                 345                 350 gtg gtg gtg gga acg acc gac agg tcg ggc gcg cct acc tac agc tgg     1104
Val Val Val Gly Thr Thr Asp Arg Ser Gly Ala Pro Thr Tyr Ser Trp
        355                 360                 365
```

| | | | | | | | | | | | | | | | | |
|---|---|---|---|---|---|---|---|---|---|---|---|---|---|---|---|---|
|ggt|gca|aat|gat|acg|gat|gtc|ttc|gtc|ctt|aac|aac|acc|agg|cca|ccg|1152|
|Gly|Ala|Asn|Asp|Thr|Asp|Val|Phe|Val|Leu|Asn|Asn|Thr|Arg|Pro|Pro| |
| | |370| | | |375| | | |380| | | | | | |
|ctg|ggc|aat|tgg|ttc|ggt|tgt|acc|tgg|atg|aac|tca|act|gga|ttc|acc|1200|
|Leu|Gly|Asn|Trp|Phe|Gly|Cys|Thr|Trp|Met|Asn|Ser|Thr|Gly|Phe|Thr| |
|385| | | | |390| | | | |395| | | | |400| |
|aaa|gtg|tgc|gga|gcg|ccc|cct|tgt|gtc|atc|gga|ggg|gtg|ggc|aac|aac|1248|
|Lys|Val|Cys|Gly|Ala|Pro|Pro|Cys|Val|Ile|Gly|Gly|Val|Gly|Asn|Asn| |
| | | | |405| | | | |410| | | | |415| | |
|acc|ttg|ctc|tgc|ccc|act|gat|tgc|ttc|cgc|aaa|cat|ccg|gaa|gcc|aca|1296|
|Thr|Leu|Leu|Cys|Pro|Thr|Asp|Cys|Phe|Arg|Lys|His|Pro|Glu|Ala|Thr| |
| | | |420| | | | |425| | | | |430| | | |
|tac|tct|cgg|tgc|ggc|tcc|ggt|ccc|tgg|att|aca|ccc|agg|tgc|atg|gtc|1344|
|Tyr|Ser|Arg|Cys|Gly|Ser|Gly|Pro|Trp|Ile|Thr|Pro|Arg|Cys|Met|Val| |
| | |435| | | | |440| | | | |445| | | | |
|gac|tac|ccg|tat|agg|ctt|tgg|cac|tat|cct|tgt|acc|atc|aat|tac|acc|1392|
|Asp|Tyr|Pro|Tyr|Arg|Leu|Trp|His|Tyr|Pro|Cys|Thr|Ile|Asn|Tyr|Thr| |
| |450| | | | |455| | | | |460| | | | | |
|ata|ttc|aaa|gtc|agg|atg|tac|gtg|gga|ggg|gtc|gag|cac|agg|ctg|gaa|1440|
|Ile|Phe|Lys|Val|Arg|Met|Tyr|Val|Gly|Gly|Val|Glu|His|Arg|Leu|Glu| |
|465| | | | |470| | | | |475| | | | |480| |
|gcg|gcc|tgc|aac|tgg|acg|cgg|ggc|gaa|cgc|tgt|gat|ctg|gaa|gac|agg|1488|
|Ala|Ala|Cys|Asn|Trp|Thr|Arg|Gly|Glu|Arg|Cys|Asp|Leu|Glu|Asp|Arg| |
| | | | |485| | | | |490| | | | |495| | |
|gac|agg|tcc|gag|ctc|agc|ccg|ttg|ctg|ctg|tcc|acc|aca|cag|tgg|cag|1536|
|Asp|Arg|Ser|Glu|Leu|Ser|Pro|Leu|Leu|Leu|Ser|Thr|Thr|Gln|Trp|Gln| |
| | | |500| | | | |505| | | | |510| | | |
|gtc|ctt|ccg|tgt|tct|ttc|acg|acc|ctg|cca|gcc|ttg|tcc|acc|ggc|ctc|1584|
|Val|Leu|Pro|Cys|Ser|Phe|Thr|Thr|Leu|Pro|Ala|Leu|Ser|Thr|Gly|Leu| |
| | |515| | | | |520| | | | |525| | | | |
|atc|cac|ctc|cac|cag|aac|att|gtg|gac|gtg|cag|tac|ttg|tac|ggg|gta|1632|
|Ile|His|Leu|His|Gln|Asn|Ile|Val|Asp|Val|Gln|Tyr|Leu|Tyr|Gly|Val| |
| |530| | | | |535| | | | |540| | | | | |
|ggg|tca|agc|atc|gcg|tcc|tgg|gcc|att|aag|tgg|gag|tac|gtc|gtt|ctc|1680|
|Gly|Ser|Ser|Ile|Ala|Ser|Trp|Ala|Ile|Lys|Trp|Glu|Tyr|Val|Val|Leu| |
|545| | | | |550| | | | |555| | | | |560| |
|ctg|ttc|ctt|ctg|ctt|gca|gac|gcg|cgc|gtc|tgc|tcc|tgc|ttg|tgg|atg|1728|
|Leu|Phe|Leu|Leu|Leu|Ala|Asp|Ala|Arg|Val|Cys|Ser|Cys|Leu|Trp|Met| |
| | | | |565| | | | |570| | | | |575| | |
|atg|tta|ctc|ata|tcc|caa|gcg|gag|gcg|gct|gga|cta|gtg|cgg|ccg|ctt|1776|
|Met|Leu|Leu|Ile|Ser|Gln|Ala|Glu|Ala|Ala|Gly|Leu|Val|Arg|Pro|Leu| |
| | | |580| | | | |585| | | | |590| | | |
|tcg|aat|cta|gag|cct|gca|gtc|tcg|agg|cat|gcg|gta|cca|agc|ttg|tcg|1824|
|Ser|Asn|Leu|Glu|Pro|Ala|Val|Ser|Arg|His|Ala|Val|Pro|Ser|Leu|Ser| |
| | |595| | | | |600| | | | |605| | | | |
|aga|agt|act|aga|gga|tca|taa| | | | | | | | | |1845|
|Arg|Ser|Thr|Arg|Gly|Ser| | | | | | | | | | | |
| | |610| | | | | | | | | | | | | | |

```
<210> SEQ ID NO 74
<211> LENGTH: 614
<212> TYPE: PRT
<213> ORGANISM: Hepatitis C virus

<400> SEQUENCE: 74
```

Met Ser Tyr Tyr His His His His His Asp Tyr Asp Ile Pro Thr
1               5                   10                  15

Thr Glu Asn Leu Tyr Phe Gln Gly Ala Met Asp Pro Glu Phe Tyr Gln
            20                  25                  30

Val Arg Asn Ser Ser Gly Leu Tyr His Val Thr Asn Asp Cys Pro Asn
        35                  40                  45

```
Ser Ser Ile Val Tyr Glu Ala Asp Ala Ile Leu His Thr Pro Gly
    50                  55                  60

Cys Val Pro Cys Val Arg Glu Gly Asn Ala Ser Arg Cys Trp Val Ala
65                  70                  75                  80

Val Thr Pro Thr Val Ala Thr Arg Asp Gly Lys Leu Pro Thr Thr Gln
                85                  90                  95

Leu Arg Arg His Ile Asp Leu Leu Val Gly Ser Ala Thr Leu Cys Ser
            100                 105                 110

Ala Leu Tyr Val Gly Asp Leu Cys Gly Ser Val Phe Leu Val Gly Gln
        115                 120                 125

Leu Phe Thr Phe Ser Pro Arg Arg His Trp Thr Thr Gln Asp Cys Asn
    130                 135                 140

Cys Ser Ile Tyr Pro Gly His Ile Thr Gly His Arg Met Ala Trp Asp
145                 150                 155                 160

Met Met Met Asn Trp Ser Pro Thr Ala Ala Leu Val Val Ala Gln Leu
                165                 170                 175

Leu Arg Ile Pro Gln Ala Ile Met Asp Met Ile Ala Gly Ala His Trp
            180                 185                 190

Gly Val Leu Ala Gly Ile Ala Tyr Phe Ser Met Val Gly Asn Trp Ala
        195                 200                 205

Lys Val Leu Val Val Leu Leu Leu Phe Ala Gly Val Asp Ala Glu Thr
    210                 215                 220

His Val Thr Gly Gly Asn Ala Gly Arg Thr Thr Ala Gly Leu Val Gly
225                 230                 235                 240

Leu Leu Thr Pro Gly Ala Lys Gln Asn Ile Gln Leu Ile Asn Thr Asn
                245                 250                 255

Gly Ser Trp His Ile Asn Ser Thr Ala Leu Asn Cys Asn Glu Ser Leu
            260                 265                 270

Asn Thr Gly Trp Leu Ala Gly Leu Phe Tyr Gln His Lys Phe Asn Ser
        275                 280                 285

Ser Gly Cys Pro Glu Arg Leu Ala Ser Cys Arg Arg Leu Thr Asp Phe
    290                 295                 300

Ala Gln Gly Trp Gly Pro Ile Ser Tyr Ala Asn Gly Ser Gly Leu Asp
305                 310                 315                 320

Glu Arg Pro Tyr Cys Trp His Tyr Pro Pro Arg Pro Cys Gly Ile Val
                325                 330                 335

Pro Ala Lys Ser Val Cys Gly Pro Val Tyr Cys Phe Thr Pro Ser Pro
            340                 345                 350

Val Val Val Gly Thr Thr Asp Arg Ser Gly Ala Pro Thr Tyr Ser Trp
        355                 360                 365

Gly Ala Asn Asp Thr Asp Val Phe Val Leu Asn Asn Thr Arg Pro Pro
    370                 375                 380

Leu Gly Asn Trp Phe Gly Cys Thr Trp Met Asn Ser Thr Gly Phe Thr
385                 390                 395                 400

Lys Val Cys Gly Ala Pro Pro Cys Val Ile Gly Gly Val Gly Asn Asn
                405                 410                 415

Thr Leu Leu Cys Pro Thr Asp Cys Phe Arg Lys His Pro Glu Ala Thr
            420                 425                 430

Tyr Ser Arg Cys Gly Ser Gly Pro Trp Ile Thr Pro Arg Cys Met Val
        435                 440                 445

Asp Tyr Pro Tyr Arg Leu Trp His Tyr Pro Cys Thr Ile Asn Tyr Thr
    450                 455                 460

Ile Phe Lys Val Arg Met Tyr Val Gly Gly Val Glu His Arg Leu Glu
```

```
                    465                 470                 475                 480
Ala Ala Cys Asn Trp Thr Arg Gly Glu Arg Cys Asp Leu Glu Asp Arg
                485                 490                 495

Asp Arg Ser Glu Leu Ser Pro Leu Leu Leu Ser Thr Thr Gln Trp Gln
            500                 505                 510

Val Leu Pro Cys Ser Phe Thr Thr Leu Pro Ala Leu Ser Thr Gly Leu
        515                 520                 525

Ile His Leu His Gln Asn Ile Val Asp Val Gln Tyr Leu Tyr Gly Val
    530                 535                 540

Gly Ser Ser Ile Ala Ser Trp Ala Ile Lys Trp Glu Tyr Val Val Leu
545                 550                 555                 560

Leu Phe Leu Leu Leu Ala Asp Ala Arg Val Cys Ser Cys Leu Trp Met
                565                 570                 575

Met Leu Leu Ile Ser Gln Ala Glu Ala Ala Gly Leu Val Arg Pro Leu
            580                 585                 590

Ser Asn Leu Glu Pro Ala Val Ser Arg His Ala Val Pro Ser Leu Ser
        595                 600                 605

Arg Ser Thr Arg Gly Ser
    610

<210> SEQ ID NO 75
<211> LENGTH: 2517
<212> TYPE: DNA
<213> ORGANISM: Artificial
<220> FEATURE:
<223> OTHER INFORMATION: Hepatitis C virus plus murine
<220> FEATURE:
<221> NAME/KEY: CDS
<222> LOCATION: (1)..(2517)

<400> SEQUENCE: 75 atg tcg tac tac cat cac cat cac cat cac gat tac gat atc cca acg       48
Met Ser Tyr Tyr His His His His His His Asp Tyr Asp Ile Pro Thr
1               5                   10                  15 acc gaa aac ctg tat ttt cag ggc gcc atg gat ccg gaa ttc tac caa       96
Thr Glu Asn Leu Tyr Phe Gln Gly Ala Met Asp Pro Glu Phe Tyr Gln
                20                  25                  30 gtg cgc aat tcc tcg ggg ctt tac cat gtc acc aat gat tgc cct aac      144
Val Arg Asn Ser Ser Gly Leu Tyr His Val Thr Asn Asp Cys Pro Asn
            35                  40                  45 tcg agt att gtg tac gag gcg gcc gat gcc atc ctg cac act ccg ggg      192
Ser Ser Ile Val Tyr Glu Ala Ala Asp Ala Ile Leu His Thr Pro Gly
        50                  55                  60 tgt gtc cct tgc gtt cgc gag ggt aac gcc tcg agg tgt tgg gtg gcg      240
Cys Val Pro Cys Val Arg Glu Gly Asn Ala Ser Arg Cys Trp Val Ala
65                  70                  75                  80 gtg acc ccc acg gtg gcc acc agg gac ggc aaa ctc ccc aca acg cag      288
Val Thr Pro Thr Val Ala Thr Arg Asp Gly Lys Leu Pro Thr Thr Gln
                85                  90                  95 ctt cga cgt cat atc gat ctg ctt gtc ggg agc gcc acc ctc tgc tcg      336
Leu Arg Arg His Ile Asp Leu Leu Val Gly Ser Ala Thr Leu Cys Ser
            100                 105                 110 gcc ctc tac gtg ggg gac ctg tgc ggg tct gtc ttt ctt gtt ggt caa      384
Ala Leu Tyr Val Gly Asp Leu Cys Gly Ser Val Phe Leu Val Gly Gln
        115                 120                 125 ctg ttt acc ttc tct ccc agg cgc cac tgg acg acg caa gac tgc aat      432
Leu Phe Thr Phe Ser Pro Arg Arg His Trp Thr Thr Gln Asp Cys Asn
    130                 135                 140 tgt tct atc tat ccc ggc cat ata acg ggt cat cgc atg gca tgg gat      480
Cys Ser Ile Tyr Pro Gly His Ile Thr Gly His Arg Met Ala Trp Asp
```

```
                145                 150                 155                 160
atg atg atg aac tgg tcc cct acg gca gcg ttg gtg gta gct cag ctg         528
Met Met Met Asn Trp Ser Pro Thr Ala Ala Leu Val Val Ala Gln Leu
                    165                 170                 175 ctc cgg atc cca caa gcc atc atg gac atg atc gct ggt gct cac tgg         576
Leu Arg Ile Pro Gln Ala Ile Met Asp Met Ile Ala Gly Ala His Trp
                180                 185                 190 gga gtc ctg gcg ggc ata gcg tat ttc tcc atg gtg ggg aac tgg gcg         624
Gly Val Leu Ala Gly Ile Ala Tyr Phe Ser Met Val Gly Asn Trp Ala
            195                 200                 205 aag gtc ctg gta gtg ctg ctg cta ttt gcc ggc gtc gac gcg gaa acc         672
Lys Val Leu Val Val Leu Leu Leu Phe Ala Gly Val Asp Ala Glu Thr
        210                 215                 220 cac gtc acc ggg gga aat gcc ggc cgc acc acg gct ggg ctt gtt ggt         720
His Val Thr Gly Gly Asn Ala Gly Arg Thr Thr Ala Gly Leu Val Gly
225                 230                 235                 240 ctc ctt aca cca ggc gcc aag cag aac atc caa ctg atc aac acc aac         768
Leu Leu Thr Pro Gly Ala Lys Gln Asn Ile Gln Leu Ile Asn Thr Asn
                245                 250                 255 ggc agt tgg cac atc aat agc acg gcc ttg aat tgc aat gaa agc ctt         816
Gly Ser Trp His Ile Asn Ser Thr Ala Leu Asn Cys Asn Glu Ser Leu
                260                 265                 270 aac acc ggc tgg tta gca ggg ctc ttc tat caa cac aaa ttc aac tct         864
Asn Thr Gly Trp Leu Ala Gly Leu Phe Tyr Gln His Lys Phe Asn Ser
            275                 280                 285 tca ggc tgt cct gag agg ttg gcc agc tgc cga cgc ctt acc gat ttt         912
Ser Gly Cys Pro Glu Arg Leu Ala Ser Cys Arg Arg Leu Thr Asp Phe
        290                 295                 300 gcc cag ggc tgg ggt cct atc agt tat gcc aac gga agc ggc ctc gac         960
Ala Gln Gly Trp Gly Pro Ile Ser Tyr Ala Asn Gly Ser Gly Leu Asp
305                 310                 315                 320 gaa cgc ccc tac tgc tgg cac tac cct cca aga cct tgt ggc att gtg        1008
Glu Arg Pro Tyr Cys Trp His Tyr Pro Pro Arg Pro Cys Gly Ile Val
                325                 330                 335 ccc gca aag agc gtg tgt ggc ccg gta tat tgc ttc act ccc agc ccc        1056
Pro Ala Lys Ser Val Cys Gly Pro Val Tyr Cys Phe Thr Pro Ser Pro
                340                 345                 350 gtg gtg gtg gga acg acc gac agg tcg ggc gcg cct acc tac agc tgg        1104
Val Val Val Gly Thr Thr Asp Arg Ser Gly Ala Pro Thr Tyr Ser Trp
            355                 360                 365 ggt gca aat gat acg gat gtc ttc gtc ctt aac aac acc agg cca ccg        1152
Gly Ala Asn Asp Thr Asp Val Phe Val Leu Asn Asn Thr Arg Pro Pro
        370                 375                 380 ctg ggc aat tgg ttc ggt tgt acc tgg atg aac tca act gga ttc acc        1200
Leu Gly Asn Trp Phe Gly Cys Thr Trp Met Asn Ser Thr Gly Phe Thr
385                 390                 395                 400 aaa gtg tgc gga gcg ccc cct tgt gtc atc gga ggg gtg ggc aac aac        1248
Lys Val Cys Gly Ala Pro Pro Cys Val Ile Gly Gly Val Gly Asn Asn
                405                 410                 415 acc ttg ctc tgc ccc act gat tgc ttc cgc aaa cat ccg gaa gcc aca        1296
Thr Leu Leu Cys Pro Thr Asp Cys Phe Arg Lys His Pro Glu Ala Thr
                420                 425                 430 tac tct cgg tgc ggc tcc ggt ccc tgg att aca ccc agg tgc atg gtc        1344
Tyr Ser Arg Cys Gly Ser Gly Pro Trp Ile Thr Pro Arg Cys Met Val
            435                 440                 445 gac tac ccg tat agg ctt tgg cac tat cct tgt acc atc aat tac acc        1392
Asp Tyr Pro Tyr Arg Leu Trp His Tyr Pro Cys Thr Ile Asn Tyr Thr
        450                 455                 460 ata ttc aaa gtc agg atg tac gtg gga ggg gtc gag cac agg ctg gaa        1440
Ile Phe Lys Val Arg Met Tyr Val Gly Gly Val Glu His Arg Leu Glu
```

```
                             465                 470                 475                 480
gcg gcc tgc aac tgg acg cgg ggc gaa cgc tgt gat ctg gaa gac agg       1488
Ala Ala Cys Asn Trp Thr Arg Gly Glu Arg Cys Asp Leu Glu Asp Arg
                    485                 490                 495 gac agg tcc gag ctc agc ccg ttg ctg ctg tcc acc aca cag tgg cag       1536
Asp Arg Ser Glu Leu Ser Pro Leu Leu Leu Ser Thr Thr Gln Trp Gln
            500                 505                 510 gtc ctt ccg tgt tct ttc acg acc ctg cca gcc ttg tcc acc ggc ctc       1584
Val Leu Pro Cys Ser Phe Thr Thr Leu Pro Ala Leu Ser Thr Gly Leu
        515                 520                 525 atc cac ctc cac cag aac att gtg gac gtg cag tac ttg tac ggg gta       1632
Ile His Leu His Gln Asn Ile Val Asp Val Gln Tyr Leu Tyr Gly Val
    530                 535                 540 ggg tca agc atc gcg tcc tgg gcc att aag tgg gag tac gtc gtt ctc       1680
Gly Ser Ser Ile Ala Ser Trp Ala Ile Lys Trp Glu Tyr Val Val Leu
545                 550                 555                 560 ctg ttc ctt ctg ctt gca gac gcg cgc gtc tgc tcc tgc ttg tgg atg       1728
Leu Phe Leu Leu Leu Ala Asp Ala Arg Val Cys Ser Cys Leu Trp Met
                565                 570                 575 atg tta ctc ata tcc caa gcg gag gcg gct gga cta gtg cgg ccg caa       1776
Met Leu Leu Ile Ser Gln Ala Glu Ala Ala Gly Leu Val Arg Pro Gln
            580                 585                 590 ggc ggc gga tcc gtg gac aag aaa att gtg ccc agg gat tgt ggt tgt       1824
Gly Gly Gly Ser Val Asp Lys Lys Ile Val Pro Arg Asp Cys Gly Cys
        595                 600                 605 aag cct tgc ata tgt aca gtc cca gaa gta tca tct gtc ttc atc ttc       1872
Lys Pro Cys Ile Cys Thr Val Pro Glu Val Ser Ser Val Phe Ile Phe
    610                 615                 620 ccc cca aag ccc aag gat gtg ctc acc att act ctg act cct aag gtc       1920
Pro Pro Lys Pro Lys Asp Val Leu Thr Ile Thr Leu Thr Pro Lys Val
625                 630                 635                 640 acg tgt gtt gtg gta gac atc agc aag gat gat ccc gag gtc cag ttc       1968
Thr Cys Val Val Val Asp Ile Ser Lys Asp Asp Pro Glu Val Gln Phe
                645                 650                 655 agc tgg ttt gta gat gat gtg gag gtg cac aca gct cag acg caa ccc       2016
Ser Trp Phe Val Asp Asp Val Glu Val His Thr Ala Gln Thr Gln Pro
            660                 665                 670 cgg gag gag cag ttc aac agc act ttc cgc tca gtc agt gaa ctt ccc       2064
Arg Glu Glu Gln Phe Asn Ser Thr Phe Arg Ser Val Ser Glu Leu Pro
        675                 680                 685 atc atg cac cag gac tgg ctc aat ggc aag gag ttc aaa tgc agg gtc       2112
Ile Met His Gln Asp Trp Leu Asn Gly Lys Glu Phe Lys Cys Arg Val
    690                 695                 700 aac agt gca gct ttc cct gcc ccc atc gag aaa acc atc tcc aaa acc       2160
Asn Ser Ala Ala Phe Pro Ala Pro Ile Glu Lys Thr Ile Ser Lys Thr
705                 710                 715                 720 aaa ggc aga ccg aag gct cca cag gtg tac acc att cca cct ccc aag       2208
Lys Gly Arg Pro Lys Ala Pro Gln Val Tyr Thr Ile Pro Pro Pro Lys
                725                 730                 735 gag cag atg gcc aag gat aaa gtc agt ctg acc tgc atg ata aca gac       2256
Glu Gln Met Ala Lys Asp Lys Val Ser Leu Thr Cys Met Ile Thr Asp
            740                 745                 750 ttc ttc cct gaa gac att act gtg gag tgg cag tgg aat ggg cag cca       2304
Phe Phe Pro Glu Asp Ile Thr Val Glu Trp Gln Trp Asn Gly Gln Pro
        755                 760                 765 gcg gag aac tac aag aac act cag ccc atc atg gac aca gat ggc tct       2352
Ala Glu Asn Tyr Lys Asn Thr Gln Pro Ile Met Asp Thr Asp Gly Ser
    770                 775                 780 tac ttc gtc tac agc aag ctc aat gtg cag aag agc aac tgg gag gca       2400
Tyr Phe Val Tyr Ser Lys Leu Asn Val Gln Lys Ser Asn Trp Glu Ala
```

```
                    785                 790                 795                 800
gga aat act ttc acc tgc tct gtg tta cat gag ggc ctg cac aac cac               2448
Gly Asn Thr Phe Thr Cys Ser Val Leu His Glu Gly Leu His Asn His
                805                 810                 815 cat act gag aag agc ctc tcc cac tct cct ggg ctg caa agc ttg tcg               2496
His Thr Glu Lys Ser Leu Ser His Ser Pro Gly Leu Gln Ser Leu Ser
            820                 825                 830 aga agt act aga gga tca taa                                                   2517
Arg Ser Thr Arg Gly Ser
            835

<210> SEQ ID NO 76
<211> LENGTH: 838
<212> TYPE: PRT
<213> ORGANISM: Artificial
<220> FEATURE:
<223> OTHER INFORMATION: Synthetic Construct

<400> SEQUENCE: 76

Met Ser Tyr Tyr His His His His Asp Tyr Asp Ile Pro Thr
 1               5                  10                  15

Thr Glu Asn Leu Tyr Phe Gln Gly Ala Met Asp Pro Glu Phe Tyr Gln
                20                  25                  30

Val Arg Asn Ser Ser Gly Leu Tyr His Val Thr Asn Asp Cys Pro Asn
            35                  40                  45

Ser Ser Ile Val Tyr Glu Ala Asp Ala Ile Leu His Thr Pro Gly
        50                  55                  60

Cys Val Pro Cys Val Arg Glu Gly Asn Ala Ser Arg Cys Trp Val Ala
 65                  70                  75                  80

Val Thr Pro Thr Val Ala Thr Arg Asp Gly Lys Leu Pro Thr Thr Gln
                85                  90                  95

Leu Arg Arg His Ile Asp Leu Leu Val Gly Ser Ala Thr Leu Cys Ser
            100                 105                 110

Ala Leu Tyr Val Gly Asp Leu Cys Gly Ser Val Phe Leu Val Gly Gln
        115                 120                 125

Leu Phe Thr Phe Ser Pro Arg Arg His Trp Thr Thr Gln Asp Cys Asn
    130                 135                 140

Cys Ser Ile Tyr Pro Gly His Ile Thr Gly His Arg Met Ala Trp Asp
145                 150                 155                 160

Met Met Met Asn Trp Ser Pro Thr Ala Ala Leu Val Val Ala Gln Leu
                165                 170                 175

Leu Arg Ile Pro Gln Ala Ile Met Asp Met Ile Ala Gly Ala His Trp
            180                 185                 190

Gly Val Leu Ala Gly Ile Ala Tyr Phe Ser Met Val Gly Asn Trp Ala
        195                 200                 205

Lys Val Leu Val Val Leu Leu Leu Phe Ala Gly Val Asp Ala Glu Thr
    210                 215                 220

His Val Thr Gly Gly Asn Ala Gly Arg Thr Thr Ala Gly Leu Val Gly
225                 230                 235                 240

Leu Leu Thr Pro Gly Ala Lys Gln Asn Ile Gln Leu Ile Asn Thr Asn
                245                 250                 255

Gly Ser Trp His Ile Asn Ser Thr Ala Leu Asn Cys Asn Glu Ser Leu
            260                 265                 270

Asn Thr Gly Trp Leu Ala Gly Leu Phe Tyr Gln His Lys Phe Asn Ser
        275                 280                 285

Ser Gly Cys Pro Glu Arg Leu Ala Ser Cys Arg Arg Leu Thr Asp Phe
    290                 295                 300
```

```
Ala Gln Gly Trp Gly Pro Ile Ser Tyr Ala Asn Gly Ser Gly Leu Asp
305                 310                 315                 320

Glu Arg Pro Tyr Cys Trp His Tyr Pro Arg Pro Cys Gly Ile Val
            325                 330                 335

Pro Ala Lys Ser Val Cys Gly Pro Val Tyr Cys Phe Thr Pro Ser Pro
            340                 345                 350

Val Val Val Gly Thr Thr Asp Arg Ser Gly Ala Pro Thr Tyr Ser Trp
            355                 360                 365

Gly Ala Asn Asp Thr Asp Val Phe Val Leu Asn Asn Thr Arg Pro Pro
            370                 375                 380

Leu Gly Asn Trp Phe Gly Cys Thr Trp Met Asn Ser Thr Gly Phe Thr
385                 390                 395                 400

Lys Val Cys Gly Ala Pro Pro Cys Val Ile Gly Gly Val Gly Asn Asn
                405                 410                 415

Thr Leu Leu Cys Pro Thr Asp Cys Phe Arg Lys His Pro Glu Ala Thr
                420                 425                 430

Tyr Ser Arg Cys Gly Ser Gly Pro Trp Ile Thr Pro Arg Cys Met Val
                435                 440                 445

Asp Tyr Pro Tyr Arg Leu Trp His Tyr Pro Cys Thr Ile Asn Tyr Thr
            450                 455                 460

Ile Phe Lys Val Arg Met Tyr Val Gly Val Glu His Arg Leu Glu
465                 470                 475                 480

Ala Ala Cys Asn Trp Thr Arg Gly Glu Arg Cys Asp Leu Glu Asp Arg
                485                 490                 495

Asp Arg Ser Glu Leu Ser Pro Leu Leu Leu Ser Thr Thr Gln Trp Gln
            500                 505                 510

Val Leu Pro Cys Ser Phe Thr Thr Leu Pro Ala Leu Ser Thr Gly Leu
            515                 520                 525

Ile His Leu His Gln Asn Ile Val Asp Val Gln Tyr Leu Tyr Gly Val
            530                 535                 540

Gly Ser Ser Ile Ala Ser Trp Ala Ile Lys Trp Glu Tyr Val Val Leu
545                 550                 555                 560

Leu Phe Leu Leu Leu Ala Asp Ala Arg Val Cys Ser Cys Leu Trp Met
                565                 570                 575

Met Leu Leu Ile Ser Gln Ala Glu Ala Ala Gly Leu Val Arg Pro Gln
                580                 585                 590

Gly Gly Gly Ser Val Asp Lys Lys Ile Val Pro Arg Asp Cys Gly Cys
            595                 600                 605

Lys Pro Cys Ile Cys Thr Val Pro Glu Val Ser Ser Val Phe Ile Phe
610                 615                 620

Pro Pro Lys Pro Lys Asp Val Leu Thr Ile Thr Leu Thr Pro Lys Val
625                 630                 635                 640

Thr Cys Val Val Val Asp Ile Ser Lys Asp Asp Pro Glu Val Gln Phe
                645                 650                 655

Ser Trp Phe Val Asp Asp Val Glu Val His Thr Ala Gln Thr Gln Pro
            660                 665                 670

Arg Glu Glu Gln Phe Asn Ser Thr Phe Arg Ser Val Ser Glu Leu Pro
            675                 680                 685

Ile Met His Gln Asp Trp Leu Asn Gly Lys Glu Phe Lys Cys Arg Val
            690                 695                 700

Asn Ser Ala Ala Phe Pro Ala Pro Ile Glu Lys Thr Ile Ser Lys Thr
705                 710                 715                 720

Lys Gly Arg Pro Lys Ala Pro Gln Val Tyr Thr Ile Pro Pro Pro Lys
```

-continued

```
            725                 730                 735
Glu Gln Met Ala Lys Asp Lys Val Ser Leu Thr Cys Met Ile Thr Asp
            740                 745                 750

Phe Phe Pro Glu Asp Ile Thr Val Glu Trp Gln Trp Asn Gly Gln Pro
            755                 760                 765

Ala Glu Asn Tyr Lys Asn Thr Gln Pro Ile Met Asp Thr Asp Gly Ser
            770                 775                 780

Tyr Phe Val Tyr Ser Lys Leu Asn Val Gln Lys Ser Asn Trp Glu Ala
785                 790                 795                 800

Gly Asn Thr Phe Thr Cys Ser Val Leu His Glu Gly Leu His Asn His
                805                 810                 815

His Thr Glu Lys Ser Leu Ser His Ser Pro Gly Leu Gln Ser Leu Ser
                820                 825                 830

Arg Ser Thr Arg Gly Ser
            835
```

CHIMERIC ANTIGENS FOR ELICITING AN IMMUNE RESPONSE

This Application claims benefit of U.S. Provisional Application Ser. No. 60/423,578, filed on Nov. 5, 2002 and claims benefit of U.S. Provisional Application Ser. No. 60/390,564, filed on Jun. 20, 2002.

FIELD OF THE INVENTION

The present invention relates to chimeric antigens (fusion proteins) for targeting and activating antigen presenting cells. In particular, the invention describes compositions and methods that contain or use one or more fusion proteins that contain a pre-selected HBV antigen or an HCV antigen, and a xenotypic immunoglobulin fragment, wherein the fusion molecule is capable of binding and activating antigen presenting cells, especially dendritic cells.

BACKGROUND OF THE INVENTION

Viral infectious diseases are major public healthcare issues. Human Hepatitis B virus (HBV) is a member of a family of DNA viruses that primarily infect the liver (Gust, 1986). Other members of this family are woodchuck hepatitis B virus (WHV) ((Summers, Smolec et al. 1978), duck hepatitis B virus (DHBV) ((Mason, Seal et al. 1980) and heron hepatitis B virus (HHBV) (Sprengel, Kaleta et al. 1988). These viruses share a common morphology and replication mechanisms, but are species specific for infectivity (Marion, 1988).

HBV primarily infects liver cells and can cause acute and chronic liver disease resulting in cirrhosis and hepatocellular carcinoma. Infection occurs through blood and other body fluids. Approximately 90% of the individuals infected by HBV are able to clear the infection, while the remaining 10% become chronic carriers of the virus with a high probability of developing cirrhosis of the liver and hepatocellular carcinoma. The world Health Organization statistics show that more than 2 billion people have been infected by HBV and among these, 350 million are chronically infected by the virus (Beasley 1988) (Law JY 1993). Prophylactic vaccines based on HBV surface antigen (HbSAg) have been very effective in providing protective immunity against HBV infections. These vaccines have been developed from HbSAg purified from plasma of chronic HBV carriers, produced by recombinant DNA techniques as well as through the use of synthetic peptides (Please see U.S. Pat. Nos. 4,599,230 and 4,599,231). These vaccines are highly effective in the prevention of infection, but are ineffective in eradicating established chronic infections.

Human Hepatitis B Virus (HBV) belongs to the family of Hepadnaviruses. Other members of this family are Duck Hepatitis B Virus (DHBV), Woodchuk Hepatitis Virus (WHV) Ground squirrel Hepatitis B Virus (GSHV) and Heron Hepatitis B Virus (HHBV). Although these viruses have similar morphology and replication mechanism, they are fairly species specific consequently, infect only very closely related species. These viruses have a DNA genome ranging in size of 3.0-3.2 Kb, with overlapping reading frames to encode several proteins. HBV genome encodes several proteins. Among these, the surface antigens: Large (S1/S2/S), Medium (S2/S) and Small (S) are proposed to be involved in the binding of the virus to the cellular receptors for uptake. The core protein (Core) forms capsids which encapsulate the partially double stranded DNA genome. Polymerase/Reverse Transcriptase (Pol) protein is a multifunctional enzyme necessary for the replication of the virus. The X protein has been proposed to have many properties, including the activation of Src kinases (Ganem and Schneider, 2001). The present invention describes DNA sequences and amino acid compositions of the surface antigen proteins S1/S2, S1/S2/S as well as Core protein fusion proteins with a xenotypic Mab fragment.

DHBV, another member of the hepdnaviral family, infects pekin ducks, are species specific, and have served as an animal model for studying the hepatitis B viruses. DHBV has a DNA genome and it codes for surface antigens PreS and PreS/S, Core protein (Core) and Polymerase/Reverse Transcriptase. The present invention also describes DNA sequences and deduced amino acid sequences of fusion proteins of the PreS, PreS/S and Core proteins with a fragment of a xenotypic Mab. These fusion proteins can be used to elicit a broad immune response in chronic viral infections, thus as therapeutic vaccine.

Hepatitis C virus (HCV) is a member of the flaviviridae family of RNA viruses. Route of infection is via blood and body fluids and over 50% of the patients become chronic carriers of the virus. Persistent infection result in chronic active hepatitis which may lead to liver cirrhosis and hepatocellular carcinoma (Saito et. al. (1990) PNAS USA 87: 6547-6549).

Approximately 170 million people worldwide are chronic carriers of HCV (Wild & Hall (2000) Mutation Res. 462: 381-393). There is no prophylactic vaccine available at present. Current therapy is Interferon $\alpha$2b and Ribavirin, either alone or as combination therapy. The significant side effects for interferon treatment and the development of mutant strains are major drawbacks to the current therapy. Moreover, interferon therapy is effective only in 20% of the patients. Therapeutic vaccines to enhance host immune system to eliminate chronic HCV infection will be a major advancement in the treatment of this disease.

HCV genome is a positive sense single stranded RNA molecule of approximately 9.5 Kb in length. This RNA which contains both 5' and 3' untranslated regions that code for a single polyprotein which is cleaved into individual proteins and catalyzed by both viral and host proteases (Clarke, B. (1997) J. Gen. Virol. 78: 2397-2410). The structural proteins are Core, Envelope E1 & E2 and P7. The non-structural proteins are NS2, NS3, NS4A, NS4B, NS5A and NS5B. Core forms capsids. E1, E2 are envelope proteins, also called "Hypervariable region" due to the high rate of mutations. NS3 is a Serine Protease, the target of several protease inhibitors as antivirals for HCV. NS5B is the RNA Polymerase enzyme. NS5A has recently been suggested to have a direct role in the replication of the virus in the host by counteracting the interferon response Tan, S-L & Katze, M. G. (2001) Virology 284: 1-12) which augments the immune function.

When a healthy host (human or animal) encounters an antigen (such as proteins derived from a bacterium, virus and/or parasite), normally the host initiates an immune response. This immune response can be a humoral response and/or a cellular response. In the humoral response, antibodies are produced by B-cells and are secreted into the blood and/or lymph in response to an antigenic stimulus. The antibody then neutralizes the antigen, e.g. a virus, by binding specifically to antigens on its surface, marking it for destruction by phagocytotic cells and/or complement-mediated mechanisms. The cellular response is characterized by the selection and expansion of specific helper and cytotoxic T-lymphocytes capable of directly eliminating the cells which contain the antigen.

In many individuals, the immune system does not respond to certain antigens. When an antigen does not stimulate the production of a specific antibody and/or killer T-cells, the immune system is unable to prevent the resultant disease. As a result, the infectious agent, e.g. virus, can establish a chronic infection and the host immune system becomes tolerant to the antigens produced by the virus. The mechanism by which the virus evades the host immune machinery is not clearly established. The best-known examples of chronic viral infections include Hepatitis B, Hepatitis C, Human Immunodeficiency Virus and Herpes Simplex Virus.

In chronic states of viral infections, the virus escapes the host immune system. Viral antigens are recognized as "self," and thus not recognized by the antigen-presenting cells. The lack of proper presentation of the appropriate viral antigen to the host immune system may be a contributing factor. The success in eliminating the virus will result from the manner in which the antigen is processed and presented by the antigen presenting cells (APCs) and the involvement of the regulatory and cytotoxic T cells. The major participant in this process is the Dendritic Cell (DC), which captures and processes antigens, expresses lymphocyte co-stimulatory molecules, migrates to lymphoid organs, and secretes cytokines to initiate immune responses. Dendritic cells also control the proliferation of B and T lymphocytes which are the mediators of immunity (Steinman et al 1999). The generation of a cytotoxic T cell (CTL) response is critical in the elimination of the virus infected cells and thus a cure of the infection.

Antigen Presenting Cells process the encountered antigens differently depending on the localization of the antigen (Steinman et al 1999). Exogenous antigens are processed within the endosomes of the APC and the generated peptide fragments are presented on the surface of the cell complexed with Major Histocompatibility Complex (MHC) Class II. The presentation of this complex to $CD4^+$ T cells stimulate the $CD4^+$ T helper cells. As a result, cytokines secreted by the helper cells stimulate B cells to produce antibodies against the exogenous antigen (humoral response). Immunizations using antigens typically generate antibody response through this endosomal antigen processing pathway.

On the other hand, intracellular antigens are processed in the proteasome and the resulting peptide fragments are presented as complexes with MHC Class I on the surface of APCs. Following binding of this complex to the co-receptor CD8 molecule, antigen presentation to $CD8^+$ T cells occurs which result in cytotoxic T cell (CTL) immune response to remove the host cells that carry the antigen.

In patients with chronic viral infections, since the virus is actively replicating, viral antigens will be produced within the host cell. Secreted antigens will be present in the circulation. As an example, in the case of chronic HBV carriers, virions, the HBV surface antigens and the core antigens can be detected in the blood. An effective therapeutic vaccine should be able to induce strong CTL responses against an intracellular antigen or an antigen delivered into the appropriate cellular compartment so as to activate the MHC Class I processing pathway.

These findings would suggest that a therapeutic vaccine that can induce a strong CTL response should be processed through the proteasomal pathway and presented via the MHC Class I (Larsson, Fonteneau et al. 2001). This can be achieved either by producing the antigen within the host cell, or it can be delivered to the appropriate cellular compartment so that it gets processed and presented so as to elicit a cellular response. Several approaches have been documented in the literature for the intracellular delivery of the antigen. Among these, viral vectors ((Lorenz, Kantor et al. 1999), the use of cDNA-transfected cells (Donnelly, Ulmer et al. 1997) (Donnelly et al 1997) as well as the expression of the antigen through injected cDNA vectors (Lai and Bennett 1998) (U.S. Pat. No. 5,589,466), have been documented.

Delivery vehicles capable of carrying the antigens to the cytosolic compartment of the cell for MHC Class I pathway processing have also been used. The use of adjuvants to achieve the same goal has been described in detail by (Hilgers et al. 1999) Another approach is the use of biodegradable microspheres in the cytoplasmic delivery of antigens (Newman, Kwon et al. 2000), exemplified by the generation of a Th1 immune response against ovalbumin peptide (Newman, Samuel et al. 1998; Newman, Kwon et al. 2000). It has also been shown that PLGA nanospheres are taken up by the most potent antigen presenting cells, dendritic cells (Newman, Elamanchili et al. 2002).

Dendritic cells derived from blood monocytes, by virtue of their capability as professional antigen presenting cells have been shown to have great potential as immune modulators which stimulate primary T cell response (Steinman, Inaba et al. 1999), (Banchereau and Steinman 1998). This unique property of the DCs to capture, process, present the antigen and stimulate naïve T cells has made them very important tools for therapeutic vaccine development (Laupeze, Fardel et al. 1999). Targeting of the antigen to the DCs is the crucial step in the antigen presentation and the presence of several receptors on the DCs for the Fc region of monoclonal antibodies have been exploited for this purpose (Regnault, Lankar et al. 1999). Examples of this approach include ovarian cancer Mab-B43.13, Anti-PSA antibody as well as Anti-HBV antibody antigen complexes (Wen, Qu et al. 1999). Cancer immunotherapy using DCs loaded with tumor associated antigens have been shown to produce tumor-specific immune responses and anti-tumor activity (Campton, Ding et al. 2000; Fong and Engleman 2000). Promising results were obtained in clinical trials in vivo using tumor-antigen-pulsed DCs (Tarte and Klein 1999). These studies clearly demonstrate the efficacy of using DCs to generate immune responses against cancer antigens.

SUMMARY OF THE INVENTION

The present invention pertains to compositions and methods for targeting and activating antigen presenting cells, one of the first steps in eliciting an immune response. The compositions of the present invention include a novel class of bifunctional molecules (hereinafter designated as "chimeric antigens") that include an immune response domain (IRD), for example a recombinant protein, linked to a target binding domain (TBD), for example, a xenotypic antibody fragment portion. More specifically, the chimeric antigens are molecules that couple viral antigens, such as Hepatitis B core and surface proteins, to a xenotypic Fc fragment, such as a murine immunoglobulin G fragment.

The compositions and methods of the present invention are useful for targeting and activating antigen presenting cells. The present invention may be useful for inducing cellular and humoral host immune responses against any viral antigen associated with a chronic viral infections, including but not limited to Hepatitis B, Hepatitis C, Human Immunodeficiency Virus, Human Papilloma Virus (HPV), and Herpes Simplex Virus. The invention may also be applicable to all autologous antigens in diseases such as cancer and autoimmune disorders.

The present invention relates to chronic infectious diseases, and in particular to chronic HBV infections. The presentation of HBV antigens to elicit a CTL response by the use of vaccine molecules designed to target the vaccines to DCs whereby the HBV-associated antigens treated as "self" during the chronic infection will be recognized as "foreign" and the host's immune system will mount a CTL response to eliminate HBV-infected cells. At the same time, through cross presentation, the antibody response to the circulating HBV antigen will bind to the antigen and remove it from the circulation. Accordingly, the present invention is designed to produce vaccines which can induce a broad immune response in patients who have chronic viral infections such as HBV.

One or more embodiments of the present invention include one or more chimeric antigens suitable for initiating an immune response against Hepatitis B virus (HBV). In these embodiments of the invention, the nucleotide and deduced amino acid sequences for pre-selected HBV antigens are linked to fragments of xenotypic antibodies. The resulting chimeric antigens are capable of targeting and activating antigen presenting cells, such as dendritic cells.

One or more embodiments of the present invention include one or more chimeric antigens suitable for initiating an immune response against Hepatitis C virus (HCV). In these embodiments of the invention, the nucleotide and deduced amino acid sequences for pre-selected HCV antigens are linked to fragments of xenotypic antibodies. The resulting chimeric antigens are capable of targeting and activating antigen presenting cells, such as dendritic cells.

The present invention also includes methods for cloning and producing fusion proteins in a heterologous expression system. In preferred embodiments of the invention, the cloning and production methods introduce unique post translational modifications including, but not limited to unique glycosylation on the expressed fusion proteins.

In order to make the efficient presentation of the antigens, the inventors have developed a novel murine monoclonal antibody Fc fragment-antigen (viral antigenic protein/peptide) fusion protein. This molecule, by virtue of the Fc fragment is recognized at a higher efficiency by the antigen-presenting cells (dendritic cells) as xenotypic, and the viral antigen is processed and presented as complexes with Major Histocompatibility Complex (MHC) Class I. This processing and antigen presentation is expected to result in the upregulation of the response by cytotoxic T-lymphocytes, resulting in the elimination of virus-infected cell population. In addition, due to cross priming and antigen presentation by MHC Class II molecules, humoral response also aids in the antibody response to the viral infection.

The bifunctional nature of the molecule targets the chimeric antigen to the proper antigen-presenting cells (dendritic cells), making it a unique approach in the therapy of chronic infectious diseases by specifically targeting the antigen presenting cells with the most effective stoichiometry of antigen to antibody. This is useful to the development of therapeutic vaccines to cure chronic viral infections such as Hepatitis B, Hepatitis C, Human Immunodeficiency Virus, Human Papilloma Virus and Herpes Simplex Virus, and may also be applicable to all autologous antigens in diseases such as cancer and autoimmune disorders.

The administration of these fusion proteins can elicit a broad immune response from the host, including both cellular and humoral responses, thus can be used as therapeutic vaccines to treat subjects that are immune tolerant to a particular infection.

BRIEF DESCRIPTION OF THE DRAWINGS

FIG. 1 is a schematic diagram illustrating the structure of the chimeric antigen of the present invention as a monomer, wherein the chimeric antigen has two portions, namely a viral antigen and a xenotypic murine Fc fragment with the hinge region present.

FIG. 1*a* is a schematic diagram illustrating the structure of the chimeric antigen of FIG. 1 in its normal, assembled state as a dimer.

FIG. 2 is a schematic diagram illustrating the structure of a modified chimeric antigen as a monomer, wherein the chimeric antigen has two portions, namely a modified viral antigen portion which incorporates in the Complementarity Determining Regions (CDR) any viral antigen or antigens, antigenic protein fragments or peptides, or any of these with glycosylation at specific sites, and a xenotypic binding agent, namely a murine Fc fragment with the hinge region present.

FIG. 2*a* is a schematic diagram illustrating the structure of the modified chimeric antigen of FIG. 2 in its normal, assembled state as a dimer. The abbreviations "Ag1," "Ag2," and "Ag3" represent different viral antigenic peptides or proteins.

FIG. 3 is a schematic diagram illustrating the structure of a modified biotinylated viral protein and a fusion protein of a streptavidin-Fc fragment with the hinge region present.

FIG. 3*a* is a schematic diagram illustrating the structure of the modified chimeric antigen of FIG. 3 in its normal, assembled state as a dimer.

FIG. 4 is a schematic diagram illustrating a recombinant bacmid.

FIG. 5 is a schematic embodiment of TBD of the present invention.

FIG. 6 shows the nucleotide sequences (SEQ ID NO: 29) of the open reading frame encoding the TBD of FIG. 5.

FIG. 7 is a schematic embodiment of an exemplary chimeric antigen of the present invention, suitable for use with an insect cell expression system.

FIG. 8 shows the nucleotide (SEQ ID NO: 33) and deduced amino acid (SEQ ID NO: 34) sequences of the chimeric antigen molecule of FIG. 7.

FIG. 9 shows the nucleotide (SEQ ID NO: 33) and deuced amino acid (SEQ ID NO: 34) sequences of the expressed HBV S1/S2 protein.

FIG. 10 is a schematic embodiment of an exemplary chimeric antigen of the present invention, illustrating an exemplary IRD of the present invention.

FIG. 11 shows the nucleotide (SEQ ID NO: 35) and deduced amino acid (SEQ ID NO: 36) sequences of the chimeric antigen molecule of FIG. 10.

FIG. 12 shows the nucleotide (SEQ ID NO: 35) and deduced amino acid (SEQ ID NO: 36) sequences of the expressed HBV S1/S2/S protein.

FIG. 13 is a schematic embodiment of an exemplary chimeric antigen of the present invention, illustrating an exemplary IRD of the present invention.

FIG. 14 shows the nucleotide (SEQ ID NO: 37) and deduced amino acid (SEQ ID NO: 38) sequences of the chimeric antigen molecule of FIG. 13.

FIG. 15 shows the nucleotide (SEQ ID NO:39) and deduced amino acid (SEQ ID NO: 40) sequences of the expressed HBV core protein.

FIG. 16 is a schematic embodiment of an exemplary chimeric antigen of the present invention, illustrating an exemplary IRD of the present invention.

FIG. 17 shows the nucleotide (SEQ ID NO: 41) and deduced amino acid (SEQ ID NO: 42) sequences of the chimeric antigen molecule of FIG. 16.

FIG. 18 shows the nucleotide (SEQ ID NO: 43) and deduced amino acid (SEQ ID NO: 44) sequences of the expressed DHBV PreS protein.

FIG. 19 is a schematic embodiment of an exemplary chimeric antigen of the present invention, illustrating an exemplary IRD of the present invention.

FIG. 20 shows the nucleotide (SEQ ID NO: 45) and deduced amino acid (SEQ ID NO: 46) sequences of the chimeric antigen molecule of FIG. 19.

FIG. 21 shows the nucleotide (SEQ ID NO: 47) and deduced amino acid (SEQ ID NO: 48) sequences of the expressed DHBV PreS/S protein.

FIG. 23 shows the nucleotide (SEQ ID NO: 49) and deduced amino acid (SEQ ID NO: 50) sequences of the chimeric antigen molecule of FIG. 22.

FIG. 24 shows the nucleotide (SEQ ID NO: 51) and deduced amino acid (SEQ ID NO: 52) sequences of the expressed DHBV core protein.

FIG. 32 shows the nucleotide (A—SEQ ID NO: 29) and amino acid (B—SEQ ID NO: 30) sequences of the ORF of TBD protein in the plasmid pFastbachta-tbd.

FIG. 33 shows the nucleotide (A—SEQ ID NO: 31) and amino acid (B—SEQ ID NO: 32) sequences of the ORF of HBV S1/S2-TBD in the plasmid pFastbachta-tbd.

FIG. 34 shows the comparison of binding of HBV S1/S2-TBD, IgG1, and IgG2 over time.

FIG. 35 shows the comparison of HBV S1/S2-TBD, IgG1, and IgG2a binding to maturing dendritic cells on day 1.

FIG. 36 shows the comparison of HBV S1/S2-TBD, IgG1, and IgG2a binding to maturing dendritic cells on day 4.

FIG. 37 shows the comparison of uptake between HBV S1/S2-TBD, IgG1, and IgG2 as a function of concentration.

FIG. 38 shows the correlation of HBV S1/S2-TBD to CD32 and CD206 expression on dendritic cells.

FIG. 39 shows that the binding of HBV S1/S2-TBD to DC32 and DC206 receptors on dendritic cells is abolished by anti-Fc Mab.

FIG. 40 shows that glycosylation of S1/S2 antigen increases the uptake via the CD206 receptor.

FIG. 41 shows intracellular interferon-gamma positive T cells after antigen presentation.

FIG. 42 shows secretion of interferon-gamma after antigen presentation.

FIG. 43 shows intracellular interferon-gamma positive cells as a function of S1/S2-TBD concentration FIG. 44 shows interferon-gamma secretion by T cells as a function of S1/S2-TBD concentration.

FIG. 45 shows the effect of glycosylation on intracellular interferon-gamma production in T cells.

FIG. 46 shows the effect of glycosylation on interferon-gamma secretion by T cells.

FIG. 47 shows the nucleotide (A—SEQ ID NO: 53) and amino acid (B—SEQ ID NO: 54) sequences of the ORF of HCV Core in the plasmid pFastbachta-HCV.

FIG. 48 shows the nucleotide (A—SEQ ID NO: 55) and amino acid (B—SEQ ID NO: 56) sequences of the ORF of HCV Core in the plasmid pFastbachta-HCV-TBD.

FIG. 49 shows the nucleotide (A—SEQ ID NO: 57) and amino acid (B—SEQ ID NO: 58) sequences of the ORF of HCV Core in the plasmid pFastbachta-HCV-core.

FIG. 50 shows the nucleotide (A—SEQ ID NO: 59) and amino acid (B—SEQ ID NO: 60) sequences of the ORF of HCV Core-TBD protein in the plasmid pFastbachta-HCV-core-TBD.

FIG. 51 shows the nucleotide (A) and amino acid (B) sequences of the ORF of HCV NS5A in the plasmid pFastbachta-HCV-NS5A.

FIG. 52 shows the nucleotide (A—SEQ ID NO: 63) and amino acid (B—SEQ ID NO: 64) sequences of the ORF of HCV NS5A-TBD in the plasmid pFastbachta-HCV-NS5A-TBD.

FIG. 53 shows the nucleotide (A—SEQ ID NO: 65) and amino acid (B—SEQ ID NO: 66) sequences of the ORF of HCV E1 in the plasmid pFastbachta-HCV-E1.

FIG. 54 shows the nucleotide (A—SEQ ID NO: 67) and amino acid (B—SEQ ID NO: 68) sequences of the ORF of HCV E1-TBD in the plasmid pFastbachta-HCV-E1-TBD.

FIG. 55 shows the nucleotide (A—SEQ ID NO: 69) and amino acid (B—SEQ ID NO: 70) sequences of the ORF of HCV E2 in the plasmid pFastbachta-HCV-E2.

FIG. 56 shows the nucleotide (A—SEQ ID NO: 71) and amino acid (B—SEQ ID NO: 72) sequences of the ORF of HCV E2-TBD in the plasmid pFastbachta-HCV-E2-TBD.

FIG. 57 shows the nucleotide (A—SEQ ID NO: 73) and amino acid (B—SEQ ID NO: 74) sequences of the ORF of HCV E1/E2 in the plasmid pFastbachta-HCV-E1/E2.

FIG. 58 shows the nucleotide (A—SEQ ID NO: 75) and amino acid (B—SEQ ID NO: 76) sequences of the ORF of HCV E1/E2-TBD in the plasmid pFastbachta-HCV-E1/E2-TBD.

DETAILED DESCRIPTION OF THE INVENTION

A composition of the present invention includes a chimeric antigen comprising an immune response domain (IRD) and a target binding domain (TBD). In preferred embodiments of the invention, the protein portion is capable of inducing humoral and/or T cell responses, and the target binding portion is capable of binding an antigen presenting cell, such as a dendritic cell. The chimeric antigen of the present invention may also include one or more of the following: a hinge region of an immunoglobulin, a $C_H1$ region of an immunoglobulin, a peptide linker, a protease cleavage site, and a tag suitable for use with a purification protocol. A chimeric antigen of the present invention is capable of binding to and activating an antigen presenting cell.

In some embodiments of the invention, the IRD of the chimeric antigen includes one or more proteins selected from the group comprising: one or more HBV proteins, one or more recombinant HBV proteins, one or more HCV proteins, or one or more recombinant HCV proteins.

In yet another embodiment of the invention, IRD of the chimeric antigen includes 6-His-peptide fused to one or more HBV proteins, one or more recombinant HBV proteins, one or more HCV proteins, or one or more recombinant HCV proteins.

Figure 1:
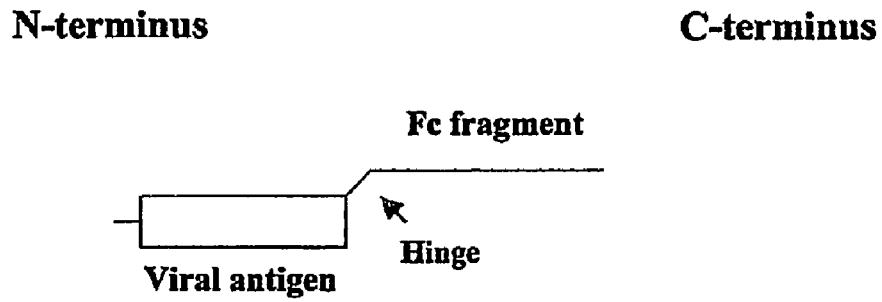
Figure 1A:
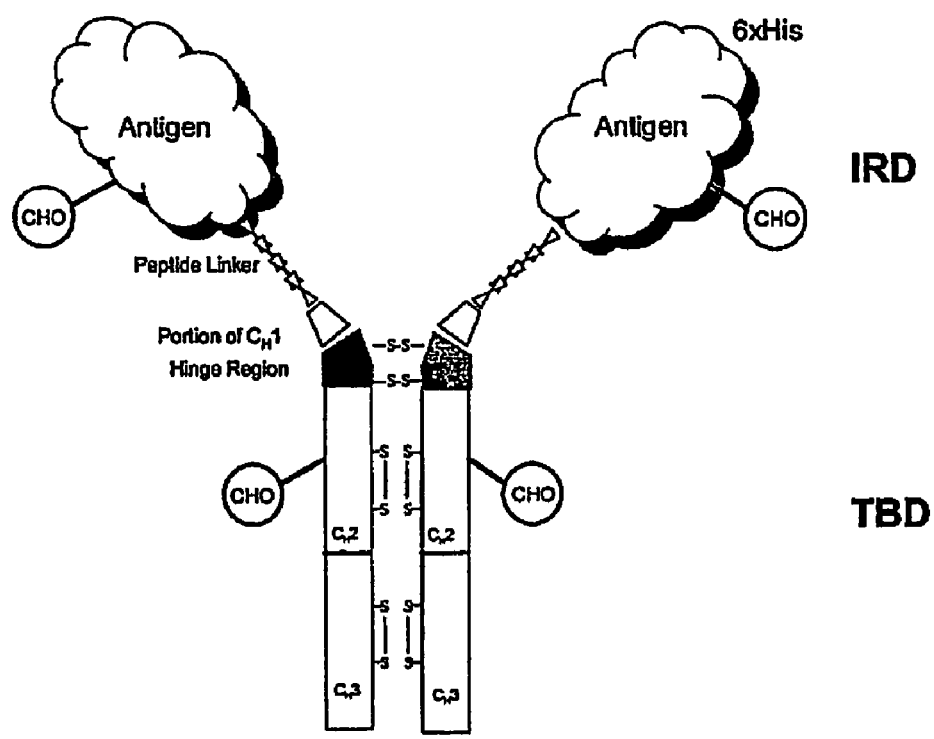
Figure 2:
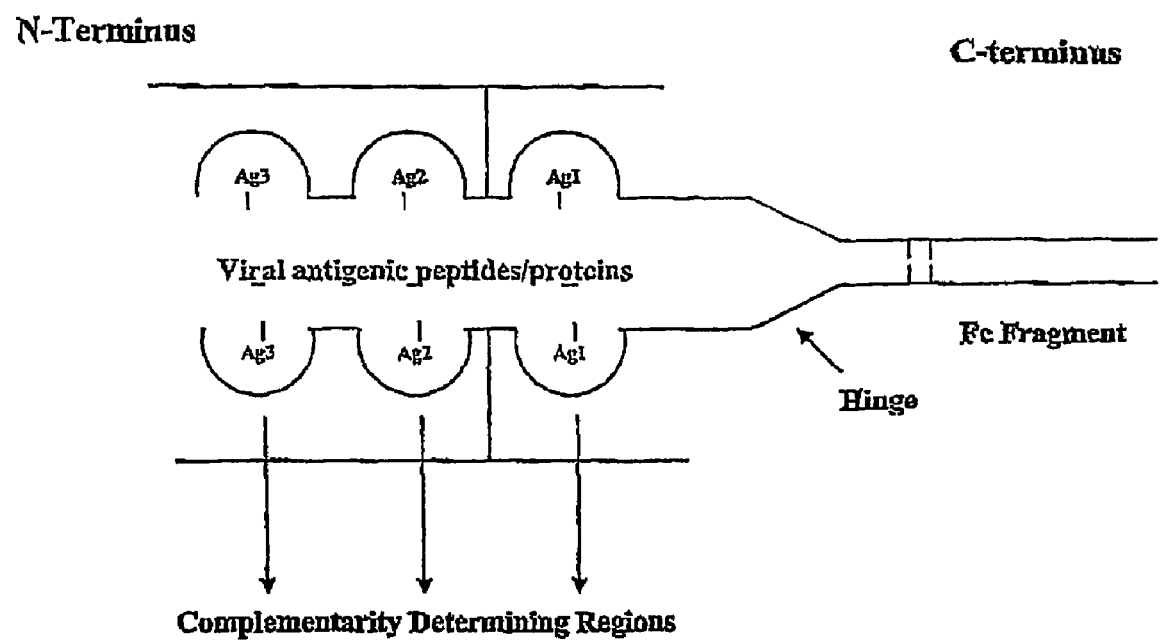
Figure 2A:
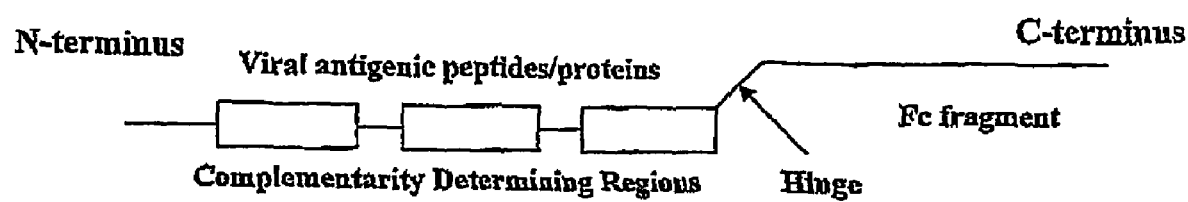
Figure 3:
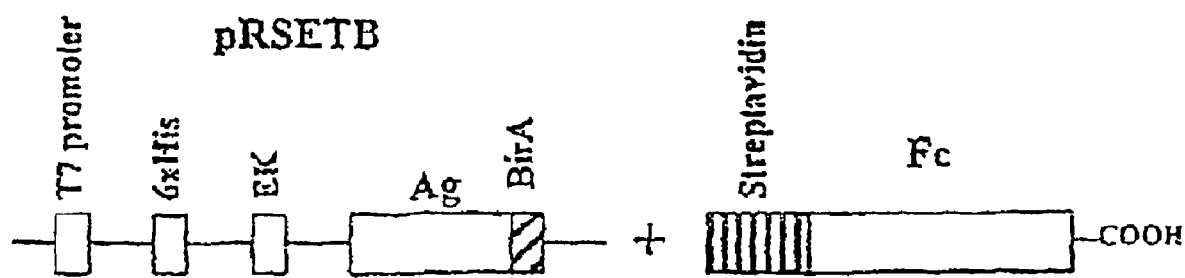
Figure 3A:
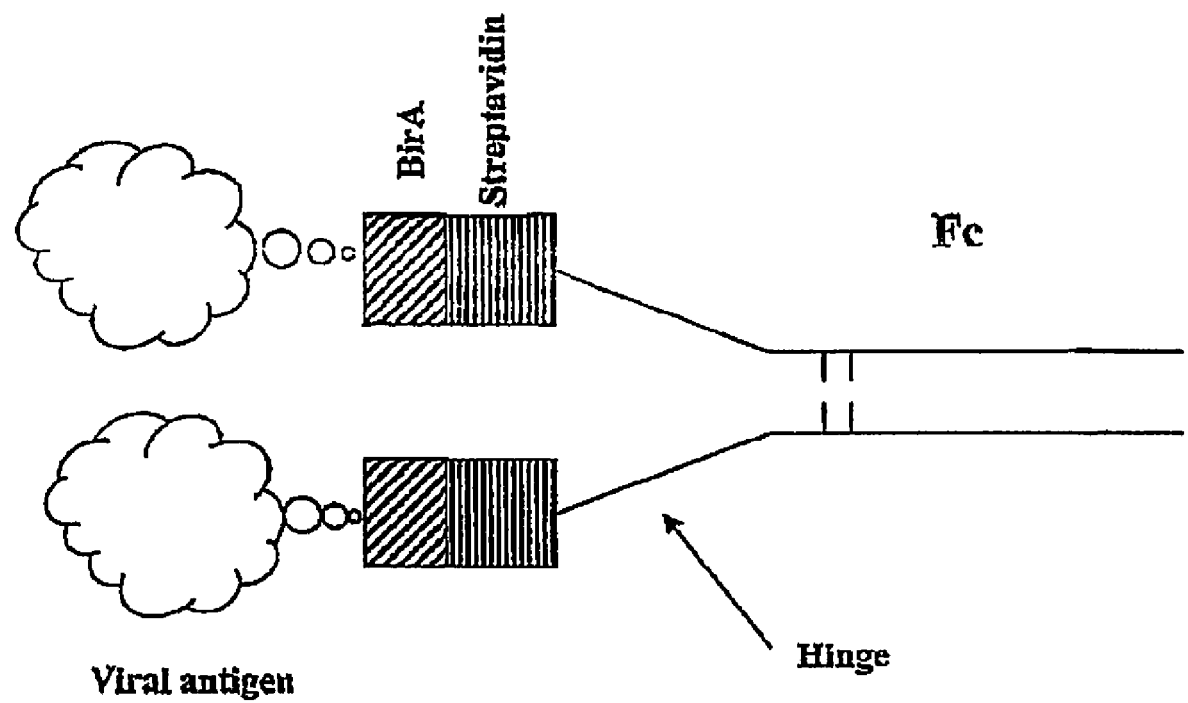
Figure 4:
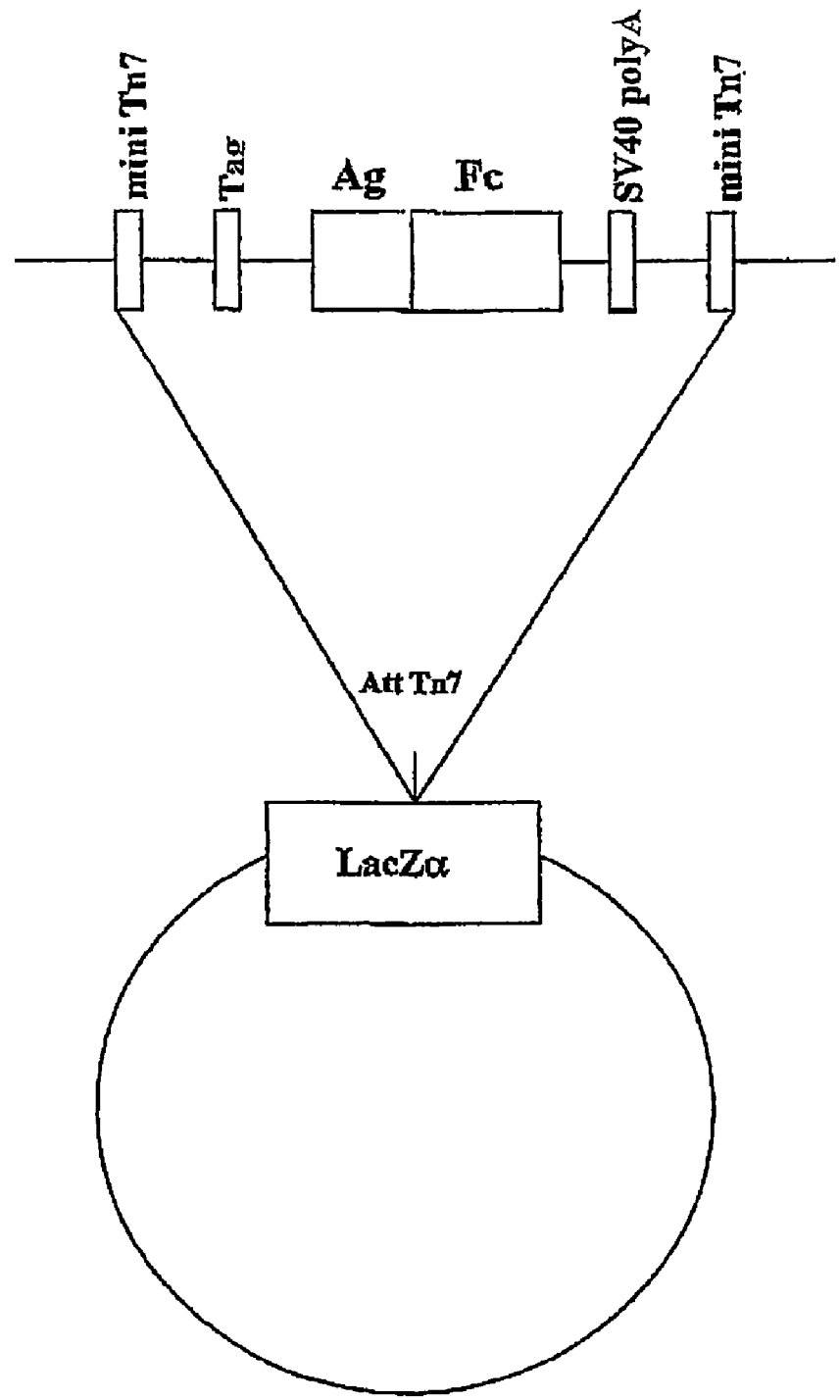
Figure 5:

In preferred embodiments of the invention, the target binding domain of the chimeric antigen is an antibody fragment xenotypic to the host. For example, if the host is a human, an exemplary xenotypic antibody fragment is a animal antibody fragment, such as from a mouse. In the preferred embodiments of the invention, the xenotypic antibody fragment comprises a murine Fc fragment. In the most preferred embodiments of the invention, the target binding domain comprises a xenotypic Fc fragment, a hinge region, a C1 region, and a peptide linkage suitable for linking the target binding domain to the IRD.

The present invention also comprises the use of linking molecules to join the IRD to the TBD. Exemplary linker molecules include leucine zippers, and biotin/avidin.

The present invention also comprises methods of using the compositions of the present invention to bind and activate antigen presenting cells, such as dendritic cells.

The present invention also comprises methods of using the compositions for the present invention to activate T-cells.

The present invention also comprises methods of making the chimeric antigens of the present invention.

The present invention also comprises a method of delivering an antigen to an immune system cell, such as an antigen presenting cell.

The present invention also comprises compositions and methods for activating a humoral and/or cellular immune response in an animal or human, said method comprising administering one or more chimeric antigens of the present invention.

The chimeric antigen of the present invention is a fusion protein having two portions, namely an IRD containing an antigenic sequence (such as a viral antigen(s)), and a TBD containing a xenotypic Fc fragment. The xenotypic murine Fc fragment with the hinge region present recruits the antigen-presenting cells, specifically dendritic cells, to take up the chimeric antigen. The binding region of the viral antigen thus targets antigen-presenting cells specifically. The internal machinery of the APC then processes the IRD to form an activated APC. The activated APC must then be capable of contacting and activating immune response cells for generating humoral and cellular immune responses to clear infected cells.

In a further embodiment, the chimeric antigen is a fusion protein having two portions, namely a modified viral antigen or antigens, antigenic protein fragments or peptides, or any of these with glycosylation at specific sites, and a xenotypic murine Fc fragment with the hinge region present.

In yet another embodiment, the invention provides a further modified chimeric antigen, wherein the antigen is biotinylated and the Fc fragment is generated with streptavidin as a fusion protein to facilitate the production of a wide assortment of antigen-Fc conjugates In yet another embodiment, the invention provides an association between the antigen and the antibody Fc fragment through chemical conjugation.

Definitions

As used herein and in the claims, the terms and phrases set out below have the meanings which follow.

"Antibody" refers to an immunoglobulin molecule produced by B lymphoid cells with a specific amino acid sequence evoked in humans or other animals by an antigen (immunogen). These molecules are characterized by reacting specifically with the antigen, each being defined in terms of the other.

"Antibody response" or "humoral response" refers to a type of immune response in which antibodies are produced by B lymphoid cells and are secreted into the blood and/or lymph in response to an antigenic stimulus. In a properly functioning immune response, the antibody binds specifically to antigens on the surface of cells (e.g., a pathogen), marking the cell for destruction by phagocytotic cells and/or complement-mediated mechanisms.

"Antigen" refers to any substance that, as a result of coming in contact with appropriate cells, induces a state of sensitivity and/or immune responsiveness and that reacts in a demonstrable way with antibodies and/or immune cells of the sensitized subject in vivo or in vitro.

"Native antigen" refers to an antigen that the body does not recognize as foreign and which will, through the present invention, be recognized as foreign.

"Antigen-presenting cell" refers to the accessory cells of antigen inductive events that function primarily by handling and presenting antigen to lymphocytes. The interaction of antigen presenting cells (APC) with antigens is an essential step in immune induction because it enables lymphocytes to encounter and recognize antigenic molecules and to become activated. Exemplary APCs include macrophages, Langerhans-dendritic cells, Follicular dendritic cells, and B cells.

"B-cell" refers to a type of lymphocyte that produces immunoglobulins or antibodies that interact with antigens.

"$C_H1$ region" refers to the heavy chain constant domain on the antigen binding fragment of an antibody.

"Cellular response" or "cellular host response" refers to a type of immune response mediated by specific helper and killer T-cells capable of directly eliminating virally infected or cancerous cells.

"Complex" or "antigen-antibody complex" refers to the product of the reaction between an antibody and an antigen. Complexes formed with polyvalent antigens tend to be insoluble in aqueous systems.

"Cytotoxic T-lymphocyte" is a specialized type of lymphocyte capable of destructing foreign cells and host cells infected with the infectious agents which produce viral antigens.

"Epitope" refers to the simplest form of an antigenic determinant, on a complex antigen molecule; this is the specific portion of an antigen that is recognized by an immunoglobulin or T-cell receptor.

"Fusion protein" or "chimeric antigen" refers to a protein formed by expression of a hybrid gene made by combining two or more gene sequences.

"Hinge region" refers to the portion of an antibody that connects the Fab fragment to the Fc fragment; the hinge region contains disulfide bonds that covalently link the two heavy chains.

"Host" refers to human or animal.

"Immunity" or "immune response" refers to the ability of the body to resist or protect itself against infectious disease.

"Immune Response Domain (IRD)" refers to the variously configured antigenic portion of a bifunctional molecule The IRD comprises one or more antigens or one or more recombinant antigens. Viral antigens may include, but are not limited to, HBV PreS1/S2 HBV PreS1/S2/S, HBV Core, HBV Core ctm $\alpha$-terminal modified), HBV e-antigen, HBV Polymerase, HCV Core, HCV E1-E2, HCV E1, HCV E2, HCV NS3-serine protease, HCV NS5A and NS4A, HIV GP120 and HSV Alkaline nuclease and HPV Antigens.

"Lymphocyte" refers to a subset of nucleated cells found in the blood, which mediate specific immune responses.

"Monoclonal antibody" or "MAb" refers to an antibody produced from a clone or genetically homogenous population of fused hybrid cells, i.e., a hybridoma cell. Hybrid cells are cloned to establish cells lines producing a specific monoclonal antibody that is chemically and immunologically homogenous, i.e., that recognizes only one type of antigen.

"Peptide linkage" or "peptide bond" refers to two or more amino acids covalently joined by a substituted amide linkage between the alpha-amino group of one amino acid and the alpha-carboxyl group of another amino acid.

"Protease cleavage site" refers to the site where proteolytic enzymes hydrolize (break) polypeptide chains.

"Tag" refers to marker or marker sequence used to isolate or purify a molecule containing the tag. An exemplary tag includes a His tag.

"T-cell" refers to a type of lymphocyte responsible for antigen-specific cellular interactions, and which mediates humoral and cellular immune responses.

"Target Binding Domain (TBD)" refers to the region of an immunoglobulin heavy chain constant region. In accordance with the present invention, the TBD is a portion capable of binding to an Fc receptor on an APC., particularly a dendritic cell, and is subsequently transported into the APC by receptor-mediated uptake. In accordance with the present invention, the presence of the Fc fragment augments the uptake of the chimeric antigen through the Fc receptor on antigen-presenting cells, specifically dendritic cells. By virtue of the specific uptake, the viral antigen is processed and presented as foreign; thus, an immune response is effectively elicited to the previously tolerant viral antigen.

"Xenotypic" refers to originating from a different species other than the host.

An embodiment of the present invention includes the use of recombinant antigens of HBV, HCV, or DHBV virus fused to a xenotypic antibody fragment by molecular biological techniques, production of the fusion proteins in baculovirus expression system and their use as therapeutic vaccines against chronic HBV and HCV infections. The present invention provides an efficient method to deliver a hitherto unrecognized antigen to APCs in vivo so as to generate a broad immune response, a Th1 response involving CTLs and a Th2 (antibody) response. The immunogenicity of the pre-selected viral antigen unrecognized by the host immune system is increased due to the presence of the xenotypic antibody fragment as well as by the presence of specific glycosylation introduced in the insect cell expression system. The antigen-antibody fragment fusion protein, due to the presence of the antibody component, will bind to specific receptors present on various immune cell types including dendritic cells, macrophages, B-cells and granulocytes. The fusion proteins administered to either humans or animals will be taken up by the APCs, especially DCs, will be hydrolysed to small peptides and presented on the cell surface, complexed with MHC Class I and/or MHC Class II, which can elicit a broad immune response and clear the viral infection.

As used herein, the term "Target Binding Domain (TBD)" refers to the region of an immunoglobulin heavy chain constant region, which is a portion capable of binding to an Fc receptor on an APC. This is derived from Mouse anti-HBVsAg Mab (Hybridoma 2C12) as cloned in pFASTBAC HTa expression vector, and expressed in High Five insect cell expression system (Invitrogen). The constant region of the heavy chain of the immunoglobulin molecule consists of part of CH1, and Hinge-CH2-CH3 from N-terminal to C-terminal. The constant region of the IgG1 molecule for the practice of the present invention contains a linker peptide, part of $C_{H1}$-hinge and the regions $C_{H2}$ and $C_{H3}$. The hinge region portion of the monomeric TBD can form disulphide bonds with a second TBD molecule. FIG. 5 illustrates a schematic representation of the TBD molecule. The protein is expressed as an N-terminal fusion protein with 6-Histidine tag, a seven amino acid recombinant tobacco etch virus (herein referred to as rTEV) protease cleavage site and the N-terminal fusion of the Target Binding Domain (TBD) of the xenotypic (murine) Mab raised against HBV sAg (Hybridoma 2C12). TBD is a fragment of the constant chain of the IgG1 Mab from 2C12 with the sequence of amino acids comprising the 8 amino acid peptide linker, five amino acids of the $C_{H1}$ region, the hinge sequences, $C_{H2}$ and $C_{H3}$ region sequences (FIG. 5). The TBD fragment defined herein forms the parent molecule for the generation of fusion proteins with antigens derived from viruses or other infectious agents. FIG. 1 A depicts the formation of dimeric TBD molecule formed via intermolecular disulphide bonds. FIG. 6 shows the nucleotide sequence of the Open Reading Frame (ORF) encoding the TBD protein and the deduced amino acid sequence as defined in FIG. 5.

FIG. 7 shows a schematic representation of chimeric antigen vaccine molecule, as produced in the insect cell expression system. This molecule is a fusion protein of N-terminal 6-His tag, rTEV protease cleavage site, HBV S1/S2 antigen, linker peptide, a part of the $C_{H1}$ as well as $C_{H2}$ and $C_{H3}$ domains of the mouse monoclonal antibody from 2C12. Cleavage and purification will result in the generation of HBV S1/S2-TBD molecule. FIG. 8 shows the nucleotide and amino acid sequences of the chimeric antigen molecule. FIG. 9 shows the nucleotide and the deduced amino acid sequences of the expressed HBVS1/S2 protein.

FIG. 10 shows a schematic representation of the fusion protein of HBV S1/S2/S-TBD. FIG. 11 shows the nucleotide and deduced amino acid sequences of the ORF of the fusion protein. FIG. 12 shows the nucleotide and deduced amino acid sequences of the HBV S1/S2/S protein.

FIG. 13 illustrates the fusion protein of HBV core-TBD molecule as expressed in the insect cells. FIG. 14 shows the nucleotide and amino acid sequences in the ORF of the fusion protein. FIG. 15 shows the nucleotide and deduced amino acid sequences of the HBV Core protein.

Another embodiment of the present invention involves the production and use of fusion proteins generated from Duck Hepatitis B Virus (DHBV) antigens and murine TBD. DHBV has been used as a very versatile animal model for the development of therapies for HBV, its human counterpart. DHBV genome encodes Surface antigen PreS/S, Core protein (Core) which form capsids and the polymerase enzyme which serves multiple functions.

FIG. 16 depicts a schematic representation of the fusion protein of DHBV PreS-TBD, as produced in High Five (Invitrogen) insect cell expression system. The nucleotide and deduced amino acid sequences of the ORF of the fusion protein as cloned in the plasmid pFastBac HTa is shown in FIG. 17. The nucleotide and deduced amino acid sequences of the DHBV PreS protein shown in FIG. 18.

FIG. 19 shows schematically, another embodiment of the present invention viz. DHBV PreS/S-TBD. The nucleotide and amino acid sequences are presented in FIG. 20. The nucleotide and deduced amino acid sequences are presented in FIG. 21.

FIG. 22 shows a schematic representation of the fusion protein of DHBV Core-TBD. FIG. 23 shows the nucleotide and deduced amino acid sequences of the DHBV Core-TBD fusion protein. The nucleotide and deduced amino acid sequences of DHBV Core protein is shown in FIG. 24.

The present invention uses established recombinant DNA technology for producing the fusion proteins of pre-selected antigen(s) and the TBD which are necessary in the practice of the invention. Fusion protein constructs are generated at the DNA level incorporating specific restriction enzyme sites which are exploited in incorporating the desired DNA fragment into expression vectors and used to express the desired fusion proteins in a heterologous expression system. As used herein, the term "vector" denotes plasmids which are capable of carrying the complimentary DNA which encode the desired protein(s). The plasmid vectors used in the present invention include, but not limited to, pFASTBACHTa and the corresponding recombinant "BACMIDS" generated in DH10BAC *E. Coli* (Invitrogen). It is possible to mobilize the ORF of the desired proteins and produce other recombinant plasmids for expression of the proteins in other systems, (bacterial or mammalian), in addition to the Baculovirus Expression System (Invitrogen), employed in the present invention. The term "expression" is used to mean the transcription of the DNA sequence into mRNA, the translation of the mRNA transcript into the fusion protein.

This is achieved by the transposition of the gene of interest into the bacmids, tranfected into Sf9 insect cells and recombinant baculovirus produced. These are used to infect High Five insect cells which produce the protein of interest. All the recombinant proteins produced have an N-terminal 6-His tag which is exploited in the purification of the proteins by using Ni-NTA Agarose (Qiagen). The proteins also have an N-terminal rTEV protease cleavage site cloned in. The Ni-purified protein are subjected to digestion with rTEV protease (Invitrogen), which also has an N-terminal 6-His tag. Following the protease digestion, the mixture can be loaded on to a Ni-NTA agarose column and the pure protein can be eluted out, while the 6-His tagged fragments will be bound to the column. This method of purification is standard procedure and one skilled in the art would be able to understand the methodology without further explanation.

Cloning and expression of the DNA sequences which encode the viral antigen and the Fc fragment of the murine monoclonal antibody to generate the chimeric antigen can be achieved through two approaches. The first approach involves cloning the two proteins as a fusion protein, while the second approach involves incorporating specific "bio-linkers" such as biotin or streptavidin in either of the molecules, purifying them separately and generating the chimeric antigen.

A monoclonal antibody (2C12) is generated against the Hepatitis B virus surface antigen, and the hybridoma which produces this monoclonal antibody is used to isolate the total RNA for the murine immunoglobulin G. This total RNA is used to clone the murine Fc fragment. Specifically, the total RNA from a hybridoma cell that expresses murine IgG is isolated using Trizol™ reagent (Invitrogen/Gibco BRL, product catalog number 10551-018, 10298-016). The mRNA is purified from total RNA by affinity chromatography on an oligo-dT column (Invitrogen/Gibco BRL, product catalog number 15939-010). A complementary DNA (cDNA) is produced using reverse transcriptase in a polymerase chain reaction. The oligonucleotide primers are designed to add unique restriction enzyme recognition sites to facilitate cloning. This cDNA is cloned into Bac-To-Bac™ baculovirus expression system (Invitrogen/Gibco BRL, product catalog number 15939-010).

The baculovirus system is used because not only are large amounts of heterologous proteins produced, but post-translational modifications, such as phosphorylation and glycosylation, of eukaryotic proteins occur within the infected insect cell. In this expression system, the cDNA can be cloned into vectors called pFASTBAC™ as illustrated schematically in FIG. 4 (Invitrogen/Gibco BRL, product catalog number 15939-010). The advantage of the Bac-To-Bac™ system over other baculovirus systems involves the method of generating recombinant baculoviruses. In other systems, the protein of interest is cloned and then co-transfected with a wild-type baculovirus. Homologous recombination is required to generate recombinants; however, this method is very inefficient and requires laborious plaque purification and screening. In the Bac-To-Bac™ system, the generation of recombinants is based on site-specific transposition with the bacterial transposon Tn7. The gene of interest is cloned into pFASTBAC™, which has mini-Tn7 elements flanking the cloning sites. The plasmid is transformed into *Escherichia coli* strain DH10BAC™ (Invitrogen/Gibco BRL, product catalog number 10361-012), which has a baculovirus shuttle plasmid (bacmid) containing the attachment site of Tn7 within a LacZ gene. Transposition disrupts the LacZ gene so that only recombinants produce white colonies and are easily selected for. The advantage of using transposition in *E. coli* is that single colonies contain only recombinants so that plaque purification and screening are not required. The recombinant bacmids are transfected in insect cells to generate baculoviruses which express recombinant proteins.

The cDNA encoding proteins of interest are generated by PCR with oligonucleotide primers bearing unique restriction enzyme sites from plasmids which contain a copy of the entire viral genome and cloned with the Fc cDNA as a fusion protein. This chimeric protein is purified by protein A or G affinity chromatography using techniques known to those skilled in the art.

The second approach involves incorporating specific "bio-linkers" such as biotin or streptavidin in either of the molecules, purifying them separately and generating the chimeric antigen. The viral antigens of interest are cloned into plasmids that control the expression of proteins by the bacteriophage T7 promoter. The recombinant plasmid is then transformed into an *E. coli* strain, e.g. BL21(DE3) Codon Plus™ RIL cells (Stratagene, product catalog number 230245), which has production of T7 RNA polymerase regulated by the lac repressor. The T7 RNA polymerase is highly specific for T7 promoters and is much more processive (~8 fold faster) than the *E. coli* host's RNA polymerase. When production of T7 RNA polymerase is induced by isopropyl-□-D-thiogalactoside, the specificity and processivity of T7 RNA polymerase results in a high level of transcription of genes under control of the T7 promoter. In order to couple two proteins together, the tight binding between biotin and streptavidin is exploited. In *E. coli*, the BirA enzyme catalyzes the covalent linkage of biotin to a defined lysine residue in a specific recognition sequence. Antigens which are thus biotinylated can be expressed at a specific site. The murine Fc fragment is expressed in the baculovirus system, as described above, as a fusion protein with streptavidin. These two proteins can be mixed to form a dimeric protein complex by biotin-streptavidin binding.

Following cloning and expression, the chimeric antigen is then evaluated for its efficacy in generating an immune response. Evaluation involves presenting the chimeric antigen to dendritic cells ex vivo or in vivo. The dendritic cells are presented to T-lymphocytes and evaluated for the production of interferon gamma as a marker of T-cell response. Specifically, in the ex vivo situation, naive dendritic cells are isolated from peripheral blood. Dendritic cells process and present antigen to naive T-lymphocytes. The chimeric antigen is then presented to naive dendritic cells for processing. These stimulated dendritic cells are in turn presented to a naive T-cells, which cause their activation into effector cells, e.g. helper T-cells or cytotoxic T-lymphocytes. Activation of the T-cells by the dendritic cells is then evaluated by measuring markers, e.g. interferon □levels, by a known procedure (Berlyn et al., 2001). In the case of the in vivo situation, the chimeric antigen is directly introduced parenterally in the host where available dendritic and other antigen-processing cells which have the capacity to interact with all antigens and process them accordingly.

The following non-limiting examples provide further illustration of the invention.

EXAMPLES

Example 1

Construction of Murine TBD Protein Expression Vector

The mouse IgG1 DNA sequences encoding amino acids of CH1-Hinge-CH2-CH3 region was generated from mRNA isolated from the hybridoma (2C12) which produces Mab against HBV surface antigen (sAg). Total mRNA was isolated using TRizol reagent (Gibco BRL cat. No. 15596-026) and the cDNA of the TBD was generated by RT-PCR using Superscript First-strand Synthesis (Invitrogen Cat. No. 11904-018). The PCR primers contained linker sequences encoding the linker peptide—SRPQGGGS—(SEQ ID NO: 28) at the 5' terminus, a unique Not I site at the 5' and a unique Hind III restriction site at the 3' end. The resulting cDNA contains (5' Not I)-linker sequence-CH1 (VDKKI)-CH2-CH3-(3' Hind III). Following digestion with the respective enzymes, the fragment is ligated with pFASTBACHTa expression vector plasmid (Invitrogen) using the same restriction enzyme sites. The 5' primer used for PCR amplification was (Sense) 5' TGTCATTCTGCGGCCGCAAG-GCGGCGGGATCCGTGGACAAGAAAATTGTGCCAGG (Seq. ID No. 1) and the 3' primer was (antisense) 5' ACGAAT-CAAGCTTTGCAGCCCAGGAGA (Seq. ID No. 2), which contained the Not I and Hind III sites, respectively. The following is the protocol used for directional cloning. The generated fragment was digested with the respective enzymes, purified on agarose gel and cloned into the vector plasmid. The DNA sequence and the correctness of the ORF were verified by standard sequencing methods.

Following the cloning of the gene of interest (eg. TBD) into the pFastBac-HTa donor plasmid, the production of recombinant proteins is based upon the Bac-to-Bac baculovirus expression system (Invitrogen). The next step is site-specific transposition of the cloned gene into a baculovirus shuttle vector (Bacmid). This is accomplished in a strain of $E.\ coli$ called DH10Bac. The DH10Bac cells contain the bacmid, which confers kanamycin resistance and a helper plasmid which encodes the transposase and confers resistance to tetracycline. The recombinant pFastBac-HTa plasmids with the gene of interest (TBD) are transformed into DH 10Bac cells for the transposition to generate recombinant bacmids. A 100 µl aliquot of competent DH10Bac cells is thawed on ice, the pFastBac-HTa based plasmids are added and the mixture is incubated on ice for 30 minutes. The mixture is given a heat shock for 45 seconds at 42° C. and then chilled on ice for 2 minutes. The mixture is then added to 900 µL of LB media and incubated for 4 hours at 37° C. The transformed cells are serially diluted with LB to $10^{-1}$ and $10^{-2}$ and 100 µl of each dilution is plated on LB agar plates supplemented with 50 µg/ml kanamycin, 7 µg/ml gentamicin, 10 µg/ml tetracycline, 100 µg/ml X-gal, and 40 µg/ml IPTG and incubated for at least 36 hours at 37° C. The gentamicin resistance is conferred by the pFastBac-HTa and the X-gal and IPTG are used to differentiate between white colonies (recombinant bacmids) from blue colonies (non recombinant). The white colonies are picked and inoculated into 2 ml of LB supplemented with 50 µg/ml kanamycin, 7 µg/ml gentamicin and 10 µg/ml tetracycline and incubated overnight at 37° C., with shaking. A sterile loop is used to sample a small amount of the overnight culture and the sample is streaked onto a fresh LB agar plate supplemented with 50 µg/ml kanamycin, 7 µg/ml gentamicin, 10 µg/ml tetracycline, 100 µg/ml X-gal, and 40 µg/ml IPTG and incubated for at least 36 hours at 37° C. to confirm a white phenotype.

Recombinant bacmids were isolated by standard protocols (Maniatis), the DNA sample was dissolved in 40 µl of TE (10 mM Tris-HCL pH 8, 1 mM EDTA) and used for transfections.

In order to produce baculoviruses, the bacmid is transfected into Sf9 insect cells. Sf9 cells ($9 \times 10^5$) were seeded into each well of a 6 well cell culture dish (35 mm wells) in 2 ml of EX-CELL 401 (JRH biosciences) and allowed to attach for at least 1 hour at 27° C. Transfections were carried out using CELLFECTIN Reagent (Invitrogen, Cat. No. 10362-010) as per the protocols provided by the supplier of the Sf 9 cells. Following transfection, the cells were incubated at 27° C. for 72 hours. The medium containing baculovirus was collected and stored at 4° C. in the dark.

The efficiency of the tranfection was verified by checking for production of baculoviral DNA. The isolated baculovirus DNA is subjected to PCR to screen for the inserted gene of interest (TBD). The primers used are pFastBac 5' (sense) TAT TCC GGA TTA TTC ATA CCG (Seq. ID No. 3) and pFastBac 3' (antisense) 5' CTCTACAAATGTGGTATGGC (Seq. ID No 4). Amplified products were on an agarose gel (0.8%). The expression of the heterologous protein in the cells was verified by SDS polyacrylamide gel electrophoresis (SDS-PAGE) and Western blots using the 6-His tag monoclonal antibody (Clonetech) as the probe.

Once production of baculovirus and the expression of protein have been confirmed, the virus production is amplified to produce a concentrated stock of the baculovirus that carry the gene of interest (e.g. TBD). It is standard practice in the art to amplify the baculovirus at least two times, and in all protocols described herein this standard practice was adhered to. After the second round of amplification, the concentration of the generated baculovirus was quantified using a plaque assay according to the protocols described by the manufacturer of the kit (Invitrogen). The most appropriate concentration of the virus to infect High Five cells and the optimum time point for the production of the desired protein was established as well.

Example 2

Figure 7:
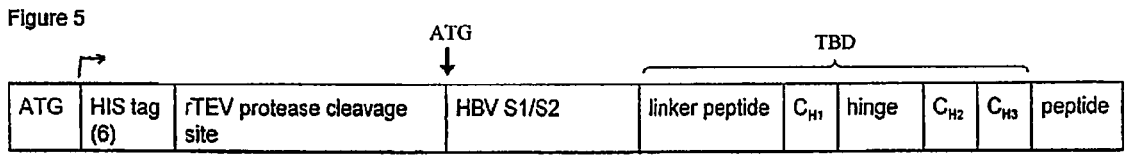

Construction of HBV Surface Antigen S1/S2 and HBV S1/S2-TBD Fusion Protein Expression Vectors The DNA encoding the HBV sAg fragment S1/S2 was generated from the plasmid pRSETB HBV S1/S2 template using PCR methodology. The primers used were: (sense) 5' GGATCCTGTACGATGACG (Seq. ID No. 5) and the 3' primer (antisense) 5' AGTCATTCTGCGGCCGCGAGT-TCGTCACAGGGTCCCCGG (Seq. ID No. 6) containing the restriction enzyme site Not I. The 5' end contained a unique Bam H I site derived from the parent plasmid which was used for ligations. Amplified DNA was digested with Bam H I/Not I and ligated with pFastBacHTa expression vector to generate the expression plasmid for HBV S1/S2 protein. The fragment was ligated with the plasmid pFastBacHTa-TBD (described in example 1) following the digestion with the respective enzymes. This produced the expression plasmid pFast-BacHTa HBV S1/S2-TBD. This plasmid was used to produce recombinant baculovirus (described in example 1) which expressed the chimeric antigen-TBD fusion protein: 6-His tag-rTEV protease cleavage site-HBVS1/S2-TBD (See FIGS. 7-9).

Example 3

Figure 10:
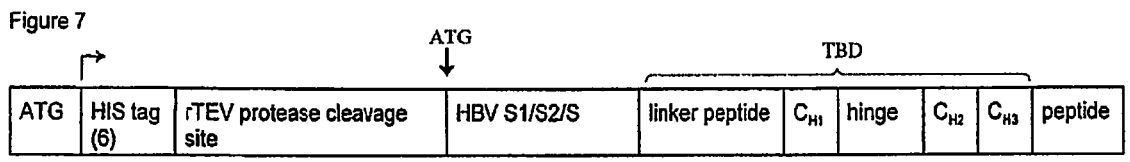

Construction of HBV Surface Antigen S1/S2/S and HBV S1/S2/S-TBD Fusion Protein Expression Vectors The DNA encoding the HBV sAg fragment S1/S2/S was generated from the plasmid pALT HBV 991 (University of Alberta) template using PCR methodology. The 5' primer used for the PCR was (sense) 5' GATAAGGATCCTATGG-GAGGTTGGTCATCAAAAC (Seq. ID No. 7), containing the restriction enzyme Nco I site. The PCR primer for 3' terminus was (antisense) 5' GTCATACTGCGGCCGC-GAAATGTATACCCAGAGACAAAAG (Seq. ID No. 8), containing the restriction enzyme Not I site. Amplified cDNA was digested with the respective enzymes and ligated with pFastBacHTa expression vector to generate either the expression plasmid for HBV S1/S2/S or the expression plasmid pFastBac HTa HBV S1/S2/S-TBD fusion protein (see FIGS. 10-11).

Example 4

Figure 13:
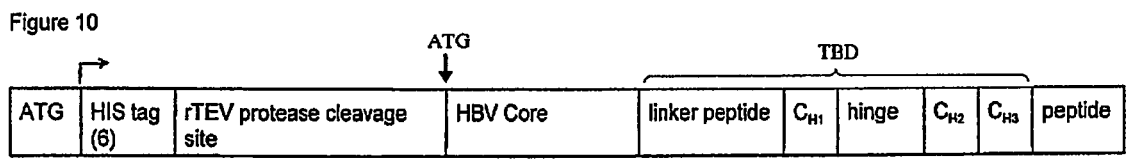
Figure 16:
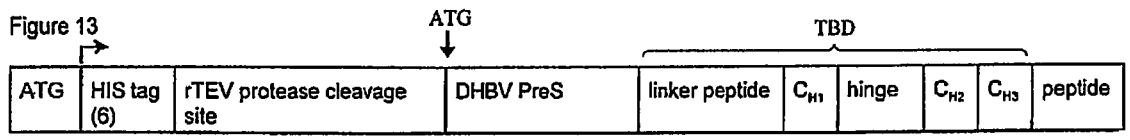
Figure 19:
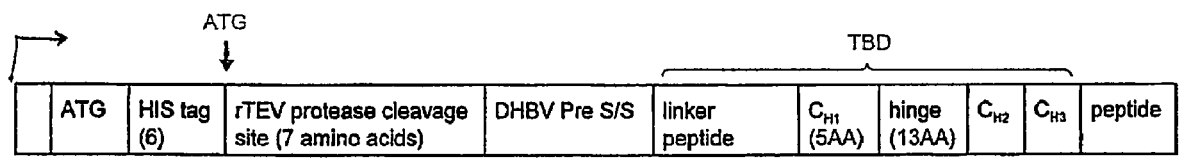
Figure 22:
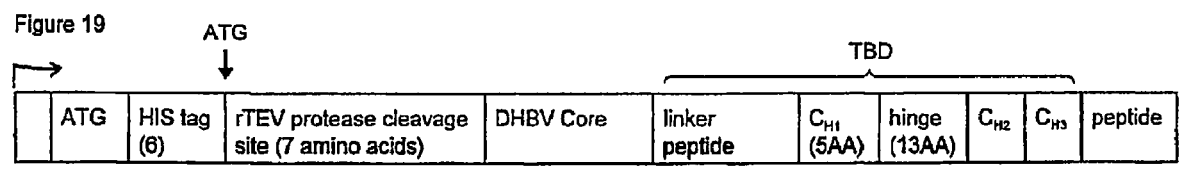
FIG. 22 is a schematic embodiment of an exemplary chimeric antigen of the present invention, illustrating an exemplary IRD of the present invention.
Figure 25:
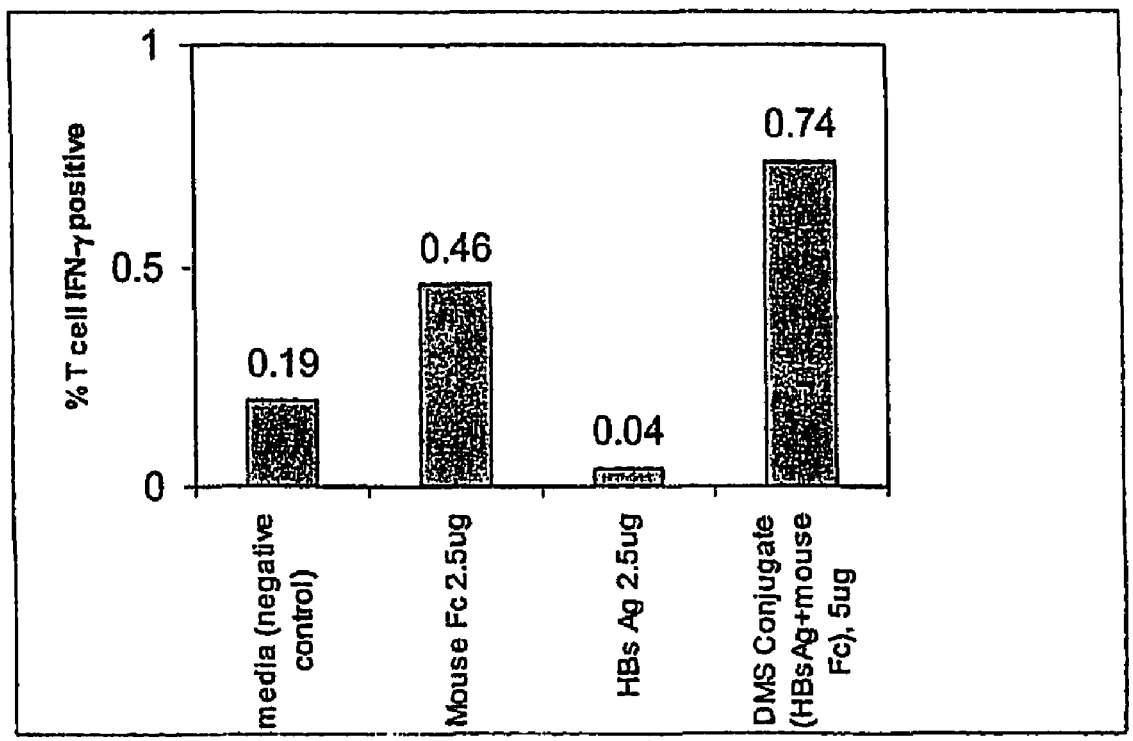
FIG. 25 shows that a chimeric antigen embodiment of the invention can be taken up by dendritic cells.
Figure 26:
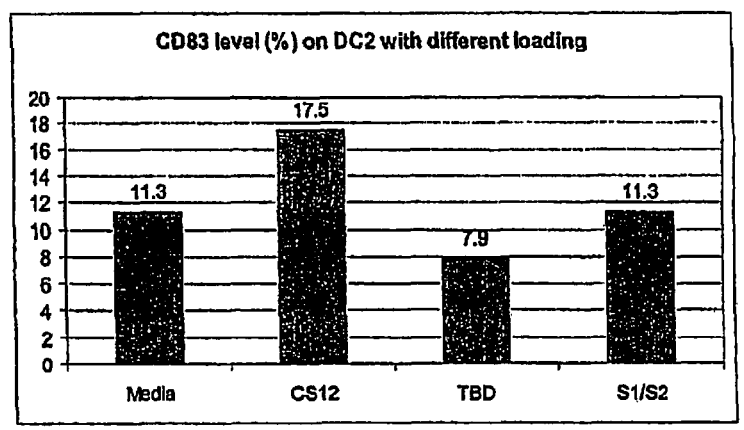
FIG. 26 shows that dendritic cells uptake a chimeric antigen of the present invention (CS12), as compared to the target binding domain (TBD) alone, or the immune response domain (IRD) alone.
Figure 27:
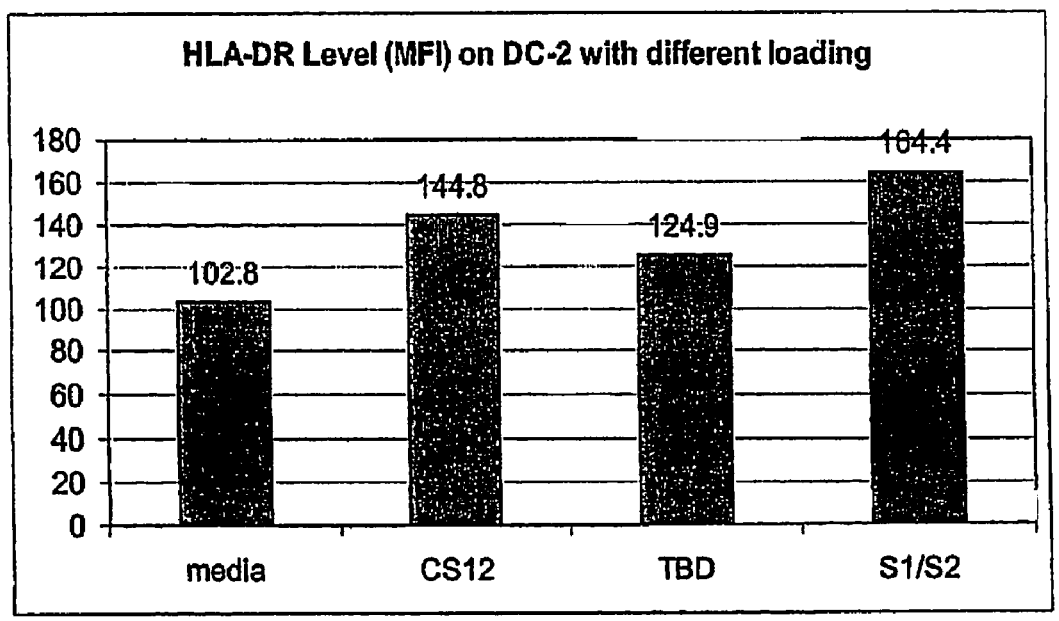
FIG. 27 shows the expression of MHC Class II by dendritic cells.
Figure 28:
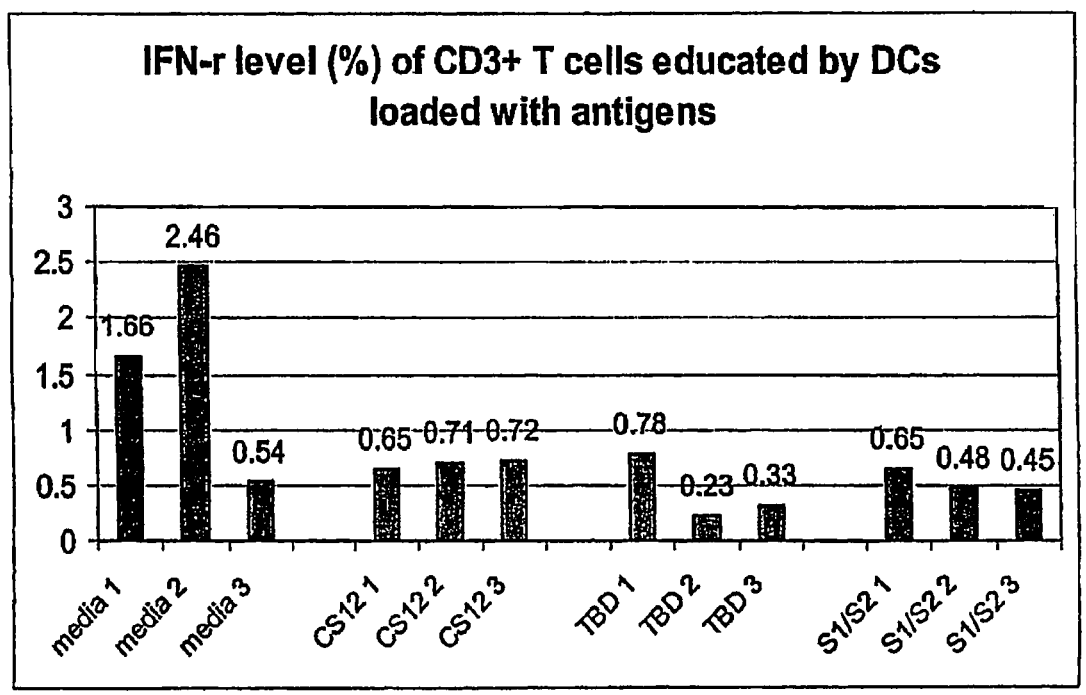
FIG. 28 shows that a cellular response is generated after contact with dendritic cells activated with a chimeric antigen of the present invention.
Figure 29:
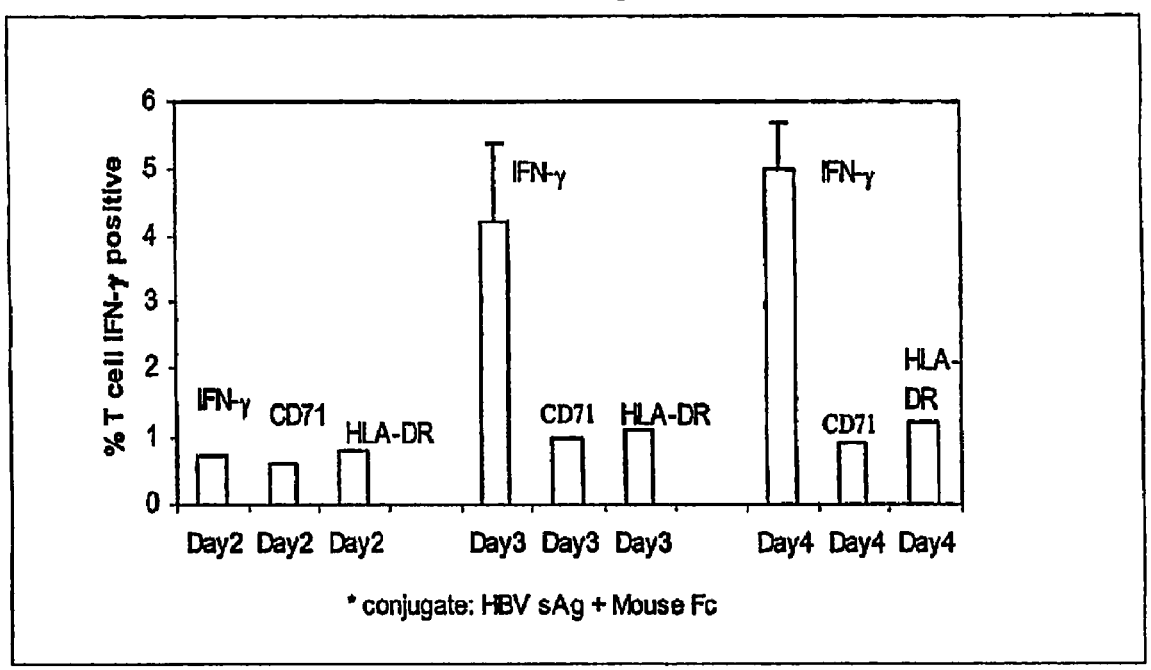
FIG. 29 shows T cell stimulation by a chemical conjugate of the present invention.

Construction of HBV Core Antigen and HBV Core-TBD Fusion Protein Expression Vectors HBV produces the core proteins (Core) to encapsidate the replicating genome of the virus. There are two forms of the core one secreted into circulation, also known as the "e" antigen and the capsid forming core protein. The present invention also relates to the generation of expression plasmids to produce the Core protein as well as the core antigen-TBD fusion protein, in insect cells. The cDNA encoding the HBV Core protein was generated from the plasmid pAL-THBV991 template using PCR technique. The 5' primer used for the PCR was (sense) 5' TGCGCTACCATGGACAT-TGACCCCTTATAAAG (Seq. ID No. 25) which contains the restriction enzyme Nco I site and the 3' primer used was (antisense) 5' TGTCATTCTGCGGCCGCGAACAT-TGAGATTCCCGAGATTGAG (Seq. ID No. 26), containing the restriction enzyme Not I site. The PCR-amplified cDNA was digested with the respective enzymes and ligated with pFastBacHTa expression vector to generate either the expression plasmid for HBV Core protein or the expression plasmid pFastBacHTa HBV Core-TBD fusion protein (see FIGS. 13-14).

Example 5

Construction of DHBV Surface Antigen Fragment PreS and DHBV PreS-TBD Fusion Protein Expression Vectors DHBV has served as a powerful animal model in the development of antiviral therapy for HBV. Pekin ducks, congenitally infected with DHBV have been used to study the mechanism of replication of the virus and for the screening of antiviral compounds. The present invention also describes the chimeric DHBV antigen-TBD molecules which could be used as therapeutic vaccines in DHBV-infected ducks, thus providing a viable animal model for the feasibility studies for a HBV therapeutic vaccines.

The cDNA encoding DHBV PreS antigen was produced by PCR from a plasmid pFastBacHTaDHBV PreS/S (University of Alberta). The 5' primer used for the PCR was (sense) 5' TATTCCGGATTATTCATACCG (SEQ. ID No. 9). The unique restriction enzyme site EcoR I, resident on the parent plasmid was used for directional cloning. The 3' primer used was (antisense) 5' TGTCATTCTGCGGCCGCGTTTTCT-TCTTCAAGGGGGGAGT (Seq. ID No. 27), containing the restriction enzyme Not I site. Following PCR amplification, the fragment was digested with the restriction enzymes EcoR I and Not I and the DNA fragment was purified on a 1% agarose gel. The fragment was ligated with the expression plasmid pFastBacHTa at the respective sites to produce pFast-BacHTa DHBV PreS, which expressed the PreS antigen. The same fragment was also used to ligate with pFastBacHTa-TBD to generate the expression plasmid pFastBacHTa DHBV PreS-TBD. The production of baculovirus stocks from these plasmids and the expression of the PreS and PreS-TBD in High Five insect cells were done as described in example 1.

Example 6

Construction of DHBV Surface Antigen Fragment PreS/S and DHBV PreS/S-TBD Fusion Protein Expression Vectors DHBV PreS/S cDNA was produced by PCR methods using 5' primer (sense) 5' TATTCCGGATTATTCATACCG (Seq. ID No. 9) and the 3' primer (antisense) 5' TGTCAT-TCAGCGGCCGCGAACTCTTGTAAAAAAGAGCAGA (Seq. ID No. 10), containing restriction enzyme Not I site. The unique restriction enzyme site Eco R I, resident on the parent plasmid pFastBacHTa PreS/S (University of Alberta) was used for directional cloning. This plasmid also was the template for generating the required cDNA by PCR. All other protocols for the production of either the DHBV PreS/S or the fusion protein PreS/S-TBD are the same as described in the example 5 above.

Example 7

Construction of DHBV Core Antigen and DHBV Core-TBD Fusion Protein Expression Vectors The cDNA coding for the DHBV Core was generated by PCR using the following primers. The 5' terminus primer used was (sense) 5' TGCGCTACCATGGATATCAATGCT-TCTAGAGCC (Seq. ID No. 11), containing the restriction enzyme Nco I site. The 3' terminus primer used was (antisense) 5' TGTCATTCTGCGGCCGCGATTTCCTAG-GCGAGGGAGATCTATG (Seq. ID No. 12), containing the restriction enzyme Not I site. All other protocols for the production of either the DHBV Core or the fusion protein DHBV Core-TBD are the same as described in the example 5 above.

Example 8

Chemically Cross-Linked HBV sAg-Fc (Murine)

HBV sAg was cross linked using the bifunctional cross linking agent DMS, a homobifunctional imidoester which react with amino groups on the proteins. The unreacted components were removed by gel filtration. The conjugate was characterized with respect to the stoichiometry of sAg/Fc in the conjugate and the fraction containing sAg:Fc at 1:1 ratio was chosen for antigen presentation assays using human monocyte-derived immature Dendritic cells (DCs). Immature DCs were cultured for four days with GM-CSF/IL4, incubated with the sAg-Fc conjugate and matured in the presence of TNFα/IFNα. Autologous CD3+ T cells were added to the mature DCs. Following three rounds of exposure to the mature DCs, T cell stimulation was quantitated by measuring the production of intracellular IFNγ, using flow cytometry. (APA Ref: Berlyn, K. A., Schultes, B., Leveugle, B., Noujaim, A. A., Alexander, R. B & Mann, D. L. 2001: Clin. Immunol. 101: 276-283)

Materials:
HBV sAg (US Biologicals; Cat# H 1910-27)
Mouse Polyclonal IgG Fc fragment (Harlan Sera-Lab Ltd., Cat# PP-19-01)
DMS (Dimethyl suberimidate. 2HCl) (Pierce Cat # 20700)
Cross-linking Buffer 0.1M HEPES pH 8.7
Stop Buffer 0.1 M Tris Hcl pH 7.8
Elution Buffer: Phosphate Buffered Saline (PBS) pH 8.3
Sephadex G 75 (Pharmacia)

Methods:
Solutions of sAg (100 µg) and Mouse Fc fragment (100 µg), were dialyzed against the cross linking buffer overnight at 4° C. The protein solutions were mixed together, DMS reagent was added immediately to a final concentration of 10 mM, and the mixture was incubated at room temperature for 1 hr. The reaction was stopped by the addition of 0.1 M Tris Hcl pH 7.8. The reaction mixture was loaded on a Sephadex G 75 column (0.7×12 cm), and fractions were eluted using elution buffer. 0.5 ml fractions were collected and the fractions containing sAg/Fc at a molar ratio of 1:1, as estimated by Elisa using the respective antibodies were pooled and used for Antigen Presentation Assays.

Results:
The levels of intracellular IFNγ produced in T cells in the presence of conjugate was substantially higher than the sAg or the Fc fragment alone.

Example 9

Chimeric Antigens of Hepatitis C Virus (HCV)

Hepatitis C virus (HCV) is a member of the flaviviridae family of RNA viruses. Route of infection is via blood and body fluids and over 50% of the patients become chronic carriers of the virus. Persistent infection result in chronic active hepatitis which may lead to liver cirrhosis and hepatocellular carcinoma (Saito et. al. (1990) PNAS USA 87: 6547-6549).

Approximately 170 million people worldwide are chronic carriers of HCV (Wild & Hall (2000) Mutation Res. 462: 381-393). There is no prophylactic vaccine available at present. Current therapy is Interferon α2b and Ribavirin, either alone or as combination therapy. The significant side effects for interferon treatment and the development of mutant strains are major drawbacks to the current therapy. Moreover, interferon therapy is effective only in 20% of the patients.

Therapeutic vaccines to enhance host immune system to eliminate chronic HCV infection will be a major advancement in the treatment of this disease.

Replication of HCV:
HCV genome is a positive sense single stranded RNA molecule of approximately 9.5 Kb in length. This RNA which contains both 5' and 3' untranslated regions codes for a single polyprotein which is cleaved into individual proteins catalyzed by both viral and host proteases (Clarke, B. (1997) J. Gen. Virol. 78: 2397-2410). The structural proteins are Core, Envelope E1 & E2 and P7. The non-structural proteins are NS2, NS3, NS4A, NS4B, NS5A and NS5B. Core forms capsids. E1, E2 are envelope proteins, also called "Hypervariable region" due to the high rate of mutations. NS3 is a Serine Protease, the target of several protease inhibitors as antivirals for HCV. NS5B is the RNA Polymerase enzyme. NS5A has recently been suggested to have a direct role in the replication of the virus in the host by counteracting the interferon response Tan, S-L & Katze, M. G. (2001) Virology 284: 1-12) which augments the immune function.

Chimeric HCV Antigens:
HCV Core-TBD:
This protein has been cloned using the pFASTBAC HTa vector and the baculovirus system and expressed in Sf-9 and High Five insect cells, similar to the HBV fusion proteins. This was done as follows. The DNA encoding the HCV core fragment was generated from the plasmid pCV-H77c (NIH) template using PCR methodology.

The primers used were: (sense) 5'CGGAATTCATGAG-CACGAATCCTAAAC (SEQ ID NO: 13) containing the restriction enzyme site Eco RI and the 3' primer (antisense) 5' GGACTAGTCCGGCTGAAGCGGGCACAGT-CAGGCAAGAG (SEQ ID NO: 14) containing the restriction enzyme site Spe I. Amplified DNA was digested with Eco RI/Spe I and ligated with fragment was ligated with the plasmid pFastBacHTa-TBD (described in example 1) following the digestion with the respective enzymes. This produced the expression plasmid pFastBacHTa HCV core-TBD. This plasmid was used to produce recombinant baculovirus (described in example 1) which expressed the chimeric antigen (HCV-core-TBD) fusion protein. 6-His tag-rTEV protease cleavage site-HCV core-TBD.

HCV Core Protein:
Amplified DNA was digested with Eco RI/Spe I and ligated with plasmid pFastBacHTa expression vector to generate the expression plasmid for HCV core protein. This protein is expressed with N-terminal $^6$His tag and rTEV protease cleavage site.

The following HCV antigens and their respective Chimeric antigens (Antigen-TBD) have been cloned and are ready for expression.
E1 & E1-TBD
E2 & E2-TBD
E1 E2 & E1 E2-TBD
NS5A & NS5A-TBD Example 10

Cloning, Expression and Purification of Recombinant Proteins Using the Baculovirus Expression System Baculovirus Expression System is commercially available from Invitrogen and the procedures used were as described in the company protocols. The gene of interest is cloned into pFastBac-HTa donor plasmid and the production of recombinant proteins is based upon the Bac-to-Bac baculovirus expression system (Invitrogen).

In the next step, the pFastBac-HTa donor plasmid containing the gene of interest is used in a site-specific transposition in order to transfer the cloned gene into a baculovirus shuttle vector (bacmid). This is accomplished in E. coli strain DH10Bac. The DH10Bac cells contain the bacmid, which confers kanamycin resistance and a helper plasmid which encodes the transposase and confers resistance to tetracycline. The recombinant pFastBac-HTa plasmids with the gene of interest are transformed into DH10Bac cells for the transposition to generate recombinant bacmids. A 100 μl aliquot of competent DH10Bac cells is thawed on ice, the pFastBac-HTa based plasmids are added and the mixture is incubated on ice for 30 minutes. The mixture is given a heat shock for 45 seconds at 42° C. and then chilled on ice for 2 minutes. The mixture is then added to 900 μL of LB media and incubated for 4 hours at 37° C. The transformed cells are serially diluted with LB to $10^{-1}$ and $10^{-2}$ and 100 μl of each dilution is plated on Luria broth (LB) agar plates (supplemented with 50 μg/ml kanamycin, 7 μg/ml gentamicin, 10 μg/ml tetracycline, 100 μg/ml X-gal, and 40 μg/ml IPTG) and incubated for at least 36 hours at 37° C. The gentamicin resistance is conferred by the pFastBac-HTa and the X-gal and IPTG are used to differentiate between white colonies (recombinant bacmids) from blue colonies (non recombinant). The white colonies are picked and inoculated into 2 ml of LB (supplemented with 50 μg/ml kanamycin, 7 μg/ml gentamicin and 10 μg/ml tetracycline) and incubated overnight at 37° C., with shaking. A sterile loop is used to sample a small amount of the overnight culture and the sample is streaked onto a fresh LB agar plate (supplemented with 50 μg/ml kanamycin, 7 μg/ml gentamicin, 10 μg/ml tetracycline, 100 μg/ml X-gal, and 40 μg/ml IPTG) and incubated for at least 36 hours at 37° C. to confirm a white phenotype.

Recombinant bacmids were isolated by standard protocols (Sambrook and Russell, 2001), the DNA sample was dissolved in 40 μl of TE (10 mM Tris-HCl pH 8, 1 mM EDTA) and used for transfections.

In order to produce baculoviruses, the bacmid is transfected into Sf9 insect cells. Sf9 cells ($9 \times 10^5$) were seeded into each well of a 6 well cell culture dish (35 mm wells) in 2 ml of SFM 900 II and allowed to attach for at least 1 hour at 27° C. Transfections were carried out using CELLFECTIN Reagent (Invitrogen, Cat. No. 10362-010) as per the protocols provided by the supplier of the Sf 9 cells. Following transfection, the cells were incubated at 27° C. for 72 hours. The medium containing baculovirus was collected and stored at 4° C. in the dark.

The efficiency of the transfection was verified by checking for production of baculoviral DNA. The isolated baculovirus DNA is subjected to PCR to screen for the inserted gene of interest. The primers used are pFastBac 5' (sense) TAT TCC GGA TTA TTC ATA CCG (Seq. ID No.3) and pFastBac 3' (antisense) 5' CTCTACAAATGTGGTATGGC (Seq. ID No 4). Amplified products were separated on an agarose gel (0.8%). The expression of the heterologous protein in the cells was verified by SDS polyacrylamide gel electrophoresis (SDS-PAGE) and Western blots using the $^6$-His tag monoclonal antibody (Clontech) as the probe.

Once production of baculovirus and the expression of protein have been confirmed, the virus stock is amplified to produce a concentrated stock of the baculovirus that carry the gene of interest. It is standard practice in the art to amplify the baculovirus at least two times, and in all protocols described herein this standard practice was adhered to. After the second round of amplification, the concentration of the generated baculovirus was quantified using a plaque assay according to the protocols described by the manufacturer of the kit (Invitrogen). The most appropriate concentration of the virus to infect High Five cells and the optimum time point for the production of the desired protein was also established.

Example 11

Expression of the Recombinant Proteins

Recombinant bacmids of standardized multiplicity of infection (MOI) were used to infect High Five insect cells. For suspension cultures, cells were seeded at a density of $3 \times 10^5$ cells/mL and incubated at 27.5° C. with shaking at 138 rpm until the cell density reached $2\text{-}3 \times 10^6$ cells/mL. Standardized amounts of the respective recombinant baculovirus was added to the cells. The incubation temperature was 27.5° C. and the appropriate infection period was standardized for individual protein expression. The cells were harvested by centrifugation at 2,500 rpm for 10 minutes at 4° C. and used for the purification of the recombinant proteins. Unused portions of cells were snap frozen in liquid nitrogen and stored at −70° C.

Example 12

Purification of Proteins

For purification under denaturing conditions, the cells were lysed in a buffer containing 6 M guanidinium-HCl in 100 mM $NaH_2PO_4$, 10 mM Tris, 300 mM NaCl, 10 mM Imidazole, pH 8.0 (lysis buffer). The suspension was sonicated on ice with 5 pulses of 1 minute per pulse at a power setting of 60 watts, and was mixed at room temperature for 1 hour. The lysate was centrifuged at $10,000 \times g$ for 10 min to remove unbroken cells and cell debris. The supernatant was loaded on to a Ni-NTA agarose (Qiagen) bead column ($1 \times 5$ cm/100 mL cell lysate), pre-equilibrated with lysis buffer. Following loading, the column was washed with 20 column volumes of 6 M guanidinium-HCl in 100 mM $NaH_2PO_4$, 10 mM Tris, 300 mM NaCl, 40 mM Imidazole, pH 8.0 (wash buffer 1), followed by washes with 20 column volumes of 8 M urea in 100 mM $NaH_2PO_4$, 10 mM Tris, 300 mM NaCl, 40 mM imidazole, pH 8.0 (wash buffer 2). The bound protein was eluted with a buffer containing 8 M urea, 100 mM $NaH_2PO_4$, 10 mM Tris, 300 mM NaCl, 250 mM imidazole, pH 8 (Elution Buffer). The fractions containing the protein was pooled and dialyzed against PBS, (Overnight, 4° C.).

Examples 13-16

Use of Chimeric Antigens to Enhance Antigen Presentation by Human PBMC-Derived Dendritic Cells and to Elicit an Immune Response in T Lymphocytes

Example 13

Human PBMC Monocyte Isolation and Differentiation to DCs

Peripheral blood mononuclear cells (PBMC) were obtained from Ficoll/Histopaque (Sigma) treatment of a leukapheresis cell preparation as described above. Monocytes were separated from the PBMC population by negative selection using a monocyte isolation kit (Dynal) as previously described. The monocytes were greater than 95% pure as assessed by antibody analysis and flow cytometry (CD3−, CD19−, CD16−, CD11a+, CD14+). Monocytes were washed twice with AIM V media containing L-glutamine, streptomycin sulfate (50 μg/mL) and gentamicin sulfate (10 μg/mL) with 1% donor matched sera (isolated as described above). Next, the monocytes were cultured in AIM V media containing 2.5% donor matched sera and the cytokines GM-CSF and IL-4 to differentiate the cells toward the dendritic cell (DC) lineage. The cells were incubated in 12-well tissue culture plates at 37° C. under a 7% $CO_2$ atmosphere. The DCs were used for APAs and ligand binding and uptake studies.

The monocyte-derived DCs (mDC) were harvested on days 1 through 4. The cells were subsequently washed once with AIM V media with 0.1% BSA (Sigma), and twice with Dulbecco's phosphate buffered saline (Invitrogen) with 0.1% (w/v) BSA (PBSB). The mDC were used in 4° C. labeling or binding assays or in 37° C. binding/uptake assays.

Example 14

Human Dendritic Cell T Cell Stimulation Assay

Antigen presentation assays were performed using human PBMC-derived dendritic cells according to established protocols (Berlyn, Schultes et al., 2001). Monocytes were generated from leukapheresis samples from healthy donors (described above) and were depleted of lineage cells by incubation with anti-CD3, CD19, and CD16 antibodies. This was followed by incubation with magnetic bead conjugated anti-mouse IgG and separation on a magnet (Dynal). Negatively selected cells were approximately 95% pure monocytes cell isolation kit (Dynal). T cells and DCs were incubated for 7 days and re-stimulated with loaded and matured DCs that were prepared as described above.

An aliquot of the cells was taken 24 hours later and prepared for intracellular cytokine staining (Day 15), while the remaining cells were incubated for another 7 days. The latter cells were stimulated with another batch of loaded and matured DCs and prepared for intracellular cytokine staining on Day 22.

For intracellular cytokine staining, cells were incubated with Brefeldin A (Golgi Plug, R&D Systems) 2 hours after DC addition and incubated for another 18 hours. Cells were stained with anti-CD3-FITC and anti-CD8-cytochrome for 30 minutes, washed, permeabilized, and stained with anti-IFN-γ-PE for 30 minutes on ice. The cells were washed, fixed and analyzed by flow cytometry (ACS Calibur, Becton Dickinson). After the third DC loading and presentation, a batch of the T cells was incubated for three days and the supernatant was used for measuring the level of secreted IFN-γ by ELISA (Pharmingen DouSet). A protocol summary for the APA is presented in schematic form.

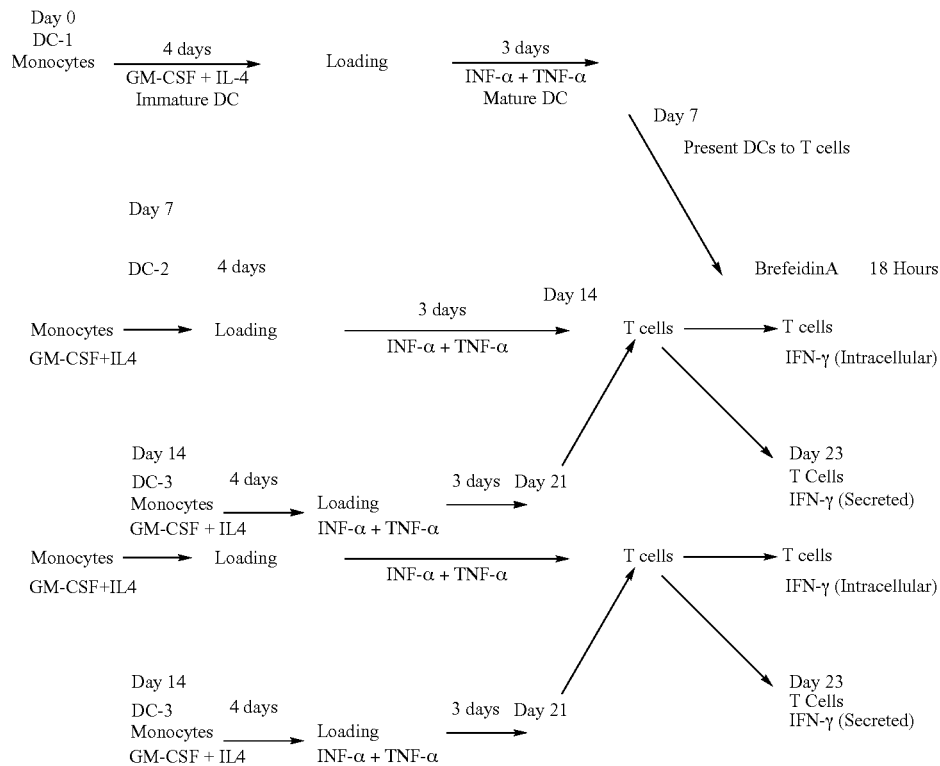

as characterized by flow cytometry using a broad CD marker panel. Next, monocytes were incubated with IL-4 and GM-CSF (R&D Systems) for 4 days in RPMI 1640+10% matched human serum to generate immature DC.

Again, an aliquot of the cells was stained with a broad CD marker panel to ensure purity and identity of the cells. The cells were harvested and loaded with antigens for 2-8 hours at 37° C., and matured with IFN-α and TNF-α for 3 days. Dendritic cell were checked again using flow cytometry for an array of CD markers to ensure that cells had undergone proper maturation. Mature DCs were washed thoroughly and added to T cells that were generated from the same monocytes as the DCs by means of negative selection using a magnetic T Example 15

Expression of Fc-γ Receptors and CD206 on Maturing DC

Figure 30:
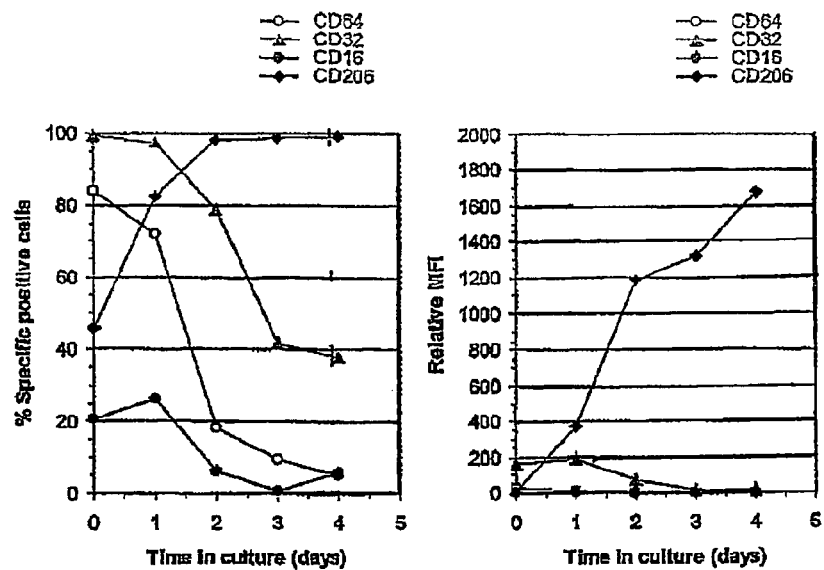
FIG. 30 shows the time course of expression of antigen binding receptors on maturing dendritic cells.
Figure 31:
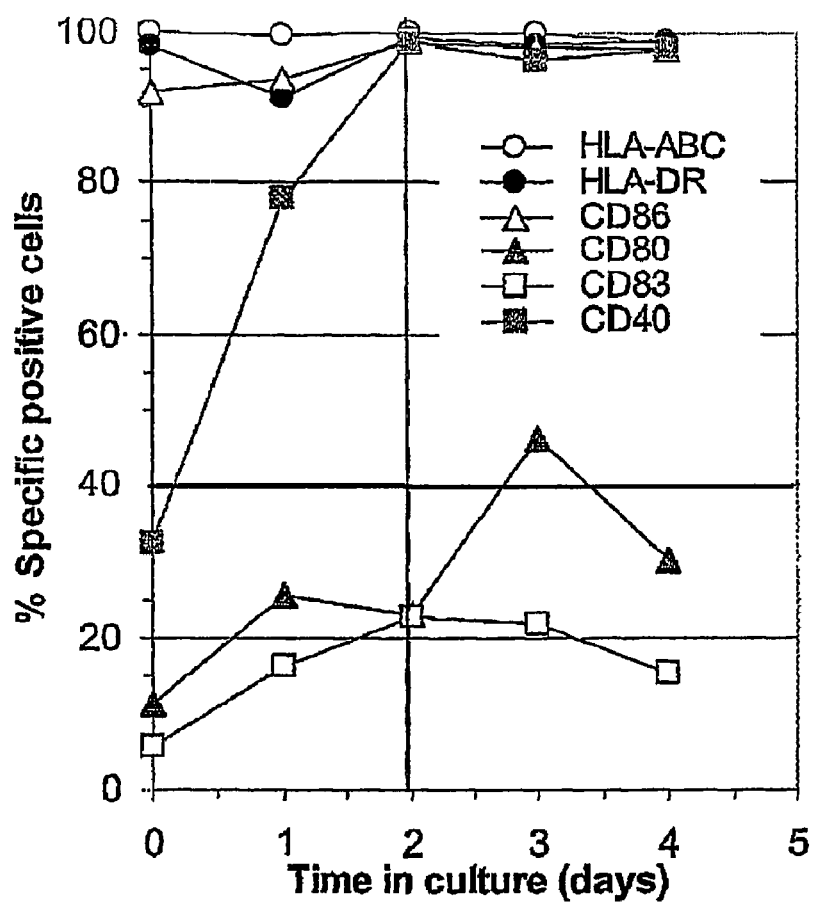
FIG. 31 shows the time course of expression of various dendritic cells activation markers.

There are several receptors on the APCs that bind and take up antigens. The abundance of these receptors on maturing DCs was evaluated using fluorescent labeled receptor-specific antibodies. FACS analysis was used to estimate percentage of specific positive cells in the total population of DCs and as a function of relative fluorescent intensity (FIG. 30). The expression of CD64 decreased with time in culture and at day 4 was almost negligible. In contrast, CD32, and to a lesser extent CD16, were expressed after 4 days of DC culture. On day 0 of culture, there was essentially no CD206 expression, but on culture with IL-4 and GM-CSF, the expression of CD206 was induced and at day 4 was expressed at very high levels. Thus at day 4, the day that antigen was loaded in the antigen presentation assays, the DCs possessed at least two potential receptors for the binding of chimeric antigens: CD32 and CD206. In addition, as shown in FIG. 30, they had the full complement of the co-stimulatory molecules. The expression of HLA-DR (Class II) and HLA-ABC (Class I) also increased with time in culture. Co-stimulatory molecules CD86 (B 7.2) and CD80 (B 7.1) were expressed at high levels throughout the period of the assay (FIG. 31). These results indicate that the monocyte-derived DCs were differentiating towards mature DCs and were capable of antigen presentation to T cells. The cells were used to evaluate the binding and uptake of the chimeric antigens in comparison to relevant antibodies.

Example 16

Phenotypic Analysis, Binding and Uptake Assay

For the phenotypic analysis and binding assay, all procedures using incubations were performed at 4° C., buffer solutions were also held at 4° C. The binding of antigens, chimeric antigens or antibodies was determined by incubating the cells with various concentrations of the agents for 60 minutes in PBSB.

For phenotypic analysis, cells were incubated with the various conjugated Mabs at the concentrations recommended by the manufacturer for 20 minutes. Incubations were performed with $1 \times 10^5$ cells/well in 96-well v-bottom plates in a volume of 25 µL. Subsequently, the cells were washed twice with PBSB.

Before conjugated Mab labeling, the cells were resuspended in PBS with 2% (w/v) paraformaldehyde (PF), and for the binding studies, the cells were treated with F(ab')$_2$ goat anti-mouse Alexa-488 (10 µg/mL) in PBSB for 20 minutes. The cells were washed twice with PBSB and either resuspended in PBSB with 2% PF and acquired by FACS or in PBSB and incubated with PE-conjugated CD32 or CD206 specific Mab for 20 minutes before washing twice with PBSB.

To determine the extent of uptake of chimeric antigens (e.g. HBV S1/S2-TBD) compared with IgG1 and IgG2a, cells were incubated with various concentrations of the antigen, IgG1 (2C12, the parent Mab from which TBD was produced) and IgG2a (G155-178) for 1 hour at 37° C. in AIM V media with 0.1% BSA. Cells were washed twice in PBSB and fixed with PBS with 2% PF overnight at 4° C. Subsequently, the cells were washed twice in PBSB and permeablized with PBS containing 0.1% (w/v) saponin (Sigma) for 40 minutes at 20° C.

The cells were washed twice with PBSB and incubated with F(ab')$_2$ goat anti-mouse Alexa-488 (10 µg/mL) in PBSB with 0.1% (w/v) saponin for 20 minutes at 4° C. After washing twice in PBSB, the cells were resuspended in PBSB. A variant of this assay involved treating the cells as above with chimeric antigen, IgG1, or IgG2a 10 minutes followed by the addition of F(ab')$_2$ goat anti-mouse Alexa-488 (10 µg/mL) for 50 minutes. Subsequently the cells were washed and resuspended in PBS with 2% PF. This procedure relied on the ability of the anti-mouse Alexa-488 Ab to directly bind the S1/S2-TBD, IgG1 or IgG2a molecules.

Cells were acquired by a Beckton Dickenson (BD) FACScan fitted with Cellquest acquisition and analysis software (BD). A gate was made on the viable cell population as determined by the FSC and SSC scatter profile and $\geq$10,000 events were acquired. To determine the percentage of positive cells, a gate was set based on negative control treated cells (isotype control labeled or cells labeled with F(ab')$_2$ goat anti-mouse Alexa-488 alone).

The percent of specific positive cells was calculated as:

$$\frac{\% \text{ positive cells test sample} - \% \text{ positive cells control}}{100 - \% \text{ positive cells of control}} \times 100$$

The relative mean fluorescent intensity (MFI) was determined as the MFI of the test sample—MFI of the control sample.

Example 17

Construction of pFASTBACHTa-TBD, TBD Protein Expression Vector

The mouse IgG1 DNA sequences encoding amino acids of CH1-Hinge-CH2-CH3 region was generated from mRNA isolated from the hybridoma (2C12) which produces Mab against HBV surface antigen (sAg). Total mRNA was isolated using TRizol reagent (Gibco BRL cat. No. 15596-026) and the cDNA of the TBD was generated by RT-PCR using Superscript First-strand Synthesis (Invitrogen Cat. No. 11904-018). The PCR primers contained linker sequences encoding the linker peptide—SRPQGGGS—(SEQ ID NO: 28) at the 5' terminus, a unique Not I site at the 5' and a unique Hind III restriction site at the 3' end. The resulting cDNA contains (5' Not I)-liner sequence-CH1 (VDKKI)-CH2-CH3-(3' Hind III). Following digestion with the respective enzymes, the fragment is ligated with pFASTBACHTa expression vector plasmid (invitrogen) using the same restriction enzyme sites to generate—pFASTBACHTa-TBD. The 5' primer used for PCR amplification was (Sense) 5' TGTCAT-TCTGCGGCCGCAAGGCGGCGGGAT CCGTGGACAA-GAAAATTGTGCCAGG (SEQ ID NO: 1) and the 3' primer was (antisense) 5' ACGAATCAAGCTTTGCAGCCCAG-GAGA (SEQ ID NO: 2), which contained the Not I and Hind III sites, respectively. The following is the protocol used for directional cloning. The generated fragment was digested with the respective enzymes, purified on agarose gel and cloned into the vector plasmid. The DNA sequence and the correctness of the ORF were verified by standard sequencing methods. Nucleotide sequence of the ORF of TBD in the plasmid pFASTBACHTa-TBD and the deduced amino acid sequences of the expressed TBD protein from the ORF is shown in FIG. 32.

Example 18

Expression and Purification of TBD Protein

Recombinant bacmids of standardized multiplicity of infection (MOI) were used to infect High Five insect cells. For suspension cultures, cells were seeded at a density of $3 \times 10^5$ cells/mL and incubated at 27.5° C. with shaking at 138 rpm until the cell density reached $2-3 \times 10^6$ cells/mL. Recombinant baculovirus was added to the cells. For the expression of TBD the MOI used was 10 pfu/cell. The incubation at 27.5° C. was continued for 48 hrs. The cells were harvested by centrifugation at 2,500 rpm for 10 minutes at 4° C. and used for the purification of the recombinant proteins.

TBD protein was expressed in Express Five Insect cells, purified as described in the methods section. The protein was subjected to electrophoresis on a 12% polyacrylamide gel and the coomassie blue-stained band is shown.

Example 19

Construction of HBV Surface Antigen S1/S2 and HBV S1/S2-TBD Chimeric Fusion Protein Plasmids The DNA encoding the HBV sAg fragment S1/S2 was generated from the plasmid pRSETB HBV S1/S2 template using PCR methodology. The primers used were: (sense) 5' GGATCCTGTACGATGACG (Seq. ID No. 5) and the 3' primer (antisense) 5' AGTCATTCTGCGGCCGCGAGT-TCGTCACAGGGTCCCCGG (Seq. ID No. 6) containing the restriction enzyme site Not I. The 5' end contained a unique Bam H I site derived from the parent plasmid which was used for ligations. Amplified DNA was digested with Bam H I/Not I and ligated with pFastBacHTa expression vector to generate the expression plasmid for HBV S1/S2 protein. The fragment was ligated with the plasmid pFastBacHTa-TBD (described in example 3) following the digestion with the respective enzymes. This produced the expression plasmid pFastBacHTa HBV S1/S2-TBD. This plasmid was used to produce recombinant baculovirus (described in example 10) which expressed the chimeric antigen-TBD fusion protein: 6-His tag-rTEV protease cleavage site-HBVS1/S2-TBD. Nucleotide and deduced amino acid sequences from the ORFs of plasmid pFastBacHTa HBV S1/S2 are shown in FIG. 8. Nucleotide and deduced amino acid sequences from the ORFs of plasmid pFastBacHTa HBV S1/S2-TBD are shown in FIG. 33.

Example 20

Expression and Purification of HBV Surface Antigen S1/S2 and HBVS1/S2-TBD Chimeric Fusion Proteins Recombinant bacmids of standardized multiplicity of infection (MOI) were used to infect High Five insect cells. For suspension cultures, cells were seeded at a density of $3 \times 10^5$ cells/mL and incubated at 27.5° C. with shaking at 138 rpm until the cell density reached $2-3 \times 10^6$ cells/mL. Recombinant baculovirus was added to the cells. For the expression of the fusion protein HBV S1/S2-TBD, the MOI was 1 pfu/cell and for S1/S2, 2 pfu/cell were used. The incubation at 27.5° C. was continued for 48 hrs. The cells were harvested by centrifugation at 2,500 rpm for 10 minutes at 4° C. and used for the purification of the recombinant proteins.

HBV S1/S2 protein and the fusion protein HBV S1/S2-TBD fusion protein were expressed in Express Five Insect cells, purified as described in example 1.b. The proteins were subjected to electrophoresis on a 12% polyacrylamide gel and stained with coomassie blue.

Example 21

Binding of Chimeric Antigens to Maturing DCs

The chimeric antigen S1/S2-TBD binds to maturing DCs with high efficiency (FIG. 34). The extent of binding of S1/S2-TBD relative to murine IgG1 and IgG2a to maturating DC was compared. DCs were isolated at various days of ex vivo culture (from day 0 to day 4) and treated with S1/S2-TBD (10 μg/mL) or with murine IgG1 (clone 2C12) or IgG2a (clone G155-178, 90 μg/mL) for 1 hour at 4° C. Subsequently, binding was detected with a F(ab')₂ anti-mouse IgG conjugated to Alexa 488 as described in the methods section. The binding of S1/S2-TBD relative to IgG1 and IgG2a on DC after 1 and 4 days of culture is shown in FIG. e. S1/S2-TBD binding was clearly much greater than the binding of either IgG1 or IgG2a with more S1/S2-TBD binding evident on day 1 than on day 4. These experiments clearly demonstrated that S1/S2-TBD was bound with high efficiency to the maturing DC.

Example 22

A High Proportion of Maturing DCs Bind Chimeric Antigen S1/S2-TBD

A large proportion of maturing DCs bind S1/S2-TBD. The binding of S1/S2-TBD in comparison to murine IgG2a and IgG1 was measured as a function of phenotypic changes on day 2 of the maturation of DCs as described in the methods section. DCs were isolated at various days of culture (from day 0 to day 4) and were treated with S1/S2-TBD (10 μg/mL), murine IgG1 (clone 2C12), or IgG2a (clone G155-178, 90 μg/ml) for 1 hour at 4° C. Subsequently, binding was detected with a F(ab')₂ anti-mouse IgG conjugated to Alexa 488. The binding of S1/S2-TBD relative to IgG1 and IgG2a on DC after 1 and 4 days of culture is shown in FIGS. 35 and 36. S1/S2-TBD binding was clearly much greater than the binding of either IgG1 or IgG2a with more S1/S2-TBD binding evident on day 1 than day 4. Thus, these experiments demonstrated that a large proportion of maturing DCs bind S1/S2-TBD The proportion of DCs that bind S1/S2-TBD was much greater than either IgG2a or IgG1. Furthermore, the degree of binding of S1/S2-TBD was several orders of magnitude greater than that of the immunoglobulins.

The chimeric Antigen S1/S2-TBD binds to DCs more efficiently than IgG1 or IgG2a on days 1 and 4 of culture.

Example 23

Chimeric Antigen S1/S2-TBD is Taken Up by DCs with High Efficiency

The uptake of S1/S2-TBD in comparison to murine IgG1 and IgG2a was estimated as a function of concentration on day 4 of DC maturation. The uptake was quantified at 37° C. for 1 hour and the results are shown in FIG. 37.

There was a linear increase in the uptake of S1/S2-TBD with concentration. IgG1 was taken up at a much lower level and there was very little uptake of IgG2a. Therefore, the chimeric antigen S1/S2-TBD is taken up by the DCs more efficiently than immunoglobulins.

Example 24

Correlation of CD32/CD206 Expression and S1/S2-TBD Binding to Maturing DCs

There is a direct correlation between the expression of CD32/CD206 receptors and S1/S2-TBD binding to maturing DCs. Since it was known that murine IgG1 binds efficiently to CD32, it was expected that S1/S2-TBD which contains the murine Fc component of IgG1 would also bind CD32. Furthermore, S1/S2-TBD by virtue of its high mannose glycosylation, would also be expected to bind to DC through the CD206 receptor.

The dot plots in FIG. 38 show S1/S2-TBD binding (10 µg/mL) and CD32 expression as well as S1/S2-TBD binding and CD206 expression. There was a direct correlation between the extent of S1/S2-TBD binding and the degree of CD32 expression, which was relatively heterogeneous, i.e., there was a broad degree of expression. These results demonstrate that S1/S2-TBD binds to CD32, and that the greater the expression of CD32, the greater was the degree of binding of the chimeric antigen S1/S2-TBD. The dot plot of S1/S2-TBD binding and CD206 expression shows that the vast majority of cells expressing CD206 also bound S1/S2-TBD A small percentage of the cell population was CD206 negative and was consequently negative for S1/S2-TBD binding. Therefore both CD32 and CD206 receptors are involved in the binding of the S1/S2-TBD.

Example 25

The Binding and Uptake of S1/S2-TBD is Primarily Via CD32, but CD206 is Involved to a Lesser Extent The uptake of S1/S2-TBD in comparison to murine IgG1 and IgG2a was estimated as a function of concentration on day 4 of DC maturation. The uptake was quantified at 37° C. for 1 hour in the presence and absence of inhibitors of CD32 and CD206 and the results are shown in FIG. 39. There was a progressive increase in the binding of the chimeric antigen with its concentration. Mab against mouse Fcγ fragment abolished this binding, whereas mannan, an inhibitor of CD206 receptor binding, had only marginal effect. Therefore, CD32 may be the primary receptor involved in the binding and uptake of the chimeric antigen.

Example 26

Glycosylation of HBV S1/S2 Antigen Produced in Insect Cells Bind to DCs through CD206 Receptors The insect cell pathway of protein glycosylation is different from that of mammalian cells in that proteins synthesized in insect cells undergo glycosylation that results in high mannose content and a lack of terminal sialic acid residues in the secreted protein (Altman, Staudacher, et al 1999).

HBV S1/S2, the antigen component of the chimeric antigen was expressed in both *E. coli* (no glycosylation) and in High Five insect cells (high mannose glycosylation). These antigens were compared for their binding to DCs. Glycosylated protein showed better binding and uptake by DCs (FIG. 40).

Example 27

Chimeric Antigen S1/S2-TBD Elicited T Cell Responses as measured by IFNγ Production The T cell response was greater with S1/S2-TBD treatment than with either of its two components measured individually. DCs were loaded with S1/S2 antigen, TBD, or S1/S2-TBD and presented to T cells in an APA as described in example 14. T cell stimulation was evaluated by measuring intracellular and secreted IFNγ levels. The results are presented in FIGS. 41 and 42. The chimeric antigen S1/S2-TBD induced the production of higher IFNγ levels compared to either the IRD or the TBD domain of the molecule when tested alone, at equivalent concentrations. It should be pointed out that 5 µg dose of S1/S2-TBD contains roughly 2.5 µg each of the components.

Example 28

IFNγ Production Following S1/S2-TBD Antigen Presentation by DCs

IFNγ production and secretion by CD3+ T cells increased in a concentration dependent manner following S1/S2-TBD antigen presentation by DCs. Purified S1/S2-TBD was used in APAs using human PBMC-derived DCs, and the secreted and intracellular IFNγ levels were measured in T cells following three rounds of antigen presentation. FIG. 43 presents intracellular levels and FIG. 44 shows the secreted levels. The results are the mean of three estimates.

Various concentrations of S1/S2-TBD were tested for the T cell response. The effect of S1/S2-TBD was greater than the tetanus toxoid treatment at similar concentrations. At concentrations lower than 5 µg/mL, the vaccine elicited a concentration dependent increase in the production and secretion of IFNγ. The positive response at low concentrations would be beneficial with respect to the dose necessary for vaccination and the cost of manufacturing of the vaccine.

Example 29

Glycosylation of HBV S1/S2 Antigen Imparts Immunogenicity to the Antigen and Generates Higher T Cell Responses Glycosylation of HBV S1/S2 elicits increased immunogenicity and T Cell responses. The insect cell pathway of protein glycosylation is different from that of mammalian cells in that proteins synthesized in insect cells undergo glycosylation that results in high mannose content and a lack of terminal sialic acid residues in the secreted protein (Altman, Staudacher, et al 1999).

HBV S1/S2, the antigen component of the chimeric antigen was expressed in both *E. coli* (no glycosylation) and in High Five insect cells (high mannose glycosylation). These antigens were compared for T cell responses when presented by DCs. Both intracellular and secreted IFNγ levels were measured and the results are presented in FIGS. 45 and 46.

Example 30

Construction of HBV Core Antigen and HBV Core-TBD Fusion Protein Expression Vectors HBV produces the core proteins (Core) to encapsidate the replicating genome of the virus. There are two forms of the core one secreted into circulation, also known as the "e" antigen and the capsid forming core protein. The present invention also relates to the generation of expression plasmids to produce the Core protein as well as the core antigen-TBD fusion protein, in insect cells similar to examples described in example 19. The DNA encoding the HBV Core protein was generated from the plasmid pALTHBV991 template using PCR technique. The 5' primer used for the PCR was (sense) 5' TGCGCTACCATGGACATTGACCCCT-TATAA AG (SEQ ID NO: 25) which contains the restriction enzyme Nco I site and the 3' primer used was (antisense) 5' TGTCATTCTGCGGCCGCGAACAT-TGAGATTCCCGAGATTGAG (SEQ ID NO: 26), containing the restriction enzyme Not I site. The PCR-amplified cDNA was digested with the respective enzymes and ligated with pFastBacHTa expression vector to generate either the expression plasmid for HBV Core protein or the expression plasmid pFastBacHTa HBV Core-TBD fusion protein.

Nucleotide and deduced amino acid sequences from the ORFs of plasmid pFastBacHTa HBV core are shown in FIG. 15. Nucleotide and deduced amino acid sequences from the ORFs of plasmid pFastBacHTa HBV Core-TBD are shown in FIG. 14.

Example 31

Construction of DHBV Surface Antigen PreS/S and DHBV PreS/S-TBD Fusion Protein Expression Vectors DHBV has served as a powerful animal model in the development of antiviral therapy for HBV. Pekin ducks, congenitally infected with DHBV have been used to study the mechanism of replication of the virus and for the screening of antiviral compounds. The present invention also describes the chimeric DHBV antigen-TBD molecules which could be used as therapeutic vaccines in DHBV-infected ducks, thus providing a viable animal model for the feasibility studies for a HBV therapeutic vaccines.

DNA encoding DHBV PreS/S was produced by PCR methods from template plasmid pFastBacHTa PreS/S (University of Alberta) using 5' primer (sense) 5' TATTCCGGAT-TATTCATACCG (Seq. ID No 9) and the 3' primer (antisense) 5' TGTCATTCAGCGGCCGCGAACTCTTG-TAAAAAAGAGCAGA (Seq. ID No 10), containing restriction enzyme Not I site. The unique restriction enzyme site Eco R I, resident on the parent plasmid pFastBacHTa PreS/S was used for directional cloning. All other protocols for the production of either the DHBV PreS/S or the fusion protein PreS/S-TBD are the same as described in example 19. Nucleotide and deduced amino acid sequences from the ORFs of plasmid pFastBacHTa DHBV PreS/S are shown in FIG. 21. Nucleotide and deduced amino acid sequences from the ORFs of plasmid pFastBacHTa DHBV PreS/S-TBD are shown in FIG. 17.

Example 32

Construction of DHBV Core antigen and DHBV Core-TBD Fusion Protein Vector Plasmids The cDNA coding for DHBV Core was generated by PCR using the following primers. The 5' terminus primer used was (sense) 5' TGCGCTACCATGGATATCAATGCTTCTA-GAGCC (Seq. ID No.11), containing the restriction enzyme Nco I site. The 3' terminus primer used was (antisense) 5' TGTCATTCTGCGGCCGCGATTTCCTAG-GCGAGGGAGATCTATG (Seq. ID No. 12), containing the restriction enzyme Not I site. All other protocols for the production of either the DHBV Core or the fusion protein DHBV Core-TBD are the same as described in the example 4 above. Nucleotide and deduced amino acid sequences from the ORFs of plasmid pFastBacHTa DHBV Core are shown in FIG. 24. Nucleotide and deduced amino acid sequences from the ORFs of plasmid pFastBacHTa DHBV Core-TBD are shown in FIG. 23.

Example 33

Construction of pFastBacHTa HCV Core (1-191) Antigen and the Chimeric Antigen pFastBacHTa HCV Core (1-191)-TBD Fusion Protein Vector Plasmids The DNA encoding the HCV core was generated from the plasmid pCV-H77C template (University of Alberta) using PCR methodology. The primers used were: (sense) 5' CGGAATTCATGAGCACGAATCCTAAAC (Sequence ID No. 13) containing the unique restriction enzyme site Eco RI and the 3' primer (antisense) 5' GGACTAGTCCGGCT-GAAGCGGGCACAGTCAGGCAAGAG (Sequence ID No. 14) containing the unique restriction enzyme site Spe I. Amplified DNA was digested with EcoR I/Spe I and ligated with pFastBacHTa expression vector digested with the same two enzymes. The expression plasmid for HCV core protein was generated with this method. The fragment was ligated with the plasmid pFastBacHTa (described in example 19) following the digestion with the respective enzymes. This produced the expression plasmid pFastBacHTa HCV Core. This plasmid was used for the transposition in DH10Bac and the recombinant Bacmids used for Sf9 insect cell transfections. The resulting baculovirus carrying the gene of interest was optimized for MOI and the time for efficient protein expression (described in example 19). The generation of recombinant expression plasimd pFastBacHTa-HCV Core-TBD was achieved through similar protocols. The PCR-amplified DNA was digested with EcoR I/Spe 1 and the purified fragment was ligated with the plasmid pFastBacHTa-TBD (described in example 19) following the digestion with the respective enzymes. This produced the expression plasmid pFastBacHTa HCV Core-TBD. This plasmid was used to produce recombinant baculovirus which expressed the chimeric antigen-TBD fusion protein: 6-His tag-rTEV protease cleavage site-HCV Core-TBD. Nucleotide and deduced amino acid sequences from the ORFs of plasmid pFastBacHTa HCV Core (1-191) are shown in FIG. 47. Nucleotide and deduced amino acid sequences from the ORFs of plasmid pFastBacHTa HCV Score (1-191)-TBD are shown in FIG. 48. All other protocols are described in example 19.

Example 34

Expression and Purification of HCV Core Antigen and HCV Core-TBD Chimeric Fusion Protein Recombinant bacmids of standardized multiplicity of infection (MOI) were used to infect High Five insect cells. For suspension cultures, cells were seeded at a density of $3 \times 1$ cells/mL and incubated at 27.5° C. with shaking at 138 rpm until the cell density reached $2-3 \times 10^6$ cells/mL. Recombinant baculovirus was added to the cells. For HCV core, infections of High Five cells were performed at an MOI=1 pfu/cell. Cells in suspension were grown to mid-log phase and infected with the recombinant baculovirus at this MOI. These infected cultures were incubated for 48 hours then the cells were harvested. For HCV core-TBD, infections of High Five cells were done at an MOI of 1 pfu/cell and for 72 hours.

Purification of Proteins

The purification of HCV Core and HCV core-TBD was done under denaturing conditions as follows. The cells were lysed in a buffer containing 6 M Guanidinium HCl, 0.1 M $Na_2HPO_4$, 0.01 M Tris-HCl pH 8.0, 0.01 M Imidazole, (lysis buffer). The suspension was sonicated on ice with 5 pulses of 1 minute per pulse at a power setting of 60 watts, and was mixed at room temperature for 1 hour. The lysate was centrifuged at $10,000 \times g$ for 10 min to remove unbroken cells and cell debris. The supernatant was mixed for 1 hr with Ni-NTA agarose (Qiagen) beads (5 mL/100 mL cell lysate), pre-equilibrated with lysis buffer. The Following the mixing step, the beads were loaded on to a column and was washed with a minimum 20 column volumes of 8M Urea, 0.1 M $Na_2HPO_4$, 0.01 M Tris-HCl pH 8.0 0.02M Imidazole (wash buffer), until the $OD_{280}$ was <0.01. The bound protein was eluted in a buffer containing 8M Urea, 0.1 M Na$_2$HPO$_4$, 0.01 M Tris-HCl pH 8, 0.25 mM imidazole.

HCV Core-TBD was separated from other proteins by gel filtration. The peak elution fractions from Ni-NTA agarose column were loaded on a Sephadex G100 (Pharmacia) gel filtration column and the column was eluted with 8M Urea, 0.1 M Na$_2$HPO$_4$, 0.01 M Tris-HCl pH 8, 0. The fractions containing HCV Core-TBD were pooled and dialyzed against PBS.

HCV core antigen and the fusion protein HCV Core-TBD fusion protein were expressed in Express Five Insect cells, and purified; coomassie blue-stained HCV core was run on a 12% polyacrylamide gel. Core-TBD was purified and a Western blot using $^6$-His monoclonal antibody.

Example 35

Construction of pFastBacHTa HCV Core (1-177) Antigen and pFastBacHTa HCV Core (1-177)-TBD Fusion Protein Plasmid Vectors The DNA coding for HCV core (1-177) was generated by PCR using the following primers. The 5' terminus primer used was (sense) 5'CCGGAATTCATGAGCACGMTC-CTAAAC (Sequence ID No. 15), containing the restriction enzyme EcoR I site. The 3' terminus primer used was (antisense) 5' GGACTAGTCCGMGATAGAGAMGAGC (SEQUENCE ID NO.16), containing the restriction enzyme Spe I site. Following digestion with the two enzymes, the DNA fragment was ligated with plasmid pFastBacHTa to generate pFastBacHTaHCV (Core 1-177) and with pFastBacHTa-TBD to generate the expression plasmid pFastBacHTaHCV Core (1-177)-TBD. All other protocols for the production of either the HCV core (1-177) antigen or the chimeric antigen fusion protein HCV core (1-177)-TBD are the same as described in example 19. Nucleotide sequence and the deduced amino acid sequence of 6-His-rTEVprotease site-HCV Core (1-177) are shown in FIG. 49. Nucleotide sequence and the deduced amino acid sequence of 6-His-rTEVprotease site-HCV Core (1-177)-TBD are shown in FIG. 50.

Example 36

Construction of pFastBacHTa HCV NS5A Antigen and pFastBacHTa HCV NS5A-TBD Fusion Protein Expression Vector Plasmids The DNA encoding the HCV NS5A fragment was generated from the plasmid pCV-H77C (University of Alberta) template using PCR methodology. The 5' primer used form the PCR was (sense) 5'CCGGAATTCTCCGGTTCCTG-GCTAAGG (Sequence ID No. 17) containing the restriction enzyme EcoR I site. The PCR primer for 3' terminus was (antisense) 5'GGACTAGTCCGCACACGACATCTTCCGT (Sequence ID No. 18) containing the restriction enzyme Spe I site. Amplified DNA was digested with the respective enzymes and ligated with pFastBacHTa expression vector to generate either the expression plasmid for HCV NS5A or it was ligated with the expression plasmid pFastBacHTa-TBD to generate the expression plasmid pFastBacHTa HCV NS5A-TBD fusion protein.

Nucleotide sequence and the deduced amino acid sequence of 6-His-rTEVprotease site-HCV NS5A are shown in FIG. 51. Nucleotide sequence and the deduced amino acid sequence of 6-His-rTEVprotease site-HCV NS5A-TBD are shown in FIG. 52.

Example 37

Construction of pFastBacHTa HCV E1 Antigen and pFastBacHTa HCV E1-TBD Fusion Protein Expression Vectors Plasmid pFastBacHTa HCV E1 and pFastBacHTa HCV E1-TBD which are used to express HCV envelope protein E1 and the respective chimeric antigen E1-TBD fusion protein, were generated as follows. The DNA encoding the E1 protein was generated from the plasmid pCV-H77C template using PCR technique. The 5' primer used for the PCR was (sense) 5'CCGGAATTCTACCAAGTGCGCAATTCCT (Sequence ID No. 19) which contains the restriction enzyme EcoR I site and the 3' primer used was (antisense) 5'GGACTAGTCCT-TCCGCGTCGACGCCGGCAAAT (Sequence ID No.20), containing the restriction enzyme Spe I site. The PCR-amplified cDNA was digested with the respective enzymes and ligated with pFastBacHTa expression vector to generate the expression plasmid pFastBacHTa HCV E1 for the expression of HCV E1 protein. The digested DNA fragment was ligated with pFastBacHTa-TBD to generate the plasmid pFastBacHTa HCV E1-TBD which was used to express HCV E-TBD fusion protein.

FIG. 53 shows the nucleotide and the deduced amino acid sequences of 6-His-rTEVprotease site-HCV E1 in the open reading frame of the expression plasmid. FIG. 54 shows nucleotide and the deduced amino acid sequences of 6-His-rTEVprotease site-HCV E1-TBD chimeric antigen fusion protein.

Example 38

Construction of pFastBacHTa HCV E2 Antigen and pFastBacHTa HCV E2-TBD Fusion Protein Expression Vectors The DNA encoding HCV E2 antigen was produced by PCR from a plasmid pCV-H77C. The 5' primer used for the PCR was (sense) 5' GCGGAATTCACCCACGTCAC-CGGGGGAMTGC (Sequence ID No. 21) containing a unique restriction enzyme site EcoR I that is used for directional cloning. The 3' primer used was (antisense) 5' GGAC-TAGTCCAGCCGCCTCCGCTTGGGATATGAGT (Sequence ID No. 22) containing the restriction enzyme Spe I site. Following PCR amplification, the fragment was digested with the restriction enzymes EcoR I and Spe I an the DNA fragment was purified and ligated with the expression plasmid pFastBacHTa at the respective sites to produce pFastBacHTa HCV E2, which expressed the E2 antigen. The same fragment was also used to ligate with pFastBacHTa-TBD to generate the expression plasmid pFastBacHTa HCV E2-TBD, which expressed the chimeric antigen fusion protein HCV E2-TBD. The production of baculovirus stocks from these plasmids and the expression of the E2 and E2-TBD in High Five insect cells were done as described in previous examples.

FIG. 55 shows the nucleotide and the deduced amino acid sequences of 6-His-rTEVprotease site-HCV E2 in the open reading frame of the expression plasmid. FIG. 56 shows nucleotide and the deduced amino acid sequences of 6-His-rTEVprotease site-HCV E2-TBD chimeric antigen fusion protein.

Example 39

Construction of pFastBacHTa HCV E1/E2 Antigen and pFastBacHTa HCV E1/E2-TBD Fusion Protein Expression Vectors DNA encoding HCV E1/E2 was produced by PCR methods from the plasmid pCV-H77C using 5' primer (sense) 5' CCGGAATTCTACCMGTGCGCAATTCCT (Sequence ID No. 23) containing the restriction enzyme site EcoR I and the 3' primer (antisense) 5' GGACTAGTCCAGCCGCCTCCGCTTGGGATATGAGT (Sequence ID No. 24) containing the restriction enzyme site Spe I. Restriction enzyme-digested DNA fragment was cloned into the respective sites of either pFastBacHTa to generate pFastBacHTaHCV E1/E2 or pFastBacHTa-TBD to generate pFastBacHTa HCV E1/E2-TBD. All other protocols for the production of either the E1/E2 antigen or the fusion protein E1/E2-TBD are the same as described in the example above.

FIG. 57 shows the nucleotide and the deduced amino acid sequences of 6-His-rTEVprotease site-HCV E1/E2 in the open reading frame of the expression plasmid. FIG. 58 shows nucleotide and the deduced amino acid sequences of 6-His-rTEVprotease site-HCV E1/E2-TBD chimeric antigen fusion protein.

Conclusions from Examples 10-39
1. A new class of Chimeric Antigens is designed in order to incorporate antigen and antibody components in the molecule.
2. Antigen components can be derived from infectious agents or cancer antigen.
3. Antibody components are Xenotypic, of murine origin, in the case of human chimeric antigens.
4. Chimeric antigen fusion proteins, TBD and the respective antigens have been produced by recombinant techniques.
5. Chimeric antigen fusion proteins, TBD and the respective antigens have been produced (expressed) in a heterologous expression system (Insect cells).
6. By virtue of the expression in insect cells, the proteins have high mannose glycosylation in the them.
7. Chimeric antigens include fusion proteins from HBV surface antigens (S1/S2), HBV Core and TBD, derived from the murine Mab 2C12.
8. Chimeric antigens include fusion proteins of DHBV surface antigens PreS/S, Core and TBD.
9. The following antigens from HCV have been cloned and expressed in insect cell expression systems. HCV Core (1-191), HCV core (1-177), HCV NS5A, HCV E1, HCV E2, HCV E1/E2.
10. Chimeric antigen fusion proteins of HCV include HCV Core (1-191), HCV core (1-177), HCV NS5A, HCV E1, HCV E2, HCV E1/E2 and TBD.
11. Chimeric antigen fusion protein HCV Core (1-191)-TBD and HCV Core (1-191) have been expressed and purified.
12. Chimeric antigen fusion protein HBV surface antigen S1/S2-TBD and HBV surface antigen S1/S2 has been purified.
13. The fusion protein by binds to antigen presenting cells (Human PBMC-derived DCs) and are taken up by the DCs.
14. Binding and uptake is via Fcγ receptors CD 32 and possibly through CD 64.
15. Binding and uptake can occur via CD 206, the Mannose Macrophage receptor.
16. High mannose Glycosylation augments the binding and uptake of the antigens via CD206.
17. Chimeric antigen fusion protein HBV surface antigen S1/S2-TBD enhances the antigen presentation by professional antigen presenting cells (DCs).
18. DCs loaded with the Chimeric antigen fusion protein HBV surface antigen S1/S2-TBD, on presentation to T cells elicit an immune response.
19. The immune response can be measured as an increase in intracellular and secreted IFNγ.

Description of Artificial Sequence: Seq. ID No. 1: TBD amplification Primer 5'
5' TGTCATTCTGCGGCCGCAAGGCGGCGGGATCCGTGGACAAGAAAATTGT GCCAGG (sense)
Type: DNA
Length: 55
Nature: Artificial sequence Description of Artificial Sequence: Seq. ID No. 2: TBD amplification primer 3'
5' ACGMTCAAGCTTTGCAGCCCAGGAGA (antisense)
Type: DNA
Length: 27
Nature: Artificial sequence Description of Artificial Sequence: Seq. ID No. 3: pFastBac 5' Sequencing primer
5' TAT TCC GGA TTA TTC ATA CCG (sense) and
Type: DNA
Length: 21
Nature: Artificial sequence Description of Artificial Sequence: Seq. ID No.4: pFastBac 3' sequencing primer
5'CTCTACAMTGTGGTATGGC (antisense)
Type: DNA
Length: 20
Nature: Artificial sequence Description of Artificial Sequence: Seq. ID No. 5: HBV S1/S2 5' PCR amplification primer
5' GGATCCTGTACGATGACG (sense)
Type: DNA
Length: 20
Nature: Artificial sequence Description of Artificial Sequence: Seq. ID No.6: HBV S1/S2 3' PCR amplification primer
5' AGTCATTCTGCGGCCGCGAGTTCGTCACAGGGTCCCCGG (antisense)
Type: DNA
Length: 39
Nature: Artificial sequence Description of Artificial Sequence: Seq. ID No. 7: HBV S1/S2/S 5' PCR Amplification Primer
5' GATAAGGATCCTATGGGAGGTTGGTCATCAAAAC (sense)
Type: DNA
Length: 34
Nature: Artificial sequence Description of Artificial Sequence: Seq. ID No. 8: HBV S1/S2/S 3' PCR Amplification Primer
5' GTCATACTGCGGCCGCGAAATGTATACCCAGAGACAAAAG (antisense)
Type: DNA
Length: 40
Nature: Artificial sequence Description of Artificial Sequence: Seq. ID No. 9: DHBV PreS/S PCR 5' Amplification Primer
5' TATTCCGGATTATTCATACCG (sense)
Type: DNA Length: 21
Nature: Artificial sequence
Description of Artificial Sequence: Seq. ID No. 10: DHBV PreS/S PCR 3' Amplification Primer
5' TGTCATTCAGCGGCCGCGAACTCTTG-TAAAAAAGAGCAGA (antisense)
Type: DNA
Length: 40
Nature: Artificial sequence
Description of Artificial Sequence: Seq. ID No. 11: DHBV Core PCR 5' Amplification Primer
5' TGCGCTACCATGGATATCAATGCTTCTAGAGCC (sense)
Type: DNA
Length: 33
Nature: Artificial sequence
Description of Artificial Sequence: Seq. ID No. 12: DHBV Core PCR 3' Amplification Primer
5' TGTCATTCTGCGGCCGCGATTTCCTAG-GCGAGGGAGATCTATG (antisense)
Type: DNA
Length: 43
Nature: Artificial sequence
Description of Artificial Sequence: Seq. ID No.13: HCV Core (1-191) PCR 5' Amplification Primer
5' CGGMTTCATGAGCACGMTCCTMAC (sense)
Type: DNA
Length: 27
Nature: Artificial sequence
Description of Artificial Sequence: Seq. ID No.14: HCV Core (1-191) PCR 3' Amplification Primer
5' GGACTAGTCCGGCTGAAGCGGGCACAGT-CAGGCAAGAG (antisense)
Type: DNA
Length: 38
Nature: Artificial sequence
Description of Artificial Sequence: Seq. ID No.15: HCV Core (1-177) PCR 5' Amplification Primer
5' CGGAATTCATGAGCACGMTCCTMAC (sense)
Type: DNA
Length: 27
Nature: Artificial sequence
Description of Artificial Sequence: Seq. ID No.16: PCR HCV Core (1-177) 3' Amplification Primer
5' GGACTAGTCCGAAGATAGAGAAAGAGC (antisense)
Type: DNA
Length: 27
Nature: Artificial sequence
Description of Artificial Sequence: Seq. ID No.17: HCV NS5A antigen PCR 5' Amplification Primer
5' CCGGAATTCTCCGGTTCCTGGCTMGG (sense)
Type: DNA
Length: 27
Nature: Artificial sequence
Description of Artificial Sequence: Seq. ID No.18: HCV NS5A antigen PCR 3' Amplification Primer
5' GGACTAGTCCGCACACGACATCTTCCGT (antisense)
Type: DNA
Length: 28
Nature: Artificial sequence
Description of Artificial Sequence: Seq. ID No.19: HCV E1 antigen PCR 5' Amplification Primer
5' CCGGAATTCTACCAAGTGCGCAATTCCT (sense)
Type: DNA
Length: 28
Nature: Artificial sequence
Description of Artificial Sequence: Seq. ID No.20: HCV E1 antigen PCR 3' Amplification Primer
5' GGACTAGTCCTTCCGCGTCGACGCCGGCAAAT (antisense)
Type: DNA
Length: 32
Nature: Artificial sequence
Description of Artificial Sequence: Seq. ID No.21: HCV E2 antigen PCR 5' Amplification Primer
5' GCGGMTTCACCCACGTCACCGGGGGAAATGC (sense)
Type: DNA
Length: 32
Nature: Artificial sequence
Description of Artificial Sequence: Seq. ID No.22: HCV E2 antigen PCR 3' Amplification Primer
5' GGACTAGTCCAGCCGCCTCCGCTTGG-GATATGAGT (antisense)
Type: DNA
Length: 35
Nature: Artificial sequence
Description of Artificial Sequence: Seq. ID No.23: HCV E1/E2 antigen PCR 5' Amplification Primer
5' CCGGAATTCTACCAAGTGCGCAATTCCT (sense)
Type: DNA
Length: 29
Nature: Artificial sequence
Description of Artificial Sequence: Seq. ID No.24: HCV E1/E2 antigen PCR 3' Amplification Primer
5' GGACTAGTCCAGCCGCCTCCGCTTGG-GATATGAGT (sense)
Type: DNA
Length: 35
Nature: Artificial sequence

REFERENCES

Banchereau, J. and R. M. Steinman (1998). "Dendritic cells and the control of immunity." *Nature* 392(6673): 245-52.

Beasley, R. P. (1988). "Hepatitis B virus. The major etiology of hepatocellular carcinoma." *Cancer* 61(10): 1942-56.

Campton, K., W. Ding, et al. (2000). "Tumor antigen presentation by dermal antigen-presenting cells." *J Invest Dermatol* 115(1): 57-61.

Donnelly, J. J., J. B. Ulmer, et al. (1997). "DNA vaccines." *Annu Rev Immunol* 15: 617-48.

Fong, L. and E. G. Engleman (2000). "Dendritic cells in cancer immunotherapy." *Annu Rev Immunol* 18: 245-73.

Hilgers, L. A., G. Lejeune, et al. (1999). "Sulfolipo-cyclodextrin in squalane-in-water as a novel and safe vaccine adjuvant." *Vaccine* 17(3): 219-28.

Lai, W. C. and M. Bennett (1998). "DNA vaccines." *Crit Rev Immunol* 18(5): 449-84.

Larsson, M., J. F. Fonteneau, et al. (2001). "Dendritic cells resurrect antigens from dead cells." *Trends Immunol* 22(3): 141-8.

Laupeze, B., O. Fardel, et al. (1999). "Differential expression of major histocompatibility complex class Ia, Ib, and II molecules on monocytes-derived dendritic and macrophagic cells." *Hum Immunol* 60(7): 591-7.

Lorenz, M. G., J. A. Kantor, et al. (1999). "Anti-tumor immunity elicited by a recombinant vaccinia virus expressing CD70 (CD27L)." *Hum Gene Ther* 10(7): 1095-103.

Mason, W. S., G. Seal, et al. (1980). "Virus of Pekin ducks with structural and biological relatedness to human hepatitis B virus." *J Virol* 36(3): 829-36.

Newman, K. D., P. Elamanchili, et al. (2002). "Uptake of poly(D,L-lactic-co-glycolic acid) microspheres by antigen-presenting cells in vivo." *J Biomed Mater Res* 60(3): 480-6.

Newman, K. D., G. S. Kwon, et al. (2000). "Cytoplasmic delivery of a macromolecular fluorescent probe by poly(d,1-lactic-co-glycolic acid) microspheres." *J Biomed Mater Res* 50(4): 591-7.

Newman, K. D., J. Samuel, et al. (1998). "Ovalbumin peptide encapsulated in poly(d,l lactic-co-glycolic acid) microspheres is capable of inducing a T helper type 1 immune response." *J Control Release* 54(1): 49-59.

Regnault, A., D. Lankar, et al. (1999). "Fcgamma receptor-mediated induction of dendritic cell maturation and major histocompatibility complex class I-restricted antigen presentation after immune complex internalization." *J Exp Med* 189(2): 371-80.

Sprengel, R., E. F. Kaleta, et al. (1988). "Isolation and characterization of a hepatitis B virus endemic in herons." *J Virol* 62(10): 3832-9.

Steinman, R. M., K. Inaba, et al. (1999). "Antigen capture, processing, and presentation by dendritic cells: recent cell biological studies." *Hum Immunol* 60(7): 562-7.

Summers, J., J. M. Smolec, et al. (1978). "A virus similar to human hepatitis B virus associated with hepatitis and hepatoma in woodchucks." *Proc Natl Acad Sci USA* 75(9): 4533-7.

Tarte, K. and B. Klein (1999). "Dendritic cell-based vaccine: a promising approach for cancer immunotherapy." *Leukemia* 13(5): 653-63.

Wen, Y. M., D. Qu, et al. (1999). "Antigen-antibody complex as therapeutic vaccine for viral hepatitis B." *Int Rev Immunol* 18(3): 251-8.

Altman, F., Staudacher, E., Wilson, I. B. H and Marz, L (1999) Insect Cells as Hosts for the Expression of Recombinant Glycoproteins. Glycoconjugate Journal 16: 109-123.

Berlyn, K. A., et al., Clin. Immunol., 101(3):276-283 (2001).

Sambrook, J and Russell, D. W (2001) in Molecular Cloning, A Laboratory Manual. Cold Spring Harbor Press.

---

The claims in the present invention are:

1. A composition for eliciting a T-cell response in vivo, the composition comprising a purified chimeric fusion protein antigen, the chimeric fusion protein antigen comprising an immune response domain and a target binding domain expressed from an open reading frame encoding the immune response domain and the target binding domain fused together genetically,
   wherein the immune response domain comprises one or more HBV surface antigens, or antigenic epitopes thereof, and
   wherein the target binding domain consists of an Ig hinge region, at least a portion of a $C_H1$ region and a xenotypic Fc antibody fragment comprising at least part of a $C_H2$ and $C_H3$ domain; and
   wherein the chimeric fusion protein antigen comprises non-mammalian glycosylation.

2. The composition of claim 1, wherein the one or more HBV surface antigens are selected from the group consisting of one or more of HBV S polypeptide, HBV S1 polypeptide, and HBV S2 polypeptide.

3. The composition of claim 1, wherein a His tag is linked to the chimeric antigen.

4. The composition of claim 1, wherein the target binding domain is capable of binding to an antigen presenting cell.

5. The composition of claim 4, wherein the antigen presenting cell is a dendritic cell.

6. The composition of claim 1, wherein the antibody fragment is a murine antibody fragment.

7. The composition of claim 1, wherein the immune response domain comprises one or more antigenic sequences.

8. The composition of claim 1, wherein the composition has the ability to induce (a) a $T_H1$ immune response, (b) a $T_H2$ immune response, or (c) a $T_H1$ immune response and a $T_H2$ immune response.

9. The composition of claim 1, wherein the immune response domain is linked to a 6-His tag and a recombinant tobacco etch virus (rTEV) protease cleavage site.

10. The composition of claim 1, wherein the one or more HBV surface antigens comprises HBV S1/S2 protein.

11. The composition of claim 1, wherein the one or more HBV surface antigens are selected from the group consisting of HBV S1/S2 protein and HBV S2/S protein.

12. The composition of claim 1, wherein the glycosylation comprises mannose glycosylation.

13. The composition of claim 1, further comprising a cell.

14. The composition of claim 13, wherein the cell is an antigen presenting cell.

15. The composition of claim 13, wherein the cell is a cultured cell.

16. The composition of claim 1, wherein the composition comprises a monomer comprising an immune response domain and a target binding domain.

17. The composition of claim 16, wherein the composition comprises a dimer of the monomer.

18. The composition of claim 3, wherein the His tag is a 6 His peptide.

19. The composition of claim 3, wherein the His tag is linked to immune response domain.

20. The composition of claim 3, wherein the His tag is linked to the target binding domain.

21. A composition for eliciting a T-cell response in vivo, the composition comprising a purified chimeric fusion protein antigen, the chimeric fusion protein antigen comprising an immune response domain and a target binding domain expressed from an open reading frame encoding the immune response domain and the target binding domain fused together genetically,
   wherein the target binding domain consists of an Ig hinge region, at least a portion of a $C_H1$ region and a xenotypic Fc antibody fragment comprising at least part of a $C_H2$ and $C_H3$ domain;
   wherein the Fc antibody fragment is capable of binding to an Ig Fc receptor or an antigen presenting cell; and
   wherein the chimeric fusion protein antigen comprises non-mammalian glycosylation.

22. The composition of claim 21, wherein the immune response domain comprises one or more HBV antigens, or antigenic epitopes thereof.

23. The composition of claim 22, wherein the one or more HBV antigens are HBV antigens comprising one or more HBV surface antigens.

24. The composition of claim 23, wherein the one or more HBV surface antigens are selected from the group consisting of one or more of HBV S protein, HBV S1 protein, and HBV S2 protein.

25. The composition of claim 24, wherein the one or more HBV surface antigens comprise HBV S1/S2 protein.

26. The composition of claim 24, wherein the one or more HBV surface antigens are selected from the group consisting of HBV S1/S2/S protein and HBV S2/S protein.

27. The composition of claim 21, wherein a 6-His-peptide is linked to the immune response domain.

28. The composition of claim 21, wherein the target binding domain is capable of binding to an antigen presenting cell.

29. The composition of claim 28, wherein the antigen presenting cell is a dendritic cell.

30. The composition of claim 21, wherein the immune response domain comprises one or more antigenic sequences.

31. The composition of claim 21, wherein the composition has the ability to induce (a) a $T_H1$ immune response, (b) a $T_H2$ immune response, or (c) a $T_H1$ immune response and a $T_H2$ immune response.

32. The composition of claim 21, wherein the glycosylation comprises mannose glycosylation.

33. The composition of claim 21, wherein the immune response domain is linked to a 6-His tag and a recombinant tobacco etch virus (rTEV) protease cleavage site.

34. The composition of claim 21, further comprising a cell.

35. The composition of claim 34, wherein the cell is an antigen presenting cell.

36. The composition of claim 34, wherein the cell is a cultured cell.

37. The composition of claim 23, wherein the one or more HBV antigens comprise human HBV antigens.

38. The composition of claim 21, wherein the composition comprises a monomer comprising an immune response domain and a target binding domain.

39. The composition of claim 38, wherein the composition comprises a dimer of the monomer.

40. The composition of claim 21, wherein a 6-His-peptide is linked to the target binding domain.

* * * * *